(12) United States Patent
Zheng et al.

(10) Patent No.: US 10,829,460 B2
(45) Date of Patent: Nov. 10, 2020

(54) [6,6] FUSED BICYCLIC HDAC8 INHIBITORS

(71) Applicant: Valo Early Discovery, Inc., Boston, MA (US)

(72) Inventors: Xiaozhang Zheng, Lexington, MA (US); Pui Yee Ng, Lexington, MA (US); Jennifer R. Thomason, Clinton, MA (US); Mary-Margaret Zablocki, Revere, MA (US); Bingsong Han, Westwood, MA (US); Nicholas Barczak, Waterford, CT (US); Cuixian Liu, Madison, CT (US); Aleksandra Rudnitskaya, Roslindale, MA (US); David R. Lancia, Jr., Boston, MA (US); Kenneth W. Bair, Wellesley, MA (US)

(73) Assignee: Valo Early Discovery, Inc., Boston, MA (US)

( * ) Notice: Subject to any disclaimer, the term of this patent is extended or adjusted under 35 U.S.C. 154(b) by 0 days.

(21) Appl. No.: 16/449,675

(22) Filed: Jun. 24, 2019

(65) Prior Publication Data
US 2019/0308946 A1 Oct. 10, 2019

Related U.S. Application Data

(63) Continuation of application No. 16/003,861, filed on Jun. 8, 2018, now Pat. No. 10,370,343, which is a continuation of application No. 15/255,817, filed on Sep. 2, 2016, now Pat. No. 10,029,995.

(60) Provisional application No. 62/214,101, filed on Sep. 3, 2015.

(51) Int. Cl.
| | | |
|---|---|---|
| C07D 265/36 | (2006.01) |
| C07D 413/12 | (2006.01) |
| C07D 413/06 | (2006.01) |
| C07D 401/04 | (2006.01) |
| C07D 279/16 | (2006.01) |
| C07D 491/107 | (2006.01) |
| C07D 413/10 | (2006.01) |
| C07D 471/04 | (2006.01) |
| C07D 417/06 | (2006.01) |
| C07D 513/04 | (2006.01) |
| C07D 487/04 | (2006.01) |
| C07D 265/34 | (2006.01) |
| C07D 279/14 | (2006.01) |

(52) U.S. Cl.
CPC ........ *C07D 265/36* (2013.01); *C07D 265/34* (2013.01); *C07D 279/14* (2013.01); *C07D 279/16* (2013.01); *C07D 401/04* (2013.01); *C07D 413/06* (2013.01); *C07D 413/10* (2013.01); *C07D 413/12* (2013.01); *C07D 417/06* (2013.01); *C07D 471/04* (2013.01); *C07D 487/04* (2013.01); *C07D 491/107* (2013.01); *C07D 513/04* (2013.01)

(58) Field of Classification Search
CPC .................................................... C07D 265/36
USPC ........................................................ 544/90
See application file for complete search history.

(56) References Cited

U.S. PATENT DOCUMENTS

| | | |
|---|---|---|
| 5,234,923 A | 8/1993 | Poss et al. |
| 5,312,820 A | 5/1994 | Ashton et al. |
| 5,393,771 A | 2/1995 | Atwal |
| 5,550,152 A | 8/1996 | Koch et al. |
| 5,595,989 A | 1/1997 | Andersen et al. |
| 5,859,010 A | 1/1999 | Petersen et al. |
| 5,939,452 A | 8/1999 | Dombroski et al. |
| 6,051,601 A | 4/2000 | Dombroski et al. |
| 6,069,156 A | 5/2000 | Oku et al. |
| 6,153,396 A | 11/2000 | Hultgren et al. |
| 6,277,885 B1 | 8/2001 | Levin et al. |
| 6,461,610 B1 | 10/2002 | Kongsbak et al. |
| 6,605,617 B2 | 8/2003 | Renhowe et al. |
| 6,653,304 B2 | 11/2003 | Leftheris et al. |
| 6,762,194 B2 | 7/2004 | Renhowe et al. |
| 6,777,413 B2 | 8/2004 | Zhu et al. |

(Continued)

FOREIGN PATENT DOCUMENTS

| | | |
|---|---|---|
| EP | 687675 A2 | 12/1995 |
| EP | 943339 A2 | 9/1999 |

(Continued)

OTHER PUBLICATIONS

Benedetti, R. et al., Targeting Histone Deacetylases in Diseases: Where Are We?, Antioxid Redox Signal., 23(1): 99-126 (2015).

(Continued)

*Primary Examiner* — Kahsay Habte
(74) *Attorney, Agent, or Firm* — Choate, Hall & Stewart LLP; Michael A. Shinall; Nicholas J. Pace

(57) ABSTRACT

The present invention is directed to compounds of Formula I:

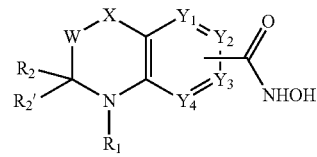

and pharmaceutically acceptable salts thereof, wherein $R_1$, $R_2$, $R_2'$, L, X, W, $Y^1$, $Y^2$, $Y^3$, and $Y^4$ are described herein, useful as inhibitors of zinc-dependent histone deacetylases (HDACs) and in the treatment of diseases or disorders associated with HDACs.

20 Claims, No Drawings

(56) References Cited

U.S. PATENT DOCUMENTS

| | | |
|---|---|---|
| 7,067,531 B2 | 6/2006 | Angibaud et al. |
| 7,615,640 B2 | 11/2009 | Horiuchi et al. |
| 7,700,592 B2 | 4/2010 | McCormick et al. |
| 7,803,828 B2 | 9/2010 | McCormick et al. |
| 7,858,635 B2 | 12/2010 | Makings et al. |
| 7,985,763 B2 | 7/2011 | Wang et al. |
| 8,003,624 B2 | 8/2011 | McCormick et al. |
| 8,138,357 B2 | 3/2012 | Naccari et al. |
| 8,173,675 B2 | 5/2012 | Koradin et al. |
| 8,394,792 B2 | 3/2013 | Ahn et al. |
| 8,497,295 B2 | 7/2013 | Makings et al. |
| 8,513,433 B2 | 8/2013 | Panicker et al. |
| 8,716,285 B2 | 5/2014 | Guo et al. |
| 8,791,090 B2 | 7/2014 | Ashikawa et al. |
| 9,630,922 B2 | 4/2017 | Ng et al. |
| 9,637,453 B2 | 5/2017 | Ng et al. |
| 9,745,253 B2 | 8/2017 | Bair et al. |
| 10,029,995 B2 | 7/2018 | Zheng et al. |
| 10,370,343 B2 | 8/2019 | Zheng et al. |
| 2002/0013314 A1 | 1/2002 | Zhu et al. |
| 2007/0155730 A1 | 7/2007 | Leit et al. |
| 2009/0136461 A1 | 5/2009 | Kim et al. |
| 2010/0173332 A1 | 7/2010 | Smaill et al. |
| 2011/0288084 A1 | 11/2011 | Cronin et al. |
| 2012/0165370 A1 | 6/2012 | Tang et al. |
| 2013/0045995 A1 | 2/2013 | Beier et al. |
| 2013/0102631 A1 | 4/2013 | Nebel et al. |
| 2014/0193337 A1 | 7/2014 | Schibli et al. |
| 2014/0234216 A1 | 8/2014 | Schibli et al. |
| 2016/0221972 A1 | 8/2016 | Zheng et al. |
| 2016/0221973 A1 | 8/2016 | Zheng et al. |
| 2016/0221997 A1 | 8/2016 | Zheng et al. |
| 2016/0222022 A1 | 8/2016 | Zheng et al. |
| 2016/0222028 A1 | 8/2016 | Zheng et al. |
| 2016/0264518 A1 | 9/2016 | Bair et al. |
| 2016/0304456 A1 | 10/2016 | Ng et al. |
| 2016/0304462 A1 | 10/2016 | Ng et al. |
| 2017/0066729 A1 | 3/2017 | Zheng et al. |
| 2018/0044282 A1 | 2/2018 | Bair et al. |
| 2018/0354919 A1 | 12/2018 | Zheng et al. |

FOREIGN PATENT DOCUMENTS

| | | |
|---|---|---|
| EP | 963755 A2 | 12/1999 |
| JP | H10-259176 A | 9/1998 |
| JP | 2011-148714 A | 8/2011 |
| KR | 2010-0052758 A | 5/2010 |
| WO | WO-9631470 A1 | 10/1996 |
| WO | WO-9631473 A1 | 10/1996 |
| WO | WO-9631474 A1 | 10/1996 |
| WO | WO-9631500 A1 | 10/1996 |
| WO | WO-9631503 A1 | 10/1996 |
| WO | WO-9903498 A1 | 1/1999 |
| WO | WO-2000068230 A1 | 11/2000 |
| WO | WO-2002072567 A2 | 9/2002 |
| WO | WO-2007/022638 A1 | 3/2007 |
| WO | WO-2008/055068 A2 | 5/2008 |
| WO | WO-2008059339 A2 | 5/2008 |
| WO | WO-2010040989 A1 | 4/2010 |
| WO | WO-2012009258 A2 | 1/2012 |
| WO | WO-2012/054332 A1 | 4/2012 |
| WO | WO-2012/117421 A1 | 9/2012 |
| WO | WO-2012117021 A2 | 9/2012 |
| WO | WO-2012137224 A1 | 10/2012 |
| WO | WO-2013/059582 A2 | 4/2013 |
| WO | WO-2013/059852 A1 | 5/2013 |
| WO | WO-2013092460 A1 | 6/2013 |
| WO | WO-2014009794 A1 | 1/2014 |
| WO | WO-2014140076 A1 | 9/2014 |
| WO | WO-2014/196328 A1 | 12/2014 |
| WO | WO-2017/040963 A1 | 3/2017 |
| WO | WO-2017/218950 A1 | 12/2017 |

OTHER PUBLICATIONS

De Ruijter, A.J. et al., Histone Deacetylases (HDACs): Characterization of the Classical HDAC Family, Biochem. J., 370 (Pt 3): 737-749 (2003).

Gobert, M. et al., Regulatory T cells recruited through CCL22/CCR4 are selectively activated in lymphoid infiltrates surrounding primary breast tumors and lead to an adverse clinical outcome, Cancer Res., 69(5): 2000-2009 (2009).

International Search Report for PCT/US2016/050152, ISA/EPO, 6 pages (dated Jan. 16, 2017).

Kannan, S. et al., Discovery of Inhibitors of Schistosoma mansoni HDAC8 by Combining Homology Modeling, Virtual Screening, and in Vitro Validation, Journal of Chemical Information and Modeling, 2014, p. 3005-3019, 54(10).

Liu, Yi-Mi et al. 1-Arylsulfonyl-5-(N-hydroxyacrylamide)tetrahydroquinolines as potent histone deacetylase inhibitors suppressing the growth of prostate cancer cells, European Journal of Medicinal Chemistry, 2015, p. 320-330, 89.

Marek, M. et al. Structural basis for the inhibition of histone deacetylase 8 (HDAC8), a key epigenetic player in the blood fluke *Schistosoma mansoni*, PLoS Pathogens, 2013, 9(9), e 1003645.

Matalon, S. et al., Histone deacetylase inhibitors for purging HIV-1 from the latent reservoir, Mol Med., 17(5-6): 466-472 (2011).

Roberti, M. et al., 1,2,3,4-tetrahydroquinolines with a weakly acid substituent at the 5-position, Farmaco, 1997, p. 257-258, 52(4).

Tang, J. et al., Histone deacetylases as targets for treatment of multiple diseases, Clin Sci. (Lond), 124(11): 651-662 (2013).

West, A.C. and Johnstone, R.W., New and emerging HDAC inhibitors for cancer treatment, J. Clin. Invest., 124(1): 30-9 (2014).

Wolfson, N.A. et al., HDAC8 Substrates: Histones and Beyond, Biopolymers, 99(2): 112-126 (2013).

Written Opinion for PCT/US2016/050152, ISA/EPO, 6 pages (dated Jan. 16, 2017).

Zdanov, S. et al., Mutant KRAS Conversion of Conventional T Cells into Regulatory T Cells, Cancer Immunol. Res., 4(4): 354-65 (2016).

[6,6] FUSED BICYCLIC HDAC8 INHIBITORS

CROSS-REFERENCE TO RELATED APPLICATIONS

This application is continuation of U.S. application Ser. No. 16/003,861, filed on Jun. 8, 2018, now U.S. Pat. No. 10,370,343, which is a continuation of U.S. application Ser. No. 15/255,817, filed on Sep. 2, 2016, now U.S. Pat. No. 10,029,995, which claims the benefit of priority of U.S. Provisional Application No. 62/214,101, filed Sep. 3, 2015, the entire content of each of which is hereby incorporated by reference.

FIELD OF THE INVENTION

The present invention relates to inhibitors of zinc-dependent histone deacetylases (HDACs) useful in the treatment of diseases or disorders associated with HDACs including cell proliferation diseases (e.g., cancer), neurological and inflammatory diseases. Specifically, this invention is concerned with compounds and compositions inhibiting HDACs, methods of treating diseases associated with HDACs, and methods of synthesizing these compounds.

BACKGROUND OF THE INVENTION

Many members of the HDAC family require zinc (Zn) to function properly. For instance, the isozyme histone deacetylase 8 (HDAC8) is a zinc-dependent histone deacetylase that possesses histone deacetylase activity. Other family members include HDACs 1-7 and 9-11. (De Ruijter et al., Histone Deacetylases (HDACs): Characterization of the Classical HDAC Family. *Biochem. J.* 370; 737-749 (2003)).

HDAC8 is a zinc-dependent histone deacetylase that is known to recognize a number of histone and non-histone substrates (Wolfson et al., HDAC8 Substrates: Histones and Beyond. Biopolymers, 99(2): 112-126 (2013)). For instance, in addition to deacetylating histones H2A/H2B, H3 and H4, HDAC8 can also deacetylate the p52 transcription factor (Wolfson et al., HDAC8 Substrates: Histones and Beyond. Biopolymers, 99(2): 112-126 (2013)). Although HDAC8 contains a nuclear localization sequence, it can also be found in the cytoplasm of smooth muscle cells (Wolfson et al., HDAC8 Substrates: Histones and Beyond. Biopolymers, 99(2): 112-126 (2013)). Northern analysis suggests that there is very little HDAC8 mRNA within the cell at any given time. (De Ruijter et al., Histone Deacetylases (HDACs): Characterization of the Classical HDAC Family. *Biochem. J.* 370; 737-749 (2003)).

Diseases in which HDAC8 inhibition may have a potential benefit include cancer, neurologic, inflammatory, autoimmune, infectious, metabolic, hematologic, or cardiovascular diseases or disorders. (See Benedetti et al., Antiox Redox. Signal. 2014 March; Tang et al., Clin Sci. (Lond). 2013 June; 124(11):651-62; West and Johnstone, J. Clin. Invest. 2014 January; 124(1):30-9.

Three HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; and belinostat (PXD101; Beleodaq®) for the treatment of peripheral T cell lymphoma. However, these drugs are of limited effectiveness and can give rise to unwanted side effects. Thus, there is a need for drugs with an improved safety-efficacy profile.

Given HDAC8's role in proliferative diseases, neurological diseases, and inflammatory diseases, there is a need for HDAC8 inhibitors with good therapeutic properties.

SUMMARY OF THE INVENTION

One aspect of the invention relates to compounds of Formula I:

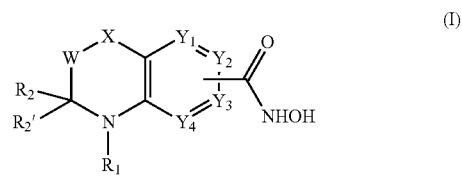

and pharmaceutically acceptable salts, prodrugs, solvates, hydrates, isomers, and tautomers thereof,
wherein:
$Y_1$, $Y_2$, $Y_3$, and $Y_4$ are each independently N, C, or $CR_3$, provided that when bonded to —C(O)NHOH any of $Y_1$, $Y_2$, $Y_3$, or $Y_4$ is C;
X is selected from the group consisting of $S(O)_2$, $S(O)$, S, O, C(=O), and $C(R_4)(R_5)$;
W is $C(R_4)(R_5)$ or O;
$R_1$ is independently $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, —$(CH_2)_n$—$R^a$, —$(CH_2)_n$—O—$(CH_2)_p$—$R^a$, —$S(O)_2R^a$, —$C(O)R^a$, or —$C(O)N(R^a)(R^b)$, wherein each alkyl, alkenyl, alkynyl, cycloalkyl, cycloalkenyl, aryl, heteroaryl, or heterocycle is optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$;
$R^a$ is at each occurrence, hydrogen, halogen, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —$C(O)N(R_{10})(R_{11})$, wherein each alkyl, alkenyl, alkynyl, cycloalkyl, cycloalkenyl, aryl, heteroaryl, or heterocycle is optionally substituted with one or more —OH, $R_4'$, $R_5'$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl;
$R^b$ is at each occurrence, hydrogen, halogen, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —$C(O)N(R_{10})(R_{11})$, wherein each alkyl, alkenyl, alkynyl, cycloalkyl, cycloalkenyl, aryl, heteroaryl, or heterocycle is optionally substituted with one or more —OH, $R_4'$, $R_5'$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl;
or $R^a$ and $R^b$ can combine with the carbon or nitrogen to which they are attached to form a $C_3$-$C_8$ cycloalkyl, or 3- to 8-membered heterocycle optionally substituted with one or more substituent selected from $R_4'$ and $R_5'$, wherein $R_4'$ and $R_5'$ independently at each occurrence are H or —$C_1$-$C_6$ alkyl; $R_2$ and $R_2'$ are each independently hydrogen, $C_1$-$C_6$ alkyl, $C_1$-$C_6$ alkoxy, —OH, halogen, —$NO_2$, —$NH_2$, —CN, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, wherein each alkyl, alkenyl, alkynyl, cycloalkyl, cycloalkenyl, aryl, heteroaryl, or heterocycle is optionally substituted with one or more —OH, halogen, oxo, —$NO_2$, —$NH_2$, —CN, —$C_1$-$C_6$ alkyl, —$C_1$-$C_6$ alkoxy; or $R_2$ and $R_2'$ can combine with the carbon to which they are attached to form an oxo group, $C_3$-$C_8$ cycloalkyl, or 3- to 8-membered heterocycle;

$R_3$ is independently, in each occurrence, hydrogen, halogen, OH, CN, $NO_2$, $NH_2$, $C_1$-$C_3$ alkyl, or $C_1$-$C_3$ alkoxy;

each $R_4$ or $R_5$ is each independently, at each occurrence, hydrogen, halogen, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —C(O)N($R_{10}$)($R_{11}$), wherein each alkyl, alkenyl, alkynyl, cycloalkyl, cycloalkenyl, aryl, heteroaryl, or heterocycle is optionally substituted with one or more —OH, $R_4$, $R_5$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl;

or $R_4$ and $R_5$ can combine with the carbon or nitrogen to which they are attached to form an oxo group, $C_3$-$C_8$ cycloalkyl, or 3- to 8-membered heterocycle optionally substituted with one or more substituent selected from $R_{4'}$ and $R_{5'}$, wherein $R_{4'}$ and $R_{5'}$ independently at each occurrence are H or —$C_1$-$C_6$ alkyl;

or $R_{4'}$ and $R_{5'}$ together when attached to the same atom form a $C_3$-$C_8$ spirocycloalkyl ring; or $R_{4'}$ and $R_{5'}$ together when attached to the same atom form a $C_3$-$C_8$ spiroheterocycloalkyl ring; or $R_{4'}$ and $R_{5'}$ together when attached to adjacent atoms form an aryl ring, a heteroaryl ring, a $C_3$-$C_8$ cycloalkyl, or a 3- to 8-membered heterocycle, wherein the spirocycloalkyl, spiroheterocycloalkyl, heteroaryl, cycloalkyl or heterocycle is optionally substituted with one or more groups selected from OH, halogen, —$C_1$-$C_6$ alkyl or $C(O)OR_6$;

$R_6$ and $R_7$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, $C_3$-$C_8$ cycloalkyl, $C_3$-$C_8$ cycloalkenyl, aryl, heteroaryl, heterocycle, —$S(O)_2NR_8R_9$, —$S(O)_2R_8$, —$C(O)R_8$, —$CO_2R_8$, —$S(O)R_8$, or —$S(O)NR_8R_9$, wherein each alkyl, alkenyl, alkynyl, cycloalkyl, cycloalkenyl, phenyl, heteroaryl, or heterocycle is optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl or $R_6$ and $R_7$ together with the atom to which they are attached form a $C_3$-$C_8$ cycloalkyl or a 3- to 8-membered heterocycle, wherein the cycloalkyl or the heterocycle is optionally substituted with one or more groups selected from halogen, oxo and $C_1$-$C_6$ alkyl;

$R_8$ and $R_9$ are each independently $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, heteroaryl, or 3- to 8-membered heterocycle, wherein each is optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl;

$R_{10}$ and $R_{11}$ are each independently hydrogen, $C_1$-$C_6$ alkyl, aryl, $C_1$-$C_6$ alkylaryl or 3- to 8-membered heterocycle, wherein aryl, arylalkyl and heterocycle are optionally substituted with one or more groups selected from halogen, $C_1$-$C_6$ alkyl, and $C_1$-$C_6$ alkoxy; or $R_{10}$ and $R_{11}$ can combine to form a 3- to 8-membered heterocycle optionally substituted with one or more $R_{12}$;

$R_{12}$ is H or $C_1$-$C_6$ alkyl or two adjacent $R_{12}$ can combine to form an aryl or heteroaryl group;

n is an integer from 1 to 6; and p is an integer from 0 to 2;

provided that the compound is not N-hydroxy-1-((4-methoxyphenyl)sulfonyl)-1,2,3,4-tetrahydroquinoline-6-carboxamide.

Another aspect of the invention relates to a method of treating a disease or disorder associated with HDAC8 modulation in a subject in need thereof, comprising administering to the subject an effective amount of a compound of Formula I.

Another aspect of the invention is directed to a method of inhibiting a histone deacetylase, for instance a zinc-dependent histone deacetylase such as HDAC8. The method involves administering to a patient in need thereof an effective amount of a compound of Formula I.

Another aspect of the invention is directed to pharmaceutical compositions comprising a compound of Formula I and a pharmaceutically acceptable carrier. The pharmaceutically acceptable carrier can further include an excipient, diluent, or surfactant. The pharmaceutical composition can be effective for treating a disease or disorder associated with HDAC8 modulation in a subject in need thereof. The pharmaceutical compositions can comprise the compounds of the present invention for use in treating diseases described herein. The compositions can contain at least one compound of the invention and a pharmaceutically acceptable carrier. The invention also provides the use of the compounds described herein in the manufacture of a medicament for the treatment of a disease associated with HDACs.

The present invention also provides methods for the treatment of human diseases or disorders including, without limitation, oncological, neurological, inflammatory, autoimmune, infectious, metabolic, hematologic, or cardiovascular diseases or disorders.

The present invention also provides compounds that are useful in inhibiting zinc-dependent HDAC enzymes, and in particular HDAC8. These compounds can also be useful in the treatment of diseases including cancer.

The present invention further provides compounds that can inhibit HDAC8. In some embodiments, the efficacy-safety profile of the compounds of the current invention can be improved relative to other known HDAC8 inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Invention, below.

DETAILED DESCRIPTION OF THE INVENTION

HDAC8 is a zinc-dependent histone deacetylase that is known to recognize a number of non-histone substrates (Wolfson et al., HDAC8 Substrates: Histones and Beyond. Biopolymers, 99(2): 112-126 (2013), herein incorporated by reference in its entirety). It contains a nuclear localization sequence and is thus commonly localized within the cell nucleus. The present invention provides inhibitors of HDAC8 and methods for using the same to treat disease.

In a first aspect of the invention, compounds of the Formula I are described:

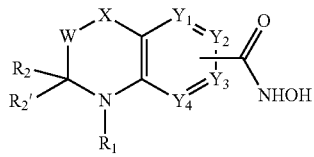

and pharmaceutically acceptable salts, prodrugs, solvates, hydrates, tautomers, and isomers thereof, wherein $R_1$, $R_2$, $R_2'$, L, X, W, $Y^1$, $Y^2$, $Y^3$, and $Y^4$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$ alkyl, —$C_1$-$C_6$ alkyl, —O—$C_2$-$C_6$alkenyl, —O—$C_2$-$C_6$ alkynyl, —$C_2$-$C_6$ alkenyl, —$C_2$-$C_6$ alkynyl, —OH, —OP(O)(OH)$_2$, —OC(O)$C_1$-$C_6$ alkyl, —C(O)$C_1$-$C_6$ alkyl, —OC(O)O$C_1$-$C_6$ alkyl, —NH$_2$, —NH ($C_1$-$C_6$ alkyl), —N($C_1$-$C_6$ alkyl)$_2$, —S(O)$_2$—$C_1$-$C_6$ alkyl, —S(O)NH$C_1$-$C_6$ alkyl, and —S(O)N($C_1$-$C_6$ alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

The term "heteroaryl" means a monovalent monocyclic or bicyclic aromatic radical of 5 to 12 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom(s) is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"Alkyl" refers to a straight or branched chain saturated hydrocarbon. $C_1$-$C_6$ alkyl groups contain 1 to 6 carbon atoms. Examples of a $C_1$-$C_6$ alkyl group include, but are not limited to, methyl, ethyl, propyl, butyl, pentyl, isopropyl, isobutyl, sec-butyl and tert-butyl, isopentyl and neopentyl.

"Alkylenyl" as herein defined refers to groups of general formula —(CH$_2$)n- where n is an integer from 1 to 6. Suitable examples of alkylenyl groups include methylenyl, ethylenyl, and propylenyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2] octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 3-18 carbon atoms. Examples of cycloalkenyl groups include, without limitation, cyclopentenyl, cyclohexenyl, cycloheptenyl, cyclooctenyl, and norborenyl. A $C_3$-$C_8$ cycloalkenyl is a cycloalkenyl group containing between 3 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized in electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

"Aralkyl" or "arylalkyl" refers to an a $C_1$-$C_6$ alkyl group, as defined herein above, substituted with an aryl ring containing from 3 to 24 ring atoms per ring. For example, arylalkyl groups herein described can have the following formula

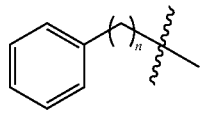

where n is an integer from 1 to 6. Non-limiting examples of suitable aralkyl groups include benzyl, 2-phenethyl and naphthalenylmethyl. The bond to the parent moiety is through the alkyl.

The term "cycloalkylalkyl refers to a monocyclic saturated carbon rings containing 3-18 carbon atoms further substituted with $C_1$-$C_6$ alkyl groups. In general cycloalkylalkyl groups herein described display the following formula

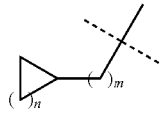

where m is an integer from 1 to 6 and n is an integer from 1 to 16.

As used herein, the term "halo" or "halogen" means fluoro, chloro, bromo, or iodo.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A $C_3$-$C_{12}$ spirocycle is a spirocycle containing between 3 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/di phosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug", as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In one embodiment of the compounds of Formula I, X is —O—;

In one embodiment of the compounds of Formula I, X is —SO$_2$—.

In one embodiment of the compounds of Formula I, X is —CR$_4$R$_5$—.

In one embodiment of the compounds of Formula I, Y$_1$, Y$_2$ and Y$_4$ are all —CR$_3$—.

In one embodiment of the compounds of Formula I, Y$_1$, Y$_3$ and Y$_4$ are all —CR$_3$—.

In one embodiment of the compounds of Formula I, Y$_2$, Y$_3$ and Y$_4$ are all —CR$_3$—.

In one embodiment of the compounds of Formula I, Y$_1$, Y$_2$ and Y$_3$ are all —CR$_3$—.

In one embodiment of the compounds of Formula I, one of Y$_1$, Y$_2$, Y$_3$, or Y$_4$ is N.

In one embodiment, R$_1$ is —(CH$_2$)$_n$—R$^a$. In another embodiment R$^a$ is optionally substituted aryl. In a further embodiment n is 1.

In one embodiment, R$_2$ and R$_2$' can combine with the carbon to form an oxo.

In another embodiment, R$_4$ is H and R$_5$ is —C(O)N(R$_{10}$)(R$_{11}$).

In one embodiment, W is CH$_2$. In another embodiment, W is O.

In one embodiment of the compounds of Formula I, the compound is of the Formula IA:

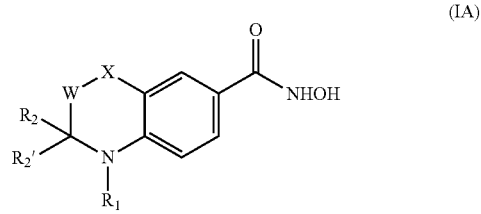

(IA)

and pharmaceutically acceptable salts, prodrugs, solvates, hydrates, tautomers and stereoisomers thereof.

In some embodiments of the compounds of IA, R$_1$ is —(CH$_2$)$_n$—R$^a$.

In one embodiment of the compounds of Formula I, the compound is of the formula IA-1a:

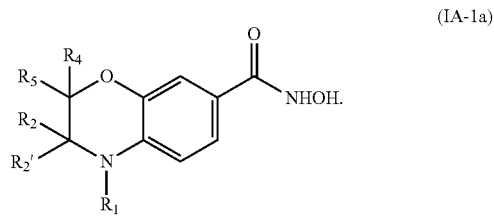

(IA-1a)

In some embodiments of the compounds of IA-1a, R$_1$ is —(CH$_2$)$_n$—R$^a$.

In one embodiment of the compounds of Formula I, the compound is of the formula IA-1b:

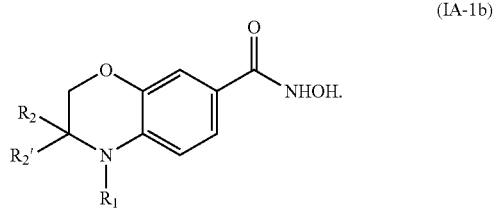

(IA-1b)

In some embodiments of the compounds of IA-1b, R$_1$ is —(CH$_2$)$_n$—R$^a$.

In one embodiment of the compounds of Formula I, the compound is of the formula IA-1c:

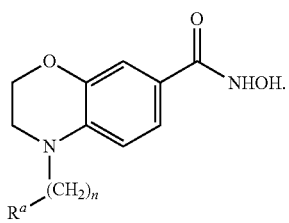
(IA-1c)

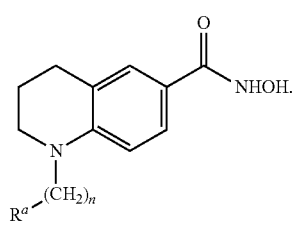
(IA-2c)

In one embodiment of the compounds of Formula I, the compound is of the formula IA-3a:

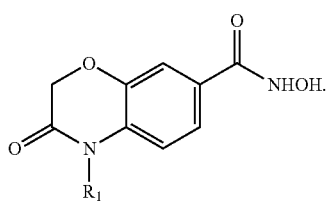
(IA-1d)

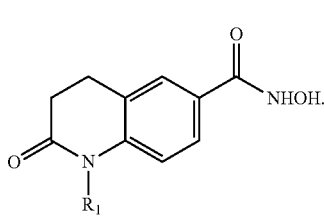
(IA-2d)

In some embodiments of the compounds of IA-2d, $R_1$ is $-(CH_2)_n-R^a$.

In one embodiment of the compounds of Formula I, the compound is of the formula IA-3a:

In some embodiments of the compounds of IA-1d, $R_1$ is $-(CH_2)_n-R^a$.

In one embodiment of the compounds of Formula I, the compound is of the formula IA-2a:

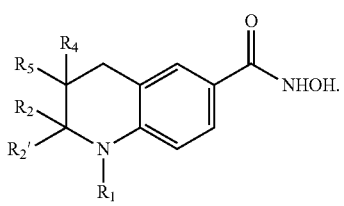
(IA-2a)

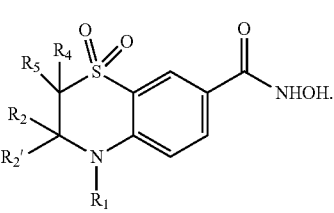
(IA-3a)

In some embodiments of the compounds of IA-2a, $R_1$ is $-(CH_2)_n-R^a$.

In some embodiments of the compounds of IA-3a, $R_1$ is $-(CH_2)_n-R^a$.

In one embodiment of the compounds of Formula I, the compound is of the formula IA-2b:

In one embodiment of the compounds of Formula I, the compound is of the formula IA-3b:

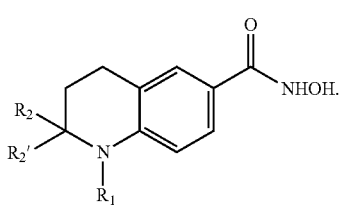
(IA-2b)

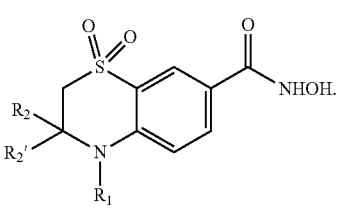
(IA-3b)

In some embodiments of the compounds of IA-2b, $R_1$ is $-(CH_2)_n-R^a$.

In some embodiments of the compounds of IA-3b, $R_1$ is $-(CH_2)_n-R^a$.

In one embodiment of the compounds of Formula I, the compound is of the formula IA-2c:

In one embodiment of the compounds of Formula I, the compound is of the formula IA-3c:

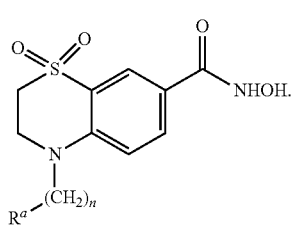
(IA-3c)

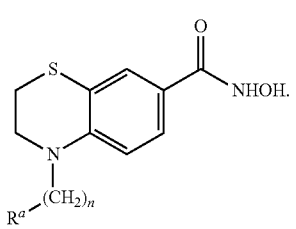
(IA-4c)

In one embodiment of the compounds of Formula I, the compound is of the formula IA-3d:

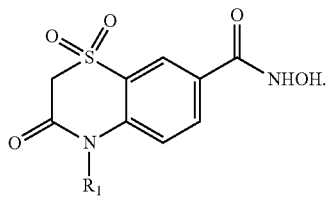
(IA-3d)

In some embodiments of the compounds of IA-3d, $R_1$ is $-(CH_2)_n-R^a$.

In one embodiment of the compounds of Formula I, the compound is of the formula IA-4a:

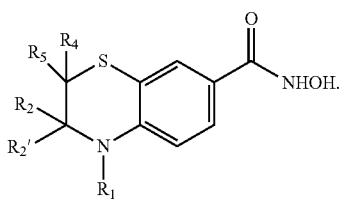
(IA-4a)

In some embodiments of the compounds of IA-4a, $R_1$ is $-(CH_2)_n-R^a$.

In one embodiment of the compounds of Formula I, the compound is of the formula IA-4b:

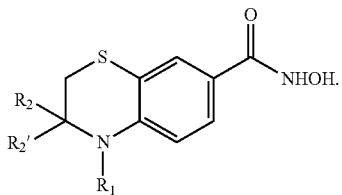
(IA-4b)

In some embodiments of the compounds of IA-4b, $R_1$ is $-(CH_2)_n-R^a$.

In one embodiment of the compounds of Formula I, the compound is of the formula IA-4c:

In one embodiment of the compounds of Formula I, the compound is of the formula IA-4d:

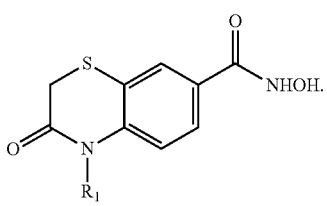
(IA-4d)

In some embodiments of the compounds of 1A-4d, $R_1$ is $-(CH_2)_n-R^a$.

In one embodiment of the compounds of Formula I, the compound is of the Formula IB:

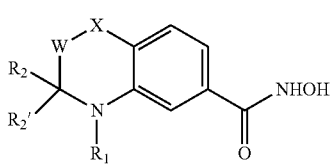
(IB)

and pharmaceutically acceptable salts, prodrugs, solvates, hydrates, tautomers and stereoisomers thereof.

In one embodiment of the compounds of Formula I, the compound is of the formula IB-1a:

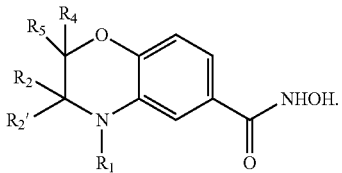
(IB-1a)

In some embodiments of the compounds of IB-1a, $R_1$ is $-(CH_2)_n-R^a$.

In one embodiment of the compounds of Formula I, the compound is of the formula IB-1b:

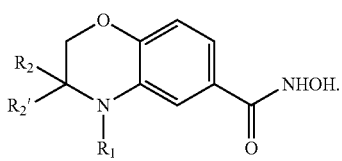
(IB-1b)

In some embodiments of the compounds of IB-1b, $R_1$ is $-(CH_2)_n-R^a$.

In one embodiment of the compounds of Formula I, the compound is of the formula IB-1c:

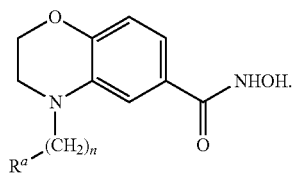
(IB-1c)

In one embodiment of the compounds of Formula I, the compound is of the formula IA-3a:

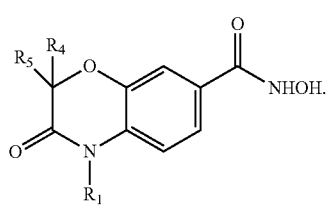
(IB-1d)

In some embodiments of the compounds of IB-1d, $R_1$ is $-(CH_2)_n-R^a$.

In one embodiment of the compounds of Formula I, the compound is of the formula IA-1e:

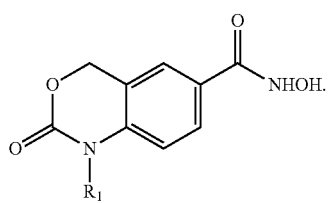
(IA-1e)

In some embodiments of the compounds of IA-1e, $R_1$ is $-(CH_2)_n-R^a$.

In one embodiment of the compounds of Formula I, the compound is of the formula IA-2a:

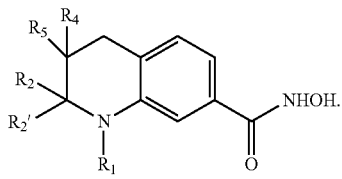
(IB-2a)

In some embodiments of the compounds of IB-2a, $R_1$ is $-(CH_2)_n-R^a$.

In one embodiment of the compounds of Formula I, the compound is of the formula IB-2b:

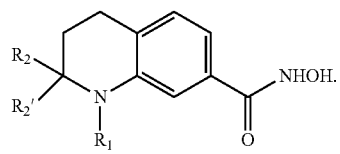
(IB-2b)

In some embodiments of the compounds of IB-2b, $R_1$ is $-(CH_2)_n-R^a$.

In one embodiment of the compounds of Formula I, the compound is of the formula IB-2c:

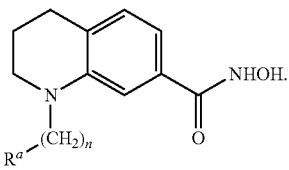
(IB-2c)

In one embodiment of the compounds of Formula I, the compound is of the formula IA-2d:

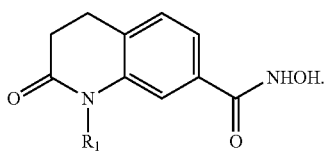
(IB-2d)

In some embodiments of the compounds of IB-2d, $R_1$ is $-(CH_2)_n-R^a$.

In one embodiment of the compounds of Formula I, the compound is of the formula IB-3a:

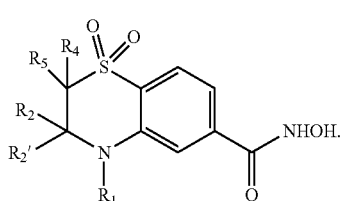
(IB-3a)

In some embodiments of the compounds of IB-3a, $R_1$ is $-(CH_2)_n-R^a$.

In one embodiment of the compounds of Formula I, the compound is of the formula IB-3b:

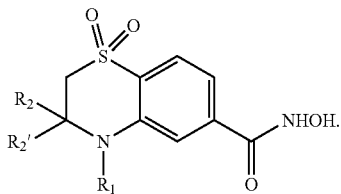
(IB-3b)

In one embodiment of the compounds of Formula I, the compound is of the formula IB-3c:

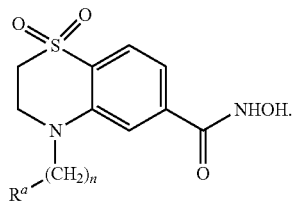
(IB-3c)

In some embodiments of the compounds of IB-3c, $R_1$ is —$(CH_2)_n$—$R^a$.

In one embodiment of the compounds of Formula I, the compound is of the formula IB-3d:

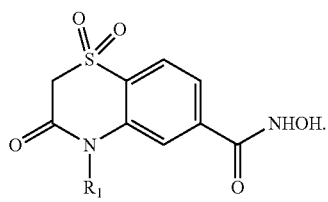
(IB-3d)

In some embodiments of the compounds of IB-3d, $R_1$ is —$(CH_2)_n$—$R^a$.

In one embodiment of the compounds of Formula I, the compound is of the formula IB-4a:

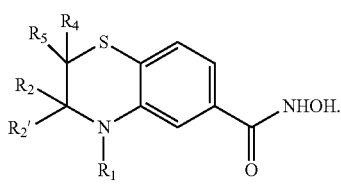
(IB-4a)

In some embodiments of the compounds of IB-4a, $R_1$ is —$(CH_2)_n$—$R^a$.

In one embodiment of the compounds of Formula I, the compound is of the formula IB-4b:

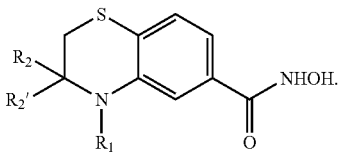
(IB-4b)

In some embodiments of the compounds of IB-4b, $R_1$ is —$(CH_2)_n$—$R^a$.

In one embodiment of the compounds of Formula I, the compound is of the formula IB-4c:

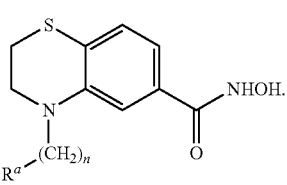
(IB-4c)

In some embodiments of the compounds of IB-4c, $R_1$ is —$(CH_2)_n$—$R^a$.

In one embodiment of the compounds of Formula I, the compound is of the formula IB-4d:

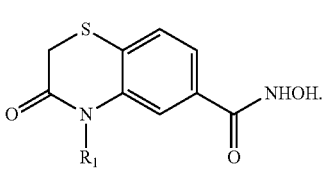
(IB-4d)

In some embodiments of the compounds of IB-4d, $R_1$ is —$(CH_2)_n$—$R^a$.

In some of the forgoing embodiments of the Formulae IA and IB, n is 1 and $R^a$ is optionally substituted aryl, optionally substituted heteroaryl, or optionally substituted 3- to 8-membered heterocycle.

In some of the forgoing embodiments of the Formulae IA and IB, n is 1 and $R^a$ is aryl optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

In some of the forgoing embodiments of the Formulae IA and IB, n is 1 and $R^a$ is heteroaryl optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

In some of the forgoing embodiments of the Formulae IA and IB, n is 1 and $R^a$ is 3- to 8-membered heterocycle optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl.

In an illustrative embodiment, the compound of Formula I is:

N6-hydroxy-4-methyl-N2-(tetrahydro-2H-pyran-4-yl)-3,4-dihydro-2H-benzo[b][1,4]oxazine-2,6-dicarboxamide (I-1);

4-benzyl-N6-hydroxy-N2-(tetrahydro-2H-pyran-4-yl)-3,4-dihydro-2H-benzo[b][1,4]oxazine-2,6-dicarboxamide (I-2);

N-hydroxy-4-methyl-2-(spiro[cyclopropane-1,3'-indoline]-1'-carbonyl)-3,4-dihydro-2H-benzo[b][1,4]oxazine-6-carboxamide (I-3);

4-benzyl-N-hydroxy-2-(spiro[cyclopropane-1,3'-indoline]-1'-carbonyl)-3,4-dihydro-2H-benzo[b][1,4]oxazine-6-carboxamide (I-4);

N2-benzyl-N6-hydroxy-4-methyl-3,4-dihydro-2H-benzo[b][1,4]oxazine-2,6-di carboxamide (I-5);

N2,4-dibenzyl-N6-hydroxy-3,4-dihydro-2H-benzo[b][1,4]oxazine-2,6-dicarboxamide (I-6);

N7-hydroxy-4-methyl-N2-(tetrahydro-2H-pyran-4-yl)-3,4-dihydro-2H-benzo[b][1,4]oxazine-2,7-dicarboxamide (I-7);

4-benzyl-N7-hydroxy-N2-(tetrahydro-2H-pyran-4-yl)-3,4-dihydro-2H-benzo[b][1,4]oxazine-2,7-dicarboxamide (I-8);

N-hydroxy-4-methyl-2-(spiro[cyclopropane-1,3'-indoline]-1'-carbonyl)-3,4-dihydro-2H-benzo[b][1,4]oxazine-7-carboxamide (I-9);

4-benzyl-N-hydroxy-2-(spiro[cyclopropane-1,3'-indoline]-1'-carbonyl)-3,4-dihydro-2H-benzo[b][1,4]oxazine-7-carboxamide (I-10);

N2-benzyl-N7-hydroxy-4-methyl-3,4-dihydro-2H-benzo[b][1,4]oxazine-2,7-dicarboxamide (I-11);

N2,4-dibenzyl-N7-hydroxy-3,4-dihydro-2H-benzo[b][1,4]oxazine-2,7-dicarboxamide (I-12);

N-hydroxy-1-(1-(2-meth oxyethyl)-1H-benzo[d]imidazol-2-yl)-1,2,3,4-tetrahydroquinoline-5-carboxamide (I-13);

1-(1H-benzo[d]imidazol-2-yl)-N-hydroxy-1,2,3,4-tetrahydroquinoline-5-carboxamide (I-14);

N-hydroxy-4-(3-((trifluoromethyl)sulfonyl)benzyl)-3,4-dihydro-2H-benzo[b][1,4]thiazine-6-carboxamide-1,1-dioxide (I-15);

N-hydroxy-4-(1-(4-(methyl sulfonyl)phenyl)ethyl)-3,4-dihydro-2H-benzo[b][1,4]thiazine-6-carboxamide-1,1-dioxide (I-16);

N-hydroxy-3-oxo-4-(4-((trifluoromethyl)sulfonyl)benzyl)-3,4-dihydro-2H-benzo[b][1,4]oxazine-6-carboxamide (I-17);

N-hydroxy-3-oxo-4-(3-((trifluoromethyl)sulfonyl)benzyl)-3,4-dihydro-2H-benzo[b][1,4]oxazine-6-carboxamide (I-18);

N-hydroxy-4-(4-(trifluoromethoxy)benzyl)-3,4-dihydro-2H-benzo[b][1,4]oxazine-6-carboxamide (I-19);

4-((2-cyclopropylthiazol-4-yl)methyl)-N-hydroxy-3,4-dihydro-2H-benzo[b][1,4]oxazine-6-carboxamide (I-20);

N-hydroxy-4-(imidazo[2,1-b]thiazol-6-ylmethyl)-3,4-dihydro-2H-benzo[b][1,4]oxazine-6-carboxamide (I-21);

N-hydroxy-4-(2-methylallyl)-3,4-dihydro-2H-benzo[b][1,4]oxazine-6-carboxamide (I-22);

4-(2,6-dichlorobenzyl)-N-hydroxy-3,4-dihydro-2H-benzo[b][1,4]oxazine-6-carboxamide (I-23);

4-(3-fluorobenzyl)-N-hydroxy-3,4-dihydro-2H-benzo[b][1,4]oxazine-6-carboxamide (I-24);

N-hydroxy-4-(2-(trifluoromethoxy)benzyl)-3,4-dihydro-2H-benzo[b][1,4]oxazine-6-carboxamide (I-25);

N-hydroxy-4-(2-morpholino-2-oxoethyl)-3,4-dihydro-2H-benzo[b][1,4]oxazine-6-carboxamide (I-26);

4-(2-fluorobenzyl)-N-hydroxy-3,4-dihydro-2H-benzo[b][1,4]oxazine-6-carboxamide (I-27);

N-hydroxy-4-((1-isopropyl-1H-benzo[d]imidazol-2-yl)methyl)-3,4-dihydro-2H-benzo[b][1,4]oxazine-6-carboxamide (I-28);

N-hydroxy-4-((1-(2-methoxyethyl)-1H-benzo[d]imidazol-2-yl)methyl)-3,4-dihydro-2H-benzo[b][1,4]oxazine-6-carboxamide (I-29);

4-((1-(cyclopropylmethyl)-1H-benzo[d]imidazol-2-yl)methyl)-N-hydroxy-3,4-dihydro-2H-benzo[b][1,4]oxazine-6-carboxamide (I-30);

4-(cyclobutylmethyl)-N-hydroxy-3-oxo-3,4-dihydro-2H-benzo[b][1,4]oxazine-6-carboxamide (I-31);

4-benzyl-N-hydroxy-3-oxo-3,4-dihydro-2H-benzo[b][1,4]oxazine-6-carboxamide (I-32);

4-(3-fluorobenzyl)-N-hydroxy-3-oxo-3,4-dihydro-2H-benzo[b][1,4]oxazine-6-carboxamide (I-33);

4-(4-chlorophenethyl)-N-hydroxy-3-oxo-3,4-dihydro-2H-benzo[b][1,4]oxazine-6-carboxamide (I-34);

N-hydroxy-3-oxo-4-(4-(trifluoromethyl)benzyl)-3,4-dihydro-2H-benzo[b][1,4]oxazine-6-carboxamide (I-35);

N-hydroxy-3-oxo-4-(4-(trifluoromethoxy)benzyl)-3,4-dihydro-2H-benzo[b][1,4]oxazine-6-carboxamide (I-36);

4-(4-fluorobenzyl)-N-hydroxy-3-oxo-3,4-dihydro-2H-benzo[b][1,4]oxazine-6-carboxamide (I-37);

N-hydroxy-4-(4-methylbenzyl)-3-oxo-3,4-dihydro-2H-benzo[b][1,4]oxazine-6-carboxamide (I-38);

N-hydroxy-3-oxo-4-propyl-3,4-dihydro-2H-benzo[b][1,4]oxazine-6-carboxamide (I-39);

N-hydroxy-3-oxo-4-(prop-2-yn-1-yl)-3,4-dihydro-2H-benzo[b][1,4]oxazine-6-carboxamide (I-40);

4-allyl-N-hydroxy-3-oxo-3,4-dihydro-2H-benzo[b][1,4]oxazine-6-carboxamide (I-41);

4-cyclopentyl-N-hydroxy-3-oxo-3,4-dihydro-2H-benzo[b][1,4]oxazine-6-carboxamide (I-42);

N-hydroxy-4-(2-methoxyethyl)-3-oxo-3,4-dihydro-2H-benzo[b][1,4]oxazine-6-carboxamide (I-43);

N-hydroxy-4-(4-methylpent-3-en-1-yl)-3-oxo-3,4-dihydro-2H-benzo[b][1,4]oxazine-6-carboxamide (I-44);

4-butyl-N-hydroxy-3-oxo-3,4-dihydro-2H-benzo[b][1,4]oxazine-6-carboxamide (I-45);

4-(sec-butyl)-N-hydroxy-3-oxo-3,4-dihydro-2H-benzo[b][1,4]oxazine-6-carboxamide (I-46);

N-hydroxy-4-((1-methylpiperidin-2-yl)methyl)-3-oxo-3,4-dihydro-2H-benzo[b][1,4]oxazine-6-carboxamide (I-47);

N-hydroxy-3-oxo-4-((tetrahydro-2H-pyran-4-yl)methyl)-3,4-dihydro-2H-benzo[b][1,4]oxazine-6-carboxamide (I-48);

4-((1,1-dioxidotetrahydro-2H-thiopyran-4-yl)methyl)-N-hydroxy-3-oxo-3,4-dihydro-2H-benzo[b][1,4]oxazine-6-carboxamide (I-49);

4-(2-(cyclopropylmethoxy)ethyl)-N-hydroxy-3-oxo-3,4-dihydro-2H-benzo[b][1,4]oxazine-6-carboxamide (I-50);

4-(2-(cyclopropyl(methyl)amino)-2-oxoethyl)-N-hydroxy-3-oxo-3,4-dihydro-2H-benzo[b][1,4]oxazine-6-carboxamide (I-51);

4-(2-(1,1-dioxidoisothiazolidin-2-yl)ethyl)-N-hydroxy-3-oxo-3,4-dihydro-2H-benzo[b][1,4]oxazine-6-carboxamide (I-52);

N-hydroxy-3-oxo-4-(2-(2,2,2-trifluoroethoxy)ethyl)-3,4-dihydro-2H-benzo[b][1,4]oxazine-6-carboxamide (I-53);

4-(2-(1,1-dioxidotetrahydrothiophen-3-yl)ethyl)-N-hydroxy-3-oxo-3,4-dihydro-2H-benzo[b][1,4]oxazine-6-carboxamide (I-54);

N-hydroxy-3-oxo-4-(2-(4-(trifluoromethyl)phenoxy)ethyl)-3,4-dihydro-2H-benzo[b][1,4]oxazine-6-carboxamide (I-55);

4-(2-(4-(N,N-dimethyl sulfamoyl)phenoxy)ethyl)-N-hydroxy-3-oxo-3,4-dihydro-2H-benzo[b][1,4]oxazine-6-carboxamide (I-56);

N-hydroxy-4-isobutyl-3-oxo-3,4-dihydro-2H-benzo[b][1,4]oxazine-6-carboxamide (I-57);

N-hydroxy-3-oxo-4-phenethyl-3,4-dihydro-2H-benzo[b][1,4]oxazine-6-carboxamide (I-58);

N-hydroxy-4-isopentyl-3-oxo-3,4-dihydro-2H-benzo[b][1,4]oxazine-6-carboxamide (I-59);

N-hydroxy-4-(3-methoxybenzyl)-3-oxo-3,4-dihydro-2H-benzo[b][1,4]oxazine-6-carboxamide (I-60);

N-hydroxy-3-oxo-4-(pyridin-2-ylmethyl)-3,4-dihydro-2H-benzo[b][1,4]oxazine-6-carboxamide (I-61);

4-(benzo[c][1,2,5]oxadiazol-5-ylmethyl)-N-hydroxy-3-oxo-3,4-dihydro-2H-benzo[b][1,4]oxazine-6-carboxamide (I-62);

N-hydroxy-4-(2-methoxybenzyl)-3-oxo-3,4-dihydro-2H-benzo[b][1,4]oxazine-6-carboxamide (I-63);

4-(4-chlorobenzyl)-N-hydroxy-3-oxo-3,4-dihydro-2H-benzo[b][1,4]oxazine-6-carboxamide (I-64);

N-hydroxy-3-oxo-4-(2-(trifluoromethyl)benzyl)-3,4-dihydro-2H-benzo[b][1,4]oxazine-6-carboxamide (I-65);

N-hydroxy-3-oxo-4-(2-(trifluoromethoxy)benzyl)-3,4-dihydro-2H-benzo[b][1,4]oxazine-6-carboxamide (I-66);

N-hydroxy-3-oxo-4-(1-phenylethyl)-3,4-dihydro-2H-benzo[b][1,4]oxazine-6-carboxamide (I-67);

N-hydroxy-4-(3-methylbenzyl)-3-oxo-3,4-dihydro-2H-benzo[b][1,4]oxazine-6-carboxamide (I-68);

4-(2-fluorobenzyl)-N-hydroxy-3-oxo-3,4-dihydro-2H-benzo[b][1,4]oxazine-6-carboxamide (I-69)

4-(4-(tert-butyl)benzyl)-N-hydroxy-3-oxo-3,4-dihydro-2H-benzo[b][1,4]oxazine-6-carboxamide (I-70);

4-(3,4-difluorobenzyl)-N-hydroxy-3-oxo-3,4-dihydro-2H-benzo[b][1,4]oxazine-6-carboxamide (I-71);

N-hydroxy-4-(2-methyl-5-(trifluoromethyl)benzyl)-3-oxo-3,4-dihydro-2H-benzo[b][1,4]oxazine-6-carboxamide (I-72);

4-(2-fluoro-5-(trifluoromethyl)benzyl)-N-hydroxy-3-oxo-3,4-dihydro-2H-benzo[b][1,4]oxazine-6-carboxamide (I-73);

4-(2-fluoro-3-methylbenzyl)-N-hydroxy-3-oxo-3,4-dihydro-2H-benzo[b][1,4]oxazine-6-carboxamide (I-74);

4-([1,1'-biphenyl]-3-ylmethyl)-N-hydroxy-3-oxo-3,4-dihydro-2H-benzo[b][1,4]oxazine-6-carboxamide (I-75);

N-hydroxy-4-((4-methyl-2-phenylthiazol-5-yl)methyl)-3-oxo-3,4-dihydro-2H-benzo[b][1,4]oxazine-6-carboxamide (I-76);

N-hydroxy-3-oxo-4-((1-phenyl-1H-1,2,3-triazol-4-yl)methyl)-3,4-dihydro-2H-benzo[b][1,4]oxazine-6-carboxamide (I-77);

N-hydroxy-4-pentyl-3,4-dihydro-2H-benzo[b][1,4]oxazine-6-carboxamide (I-78);

N-hydroxy-4-(4-(trifluoromethyl)benzyl)-3,4-dihydro-2H-benzo[b][1,4]thiazine-6-carboxamide 1,1-dioxide (I-79);

N-hydroxy-4-(4-methoxybenzyl)-3,4-dihydro-2H-benzo[b][14]thiazine-7-carboxamide-1,1-dioxide (I-80);

N-hydroxy-4-(3-(trifluoromethyl)benzyl)-3,4-dihydro-2H-benzo[b][1,4]thiazine-6-carboxamide-1,1-dioxide (I-81);

N-hydroxy-4-(4-(methyl sulfonyl)benzyl)-3,4-dihydro-2H-benzo[b][1,4]thiazine-6-carboxamide-1,1-dioxide (I-82);

4-benzyl-N-hydroxy-2-methyl-3,4-dihydro-2H-benzo[b][1,4]oxazine-6-carboxamide (I-83);

N-hydroxy-4-(4-methoxybenzyl)-2-methyl-3,4-dihydro-2H-benzo[b][1,4]oxazine-6-carboxamide (I-84);

N-hydroxy-2-methyl-4-(4-(methylsulfonyl)benzyl)-3,4-dihydro-2H-benzo[b][1,4]oxazine-6-carboxamide (I-85);

N-hydroxy-4-(phenylsulfonyl)-3,4-dihydro-2H-benzo[b][1,4]oxazine-6-carboxamide (I-86);

N-hydroxy-4-((4-methoxyphenyl)sulfonyl)-3,4-dihydro-2H-benzo[b][1,4]oxazine-6-carboxamide (I-87);

4-(4-((difluoromethyl)sulfonyl)benzyl)-N-hydroxy-3-oxo-3,4-dihydro-2H-benzo[b][1,4]oxazine-6-carboxamide (I-88);

N-hydroxy-4-(4-methoxybenzyl)-3-oxo-3,4-dihydro-2H-benzo[b][1,4]oxazine-7-carboxamide (I-89);

N-hydroxy-4-(4-(methylsulfonyl)benzyl)-3-oxo-3,4-dihydro-2H-benzo[b][1,4]oxazine-7-carboxamide (I-90);

N-hydroxy-4-(4-meth oxybenzyl)-2-methyl-3-oxo-3,4-dihydro-2H-benzo[b][1,4]oxazine-7-carboxamide (I-91);

N-hydroxy-2-methyl-4-(4-(methylsulfonyl)benzyl)-3-oxo-3,4-dihydro-2H-benzo[b][1,4]oxazine-7-carboxamide (I-92);

4-(2-chloro-4-(methylsulfonyl)benzyl)-N-hydroxy-3-oxo-3,4-dihydro-2H-benzo[b][1,4]oxazine-6-carboxamide (I-93);

N-hydroxy-4-(1-(4-(methylsulfonyl)phenyl)ethyl)-3-oxo-3,4-dihydro-2H-benzo[b][1,4]oxazine-6-carboxamide (I-94);

4-(1-(2-fluorophenyl)ethyl)-N-hydroxy-3-oxo-3,4-dihydro-2H-benzo[b][1,4]oxazine-6-carboxamide (I-95);

4-(1-(2,6-difluorophenyl)ethyl)-N-hydroxy-3-oxo-3,4-dihydro-2H-benzo[b][1,4]oxazine-6-carboxamide (I-96);

N-hydroxy-4-(piperidine-1-carbonyl)-3,4-dihydro-2H-benzo[b][1,4]oxazine-6-carboxamide (I-97);

N-hydroxy-4-(4-methoxybenzyl)-2,2-dimethyl-3-oxo-3,4-dihydro-2H-benzo[b][1,4]oxazine-6-carboxamide (I-98);

2-ethyl-N-hydroxy-4-(4-methoxybenzyl)-3-oxo-3,4-dihydro-2H-benzo[b][1,4]oxazine-6-carboxamide (I-99);

N-hydroxy-2-isopropyl-4-(4-methoxybenzyl)-3-oxo-3,4-dihydro-2H-benzo[b][1,4]oxazine-6-carboxamide (I-100);

N-hydroxy-4-(4-methoxybenzyl)-3-oxo-2-phenyl-3,4-dihydro-2H-benzo[b][1,4]oxazine-6-carboxamide (I-101);

2-benzyl-N-hydroxy-4-(4-methoxybenzyl)-3-oxo-3,4-dihydro-2H-benzo[b][1,4]oxazine-6-carboxamide (I-102);

2-(tert-butyl)-N-hydroxy-4-(4-methoxybenzyl)-3-oxo-3,4-dihydro-2H-benzo[b][1,4]oxazine-6-carboxamide (I-103);

2-(2-aminoethyl)-N-hydroxy-4-(4-methoxybenzyl)-3-oxo-3,4-dihydro-2H-benzo[b][1,4]oxazine-6-carboxamide (I-104);

2-(2-(dimethylamino)ethyl)-N-hydroxy-4-(4-methoxybenzyl)-3-oxo-3,4-dihydro-2H-benzo[b][1,4]oxazine-6-carboxamide (I-105);

1-(1H-benzo[d]imidazol-2-yl)-N-hydroxy-1,2,3,4-tetrahydroquinoline-7-carboxamide (I-106);

1-(1H-benzo[d]imidazol-2-yl)-N-hydroxy-1,2,3,4-tetrahydroquinoline-6-carboxamide (I-107);

4-(1H-benzo[d]imidazol-2-yl)-N-hydroxy-3,4-dihydro-2H-benzo[b][1,4]oxazine-6-carboxamide (I-108);

4-(1H-benzo[d]imidazol-2-yl)-N-hydroxy-3,4-dihydro-2H-benzo[b][1,4]oxazine-7-carboxamide (I-109);

N-hydroxy-1-(1-(2-methoxyethyl)-1H-benzo[d]imidazol-2-yl)-1,2,3,4-tetrahydroquinoline-7-carboxamide (I-110);

N-hydroxy-1-(1-(2-methoxyethyl)-1H-benzo[d]imidazol-2-yl)-1,2,3,4-tetrahydroquinoline-6-carboxamide (I-111);

N-hydroxy-1-(4-methoxybenzoyl)-1,2,3,4-tetrahydroquinoline-7-carboxamide (I-112);

N-hydroxy-4-(4-methoxybenzoyl)-3,4-dihydro-2H-benzo[b][1,4]oxazine-6-carboxamide (I-113);
4-(cyclohexanecarbonyl)-N-hydroxy-3,4-dihydro-2H-benzo[b][1,4]oxazine-6-carboxamide (I-114);
N-hydroxy-4-(4-methoxybenzyl)-3,4-dihydro-2H-benzo[b][1,4]oxazine-6-carboxamide (I-115);
4-benzyl-N-hydroxy-3,4-dihydro-2H-benzo[b][1,4]oxazine-6-carboxamide (I-116);
N-hydroxy-4-(4-methylbenzyl)-3,4-dihydro-2H-benzo[b][1,4]oxazine-6-carboxamide (I-117);
4-(4-chlorobenzyl)-N-hydroxy-3,4-dihydro-2H-benzo[b][1,4]oxazine-6-carboxamide (I-118);
N-hydroxy-4-(4-(trifluoromethyl)benzyl)-3,4-dihydro-2H-benzo[b][1,4]oxazine-6-carboxamide (I-119);
N-hydroxy-4-(4-(methylsulfonyl)benzyl)-3,4-dihydro-2H-benzo[b][1,4]oxazine-6-carboxamide (I-120);
N-hydroxy-4-(3-methoxybenzyl)-3,4-dihydro-2H-benzo[b][1,4]oxazine-6-carboxamide (I-121);
N-hydroxy-4-(3-methyl benzyl)-3,4-dihydro-2H-benzo[b][1,4]oxazine-6-carboxamide (I-122);
4-(3-chlorobenzyl)-N-hydroxy-3,4-dihydro-2H-benzo[b][1,4]oxazine-6-carboxamide (I-123);
N-hydroxy-4-(3-(trifluoromethyl)benzyl)-3,4-dihydro-2H-benzo[b][1,4]oxazine-6-carboxamide (I-124);
N-hydroxy-4-(3-(methyl sulfonyl)benzyl)-3,4-dihydro-2H-benzo[b][1,4]oxazine-6-carboxamide (I-125);
N-hydroxy-4-(2-methoxybenzyl)-3,4-dihydro-2H-benzo[b][1,4]oxazine-6-carboxamide (I-126);
N-hydroxy-4-(2-m ethylbenzyl)-3,4-dihydro-2H-benzo[b][1,4]oxazine-6-carboxamide (I-127);
4-(2-chlorobenzyl)-N-hydroxy-3,4-dihydro-2H-benzo[b][1,4]oxazine-6-carboxamide (I-128);
N-hydroxy-4-(2-(trifluoromethyl)benzyl) 3,4-dihydro-2H-benzo[b][1,4]oxazine-6-carboxamide (I-129);
N-hydroxy-4-(2-(methyl sulfonyl)benzyl)-3,4-dihydro-2H-benzo[b][1,4]oxazine-6-carboxamide (I-130);
4-(2-(difluoromethoxy)benzyl)-N-hydroxy-3,4-dihydro-2H-benzo[b][1,4]oxazine-6-carboxamide (I-131);
4-(3-(difluoromethoxy)benzyl)-N-hydroxy-3,4-dihydro-2H-benzo[b][1,4]oxazine-6-carboxamide (I-132);
4-(cyclohexylmethyl)-N-hydroxy-3,4-dihydro-2H-benzo[b][1,4]oxazine-6-carboxamide (I-133);
4-(2-chloro-4-(methylsulfonyl)benzyl)-N-hydroxy-3,4-dihydro-2H-benzo[b][1,4]oxazine-6-carboxamide (I-134);
N-hydroxy-4-(1-(4-(methylsulfonyl)phenyl)ethyl)-3,4-dihydro-2H-benzo[b][1,4]oxazine-6-carboxamide (I-135);
4-(1-(2-chlorophenyl)ethyl)-N-hydroxy-3,4-dihydro-2H-benzo[b][1,4]oxazine-6-carboxamide (I-136);
N-hydroxy-4-(4-(methyl sulfonyl)-2-(trifiuoromethyl)benzyl)-3,4-dihydro-2H-benzo[b][1,4]oxazine-6-carboxamide (I-137);
N-hydroxy-4-(3-methoxy-4-(methyl sulfonyl)benzyl)-3,4-dihydro-2H-benzo[b][1,4]oxazine-6-carboxamide (I-138);
N-hydroxy-4-(4-methoxy-3-(methylsulfonyl)benzyl)-3,4-dihydro-2H-benzo[b][1,4]oxazine-6-carboxamide (I-139);
4-benzoyl-N-hydroxy-3,4-dihydro-2H-benzo[b][1,4]oxazine-6-carboxamide (I-140);
N-hydroxy-4-(4-methoxybenzyl)-3-oxo-3,4-dihydro-2H-benzo[b][1,4]oxazine-6-carboxamide (I-141);
N-hydroxy-4-(4-(methyl sulfonyl)benzyl)-3-oxo-3,4-dihydro-2H-benzo[b][1,4]oxazine-6-carboxamide (I-142);
4-(3-chlorobenzyl)-N-hydroxy-3-oxo-3,4-dihydro-2H-benzo[b][1,4]oxazine-6-carboxamide (I-143);
N-hydroxy-3-oxo-4-(3-(trifluoromethyl)benzyl)-3,4-dihydro-2H-benzo[b][1,4]oxazine-6-carboxamide (I-144);
N-hydroxy-4-(3-(methylsulfonyl)benzyl)-3-oxo-3,4-dihydro-2H-benzo[b][1,4]oxazine-6-carboxamide (I-145);
N-hydroxy-3-oxo-4-(3-(trifluoromethoxy)benzyl)-3,4-dihydro-2H-benzo[b][1,4]oxazine-6-carboxamide (I-146);
4-(2-chlorobenzyl)-N-hydroxy-3-oxo-3,4-dihydro-2H-benzo[b][1,4]oxazine-6-carboxamido (I-147);
N-hydroxy-4-(2-m ethylbenzyl)-3-oxo-3,4-dihydro-2H-benzo[b][1,4]oxazine-6-carboxamide (I-148);
4-(cyclohexylmethyl)-N-hydroxy-3-oxo-3,4-dihydro-2H-benzo[b][1,4]oxazine-6-carboxamide (I-149);
N-hydroxy-3-oxo-4-(4-(piperidine-1-carbonyl)benzyl)-3,4-dihydro-2H-benzo[b][1,4]oxazine-6-carboxamide (I-150);
N-hydroxy-4-(4-methoxybenzyl)-2-methyl-3-oxo-3,4-dihydro-2H-benzo[b][1,4]oxazine-6-carboxamide (I-151);
N-hydroxy-2-methyl-4-(4-(methylsulfonyl)benzyl)-3-oxo-3,4-dihydro-2H-benzo[b][1,4]oxazine-6-carboxamide (I-152);
4-benzyl-N-hydroxy-2-methyl-3-oxo-3,4-dihydro-2H-benzo[b][1,4]oxazine-6-carboxamide (I-153);
4-benzyl-N-hydroxy-3-methyl-3,4-dihydro-2H-benzo[b][1,4]oxazine-6-carboxamide (I-154);
N-hydroxy-4-(4-methoxybenzyl)-3-methyl-3,4-dihydro-2H-benzo[b][1,4]oxazine-6-carboxamide (I-155);
N-hydroxy-4-(2',3',5',6'-tetrahydrospiro[indoline-3,4'-pyran]-1-carbonyl)-3,4-dihydro-2H-benzo[b][1,4]oxazine-6-carboxamide (I-156);
N-hydroxy-4-(4-methoxybenzyl)-3-oxo-3,4-dihydrospiro[benzo[b][1,4]oxazine-2,1'-cyclobutane]-6-carboxamide (I-157);
N-hydroxy-4-(4-methoxybenzyl)-3-oxo-3,4-dihydrospiro[benzo[b][1,4]oxazine-2,1'-cyclohexane]-6-carboxamide (I-158);
4-(2-chloro-4-methoxybenzyl)-N-hydroxy-2,2-dimethyl-3-oxo-3,4-dihydro-2H-benzo[b][1,4]oxazine-6-carboxamide (I-159);
4-(2-fluoro-4-methoxybenzyl)-N-hydroxy-2,2-dimethyl-3-oxo-3,4-dihydro-2H-benzo[b][1,4]oxazine-6-carboxamide (I-160);
4-(4-chloro-2-fluorobenzyl)-N-hydroxy-2,2-dimethyl-3-oxo-3,4-dihydro-2H-benzo[b][1,4]oxazine-6-carboxamide (I-161);
(R)—N-hydroxy-4-(4-methoxybenzyl)-2-methyl-3-oxo-3,4-dihydro-2H-benzo[b][1,4]oxazine-6-carboxamide (I-162);
8-fluoro-N-hydroxy-4-(4-methoxybenzyl)-3-oxo-3,4-dihydro-2H-benzo[b][1,4]oxazine-6-carboxamide (I-163);
4-(4-(1H-pyrazol-1-yl)benzyl)-8-fluoro-N-hydroxy-3-oxo-3,4-dihydro-2H-benzo[b][1,4]oxazine-6-carboxamide (I-164);
N-hydroxy-1-(4-methoxybenzyl)-2-oxo-2,4-dihydro-1H-benzo[d][1,3]oxazine-7-carboxamide (I-165);
1-(4-(1H-pyrazol-1-yl)benzyl)-N-hydroxy-2-oxo-1,4-dihydro-2H-benzo[d][1,3]oxazine-7-carboxamide (I-166);
N-hydroxy-4-(4-methoxybenzyl)-3,3-dimethyl-3,4-dihydro-2H-benzo[b][1,4]oxazine-6-carboxamide (I-167);
4-(4-(1H-pyrazol-1-yl)benzyl)-N-hydroxy-3,3-dimethyl-3,4-dihydro-2H-benzo[b][1,4]oxazine-6-carboxamide (I-168);
N6-hydroxy-4-(4-methoxybenzyl)-N2,N2-dimethyl-3,4-dihydro-2H-benzo[b][1,4]oxazine-2,6-dicarboxamide (I-169);
$N^6$-hydroxy-4-(4-methoxybenzyl)-$N^2$-methyl-3,4-dihydro-2H-benzo[b][1,4]oxazine-2,6-dicarboxamide (I-170);
N-hydroxy-4-(4-methoxybenzyl)-2-(morpholine-4-carbonyl)-3,4-dihydro-2H-benzo[b][1,4]oxazine-6-carboxamide (I-171);

N6-hydroxy-4-(4-methoxybenzyl)-N2-(tetrahydro-2H-pyran-4-yl)-3,4-dihydro-2H-benzo[b][1,4]oxazine-2,6-dicarboxamide (I-172);

4-((2,3-dihydro-[1,4]dioxino[2,3-b]pyridin-7-yl)methyl)-N-hydroxy-3-oxo-3,4-dihydro-2H-benzo[b][1,4]oxazine-6-carboxamide (I-173);

tert-butyl 2-((6-(hydroxycarbamoyl)-3-oxo-2,3-dihydro-4H-benzo[b][1,4]oxazin-4-yl)methyl)-7,8-dihydro-1,6-naphthyridine-6(5H)-carboxylate (I-174);

4-(4-(1H-1,2,4-triazol-1-yl)benzyl)-N-hydroxy-3-oxo-3,4-dihydro-2H-benzo[b][1,4]oxazine-6-carboxamide (I-175);

N-hydroxy-3-oxo-4-(4-(pyrrolidin-1-yl)benzyl)-3,4-dihydro-2H-benzo[b][1,4]oxazine-6-carboxamide (I-176);

N-hydroxy-4-(4-morpholinobenzyl)-3-oxo-3,4-dihydro-2H-benzo[b][1,4]oxazine-6-carboxamide (I-177);

N-hydroxy-3-oxo-4-((2-phenyl oxazol-5-yl)methyl)-3,4-dihydro-2H-benzo[b][1,4]oxazine-6-carboxamide (I-178);

N-hydroxy-3-oxo-4-((2-phenyloxazol-4-yl)methyl)-3,4-dihydro-2H-benzo[b][1,4]oxazine-6-carboxamide (I-179);

N-hydroxy-3-oxo-4-((2-phenyl-2H-1,2,3-triazol-4-yl)methyl)-3,4-dihydro-2H-benzo[b][1,4]oxazine-6-carboxamide (I-180);

tert-butyl 6-((6-(hydroxycarbamoyl)-3-oxo-2,3-dihydrobenzo[b][1,4]oxazin-4-yl)methyl)-3,4-dihydroisoquinoline-2(1H)-carboxylate (I-181);

N-hydroxy-4-((1-methyl-1,2,3,4-tetrahydroquinolin-6-yl)methyl)-3-oxo-3,4-dihydro-2H-benzo[b][1,4]oxazine-6-carboxamide (I-182);

N-hydroxy-4-((1-methyl-2-oxo-1,2,3,4-tetrahydroquinolin-6-yl)methyl)-3-oxo-3,4-dihydro-2H-benzo[b][1,4]oxazine-6-carboxamide (I-183);

(+/−)-4-(chroman-2-ylmethyl)-N-hydroxy-3-oxo-3,4-dihydro-2H-benzo[b][1,4]oxazine-6-carboxamide (I-184);

(+/−)-4-((2,3-dihydrobenzo[b][1,4]dioxin-2-yl)methyl)-N-hydroxy-3-oxo-3,4-dihydro-2H-benzo[b][1,4]oxazine-6-carboxamide (I-185);

4-(4-acetamidobenzyl)-N-hydroxy-3-oxo-3,4-dihydro-2H-benzo[b][1,4]oxazine-6-carboxamide (I-186);

4-(4-(1H-imidazol-1-yl)benzyl)-N-hydroxy-3-oxo-3,4-dihydro-2H-benzo[b][1,4]oxazine-6-carboxamide (I-187);

N-hydroxy-3-oxo-4-(4-(2-oxopyrrolidin-1-yl)benzyl)-3,4-dihydro-2H-benzo[b][1,4]oxazine-6-carboxamide (I-188);

4-(4-(N,N-dimethylsulfamoyl)benzyl)-N-hydroxy-3-oxo-3,4-dihydro-2H-benzo[b][1,4]oxazine-6-carboxamide (I-189);

N-hydroxy-4-(4-(morpholine-4-carbonyl)benzyl)-3-oxo-3,4-dihydro-2H-benzo[b][1,4]oxazine-6-carboxamide (I-190);

N-hydroxy-3-oxo-4-((5-phenyl oxazol-2-yl)methyl)-3,4-dihydro-2H-benzo[b][1,4]oxazine-6-carboxamide (I-191);

N-hydroxy-3-oxo-4-(4-(pyrrolidine-1-carbonyl)benzyl)-3,4-dihydro-2H-benzo[b][1,4]oxazine-6-carboxamide (I-192);

N-hydroxy-3-oxo-4-((1-phenyl-1H-1,2,4-triazol-3-yl)methyl)-3,4-dihydro-2H-benzo[b][1,4]oxazine-6-carboxamide (I-193);

4-(2,4-dimethoxybenzyl)-N-hydroxy-3-oxo-3,4-dihydro-2H-benzo[b][1,4]oxazine-6-carboxamide (I-194);

4-(2-(4-fluorophenylamino)-2-oxoethyl)-N-hydroxy-3-oxo-3,4-dihydro-2H-benzo[b][1,4]oxazine-6-carboxamide (I-195);

N-hydroxy-4-(4-(2-methoxyethoxy)benzyl)-3-oxo-3,4-dihydro-2H-benzo[b][1,4]oxazine-6-carboxamide (I-196);

N-hydroxy-4-(3-(2-methoxyethoxy)benzyl)-3-oxo-3,4-dihydro-2H-benzo[b][1,4]oxazine-6-carboxamide (I-197);

N-hydroxy-3-oxo-4-((1-phenylpiperidin-4-yl)methyl)-3,4-dihydro-2H-benzo[b][1,4]oxazine-6-carboxamide (I-198);

N-hydroxy-4-((1-isobutyrylpiperidin-4-yl)methyl)-3-oxo-3,4-dihydro-2H-benzo[b][1,4]oxazine-6-carboxamide (I-199);

4-((1H-indol-3-yl)methyl)-N-hydroxy-3-oxo-3,4-dihydro-2H-benzo[b][1,4]oxazine-6-carboxamide (I-200);

4(1-cyanoindolizin-2-yl)methyl)-N-hydroxy-3-oxo-3,4-dihydro-2H-benzo[b][1,4]oxazine-6-carboxamide (I-201);

N-hydroxy-3-oxo-4-((4-phenyloxazol-2-yl)methyl)-3,4-dihydro-2H-benzo[b][1,4]oxazine-6-carboxamide (I-202);

4-((1H-indazol-3-yl)methyl)-N-hydroxy-3-oxo-3,4-dihydro-2H-benzo[b][1,4]oxazine-6-carboxamide (I-203);

N-hydroxy-3-oxo-4-[(5-phenyl-1H-pyrazol-3-yl)methyl]-3,4-dihydro-2H-1,4-benzoxazine-6-carboxamide (I-204);

N-hydroxy-3-oxo-4-((1-phenyl-1H-imidazol-4-yl)methyl)-3,4-dihydro-2H-benzo[b][1,4]oxazine-6-carboxamide (I-205);

4-((1-cyclopropyl-1H-pyrazol-4-yl)methyl)-N-hydroxy-3-oxo-3,4-dihydro-2H-benzo[b][1,4]oxazine-6-carboxamide (I-206);

N-hydroxy-4-((6-methylthiazolo[5,4-b]pyridin-2-yl)methyl)-3-oxo-3,4-dihydro-2H-benzo[b][1,4]oxazine-6-carboxamide (I-207);

N-hydroxy-4-((6-methoxythiazolo[5,4-b]pyridin-2-yl)methyl)-3-oxo-3,4-dihydro-2H-benzo[b][1,4]oxazine-6-carboxamide (I-208);

4-((6-chlorothiazolo[5,4-b]pyridin-2-yl)methyl)-N-hydroxy-3-oxo-3,4-dihydro-2H-benzo[b][1,4]oxazine-6-carboxamide (I-209);

N-hydroxy-4-((5-methylthiazolo[5,4-b]pyridin-2-ylmethyl)-3-oxo-3,4-dihydro-2H-benzo[b][1,4]oxazine-6-carboxamide (I-210);

N-hydroxy-4-((5-methoxythiazolo[5,4-b]pyridin-2-yl)methyl)-3-oxo-3,4-dihydro-2H-benzo[b][1,4]oxazine-6-carboxamide (I-211);

N-hydroxy-3-oxo-4-((5-(trifluoromethyl)thiazolo[5,4-b]pyridin-2-yl)methyl)-3,4-dihydro-2H-benzo[b][1,4]oxazine-6-carboxamide (I-212);

N-hydroxy-4-((6-methylbenzo[d]oxazol-2-yl)methyl)-3-oxo-3,4-dihydro-2H-benzo[b][1,4]oxazine-6-carboxamide (I-213);

N-hydroxy-3-oxo-4-(pyridin-3-ylmethyl)-3,4-dihydro-2H-benzo[b][1,4]oxazine-6-carboxamide (I-214);

N-hydroxy-3-oxo-4-(pyridin-4-ylmethyl)-3,4-dihydro-2H-benzo[b][1,4]oxazine-6-carboxamide (I-215);

N-hydroxy-4-(imidazo[1,2-a]pyridin-2-ylmethyl)-3-oxo-3,4-dihydro-2H-benzo[b][1,4]oxazine-6-carboxamide (I-216);

4-((5-fluorobenzo[d]oxazol-2-yl)methyl)-N-hydroxy-3-oxo-3,4-dihydro-2H-benzo[b][1,4]oxazine-6-carboxamide (I-217);

4-((6-fluorobenzo[d]oxazol-2-yl)methyl)-N-hydroxy-3-oxo-3,4-dihydro-2H-benzo[b][1,4]oxazine-6-carboxamide (I-218);

4-(3,4-dimethyl benzyl)-N-hydroxy-3-oxo-3,4-dihydro-2H-benzo[b][1,4]oxazine-6-carboxamide (I-219);

N-hydroxy-3-oxo-4-(3-phenoxybenzyl)-3,4-dihydro-2H-benzo[b][1,4]oxazine-6-carboxamide (I-220);

N-hydroxy-4-(4-(oxazol-2-yl)benzyl)-3-oxo-3,4-dihydro-2H-benzo[b][1,4]oxazine-6-carboxamide (I-221);

N-hydroxy-3-oxo-4-((1-phenyl-1H-pyrazol-3-yl)methyl)-3,4-dihydro-2H-benzo[b][1,4]oxazine-6-carboxamide (I-222);

N-hydroxy-3-oxo-4-((1-phenyl-1H-pyrazol-4-yl)methyl)-3,4-dihydro-2H-benzo[b][1,4]oxazine-6-carboxamide (I-223);

4-(4-(1H-pyrazol-1-yl)benzyl)-N-hydroxy-3-oxo-3,4-dihydro-2H-benzo[b][1,4]oxazine-6-carboxamide (I-224);

N-hydroxy-2,2-dimethyl-3-oxo-4-(3-phenoxybenzyl)-3,4-dihydro-2H-benzo[b][1,4]oxazine-6-carboxamide (I-225);

4-(3-(4-chlorophenoxy)benzyl)-N-hydroxy-3-oxo-3,4-dihydro-2H-benzo[b][1,4]oxazine-6-carboxamide (I-226);

4-(3-(4-chlorophenoxy)benzyl)-N-hydroxy-2,2-dimethyl-3-oxo-3,4-dihydro-2H-benzo[b][1,4]oxazine-6-carboxamide (I-227);

N-hydroxy-3-oxo-4-(2-phenoxybenzyl)-3,4-dihydro-2H-benzo[b][1,4]oxazine-6-carboxamide (I-228);

N-hydroxy-3-oxo-4-(4-phenoxybenzyl)-3,4-dihydro-2H-benzo[b][1,4]oxazine-6-carboxamide (I-229);

N-hydroxy-4-(naphthalen-1-ylmethyl)-3-oxo-3,4-dihydro-2H-benzo[b][1,4]oxazine-6-carboxamide (I-230);

N-hydroxy-3-oxo-4-(quinolin-6-ylmethyl)-3,4-dihydro-2H-benzo[b][1,4]oxazine-6-carboxamide (I-231);

N-hydroxy-3-oxo-4-(quinolin-2-ylmethyl)-3,4-dihydro-2H-benzo[b][1,4]oxazine-6-carboxamide (I-232);

N-hydroxy-3-oxo-4-((6-(trifluoromethyl)benzo[d]oxazol-2-yl)methyl)-3,4-dihydro-2H-benzo[b][1,4]oxazine-6-carboxamide (I-233);

N-hydroxy-3-oxo-4-((5-(trifluoromethyl)benzo[d]oxazol-2-yl)methyl)-3,4-dihydro-2H-benzo[b][1,4]oxazine-6-carboxamide (I-234);

4-(2-cyanobenzyl)-N-hydroxy-3-oxo-3,4-dihydro-2H-benzo[b][1,4]oxazine-6-carboxamide (I-235);

4-(3-cyanobenzyl)-N-hydroxy-3-oxo-3,4-dihydro-2H-benzo[b][1,4]oxazine-6-carboxamide (I-236);

4-(4-cyanobenzyl)-N-hydroxy-3-oxo-3,4-dihydro-2H-benzo[b][1,4]oxazine-6-carboxamide (I-237);

N-hydroxy-4-((2-methyl-2H-indazol-5-yl)methyl)-3-oxo-3,4-dihydro-2H-benzo[b][1,4]oxazine-6-carboxamide (I-238);

N-hydroxy-4-((2-methylbenzo[d]oxazol-6-yl)methyl)-3-oxo-3,4-dihydro-2H-benzo[b][1,4]oxazine-6-carboxamide (I-239);

N-hydroxy-4-((2-methyl-2H-indazol-6-yl)methyl)-3-oxo-3,4-dihydro-2H-benzo[b][1,4]oxazine-6-carboxamide (I-240);

N-hydroxy-1-(4-methoxybenzyl)-2-oxo-2,3-dihydro-1H-pyrido[2,3-b][1,4]oxazine-7-carboxamide (I-241);

4-(2-chloro-4-methoxybenzyl)-N-hydroxy-3-oxo-3,4-dihydro-2H-benzo[b][1,4]oxazine-6-carboxamide (I-242);

4-(3-chloro-4-methoxybenzyl)-N-hydroxy-3-oxo-3,4-dihydro-2H-benzo[b][1,4]oxazine-6-carboxamide (I-243);

N-hydroxy-4-(4-methoxy-3-methylbenzyl)-3-oxo-3,4-dihydro-2H-benzo[b][1,4]oxazine-6-carboxamide (I-244);

4-(3-fluoro-4-methoxybenzyl)-N-hydroxy-3-oxo-3,4-dihydro-2H-benzo[b][1,4]oxazine-6-carboxamide (I-245);

N-hydroxy-4-(4-methoxy-3-(trifluoromethyl)benzyl)-3-oxo-3,4-dihydro-2H-benzo[b][1,4]oxazine-6-carboxamide (I-246);

4-(2,3-difluoro-4-methoxybenzyl)-N-hydroxy-3-oxo-3,4-dihydro-2H-benzo[b][1,4]oxazine-6-carboxamide (I-247);

4-(2,6-difluoro-4-methoxybenzyl)-N-hydroxy-3-oxo-3,4-dihydro-2H-benzo[b][1,4]oxazine-6-carboxamide (I-248);

N-hydroxy-4-(4-methoxy-2-(trifluoromethyl)benzyl)-3-oxo-3,4-dihydro-2H-benzo[b][1,4]oxazine-6-carboxamide (I-249);

4-(4-ethoxy-3,5-difluorobenzyl)-N-hydroxy-3-oxo-3,4-dihydro-2H-benzo[b][1,4]oxazine-6-carboxamide (I-250);

4-([1,1'-biphenyl]-4-ylmethyl)-N-hydroxy-3-oxo-3,4-dihydro-2H-benzo[b][1,4]oxazine-6-carboxamide (I-251);

4-(2,5-dichlorobenzyl)-N-hydroxy-3-oxo-3,4-dihydro-2H-benzo[b][1,4]oxazine-6-carboxamide (I-252);

4-(2,6-dichlorobenzyl)-N-hydroxy-3-oxo-3,4-dihydro-2H-benzo[b][1,4]oxazine-6-carboxamide (I-253);

4-(2,3-dichlorobenzyl)-N-hydroxy-3-oxo-3,4-dihydro-2H-benzo[b][1,4]oxazine-6-carboxamide (I-254);

4-((5-chloro-2-phenylthiazol-4-yl)methyl)-N-hydroxy-3-oxo-3,4-dihydro-2H-benzo[b][1,4]oxazine-6-carboxamide (I-255);

4-(2,4-dichlorobenzyl)-N-hydroxy-3-oxo-3,4-dihydro-2H-benzo[b][1,4]oxazine-6-carboxamide (I-256);

4-([1,1'-biphenyl]-2-ylmethyl)-N-hydroxy-3-oxo-3,4-dihydro-2H-benzo[b][1,4]oxazine-6-carboxamide (I-257);

4-(3,4-dichlorobenzyl)-N-hydroxy-3-oxo-3,4-dihydro-2H-benzo[b][1,4]oxazine-6-carboxamide (I-258);

4-(2-chloro-5-(trifluoromethyl)benzyl)-N-hydroxy-3-oxo-3,4-dihydro-2H-benzo[b][1,4]oxazine-6-carboxamide (I-259);

4-((6-chloro-1-(cyclopropylmethyl)-1H-benzo[d]imidazol-2-yl)methyl)-N-hydroxy-3-oxo-3,4-dihydro-2H-benzo[b][1,4]oxazine-6-carboxamide (I-260);

4-((5-chloro-6-methylbenzo[d]oxazol-2-yl)methyl)-N-hydroxy-3-oxo-3,4-dihydro-2H-benzo[b][1,4]oxazine-6-carboxamide (I-261);

N-hydroxy-3-oxo-4-(2-((trifluoromethyl)thio)benzyl)-3,4-dihydro-2H-benzo[b][1,4]oxazine-6-carboxamide (I-262);

N-hydroxy-3-oxo-4-(3-((trifluoromethyl)thio)benzyl)-3,4-dihydro-2H-benzo[b][1,4]oxazine-6-carboxamide (I-263);

N-hydroxy-3-oxo-4-(4-((trifluoromethyl)thio)benzyl)-3,4-dihydro-2H-benzo[b][1,4]oxazine-6-carboxamide (I-264);

4-(2-fluoro-3-(trifluoromethyl)benzyl)-N-hydroxy-3-oxo-3,4-dihydro-2H-benzo[b][1,4]oxazine-6-carboxamide (I-265);

4-(3-fluoro-4-(trifluoromethyl)benzyl)-N-hydroxy-3-oxo-3,4-dihydro-2H-benzo[b][1,4]oxazine-6-carboxamide (I-266);

4-(4-fluoro-3-(trifluoromethyl)benzyl)-N-hydroxy-3-oxo-3,4-dihydro-2H-benzo[b][1,4]oxazine-6-carboxamide (I-267);

4-(5-fluoro-2-(trifluoromethyl)benzyl)-N-hydroxy-3-oxo-3,4-dihydro-2H-benzo[b][1,4]oxazine-6-carboxamide (I-268);

4-((6-chloro-1-ethyl-1H-benzo[d]imidazol-2-yl)methyl)-N-hydroxy-3-oxo-3,4-dihydro-2H-benzo[b][1,4]oxazine-6-carboxamide (I-269);

4-(2-chloro-4-fluorobenzyl)-N-hydroxy-3-oxo-3,4-dihydro-2H-benzo[b][1,4]oxazine-6-carboxamide (I-270);

N-hydroxy-3-oxo-4-((2-phenylthiazol-4-yl)methyl)-3,4-dihydro-2H-benzo[b][1,4]oxazine-6-carboxamide (I-271);

4-((5-chlorobenzo[d]oxazol-2-yl)methyl)-N-hydroxy-3-oxo-3,4-dihydro-2H-benzo[b][1,4]oxazine-6-carboxamide (I-272);

4-(2-chloro-6-fluorobenzyl)-N-hydroxy-3-oxo-3,4-dihydro-2H-benzo[b][1,4]oxazine-6-carboxamide (I-273);

4-(2-fluoro-4-(trifluoromethyl)benzyl)-N-hydroxy-3-oxo-3,4-dihydro-2H-benzo[b][1,4]oxazine-6-carboxamide (I-274);

4-(2-fluoro-6-(trifluoromethyl)benzyl)-N-hydroxy-3-oxo-3,4-dihydro-2H-benzo[b][1,4]oxazine-6-carboxamide (I-275);

4-(3-fluoro-5-(trifluoromethyl)benzyl)-N-hydroxy-3-oxo-3,4-dihydro-2H-benzo[b][1,4]oxazine-6-carboxamide (I-276);

4-(4-fluoro-2-(trifluoromethyl)benzyl)-N-hydroxy-3-oxo-3,4-dihydro-2H-benzo[b][1,4]oxazine-6-carboxamide (I-277);

4-((6-chloro-1-methyl-1H-benzo[d]imidazol-2-yl)methyl)-N-hydroxy-3-oxo-3,4-dihydro-2H-benzo[b][1,4]oxazine-6-carboxamide (I-278);

4-((1-(cyclopropylmethyl)-1H-benzo[d]imidazol-2-yl)methyl)-N-hydroxy-3-oxo-3,4-dihydro-2H-benzo[b][1,4]oxazine-6-carboxamide (I-279);

4-(2,4-dimethylbenzyl)-N-hydroxy-3-oxo-3,4-dihydro-2H-benzo[b][1,4]oxazine-6-carboxamide (I-280);

N-hydroxy-4-((I-isopropyl-1H-benzo[d]imidazol-2-yl)methyl)-3-oxo-3,4-dihydro-2H-benzo[b][1,4]oxazine-6-carboxamide (I-281);

N-hydroxy-3-oxo-4-((1-propyl-1H-benzo[d]imidazol-2-yl)methyl)-3,4-dihydro-2H-benzo[b][1,4]oxazine-6-carboxamide (I-282);

N-hydroxy-4-((2-methyl-4-propylthiazol-5-yl)methyl)-3-oxo-3,4-dihydro-2H-benzo[b][1,4]oxazine-6-carboxamide (I-283);

4-((3-benzyl-3H-imidazo[4,5-b]pyridin-2-yl)methyl)-N-hydroxy-3-oxo-3,4-dihydro-2H-benzo[b][1,4]oxazine-6-carboxamide (I-284);

N-hydroxy-4-((5-methoxybenzo[d]oxazol-2-yl)methyl)-3-oxo-3,4-dihydro-2H-benzo[b][1,4]oxazine-6-carboxamide (I-285);

N-hydroxy-4-((5-m ethylbenzo[d]oxazol-2-yl)methyl)-3-oxo-3,4-dihydro-2H-benzo[b][1,4]oxazine-6-carboxamide (I-286);

4-((6-chlorobenzo[d]oxazol-2-yl)methyl)-N-hydroxy-3-oxo-3,4-dihydro-2H-benzo[b][1,4]oxazine-6-carboxamide (I-287);

4-(benzo[d]oxazol-2-ylmethyl)-N-hydroxy-3-oxo-3,4-dihydro-2H-benzo[b][1,4]oxazine-6-carboxamide (I-288);

4-(benzo[d]thiazol-2-ylmethyl)-N-hydroxy-3-oxo-3,4-dihydro-2H-benzo[b][1,4]oxazine-6-carboxamide (I-289);

4-((5-chlorobenzo[d]thiazol-2-yl)methyl)-N-hydroxy-3-oxo-3,4-dihydro-2H-benzo[b][1,4]oxazine-6-carboxamide (I-290);

4-((6-fluorobenzo[d]oxazol-2-yl)methyl)-N-hydroxy-2,2-dimethyl-3-oxo-3,4-dihydro-2H-benzo[b][1,4]oxazine-6-carboxamide (I-291);

N-hydroxy-2,2-dimethyl-4-((6-m ethylbenzo[d]oxazol-2-yl)methyl)-3-oxo-3,4-dihydro-2H-benzo[b][1,4]oxazine-6-carboxamide (I-292);

N-hydroxy-4-(imidazo[1,2-a]pyridin-2-ylmethyl)-2,2-dimethyl-3-oxo-3,4-dihydro-2H-benzo[b][1,4]oxazine-6-carboxamide (I-293);

4-((6-chlorobenzo[d]oxazol-2-yl)methyl)-N-hydroxy-2,2-dimethyl-3-oxo-3,4-dihydro-2H-benzo[b][1,4]oxazine-6-carboxamide (I-294);

4-(benzo[d]thiazol-2-ylmethyl)-N-hydroxy-2,2-dimethyl-3-oxo-3,4-dihydro-2H-benzo[b][1,4]oxazine-6-carboxamide (I-295);

4-((5-chlorobenzo[d]thiazol-2-yl)methyl)-N-hydroxy-2,2-dimethyl-3-oxo-3,4-dihydro-2H-benzo[b][1,4]oxazine-6-carboxamide (I-296);

N-hydroxy-2,2-dimethyl-3-oxo-4-phenethyl-3,4-dihydro-2H-benzo[b][1,4]oxazine-6-carboxamide (I-297);

N-hydroxy-2,2-dimethyl-3-oxo-4-(3-phenylpropyl)-3,4-dihydro-2H-benzo[b][1,4]oxazine-6-carboxamide (I-298);

4-(2,6-dichlorobenzyl)-N-hydroxy-2,2-dimethyl-3-oxo-3,4-dihydro-2H-benzo[b][1,4]oxazine-6-carboxamide (I-299);

N-hydroxy-2,2-dimethyl-3-oxo-4-(3-(trifluoromethyl)benzyl)-3,4-dihydro-2H-benzo[b][1,4]oxazine-6-carboxamide (I-300);

4-(4-chlorophenethyl)-N-hydroxy-2,2-dimethyl-3-oxo-3,4-dihydro-2H-benzo[b][1,4]oxazine-6-carboxamide (I-301);

N-hydroxy-2,2-dimethyl-3-oxo-4-(2-(trifluoromethoxy)benzyl)-3,4-dihydro-2H-benzo[b][1,4]oxazine-6-carboxamide (I-302);

(S)—N-hydroxy-2,2-dimethyl-3-oxo-4-(1-phenylethyl)-3,4-dihydro-2H-benzo[b][1,4]oxazine-6-carboxamide (I-303);

4-(cyclohexylmethyl)-N-hydroxy-2,2-dimethyl-3-oxo-3,4-dihydro-2H-benzo[b][1,4]oxazine-6-carboxamide (I-304);

N-hydroxy-2,2-dimethyl-3-oxo-4-(4-(trifluoromethyl)benzyl)-3,4-dihydro-2H-benzo[b][1,4]oxazine-6-carboxamide (I-305);

4-([1,1'-biphenyl]-4-ylmethyl)-N-hydroxy-2,2-dimethyl-3-oxo-3,4-dihydro-2H-benzo[b][1,4]oxazine-6-carboxamide (I-306);

N-hydroxy-2,2-dimethyl-3-oxo-4-((2-phenylthiazol-4-yl)methyl)-3,4-dihydro-2H-benzo[b][1,4]oxazine-6-carboxamide (I-307);

4-((5-chloro-2-phenylthiazol-4-yl)methyl)-N-hydroxy-2,2-dimethyl-3-oxo-3,4-dihydro-2H-benzo[b][1,4]oxazine-6-carboxamide (I-308);

4-((5-benzyl-2-phenylthiazol-4-yl)methyl)-N-hydroxy-2,2-dimethyl-3-oxo-3,4-dihydro-2H-benzo[b][1,4]oxazine-6-carboxamide (I-309);

N-hydroxy-2,2-dimethyl-3-oxo-4-(4-(trifluoromethoxy)benzyl)-3,4-dihydro-2H-benzo[b][1,4]oxazine-6-carboxamide (I-310);

4-([1,1'-biphenyl]-3-ylmethyl)-N-hydroxy-2,2-dimethyl-3-oxo-3,4-dihydro-2H-benzo[b][1,4]oxazine-6-carboxamide (I-311);

4-(3,4-di chlorobenzyl)-N-hydroxy-2,2-dimethyl-3-oxo-3,4-dihydro-2H-benzo[b][1,4]oxazine-6-carboxamide (I-312);

4-(4-(tert-butyl)benzyl)-N-hydroxy-2,2-dimethyl-3-oxo-3,4-dihydro-2H-benzo[b][1,4]oxazine-6-carboxamide (I-313);

4-(4-(benzyloxy)benzyl)-N-hydroxy-2,2-dimethyl-3-oxo-3,4-dihydro-2H-benzo[b][1,4]oxazine-6-carboxamide (I-314);

4-([1,1'-biphenyl]-2-ylmethyl)-N-hydroxy-2,2-dimethyl-3-oxo-3,4-dihydro-2H-benzo[b][1,4]oxazine-6-carboxamide (I-315);

4-(3,4-dimethylbenzyl)-N-hydroxy-2,2-dimethyl-3-oxo-3,4-dihydro-2H-benzo[b][1,4]oxazine-6-carboxamide (I-316);

N-hydroxy-2,2-dimethyl-4-(naphthalen-2-ylmethyl)-3-oxo-3,4-dihydro-2H-benzo[b][1,4]oxazine-6-carboxamide (I-317);

4-cinnamyl-N-hydroxy-2,2-dimethyl-3-oxo-3,4-dihydro-2H-benzo[b][1,4]oxazine-6-carboxamide (I-318);

N-hydroxy-2,2-dimethyl-3-oxo-4-(3-(trifluoromethoxy)benzyl)-3,4-dihydro-2H-benzo[b][1,4]oxazine-6-carboxamide (I-319);

N-hydroxy-2,2-dimethyl-3-oxo-4-((5-phenylisoxazol-3-yl)methyl)-3,4-dihydro-2H-benzo[b][1,4]oxazine-6-carboxamide (I-320);

4-(2-fluoro-4-(trifluoromethyl)benzyl)-N-hydroxy-2,2-dimethyl-3-oxo-3,4-dihydro-2H-benzo[b][1,4]oxazine-6-carboxamide (I-321);

4-(2-fluoro-4-(trifluoromethoxy)benzyl)-N-hydroxy-2,2-dimethyl-3-oxo-3,4-dihydro-2H-benzo[b][1,4]oxazine-6-carboxamide (I-322);

N-hydroxy-4-(naphthalen-2-ylmethyl)-3-oxo-3,4-dihydro-2H-benzo[b][1,4]oxazine-6-carboxamide (I-323);

4-((1H-pyrrolo[2,3-b]pyridin-5-yl)methyl)-N-hydroxy-3-oxo-3,4-dihydro-2H-benzo[b][1,4]oxazine-6-carboxamide (I-324);

4-((1,3-dimethyl-1H-pyrazolo[3,4-b]pyridin-5-yl)methyl)-N-hydroxy-3-oxo-3,4-dihydro-2H-benzo[b][1,4]oxazine-6-carboxamide (I-325);

N-hydroxy-3-oxo-4-((2-oxo-1,2-dihydroquinolin-3-yl)methyl)-3,4-dihydro-2H1-benzo[b][1,4]oxazine-6-carboxamide (I-326);

N-hydroxy-4-((6-methyl-4-oxo-4H-pyrido[1,2-a]pyrimidin-2-yl)methyl)-3-oxo-3,4-dihydro-2H-benzo[b][1,4]oxazine-6-carboxamide (I-327);

N-hydroxy-3-oxo-4-((7-oxo-4,7-dihydropyrazolo[1,5-a]pyrimidin-5-yl)methyl)-3,4-dihydro-2H-benzo[b][1,4]oxazine-6-carboxamide (I-328);

N-hydroxy-3-oxo-4-((7-oxo-4,7-dihydro-[1,2,4]triazolo[1,5-a]pyrimidin-5-yl)methyl)-3,4-dihydro-2H-benzo[b][1,4]oxazine-6-carboxamide (I-329);

N-hydroxy-4-(4-isopropoxybenzyl)-3-oxo-3,4-dihydro-2H-benzo[b][1,4]oxazine-6-carboxamide (I-330);

4-(4-cyclobutoxybenzyl)-N-hydroxy-3-oxo-3,4-dihydro-2H-benzo[b][1,4]oxazine-6-carboxamide (I-331);

N-hydroxy-4-((6-methoxypyridin-3-yl)methyl)-3-oxo-3,4-dihydro-2H-benzo[b][1,4]oxazine-6-carboxamide (I-332);

N-hydroxy-3-oxo-4-(quinolin-3-ylmethyl)-3,4-dihydro-2H-benzo[b][1,4]oxazine-6-carboxamide (I-333);

N-hydroxy-4-(isoquinolin-3-ylmethyl)-3-oxo-3,4-dihydro-2H-benzo[b][1,4]oxazine-6-carboxamide (I-334);

N-hydroxy-3-oxo-4-(quinolin-7-ylmethyl)-3,4-dihydro-2H-benzo[b][1,4]oxazine-6-carboxamide (I-335);

N-hydroxy-4-(isoquinolin-6-ylmethyl)-3-oxo-3,4-dihydro-2H-benzo[b][1,4]oxazine-6-carboxamide (I-336);

N-hydroxy-4-(isoquinolin-7-ylmethyl)-3-oxo-3,4-dihydro-2H-benzo[b][1,4]oxazine-6-carboxamide (I-337);

N-hydroxy-4-(imidazo[1,2-a]pyridin-7-ylmethyl)-3-oxo-3,4-dihydro-2H-benzo[b][1,4]oxazine-6-carboxamide (I-338);

N-hydroxy-3-oxo-4-(pyrazolo[1,5-a]pyridin-5-ylmethyl)-3,4-dihydro-2H-benzo[b][1,4]oxazine-6-carboxamide (I-339);

4-(3-chloro-2-fluorobenzyl)-N-hydroxy-3-oxo-3,4-dihydro-2H-benzo[b][1,4]oxazine-6-carboxamide (I-340);

4-(2-fluoro-4-methoxybenzyl)-N-hydroxy-3-oxo-3,4-dihydro-2H-benzo[b][1,4]oxazine-6-carboxamide (I-341);

4-(3-fluoro-5-methoxybenzyl)-N-hydroxy-3-oxo-3,4-dihydro-2H-benzo[b][1,4]oxazine-6-carboxamide (I-342);

4-(3-chloro-5-fluorobenzyl)-N-hydroxy-3-oxo-3,4-dihydro-2H-benzo[b][1,4]oxazine-6-carboxamide (I-343);

4-(4-chloro-2-fluorobenzyl)-N-hydroxy-3-oxo-3,4-dihydro-2H-benzo[b][1,4]oxazine-6-carboxamide (I-344);

4-(4-chloro-3-(trifluoromethyl)benzyl)-N-hydroxy-3-oxo-3,4-dihydro-2H-benzo[b][1,4]oxazine-6-carboxamide (I-345);

4-(4-chloro-3-methoxybenzyl)-N-hydroxy-3-oxo-3,4-dihydro-2H-benzo[b][1,4]oxazine-6-carboxamide (I-346);

4-(2-chloro-5-methoxybenzyl)-N-hydroxy-3-oxo-3,4-dihydro-2H-benzo[b][1,4]oxazine-6-carboxamide (I-347);

4-(5-chloro-2-fluorobenzyl)-N-hydroxy-3-oxo-3,4-dihydro-2H-benzo[b][1,4]oxazine-6-carboxamide (I-348);

4-(3-chloro-5-(trifluoromethyl)benzyl)-N-hydroxy-3-oxo-3,4-dihydro-2H-benzo[b][1,4]oxazine-6-carboxamide (I-349);

4-(4-chloro-3-methoxybenzyl)-N-hydroxy-3-oxo-3,4-dihydro-2H-benzo[b][1,4]oxazine-6-carboxamide (I-350);

4-(3-chloro-4-fluorobenzyl)-N-hydroxy-3-oxo-3,4-dihydro-2H-benzo[b][1,4]oxazine-6-carboxamide (I-351);

4-(2-chloro-5-fluorobenzyl)-N-hydroxy-3-oxo-3,4-dihydro-2H-benzo[b][1,4]oxazine-6-carboxamide (I-352);

4-(4-fluoro-3-methoxybenzyl)-N-hydroxy-3-oxo-3,4-dihydro-2H-benzo[b][1,4]oxazine-6-carboxamide (I-353);

4-(2-chloro-3-(trifluoromethyl)benzyl)-N-hydroxy-3-oxo-3,4-dihydro-2H-benzo[b][1,4]oxazine-6-carboxamide (I-354);

4-(3,5-dichlorobenzyl)-N-hydroxy-3-oxo-3,4-dihydro-2H-benzo[b][1,4]oxazine-6-carboxamide (I-355);

4-(2-chloro-4-(trifluoromethyl)benzyl)-N-hydroxy-3-oxo-3,4-dihydro-2H-benzo[b][1,4]oxazine-6-carboxamide (I-356);

N-hydroxy-3-oxo-4-phenyl-3,4-dihydro-2H-benzo[b][1,4]oxazine-6-carboxamide (I-357);

N-hydroxy-4-(3-methoxyphenyl)-3-oxo-3,4-dihydro-2H-1,4-benzoxazine-6-carboxamide (I-358);

N-hydroxy-3-oxo-4-(thiazolo[5,4-b]pyridin-2-ylmethyl)-3,4-dihydro-2H-benzo[b][1,4]oxazine-6-carboxamide (I-359);

4-(4-(dimethylcarbamoyl)benzyl)-N-hydroxy-3-oxo-3,4-dihydro-2H-benzo[b][1,4]oxazine-6-carboxamide (I-360);

4-(4-(dimethylamino)benzyl)-N-hydroxy-3-oxo-3,4-dihydro-2H-benzo[b][1,4]oxazine-6-carboxamide (I-361);

4-(4-carbamoylbenzyl)-N-hydroxy-3-oxo-3,4-dihydro-2H-benzo[b][1,4]oxazine-6-carboxamide (I-362);

N-hydroxy-4-(imidazo[2,1-b]thiazol-6-ylmethyl)-3-oxo-3,4-dihydro-2H-benzo[b][1,4]oxazine-6-carboxamide (I-363);

N-hydroxy-4-((7-methylimidazo[1,2-a]pyridin-2-yl)methyl)-3-oxo-3,4-dihydro-2H-benzo[b][1,4]oxazine-6-carboxamide (I-364);

N-hydroxy-4-((6-methylimidazo[1,2-a]pyridin-2-yl)methyl)-3-oxo-3,4-dihydro-2H-benzo[b][1,4]oxazine-6-carboxamide (I-365);

4-(3-carbamoylbenzyl)-N-hydroxy-3-oxo-3,4-dihydro-2H-benzo[b][1,4]oxazine-6-carboxamide (I-366);

4-(3-(dimethylcarbamoyl)benzyl)-N-hydroxy-3-oxo-3,4-dihydro-2H-benzo[b][1,4]oxazine-6-carboxamide (I-367);

4-((6-fluoroimidazo[1,2-a]pyridin-2-yl)methyl)-N-hydroxy-3-oxo-3,4-dihydro-2H-benzo[b][1,4]oxazine-6-carboxamide (I-368);

N-hydroxy-4-(3-(isopropylcarbamoyl)benzyl)-3-oxo-3,4-dihydro-2H-benzo[b][1,4]oxazine-6-carboxamide (I-369);

N-hydroxy-3-oxo-4-(3-(pyrrolidine-1-carbonyl)benzyl)-3,4-dihydro-2H-benzo[b][1,4]oxazine-6-carboxamide (I-370);

4-(2-fluoro-5-methoxybenzyl)-N-hydroxy-3-oxo-3,4-dihydro-2H-benzo[b][1,4]oxazine-6-carboxamide (I-371);

4-(2-chloro-4-cyanobenzyl)-N-hydroxy-3-oxo-3,4-dihydro-2H-benzo[b][1,4]oxazine-6-carboxamide (I-372); or 4-(2-chloro-5-cyanobenzyl)-N-hydroxy-3-oxo-3,4-dihydro-2H-benzo[b][1,4]oxazine-6-carboxamide (I-373).

In some embodiments, the compound of Formula I comprises a compound selected from N-hydroxy-3-oxo-4-((1-phenyl-1H-1,2,3-triazol-4-yl)methyl)-3,4-dihydro-2H-benzo[b][1,4]oxazine-6-carboxamide (I-77); N-hydroxy-4-((6-methylbenzo[d]oxazol-2-yl)methyl)-3-oxo-3,4-dihydro-2H-benzo[b][1,4]oxazine-6-carboxamide (I-213); 4-(benzo[d]oxazol-2-ylmethyl)-N-hydroxy-3-oxo-3,4-dihydro-2H- benzo[b][1,4]oxazine-6-carboxamide (I-288); N-hydroxy-3-oxo-4-((4-phenyloxazol-2-yl)methyl)-3,4-dihydro-2H-benzo[b][1,4]oxazine-6-carboxamide (I-202); 4-(benzo[d]thiazol-2-ylmethyl)-N-hydroxy-3-oxo-3,4-dihydro-2H-benzo[b][1,4]oxazine-6-carboxamide (I-289); N-hydroxy-4-((6-methylthiazolo[5,4-b]pyridin-2-yl)methyl)-3-oxo-3,4-dihydro-2H-benzo[b][1,4]oxazine-6-carboxamide (I-207); N-hydroxy-3-oxo-4-(quinolin-7-ylmethyl)-3,4-dihydro-2H-benzo[b][1,4]oxazine-6-carboxamide (I-335); or N-hydroxy-4-(isoquinolin-7-ylmethyl)-3-oxo-3,4-dihydro-2H-benzo[b][1,4]oxazine-6-carboxamide (I-337).

In some embodiments, the compound of Formula I comprises a compound selected from 4-(2-chloro-5-(trifluoromethyl)benzyl)-N-hydroxy-3-oxo-3,4-dihydro-2H-benzo[b][1,4]oxazine-6-carboxamide (I-259); N-hydroxy-4-(4-(oxazol-2-yl)benzyl)-3-oxo-3,4-dihydro-2H-benzo[b][1,4]oxazine-6-carboxamide (I-221); 4-(2-fluoro-5-methoxybenzyl)-N-hydroxy-3-oxo-3,4-dihydro-2H-benzo[b][1,4]oxazine-6-carboxamide (I-371); N-hydroxy-4-(4-methoxybenzyl)-3-oxo-3,4-dihydro-2H-benzo[b][1,4]oxazine-6-carboxamide (I-141); 4-(2-chloro-5-cyanobenzyl)-N-hydroxy-3-oxo-3,4-dihydro-2H-benzo[b][1,4]oxazine-6-carboxamide (I-373); 4-(2-chloro-4-cyanobenzyl)-N-hydroxy-3-oxo-3,4-dihydro-2H-benzo[b][1,4]oxazine-6-carboxamide (I-372); 4-(2-fluoro-4-methoxybenzyl)-N-hydroxy-2,2-dimethyl-3-oxo-3,4-dihydro-2H-benzo[b][1,4]oxazine-6-carboxamide (I-160); or 4-(4-chloro-2-fluorobenzyl)-N-hydroxy-2,2-dimethyl-3-oxo-3,4-dihydro-2H-benzo[b][1,4]oxazine-6-carboxamide (I-161).

In some embodiments, the compound of Formula I is N-hydroxy-3-oxo-4-((1-phenyl-1H-1,2,3-triazol-4-yl)methyl)-3,4-dihydro-2H-benzo[b][1,4]oxazine-6-carboxamide (I-77).

In some embodiments, the compound of Formula I is N-hydroxy-4-((6-methylbenzo[d]oxazol-2-yl)methyl)-3-oxo-3,4-dihydro-2H-benzo[b][1,4]oxazine-6-carboxamide (I-213).

In some embodiments, the compound of Formula I is 4-(benzo[d]oxazol-2-ylmethyl)-N-hydroxy-3-oxo-3,4-dihydro-2H-benzo[b][1,4]oxazine-6-carboxamide (I-288).

In some embodiments, the compound of Formula I is N-hydroxy-3-oxo-4-((4-phenyloxazol-2-yl)methyl)-3,4-dihydro-2H-benzo[b][1,4]oxazine-6-carboxamide (I-202).

In some embodiments, the compound of Formula I is 4-(benzo[d]thiazol-2-ylmethyl)-N-hydroxy-3-oxo-3,4-dihydro-2H-benzo[b][1,4]oxazine-6-carboxamide (I-289).

In some embodiments, the compound of Formula I is N-hydroxy-4-((6-methylthiazolo[5,4-b]pyridin-2-yl)methyl)-3-oxo-3,4-dihydro-2H-benzo[b][1,4]oxazine-6-carboxamide (I-207).

In some embodiments, the compound of Formula I is N-hydroxy-3-oxo-4-(quinolin-7-ylmethyl)-3,4-dihydro-2H-benzo[b][1,4]oxazine-6-carboxamide (I-335).

In some embodiments, the compound of Formula I is N-hydroxy-4-(isoquinolin-7-ylmethyl)-3-oxo-3,4-dihydro-2H-benzo[b][1,4]oxazine-6-carboxamide (I-337).

In some embodiments, the compound of Formula I is 4-(2-chloro-5-(trifluoromethyl)benzyl)-N-hydroxy-3-oxo-3,4-dihydro-2H-benzo[b][1,4]oxazine-6-carboxamide (I-259).

In some embodiments, the compound of Formula I is N-hydroxy-4-(4-(oxazol-2-yl)benzyl)-3-oxo-3,4-dihydro-2H-benzo[b][1,4]oxazine-6-carboxamide (I-221).

In some embodiments, the compound of Formula I is 4-(2-fluoro-5-methoxybenzyl)-N-hydroxy-3-oxo-3,4-dihydro-2H-benzo[b][1,4]oxazine-6-carboxamide (I-371).

In some embodiments, the compound of Formula I is N-hydroxy-4-(4-methoxybenzyl)-3-oxo-3,4-dihydro-2H-benzo[b][1,4]oxazine-6-carboxamide (I-141).

In some embodiments, the compound of Formula I is 4-(2-chloro-5-cyanobenzyl)-N-hydroxy-3-oxo-3,4-dihydro-2H-benzo[b][1,4]oxazine-6-carboxamide (I-373).

In some embodiments, the compound of Formula I is 4-(2-chloro-4-cyanobenzyl)-N-hydroxy-3-oxo-3,4-dihydro-2H-benzo[b][1,4]oxazine-6-carboxamide (I-372).

In some embodiments, the compound of Formula I is 4-(2-fluoro-4-methoxybenzyl)-N-hydroxy-2,2-dimethyl-3-oxo-3,4-dihydro-2H-benzo[b][1,4]oxazine-6-carboxamide (I-160).

In some embodiments, the compound of Formula I is 4-(4-chloro-2-fluorobenzyl)-N-hydroxy-2,2-dimethyl-3-oxo-3,4-dihydro-2H-benzo[b][1,4]oxazine-6-carboxamide (I-161).

In some embodiments, $Y_1$ is $CR_3$. In other embodiments, $Y_2$ is $CR_3$. In other embodiments, $Y_3$ is $CR_3$. In other embodiments, $Y_4$ is $CR_3$. In other embodiments, $Y_1$ is N. In other embodiments, $Y_2$ is N. In other embodiments, $Y_3$ is N. In other embodiments, $Y_4$ is N. In other embodiments, $Y_1$ is C when attached to C(O)NHOH. In other embodiments, $Y_2$ is C when attached to C(O)NHOH. In other embodiments, $Y_3$ is C when attached to C(O)NHOH. In other embodiments, $Y_4$ is C when attached to C(O)NHOH.

In some embodiments, W is $C(R_4)(R_5)$. In some embodiments, W is O.

In some embodiments, $R_1$ is $C_1$-$C_6$ alkyl. In some embodiments, $R_1$ is $C_1$-$C_6$ alkoxy. In some embodiments, $R_1$ is $C_2$-$C_6$ alkenyl. In some embodiments, $R_1$ is $C_2$-$C_6$ alkynyl. In some embodiments, $R_1$ is $C_3$-$C_8$ cycloalkyl. In some embodiments, $R_1$ is $C_4$-$C_8$ cycloalkenyl. In some embodiments, $R_1$ is aryl. In some embodiments, $R_1$ is heteroaryl. In some embodiments, $R_1$ is 3- to 8-membered heterocycle. In some embodiments, $R_1$ is —$(CH_2)_n$—$R_4$. In some embodiments, $R_1$ is —$(CH_2)_n$—O—$(CH_2)_p$—$R_4$. In some embodiments, $R_1$ is —$S(O)_2R_4$. In some embodiments, $R_1$ is —$C(O)R_4$. In some embodiments, $R_1$ is —$C(O)N(R_4)(R_5)$. In some embodiments, $R_1$ is $C_1$-$C_6$ alkyl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is $C_1$-$C_6$ alkoxy optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is $C_2$-$C_6$ alkenyl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is $C_2$-$C_6$ alkynyl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is $C_3$-$C_8$ cycloalkyl optionally substituted with one or more —OH, halogen, oxo, —$NO_2$, —$NH_2$, —CN, —$C_1$-$C_6$ alkyl, —$C_1$—$C_6$ alkoxy, heterocycle, aryl, heteroaryl, or $R_4$. In some embodiments, $R_1$ is $C_4$-$C_8$ cycloalkenyl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is aryl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is heteroaryl optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$. In some embodiments, $R_1$ is 3- to 8-membered heterocycle optionally substituted with one or more —OH, halogen, oxo, —NO$_2$, —NH$_2$, —CN, —C$_1$-C$_6$ alkyl, —C$_1$-C$_6$ alkoxy, heterocycle, aryl, heteroaryl, or R$_4$.

In some embodiments, R$_2$ is H. In some embodiments, R$_2$ is C$_1$-C$_6$ alkyl. In some embodiments, R$_2$ is C$_1$-C$_6$ alkoxy. In some embodiments, R$_2$ is C$_2$-C$_6$ alkenyl. In some embodiments, R$_2$ is C$_2$-C$_6$ alkynyl. In some embodiments, R$_2$ is C$_3$-C$_8$ cycloalkyl. In some embodiments, R$_2$ is C$_4$-C$_8$ cycloalkenyl. In some embodiments, R$_2$ is aryl. In some embodiments, R$_2$ is heteroaryl. In some embodiments, R$_2$ is 3- to 8-membered heterocycle. In some embodiments, R$_2$ is C$_1$-C$_6$ alkyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is C$_1$-C$_6$ alkoxy optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is C$_2$-C$_6$ alkenyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is C$_2$-C$_6$ alkynyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is C$_3$-C$_8$ cycloalkyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is C$_4$-C$_8$ cycloalkenyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is aryl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is heteroaryl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$ is 3- to 8-membered heterocycle optionally substituted with one or more —OH, halogen, oxo, —NO$_2$, —NH$_2$, —CN, —C$_1$-C$_6$ alkyl, or —C$_1$-C$_6$ alkoxy.

In some embodiments, R$_2$' is H. In some embodiments, R$_2$' is C$_1$-C$_6$ alkyl. In some embodiments, R$_2$' is C$_1$-C$_6$ alkoxy. In some embodiments, R$_2$' is C$_2$-C$_6$ alkenyl. In some embodiments, R$_2$' is C$_2$-C$_6$ alkynyl. In some embodiments, R$_2$' is C$_3$-C$_8$ cycloalkyl. In some embodiments, R$_2$' is C$_4$-C$_8$ cycloalkenyl. In some embodiments, R$_2$' is aryl. In some embodiments, R$_2$' is heteroaryl. In some embodiments, R$_2$' is 3- to 8-membered heterocycle. In some embodiments, R$_2$' is C$_1$-C$_6$ alkyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is C$_1$-C$_6$ alkoxy optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is C$_2$—C alkenyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is C$_2$-C$_6$ alkynyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is C$_3$-C$_8$ cycloalkyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is C$_4$-C$_8$ cycloalkenyl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is aryl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is heteroaryl optionally substituted with one or more —OH, halogen, oxo, —NO$_2$, —NH$_2$, —CN, —C$_1$-C$_6$ alkyl, or —C$_1$-C$_6$ alkoxy. In some embodiments, R$_2$' is 3- to 8-membered heterocycle optionally substituted with one or more —OH, halogen, oxo, —NO$_2$, —NH$_2$, —CN, —C$_1$-C$_6$ alkyl, or —C$_1$-C$_6$ alkoxy.

In some embodiments, R$_2$ and R$_2$' may combine with the carbon to which they are attached to form an oxo group, In some embodiments, R$_2$ and R$_2$' can combine with the carbon to which they are attached to form C$_3$-C$_8$ cycloalkyl, In some embodiments, R$_2$ and R$_2$' can combine with the carbon to which they are attached to form 3- to 8-membered heterocycle.

In some embodiments, R$_3$ is hydrogen. In other embodiments, R$_3$ is halogen. In other embodiments, R$_3$ is OH. In other embodiments, R$_3$ is CN. In other embodiments, R$_3$ is NO$_2$. In other embodiments, R$_3$ is NH$_2$. In other embodiments, R$_3$ is C$_1$-C$_3$ alkyl. In other embodiments, R$_3$ is C$_1$-C$_3$ alkoxy.

In some embodiments, R$_4$ is H. In some embodiments, R$_4$ is halogen. In some embodiments, R$_4$ is OH. In some embodiments, R$_4$ is NH$_2$. In some embodiments, R$_4$ is —C(O)N(R$_{10}$)(R$_{11}$). In some embodiments, R$_4$ is C$_1$-C$_6$ alkyl. In some embodiments, R$_4$ is C$_1$-C$_6$ alkoxy. In some embodiments, R$_4$ is C$_2$-C$_6$ alkenyl. In some embodiments, R$_4$ is C$_2$-C$_6$ alkynyl. In some embodiments, R$_4$ is C$_3$-C$_8$ cycloalkyl. In some embodiments, R$_4$ is C$_4$-C$_8$ cycloalkenyl. In some embodiments, R$_4$ is aryl. In some embodiments, R$_4$ is heteroaryl. In some embodiments, R$_4$ is 3- to 8-membered heterocycle. In some embodiments, R$_4$ is C$_1$-C$_6$ alkyl optionally substituted with one or more —OH, R$_{4'}$, R$_{5'}$, halogen, oxo, —(CH$_2$)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl. In some embodiments, R$_4$ is C$_1$-C$_6$ alkoxy optionally substituted with one or more —OH, R$_{4'}$, R$_{5'}$, halogen, oxo, —(CH$_2$)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl. In some embodiments, R$_4$ is C$_2$-C$_6$ alkenyl optionally substituted with one or more —OH, R$_{4'}$, R$_{5'}$, halogen, oxo, —(CH$_2$)OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl. In some embodiments, R$_4$ is C$_2$-C$_6$ alkynyl optionally substituted with one or more —OH, R$_{4'}$, R$_{5'}$, halogen, oxo, —(CH$_2$-)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl. In some embodiments, R$_4$ is C$_3$-C$_8$ cycloalkyl optionally substituted with one or more —OH, R$_{4'}$, R$_{5'}$, halogen, oxo, —(CH$_2$)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —C$_1$-C$_6$ alkyl, —C$_1$-C$_6$ haloalkyl, —C$_1$-C$_6$ alkoxy, C$_1$-C$_6$ alkylamino, C$_1$-C$_6$ dialkylamino, C$_1$-C$_6$ hydroxyalkyl, C$_3$-C$_8$ cycloalkyl, C$_3$-C$_8$ cycloalkylalkyl, arylalkyl, heterocycle, aryl, or heteroaryl. In some embodiments, R$_4$ is C$_4$-C$_8$ cycloalkenyl optionally substituted with one or more —OH, $R_{4'}$, $R_{5'}$, halogen, oxo, —$(CH_2)OR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_4$ is aryl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_4$ is heteroaryl optionally substituted with one or more —OH, $R_{4'}$, $R_{5'}$, halogen, oxo, —$(CH_2)OR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_4$ is 3- to 8-membered heterocycle optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

In some embodiments, $R_5$ is H. In some embodiments, $R_5$ is halogen. In some embodiments, $R_5$ is OH. In some embodiments, $R_5$ is $NH_2$. In some embodiments, $R_5$ is —$C(O)N(R_{10})(R_{11})$. In some embodiments, $R_5$ is $C_1$-$C_6$ alkyl. In some embodiments, $R_5$ is $C_1$-$C_6$ alkoxy. In some embodiments, $R_5$ is $C_2$-$C_6$ alkenyl. In some embodiments, $R_5$ is $C_2$-$C_6$ alkynyl. In some embodiments, $R_5$ is $C_3$-$C_8$ cycloalkyl. In some embodiments, $R_5$ is $C_4$-$C_8$ cycloalkenyl. In some embodiments, $R_5$ is aryl. In some embodiments, $R_5$ is heteroaryl. In some embodiments, $R_5$ is 3- to 8-membered heterocycle. In some embodiments, $R_5$ is $C_1$-$C_6$ alkyl optionally substituted with one or more —OH, $R_{4'}$, $R_{5'}$, halogen, oxo, —$(CH_2)$, $OR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is $C_1$-$C_6$ alkoxy optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is $C_2$-$C_6$ alkenyl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is $C_2$-$C_6$ alkynyl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is $C_3$-$C_8$ cycloalkyl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is $C_4$-$C_8$ cycloalkenyl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is aryl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is heteroaryl optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl. In some embodiments, $R_5$ is 3- to 8-membered heterocycle optionally substituted with one or more —OH, $R_{4'}$, $R_{5'}$, halogen, oxo, —$(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

In other embodiments, $R_4$ and $R_5$ may combine with the carbon to which they are attached to form an oxo group. In other embodiments, $R_4$ and $R_5$ may combine with the carbon to which they are attached to form $C_3$-$C_8$ cycloalkyl. In other embodiments, $R_4$ and $R_5$ may combine with the carbon to which they are attached to form 3- to 8-membered heterocycle. In other embodiments, $R_4$ and $R_5$ may combine with the carbon to which they are attached to form 3- to 8-membered heterocycle optionally substituted with one or more substituent selected from $R_{4'}$ and $R_{5'}$. In other embodiments, $R_4$ and $R_5$ may combine with the nitrogen to which they are attached to form 3- to 8-membered heterocycle. In other embodiments, $R_4$ and $R_5$ may combine with the nitrogen to which they are attached to form 3- to 8-membered heterocycle optionally substituted with one or more substituent selected from $R_{4'}$ and $R_{5'}$.

In one embodiment, $R_{4'}$ is H. In another embodiment, $R_{4'}$ is —$C_1$-$C_6$ alkyl. In a further embodiment, one embodiment, $R_{5'}$ is H. In another embodiment, $R_{5'}$ is —$C_1$-$C_6$ alkyl. In yet other embodiments, $R_{4'}$ and $R_{5'}$ together when attached to the same atom may form a $C_3$-$C_8$ spirocycloalkyl ring. In other embodiments $R_{4'}$ and $R_{5'}$ together when attached to the same atom may also form a spiroheterocycloalkyl. In other embodiments, $R_{4'}$ and $R_{5'}$ together when attached to adjacent atoms may form an aryl. In other embodiments, $R_{4'}$ and $R_{5'}$ together when attached to adjacent atoms may form a heteroaryl. In other embodiments, $R_{4'}$ and $R_{5'}$ together when attached to adjacent atoms may form a $C_3$-$C_8$ cycloalkyl. In other embodiments, $R_{4'}$ and $R_{5'}$ together when attached to adjacent atoms form a 3- to 8-membered heterocycle. In yet other embodiments, $R_{4'}$ and $R_{5'}$ together when attached to the same atom may form a $C_3$-$C_8$ spirocycloalkyl ring optionally substituted with one or more OH, halogen, —$C_1$-$C_6$ alkyl or $C(O)OR_6$. In other embodiments $R_{4'}$ and $R_{5'}$ together when attached to the same atom may also form a spiroheterocycloalkyl optionally substituted with one or more OH, halogen, —$C_1$-$C_6$ alkyl or $C(O)OR_6$. In other embodiments, $R_{4'}$ and $R_{5'}$ together when attached to adjacent atoms may form an aryl optionally substituted with one or more OH, halogen, —$C_1$-$C_6$ alkyl or $C(O)OR_6$. In other embodiments, $R_{4'}$ and $R_{5'}$ together when attached to adjacent atoms may form a heteroaryl optionally substituted with one or more OH, halogen, —$C_1$-$C_6$ alkyl or $C(O)OR_6$. In other embodiments, $R_{4'}$ and $R_{5'}$ together when attached to adjacent atoms may form a $C_3$-$C_8$ cycloalkyl optionally substituted with one or more OH, halogen, —$C_1$-$C_6$ alkyl or $C(O)OR_6$. In other embodiments, $R_{4'}$ and $R_{5'}$ together when attached to adjacent atoms form a 3- to 8-membered heterocycle optionally substituted with one or more OH, halogen, —$C_1$-$C_6$ alkyl or $C(O)OR_6$.

In some embodiments, $R_6$ is H. In some embodiments, $R_6$ is amino. In some embodiments, $R_6$ is $C_1$-$C_6$ dialkylamino. In some embodiments, $R_6$ is $C_1$-$C_6$ alkylamino. In some embodiments, $R_6$ is —$S(O)_2N(R_8)(R_9)$. In some embodiments, $R_6$ is $C_1$-$C_6$ alkyl. In some embodiments, $R_6$ is $C_1$-$C_6$ alkoxy. In some embodiments, $R_6$ is $C_2$-$C_6$ alkenyl. In some embodiments, $R_6$ is $C_2$-$C_6$ alkynyl. In some embodiments, $R_6$ is $C_3$-$C_8$ cycloalkyl. In some embodiments, $R_6$ is $C_4$-$C_8$ cycloalkenyl. In some embodiments, $R_6$ is aryl. In some embodiments, $R_6$ is heteroaryl. In some embodiments, $R_6$ is 3- to 8-membered heterocycle. In some embodiments, $R_6$ is —$S(O)_2R_8$. In some embodiments, $R_6$ is —$C(O)R_8$. In some embodiments, $R_6$ is —$C(O)OR_8$. In some embodiments, $R_6$ is -is $s_8$. In some embodiments, $R_6$ is —$S(O)N(R_8)(R_9)$. In some embodiments, $R_6$ is $C_1$-$C_6$ alkyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is $C_1$-$C_6$ alkoxy optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is $C_2$-$C_6$ alkenyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is $C_2$-$C_6$ alkynyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is $C_3$-$C_8$ cycloalkyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is $C_4$-$C_8$ cycloalkenyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is aryl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is heteroaryl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_6$ is 3- to 8-membered heterocycle optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl.

In some embodiments, $R_7$ is H. In some embodiments, $R_7$ is amino. In some embodiments, $R_7$ is $C_1$-$C_6$ dialkylamino. In some embodiments, $R_7$ is $C_1$-$C_6$ alkylamino. In some embodiments, $R_7$ is —$S(O)_2N(R_8)(R_9)$. In some embodiments, $R_7$ is $C_1$-$C_6$ alkyl. In some embodiments, $R_7$ is $C_1$-$C_6$ alkoxy. In some embodiments, $R_7$ is $C_2$-$C_6$ alkenyl. In some embodiments, $R_7$ is $C_2$-$C_6$ alkynyl. In some embodiments, $R_7$ is $C_3$-$C_8$ cycloalkyl. In some embodiments, $R_7$ is $C_4$-$C_8$ cycloalkenyl. In some embodiments, $R_7$ is aryl. In some embodiments, $R_7$ is heteroaryl. In some embodiments, $R_7$ is 3- to 8-membered heterocycle. In some embodiments, $R_7$ is —$S(O)_2R_8$. In some embodiments, $R_7$ is —$C(O)R_8$. In some embodiments, $R_7$ is —$C(O)OR_8$. In some embodiments, $R_7$ is -is $s_8$. In some embodiments, $R_7$ is —$S(O)N(R_8)(R_9)$. In some embodiments, $R_7$ is $C_1$-$C_6$ alkyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is $C_1$-$C_6$ alkoxy optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, heteroaryl. In some embodiments, $R_7$ is $C_2$-$C_6$ alkenyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is $C_2$-$C_6$ alkynyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is $C_3$-$C_8$ cycloalkyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is $C_4$-$C_8$ cycloalkenyl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is aryl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is heteroaryl optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl. In some embodiments, $R_7$ is 3- to 8-membered heterocycle optionally substituted with one or more —OH, halogen, oxo, —$NO_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl.

In some embodiments, R$_6$ and R$_7$ together with the atom to which they are attached may form a C$_3$-C$_8$ cycloalkyl. In other embodiments, R$_6$ and R$_7$ together with the atom to which they are attached may form a 3- to 8-membered heterocycle. In some embodiments, R$_6$ and R$_7$ together with the atom to which they are attached may form a C$_3$-C$_8$ cycloalkyl optionally substituted with one or more halogen, oxo or C$_1$-C$_6$ alkyl. In other embodiments, R$_6$ and R$_7$ together with the atom to which they are attached may form a 3- to 8-membered heterocycle optionally substituted with one or more halogen, oxo or C$_1$-C$_6$ alkyl.

In some embodiments, R$_8$ is C$_1$-C$_6$ alkyl. In some embodiments, R is C$_2$-C$_6$ alkenyl. In some embodiments, R$_8$ is C$_2$-C$_6$ alkynyl. In some embodiments, R$_8$ is C$_3$-C$_8$ cycloalkyl. In some embodiments, R$_8$ is C$_4$-C$_8$ cycloalkenyl. In some embodiments, R$_8$ is heteroaryl. In some embodiments, R$_8$ is 3- to 8-membered heterocycle. In some embodiments, R$_8$ is C$_1$-C$_6$ alkyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is C$_2$-C$_6$ alkenyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is C$_2$-C$_6$ alkynyl optionally substituted with one or more —OH, halogen, oxo, —NO$_2$, —NH$_2$, —CN, —C$_1$—C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is C$_3$-C$_8$ cycloalkyl optionally substituted with one or more —OH, halogen, oxo, —NO$_2$; —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is C$_4$-C$_8$ cycloalkenyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is heteroaryl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_8$ is 3- to 8-membered heterocycle optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl.

In some embodiments, R$_9$ is C$_1$-C$_6$ alkyl. In some embodiments, R$_9$ is C$_2$-C$_6$ alkenyl. In some embodiments, R$_9$ is C$_2$-C$_6$ alkynyl. In some embodiments, R$_9$ is C$_3$-C$_8$ cycloalkyl. In some embodiments, R$_9$ is C$_4$-C$_8$ cycloalkenyl. In some embodiments, R$_9$ is heteroaryl. In some embodiments, R$_9$ is 3- to 8-membered heterocycle. In some embodiments, R$_9$ is C$_1$-C$_6$ alkyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is C$_2$-C$_6$ alkenyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is C$_2$-C$_6$ alkynyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is C$_3$-C$_8$ cycloalkyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is C$_4$-C$_8$ cycloalkenyl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is heteroaryl optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl. In some embodiments, R$_9$ is 3- to 8-membered heterocycle optionally substituted with one or more —OH, halogen, oxo, —NO$_2$, —NH$_2$, —CN, —C$_1$-C$_6$ alkyl, —C$_1$-C$_6$ alkoxy, C$_1$-C$_6$ alkylamino, C$_1$-C$_6$ dialkylamino, C$_1$-C$_6$ hydroxyalkyl, heterocycle, aryl, or heteroaryl.

In another embodiment, R$_{10}$ is H. In some embodiments, R$_{10}$ is C$_1$-C$_6$ alkyl. In some embodiments, R$_{10}$ is aryl. In some embodiments, R$_{10}$ is arylalkyl. In some embodiments, R$_{10}$ is 3- to 8-membered heterocycle. In another embodiment, R$_{10}$ is H. In some embodiments, R$_{10}$ is C$_1$-C$_6$ alkyl optionally substituted with one or more halogen, C$_1$-C$_6$ alkyl, or C$_1$-C$_6$ alkoxy. In some embodiments, R$_{10}$ is aryl optionally substituted with one or more halogen, C$_1$-C$_6$ alkyl, or C$_1$-C$_6$ alkoxy. In some embodiments, R$_{10}$ is arylalkyl optionally substituted with one or more halogen, C$_1$-C$_6$ alkyl, or C$_1$-C$_6$ alkoxy. In some embodiments, R$_{10}$ is 3- to 8-membered heterocycle optionally substituted with one or more halogen, C$_1$-C$_6$ alkyl, or C$_1$-C$_6$ alkoxy.

In another embodiment, R$_{11}$ is H. In some embodiments, R$_{11}$ is C$_1$-C$_6$ alkyl. In some embodiments, R$_{11}$ is aryl. In some embodiments, R$_{11}$ is arylalkyl. In some embodiments, R$_{11}$ is 3- to 8-membered heterocycle. In another embodiment, R$_{11}$ is H. In some embodiments, R$_{11}$ is C$_1$-C$_6$ alkyl optionally substituted with one or more halogen, C$_1$-C$_6$ alkyl, or C$_1$-C$_6$ alkoxy. In some embodiments, R$_{11}$ is aryl optionally substituted with one or more halogen, C$_1$-C$_6$ alkyl, or C$_1$-C$_6$ alkoxy. In some embodiments, R$_{11}$ is arylalkyl optionally substituted with one or more halogen, C$_1$-C$_6$ alkyl, or C$_1$-C$_6$ alkoxy. In some embodiments, R$_{11}$ is 3- to 8-membered heterocycle optionally substituted with one or more halogen, C$_1$-C$_6$ alkyl, or C$_1$-C$_6$ alkoxy.

In other embodiments, R$_{10}$ and R$_{11}$ may combine to form a 3- to 8-membered heterocycle. In other embodiments, R$_{10}$ and R$_{11}$ may combine to form a 3- to 8-membered heterocycle optionally substituted with one or more R$_{12}$.

In some embodiments, R$_{12}$ is H. In some embodiments, R$_{12}$ is C$_1$-C$_6$ alkyl. In yet other embodiments, two adjacent R$_{12}$ can combine to form an aryl. In yet other embodiments, two adjacent R$_{12}$ can combine to form a heteroaryl.

In some embodiments, n is 1. In other embodiments, n is 2. In other embodiments, n is 3. In other embodiments, n is 4. In other embodiments, n is 5. In other embodiments, n is 6. In some embodiments, p is 0. In some embodiments, p is 1. In some embodiments, p is 2.

In some embodiments, R$_1$ is —(CH$_2$)$_n$—R$_4$, X is S(O)$_2$ and Y$_1$ is CR$_3$. In other embodiments, R$_1$ is —(CH$_2$)$_n$—R$_4$, X is S(O)$_2$ and Y$_2$ is CR$_3$. In other embodiments, R$_1$ is —(CH$_2$)$_n$—R$_4$, X is S(O)$_2$ and Y$_3$ is CR$_3$. In other embodiments, R$_1$ is —(CH$_2$)$_n$—R$_4$, X is S(O)$_2$ and Y$_4$ is CR$_3$. In other embodiments, $R_1$ is $-(CH_2)_n-R_4$, X is $S(O)_2$ and $Y_1$ is N. In other embodiments, $R_1$ is $-(CH_2)_n-R_4$, X is $S(O)_2$ and $Y_2$ is N. In other embodiments, $R_1$ is $-(CH_2)_n-R_4$, X is $S(O)_2$ and $Y_3$ is N. In other embodiments, $R_1$ is $-(CH_2)_n-R_4$, X is $S(O)_2$ and $Y_4$ is N. In other embodiments, $R_1$ is $-(CH_2)_n-R_4$, X is $S(O)_2$ and $Y_1$ is C when attached to C(O)NHOH. In other embodiments, $R_1$ is $-(CH_2)_n-R_4$, X is $S(O)_2$ and $Y_2$ is C when attached to C(O)NHOH. In other embodiments, $R_1$ is $-(CH_2)_n-R_4$, X is $S(O)_2$ and $Y_3$ is C when attached to C(O)NHOH. In other embodiments, $R_1$ is $-(CH_2)_n-R_4$, X is $S(O)_2$ and $Y_4$ is C when attached to C(O)NHOH.

In some embodiments, $R_1$ is $-(CH_2)_n-R_4$, X is O and $Y_1$ is $CR_3$. In other embodiments, $R_1$ is $-(CH_2)_n-R_4$, X is O and $Y_2$ is $CR_3$. In other embodiments, $R_1$ is $-(CH_2)_n-R_4$, X is O and $Y_3$ is $CR_3$. In other embodiments, $R_1$ is $-(CH_2)_n-R_4$, X is O and $Y_4$ is $CR_3$. In other embodiments, $R_1$ is $-(CH_2)_n-R_4$. X is O and $Y_1$ is N. In other embodiments, $R_1$ is $-(CH_2)_n-R_4$, X is O and $Y_2$ is N. In other embodiments, $R_1$ is $-(CH_2)_n-R_4$, X is O and $Y_3$ is N. In other embodiments, $R_1$ is $-(CH_2)_n-R_4$, X is O and $Y_4$ is N. In other embodiments, $R_1$ is $-(CH_2)_n-R_4$, X is O and $Y_1$ is C when attached to C(O)NHOH. In other embodiments, $R_1$ is $-(CH_2)_n-R_4$, X is O and $Y_2$ is C when attached to C(O)NHOH. In other embodiments, $R_1$ is $-(CH_2)_n-R_4$, X is O and $Y_3$ is C when attached to C(O)NHOH. In other embodiments, $R_1$ is $-(CH_2)_n-R_4$. X is O and $Y_4$ is C when attached to C(O)NHOH.

In some embodiments, $R_1$ is $-(CH_2)_n-R_4$, X is $C(R_4)(R_5)$ and $Y_1$ is $CR_3$. In other embodiments, $R_1$ is $-(CH_2)_n-R_4$. X is $C(R_4)(R_5)$ and $Y_2$ is $CR_3$. In other embodiments, $R_1$ is $-(CH_2)_n-R_4$, X is $C(R_4)(R_5)$ and $Y_3$ is $CR_3$. In other embodiments, $R_1$ is $-(CH_2)_n-R_4$, X is $C(R_4)(R_5)$ and $Y_4$ is $CR_3$. In other embodiments, $R_1$ is $-(CH_2)_n-R_4$, X is $C(R_4)(R_5)$ and $Y_1$ is N. In other embodiments, $R_1$ is $-(CH_2)_n-R_4$, X is $C(R_4)(R_5)$ and $Y_2$ is N. In other embodiments, $R_1$ is $-(CH_2)_n-R_4$, X is $C(R_4)(R_5)$ and $Y_3$ is N. In other embodiments, $R_1$ is $-(CH_2)_n-R_4$, X is $C(R_4)(R_5)$ and $Y_4$ is N. In other embodiments, $R_1$ is $-(CH_2)_n-R_4$, X is $C(R_4)(R_5)$ and $Y_1$ is C when attached to C(O)NHOH. In other embodiments, $R_1$ is $-(CH_2)_n-R_4$, X is $C(R_4)(R_5)$ and $Y_2$ is C when attached to C(O)NHOH. In other embodiments, $R_1$ is $-(CH_2)_nR_4$, X is $C(R_4)(R_5)$ and $Y_3$ is C when attached to C(O)NHOH. In other embodiments, $R_1$ is $-(CH_2)_n-R_4$, X is $C(R_4)(R_5)$ and $Y_4$ is C when attached to C(O)NHOH.

In some embodiments, $R_1$ is $-(CH_2)_n-R_4$, X is S(O) and $Y_1$ is $CR_3$. In other embodiments, $R_1$ is $-(CH_2)_n-R_4$, X is S(O) and $Y_2$ is $CR_3$. In other embodiments, $R_1$ is $-(CH_2)_n-R_4$, X is S(O) and $Y_3$ is $CR_3$. In other embodiments, $R_1$ is $-(CH_2)_n-R_4$, X is S(O) and $Y_4$ is $CR_3$. In other embodiments, $R_1$ is $-(CH_2)_n-R_4$, X is S(O) and $Y_1$ is N. In other embodiments, $R_1$ is $-(CH_2)_n-R_4$, X is S(O) and $Y_2$ is N. In other embodiments, $R_1$ is $-(CH_2)_n-R_4$, X is S(O) and $Y_3$ is N. In other embodiments, $R_1$ is $-(CH_2)_n-R_4$, X is S(O) and $Y_4$ is N. In other embodiments, $R_1$ is $-(CH_2)_n-R_4$, X is S(O) and $Y_1$ is C when attached to C(O)NHOH. In other embodiments, $R_1$ is $-(CH_2)_n-R_4$, X is S(O) and $Y_2$ is C when attached to C(O)NHOH. In other embodiments, $R_1$ is $-(CH_2)_n-R_4$, X is S(O) and $Y_3$ is C when attached to C(O)NHOH. In other embodiments, $R_1$ is $-(CH_2)_n-R_4$, X is S(O) and $Y_4$ is C when attached to C(O)NHOH.

In some embodiments, $R_1$ is $-(CH_2)_n-R_4$, X is S and $Y_1$ is $CR_3$. In other embodiments, $R_1$ is $-(CH_2)_n-R_4$, X is S and $Y_2$ is $CR_3$. In other embodiments, $R_1$ is $-(CH_2)_n-R_4$, X is S and $Y_3$ is $CR_3$. In other embodiments, $R_1$ is $-(CH_2)_n-R_4$, X is S and $Y_4$ is $CR_3$. In other embodiments, $R_1$ is $-(CH_2)_n-R_4$, X is S and $Y_1$ is N. In other embodiments, $R_1$ is $-(CH_2)_n-R_4$, X is S and $Y_2$ is N. In other embodiments, $R_1$ is $-(CH_2)_n-R_4$, X is S and $Y_3$ is N. In other embodiments, $R_1$ is $-(CH_2)_n-R_4$, X is S and $Y_4$ is N. In other embodiments, $R_1$ is $-(CH_2)_n-R_4$, X is S and $Y_1$ is C when attached to C(O)NHOH. In other embodiments, $R_1$ is $-(CH_2)_n-R_4$, X is S and $Y_2$ is C when attached to C(O)NHOH. In other embodiments, $R_1$ is $-(CH_2)_n-R_4$, X is S and $Y_3$ is C when attached to C(O)NHOH. In other embodiments, $R_1$ is $-(CH_2)_n-R_4$, X is S and $Y_4$ is C when attached to C(O)NHOH.

In some embodiments, $R_1$ is $-(CH_2)_n-R_4$, X is C(=O) and $Y_1$ is $CR_3$. In other embodiments, $R_1$ is $-(CH_2)_n-R_4$, X is C(=O) and $Y_2$ is $CR_3$. In other embodiments, $R_1$ is $-(CH_2)_n-R_4$, X is C(=O) and $Y_3$ is $CR_3$. In other embodiments, $R_1$ is $-(CH_2)_n-R_4$, X is C(=O) and $Y_4$ is $CR_3$. In other embodiments, $R_1$ is $-(CH_2)_n-R_4$, X is C(=O) and $Y_1$ is N. In other embodiments, $R_1$ is $-(CH_2)_n-R_4$. X is C(=O) and $Y_2$ is N. In other embodiments, $R_1$ is $-(CH_2)_n-R_4$, X is C(=O) and $Y_3$ is N. In other embodiments, $R_1$ is $-(CH_2)_n-R_4$. X is C(=O) and $Y_4$ is N. In other embodiments, $R_1$ is $-(CH_2)_n-R_4$, X is C(=O) and $Y_1$ is C when attached to C(O)NHOH. In other embodiments, $R_1$ is $-(CH_2)_n-R_4$, X is C(=O) and $Y_2$ is C when attached to C(O)NHOH. In other embodiments, $R_1$ is $-(CH_2)_n-R_4$, X is C(=O) and $Y_3$ is C when attached to C(O)NHOH. In other embodiments, $R_1$ is $-(CH_2)_n-R_4$. X is C(=O) and $Y_4$ is C when attached to C(O)NHOH.

In some embodiments, X is $S(O)_2$ and $Y_1$ is $CR_3$. In other embodiments, X is $S(O)_2$ and $Y_2$ is $CR_3$. In other embodiments, X is $S(O)_2$ and $Y_3$ is $CR_3$. In other embodiments, X is $S(O)_2$ and $Y_4$ is $CR_3$. In other embodiments, X is $S(O)_2$ and $Y_1$ is N. In other embodiments, X is $S(O)_2$ and $Y_2$ is N. In other embodiments, X is $S(O)_2$ and $Y_3$ is N. In other embodiments, X is $S(O)_2$ and $Y_4$ is N. In other embodiments, X is $S(O)_2$ and $Y_1$ is C when attached to C(O)NHOH. In other embodiments, X is $S(O)_2$ and $Y_2$ is C when attached to C(O)NHOH. In other embodiments, X is $S(O)_2$ and $Y_3$ is C when attached to C(O)NHOH. In other embodiments, X is $S(O)_2$ and $Y_4$ is C when attached to C(O)NHOH.

In some embodiments, X is O and $Y_1$ is $CR_3$. In other embodiments, X is O and $Y_2$ is $CR_3$. In other embodiments, X is O and $Y_3$ is $CR_3$. In other embodiments, X is O and $Y_4$ is $CR_3$. In other embodiments, X is O and $Y_1$ is N. In other embodiments, X is O and $Y_2$ is N. In other embodiments, X is O and $Y_3$ is N. In other embodiments, X is O and $Y_4$ is N. In other embodiments, X is O and $Y_1$ is C when attached to C(O)NHOH. In other embodiments, X is O and $Y_2$ is C when attached to C(O)NHOH. In other embodiments, X is O and $Y_3$ is C when attached to C(O)NHOH. In other embodiments, X is O and $Y_4$ is C when attached to C(O)NHOH.

In some embodiments, X is $C(R_4)(R_5)$ and $Y_1$ is $CR_3$. In other embodiments, X is $C(R_4)(R_5)$ and $Y_2$ is $CR_3$. In other embodiments, X is $C(R_4)(R_5)$ and $Y_3$ is $CR_3$. In other embodiments, X is $C(R_4)(R_5)$ and $Y_4$ is $CR_3$. In other embodiments, X is $C(R_4)(R_5)$ and $Y_1$ is N. In other embodiments, X is $C(R_4)(R_5)$ and $Y_2$ is N. In other embodiments, X is $C(R_4)(R_5)$ and $Y_3$ is N. In other embodiments, X is $C(R_4)(R_5)$ and $Y_4$ is N. In other embodiments, X is $C(R_4)(R_5)$ and $Y_1$ is C when attached to C(O)NHOH. In other embodiments, X is $C(R_4)(R_5)$ and $Y_2$ is C when attached to C(O)NHOH. In other embodiments, X is $C(R_4)(R_5)$ and $Y_3$ is C when attached to C(O)NHOH. In other embodiments, X is $C(R_4)(R_5)$ and $Y_4$ is C when attached to C(O)NHOH.

In some embodiments, X is S(O) and $Y_1$ is $CR_3$. In other embodiments, X is S(O) and $Y_2$ is $CR_3$. In other embodiments, X is S(O) and $Y_3$ is $CR_3$. In other embodiments, X is S(O) and $Y_4$ is $CR_3$. In other embodiments, X is S(O) and $Y_1$ is N. In other embodiments, X is S(O) and $Y_2$ is N. In other embodiments, X is S(O) and $Y_3$ is N. In other embodiments, X is S(O)) and $Y_4$ is N. In other embodiments, X is S(O) and $Y_1$ is C when attached to C(O)NHOH. In other embodiments, X is S(O) and $Y_2$ is C when attached to C(O)NHOH. In other embodiments, X is S(O) and $Y_3$ is C when attached to C(O)NHOH. In other embodiments, X is S(O) and $Y_4$ is C when attached to C(O)NHOH.

In some embodiments, X is S and $Y_1$ is $CR_3$. In other embodiments, X is S and $Y_2$ is $CR_3$. In other embodiments, X is S and $Y_3$ is $CR_3$. In other embodiments, X is S and $Y_4$ is $CR_3$. In other embodiments, X is S and $Y_1$ is N. In other embodiments, X is S and $Y_2$ is N. In other embodiments, X is S and $Y_3$ is N. In other embodiments, X is S and $Y_4$ is N. In other embodiments, X is S and $Y_1$ is C when attached to C(O)NHOH. In other embodiments, X is S and $Y_2$ is C when attached to C(O)NHOH. In other embodiments, X is S and $Y_3$ is C when attached to C(O)NHOH. In other embodiments, X is S and $Y_4$ is C when attached to C(O)NHOH.

In some embodiments, X is C(=O) and $Y_1$ is $CR_3$. In other embodiments, X is C(=O) and $Y_2$ is $CR_3$. In other embodiments, X is C(=O) and $Y_3$ is $CR_3$. In other embodiments, X is C(=O) and $Y_4$ is $CR_3$. In other embodiments, X is C(=O) and $Y_1$ is N. In other embodiments, X is C(=O) and $Y_2$ is N. In other embodiments, X is C(=O) and $Y_3$ is N. In other embodiments, X is C(=O) and $Y_4$ is N. In other embodiments, X is C(=O) and $Y_1$ is C when attached to C(O)NHOH. In other embodiments, X is C(=O) and $Y_2$ is C when attached to C(O)NHOH. In other embodiments, X is C(=O) and $Y_3$ is C when attached to C(O)NHOH. In other embodiments, X is C(=O) and $Y_4$ is C when attached to C(O)NHOH.

In some embodiments, n is 1, $R_1$ is $-(CH_2)_n-R_4$, X is $S(O)_2$ and $Y_1$ is $CR_3$. In other embodiments, n is 1, $R_1$ is $-(CH_2)_n-R_4$, X is $S(O)_2$ and $Y_2$ is $CR_3$. In other embodiments, n is 1, $R_1$ is $-(CH_2)_n-R_4$, X is $S(O)_2$ and $Y_3$ is $CR_3$. In other embodiments, n is 1, $R_1$ is $-(CH_2)_n-R_4$, X is $S(O)_2$ and $Y_4$ is $CR_3$. In other embodiments, n is 1, $R_1$ is $-(CH_2)_n-R_4$, X is $S(O)_2$ and $Y_1$ is N. In other embodiments, n is 1, $R_1$ is $-(CH_2)_n-R_4$, X is $S(O)_2$ and $Y_2$ is N. In other embodiments, n is 1, $R_1$ is $-(CH_2)_n-R_4$, X is $S(O)_2$ and $Y_3$ is N. In other embodiments, n is 1, $R_1$ is $-(CH_2)_n-R_4$, X is $S(O)_2$ and $Y_4$ is N. In other embodiments, n is 1, $R_1$ is $-(CH_2)_n-R_4$, X is $S(O)_2$ and $Y_1$ is C when attached to C(O)NHOH. In other embodiments, n is 1, $R_1$ is $-(CH_2)_n-R_4$, X is $S(O)_2$ and $Y_2$ is C when attached to C(O)NHOH. In other embodiments, n is 1, $R_1$ is $-(CH_2)_n-R_4$, X is $S(O)_2$ and $Y_3$ is C when attached to C(O)NHOH. In other embodiments, n is 1, $R_1$ is $-(CH_2)_n-R_4$, X is $S(O)_2$ and $Y_4$ is C when attached to C(O)NHOH.

In some embodiments, n is 1, $R_1$ is $-(CH_2)_n-R_4$, X is O and $Y_1$ is $CR_3$. In other embodiments, n is 1, $R_1$ is $-(CH_2)_n-R_4$, X is O and $Y_2$ is $CR_3$. In other embodiments, n is 1, $R_1$ is $-(CH_2)_n-R_4$, X is O and $Y_3$ is $CR_3$. In other embodiments, n is 1, $R_1$ is $-(CH_2)_n-R_4$, X is O and $Y_4$ is $CR_3$. In other embodiments, n is 1, $R_1$ is $-(CH_2)_n-R_4$, X is O and $Y_1$ is N. In other embodiments, n is 1, $R_1$ is $-(CH_2)_n-R_4$, X is O and $Y_2$ is N. In other embodiments, n is 1, $R_1$ is $-(CH_2)_n-R_4$, X is O and $Y_3$ is N. In other embodiments, n is 1, $R_1$ is $-(CH_2)_n-R_4$, X is O and $Y_4$ is N. In other embodiments, n is 1, $R_1$ is $-(CH_2)_n-R_4$, X is O and $Y_1$ is C when attached to C(O)NHOH. In other embodiments, n is 1, $R_1$ is $-(CH_2)_n-R_4$, X is O and $Y_2$ is C when attached to C(O)NHOH. In other embodiments, n is 1, $R_1$ is $-(CH_2)_n-R_4$, X is O and $Y_3$ is C when attached to C(O)NHOH. In other embodiments, n is 1, $R_1$ is $-(CH_2)_n-R_4$, X is O and $Y_4$ is C when attached to C(O)NHOH.

In some embodiments, n is 1, $R_1$ is $-(CH_2)_n-R_4$, X is $C(R_4)(R_5)$ and $Y_1$ is $CR_3$. In other embodiments, n is 1, $R_1$ is $-(CH_2)_n-R_4$, X is $C(R_4)(R_5)$ and $Y_2$ is $CR_3$. In other embodiments, n is 1, $R_1$ is $-(CH_2)_n-R_4$, X is $C(R_4)(R_5)$ and $Y_3$ is $CR_3$. In other embodiments, n is 1, $R_1$ is $-(CH_2)_n-R_4$, X is $C(R_4)(R_5)$ and $Y_4$ is $CR_3$. In other embodiments, n is 1, $R_1$ is $-(CH_2)_n-R_4$, X is $C(R_4)(R_5)$ and $Y_1$ is N. In other embodiments, n is 1, $R_1$ is $-(CH_2)_n-R_4$, X is $C(R_4)(R_5)$ and $Y_2$ is N. In other embodiments, n is 1, $R_1$ is $-(CH_2)_n-R_4$, X is $C(R_4)(R_5)$ and $Y_3$ is N. In other embodiments, n is 1, $R_1$ is $-(CH_2)_n-R_4$, X is $C(R_4)(R_5)$ and $Y_4$ is N. In other embodiments, n is 1, $R_1$ is $-(CH_2)_n-R_4$, X is $C(R_4)(R_5)$ and $Y_1$ is C when attached to C(O)NHOH. In other embodiments, n is 1, $R_1$ is $-(CH_2)_n-R_4$, X is $C(R_4)(R_5)$ and $Y_2$ is C when attached to C(O)NHOH. In other embodiments, n is 1, $R_1$ is $-(CH_2)_n-R_4$, X is $C(R_4)(R_5)$ and $Y_3$ is C when attached to C(O)NHOH. In other embodiments, n is 1, $R_1$ is $-(CH_2)_n-R_4$, X is $C(R_4)(R_5)$ and $Y_4$ is C when attached to C(O)NHOH.

In some embodiments, n is 1, $R_1$ is $-(CH_2)_n-R_4$, X is S(O) and $Y_1$ is $CR_3$. In other embodiments, n is 1, $R_1$ is $-(CH_2)_n-R_4$, X is S(O) and $Y_2$ is $CR_3$. In other embodiments, n is 1, $R_1$ is $-(CH_2)_n-R_4$, X is S(O) and $Y_3$ is $CR_3$. In other embodiments, n is 1, $R_1$ is $-(CH_2)_n-R_4$, X is S(O) and $Y_4$ is $CR_3$. In other embodiments, n is 1, $R_1$ is $-(CH_2)_n-R_4$, X is S(O) and $Y_1$ is N. In other embodiments, n is 1, $R_1$ is $-(CH_2)_n-R_4$, X is S(O) and $Y_2$ is N. In other embodiments, n is 1, $R_1$ is $-(CH_2)_n-R_4$, X is S(O) and $Y_3$ is N. In other embodiments, n is 1, $R_1$ is $-(CH_2)_n-R_4$, X is S(O) and $Y_4$ is N. In other embodiments, n is 1, $R_1$ is $-(CH_2)_n-R_4$, X is S(O) and $Y_1$ is C when attached to C(O)NHOH. In other embodiments, n is 1, $R_1$ is $-(CH_2)_n-R_4$, X is S(O) and $Y_2$ is C when attached to C(O)NHOH. In other embodiments, n is 1, $R_1$ is $-(CH_2)_n-R_4$, X is S(O) and $Y_3$ is C when attached to C(O)NHOH. In other embodiments, n is 1, $R_1$ is $-(CH_2)_n-R_4$, X is S(O) and $Y_4$ is C when attached to C(O)NHOH.

In some embodiments, n is 1, $R_1$ is $-(CH_2)_n-R_4$, X is S and $Y_1$ is $CR_3$. In other embodiments, n is 1, $R_1$ is $-(CH_2)_n-R_4$, X is S and $Y_2$ is $CR_3$. In other embodiments, n is 1, $R_1$ is $-(CH_2)_n-R_4$, X is S and $Y_3$ is $CR_3$. In other embodiments, n is 1, $R_1$ is $-(CH_2)_n-R_4$, X is S and $Y_4$ is $CR_3$. In other embodiments, n is 1, $R_1$ is $-(CH_2)_n-R_4$, X is S and $Y_1$ is N. In other embodiments, n is 1, $R_1$ is $-(CH_2)_n-R_4$, X is S and $Y_2$ is N. In other embodiments, n is 1, $R_1$ is $-(CH_2)_n-R_4$, X is S and $Y_3$ is N. In other embodiments, n is 1, $R_1$ is $-(CH_2)_n-R_4$, X is S and $Y_4$ is N. In other embodiments, n is 1, $R_1$ is $-(CH_2)_n-R_4$, X is S and $Y_1$ is C when attached to C(O)NHOH. In other embodiments, n is 1, $R_1$ is $-(CH_2)_n-R_4$, X is S and $Y_2$ is C when attached to C(O)NHOH. In other embodiments, n is 1, $R_1$ is $-(CH_2)_n-R_4$, X is S and $Y_3$ is C when attached to C(O)NHOH. In other embodiments, n is 1, $R_1$ is $-(CH_2)_n-R_4$, X is S and $Y_4$ is C when attached to C(O)NHOH.

In some embodiments, n is 1, $R_1$ is $-(CH_2)_n-R_4$, X is C(=O) and $Y_1$ is $CR_3$. In other embodiments, n is 1, $R_1$ is $-(CH_2)_n-R_4$, X is C(=O) and $Y_2$ is $CR_3$. In other embodiments, n is 1, $R_1$ is $-(CH_2)_n-R_4$, X is C(=O) and $Y_3$ is $CR_3$. In other embodiments, n is 1, $R_1$ is $-(CH_2)_n-R_4$, X is C(=O) and $Y_4$ is $CR_3$. In other embodiments, n is 1, $R_1$ is $-(CH_2)_n-R_4$, X is C(=O) and $Y_1$ is N. In other embodiments, n is 1, $R_1$ is —$(CH_2)_n$—$R_4$, X is C(═O) and $Y_2$ is N. In other embodiments, n is 1, $R_1$ is —$(CH_2)_n$—$R_4$, X is C(═O) and $Y_3$ is N. In other embodiments, n is 1, $R_1$ is —$(CH_2)_n$—$R_4$. X is C(═O) and $Y_4$ is N. In other embodiments, n is 1, $R_1$ is —$(CH_2)_n$—$R_4$, X is C(═O) and $Y_1$ is C when attached to C(O)NHOH. In other embodiments, n is 1, $R_1$ is —$(CH_2)_n$—$R_4$, X is C(═O) and $Y_2$ is C when attached to C(O)NHOH. In other embodiments, n is 1, $R_1$ is —$(CH_2)_n$—$R_4$, X is C(═O) and $Y_3$ is C when attached to C(O)NHOH. In other embodiments, n is 1, $R_1$ is —$(CH_2)_n$—$R_4$, X is C(═O) and $Y_4$ is C when attached to C(O)NHOH.

In another embodiment of the invention, the compounds of Formula I are enantiomers. In some embodiments the compounds are the (S)-enantiomer. In other embodiments the compounds are the (R)-enantiomer. In yet other embodiments, the compounds of Formula I may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Methods of Synthesizing the Disclosed Compounds

The compounds of the present invention may be made by a variety of methods, including standard chemistry. Suitable synthetic routes are depicted in the schemes given below.

The compounds of Formula I may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994, herein incorporated by reference in its entirety).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below.

Scheme 1. Generl Synthesis of compounds of the invention

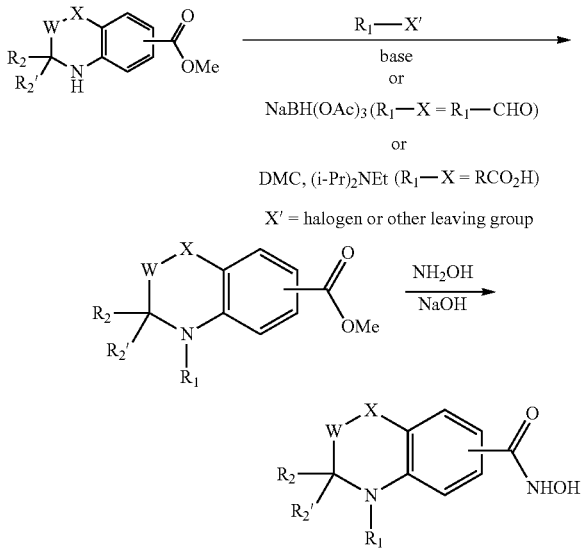

Scheme 2. General synthesis scheme where $X = SO_2$.

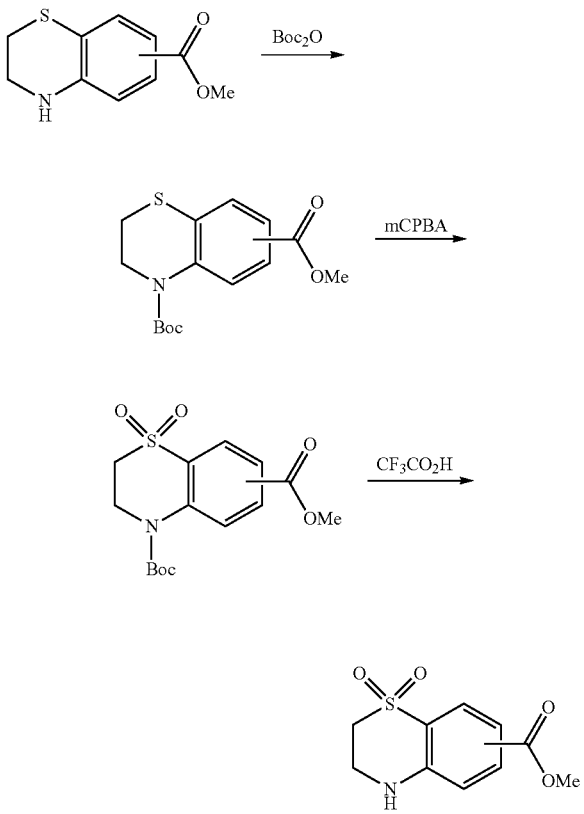

Scheme 3. General synthesis for Examples where X = O or X = C(H)C(O)N(R_{10})(R_{11})

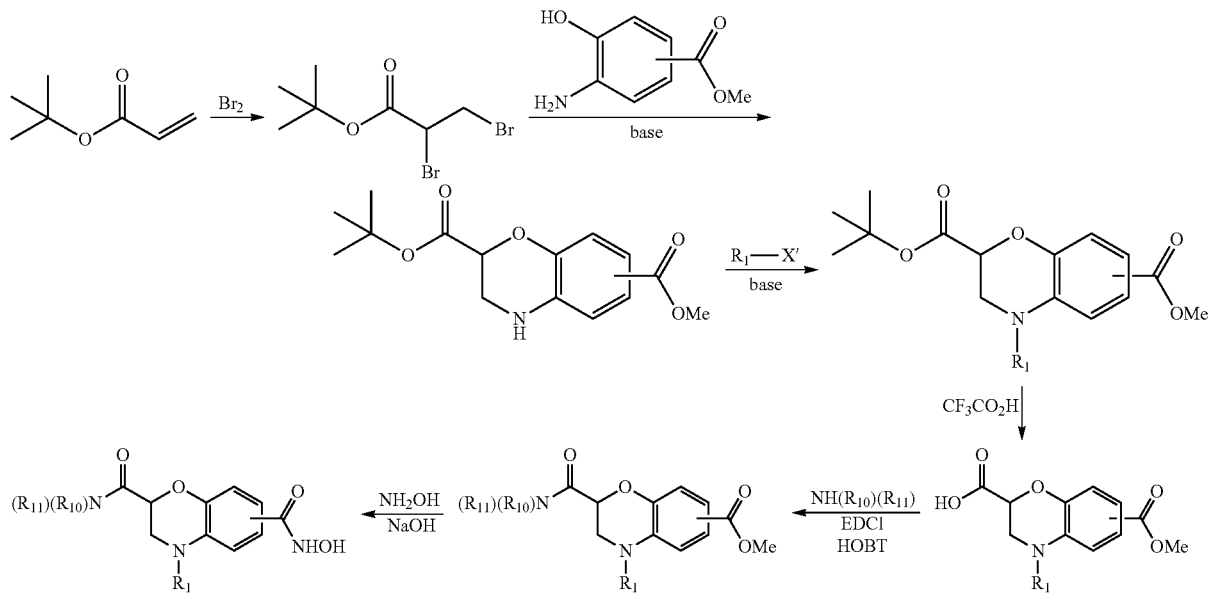

X' = halogen or other leaving group

Methods of Using the Disclosed Compounds

One aspect of the present invention relates to a method of modulating HDAC8, comprising administering to a patient in need thereof a therapeutically effective amount of a compound of Formula (I).

Another aspect of the present invention relates to a method of inhibiting HDAC8, comprising administering to a patient in need thereof a therapeutically effective amount of a compound of Formula (I).

In another aspect, the present invention relates to a method of inhibiting HDAC8, comprising administering to a patient in need thereof a therapeutically effective amount of the pharmaceutical composition comprising a compound of Formula (I).

Another aspect of the present invention relates to a method of treating, preventing, inhibiting, or eliminating a disease or disorder in a patient associated with the inhibition of HDAC8, the method comprising administering a therapeutically effective amount of a compound of Formula (I).

One therapeutic use of the compounds of the present invention is to treat proliferative diseases or disorders such as cancer. Cancer can be understood as abnormal or unregulated cell growth within a patient and can include colon cancer, lung cancer, neuroblastoma, ovarian cancer, hepatocellular carcinoma, gastric cancer, prostate cancer, pancreatic cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), B-cell lymphoma and multiple myeloma. In other embodiments, treating proliferative diseases or disorders can include any cancer where there is evidence of an increase in Treg/effector T cell ratio or in an absolute Treg number, either in the periphery or in the tumor microenvironment or tertiary lymphoid structures, or increased expression of T cell tolerance-related genes. Such proliferative diseases or disorders can include but are not limited to: any Kras mutant carrying tumor (Zdanov, S. et. al. (2016) Cancer Immunol Res. 4, 354-65); renal cell carcinoma; lung carcinoma; cervical cancer; prostate cancer; ovarian cancer; head and neck cancer; lymphoma; colorectal cancer, non small cell lung carcinoma; breast cancers (Gobert, M. et al. (2009) Cancer Res. 69, 2000-2009); and bladder cancer.

One therapeutic use of the compounds of the present invention is to treat neurological diseases or disorders or neurodegeneration. Neurological disorders are understood as disorders of the nervous system (e.g., the brain and spinal cord). Neurological disorders and diseases can include but are not limited to epilepsy, attention deficit disorder (ADD), Alzheimer's disease, Parkinson's Disease, Huntington's Disease, Muscular dystrophy, essential tremor, central nervous system trauma caused by tissue injury, oxidative stress-induced neuronal or axomal degeneration, ALS, and multiple sclerosis.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor. In some embodiments, the inflammatory diseases include fibrosis or fibrotic diseases. Types of fibrotic diseases include but are not limited to lung fibrosis or pulmonary fibrosis, Liver fibrosis; Heart fibrosis; Mediastinal fibrosis; Retroperitoneal cavity fibrosis; Bone marrow fibrosis; Skin fibrosis; and Scleroderma or systemic sclerosis.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to rheumatoid arthritis, Crohn's disease, type-1 diabetes, systemic juvenile idiopathic arthritis; inflammatory bowel disease; allograft transplantation; eczema, psoriasis, idiopathic thrombocytopenic purpra, autoimmune thrombocytopenia, acquired immune thrombocytopenia, autoimmune neutropenia, autoimmune hemolyitic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lamber-Eaton myasthenic syndeom, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atomic dermatis, systemic and diffuse sclerosis, primary biliary cirrhosis, Celiac disease, dermatitis herpetiformis, cryptogenic cirrhosis, reactive arthritis, Hashimoto's thryroditis, Wegner's granulomoatosis, micropolyarterits, Churg-Strauss syndrome Type I and Type II autoimmune polygalndular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Bechet's syndrome temporal arteritis, Takayasu's arteritis, autoimmune urticaria, and Kawasaki's disease.

Another therapeutic use of the compounds of the present invention is also to treat infectious diseases or disorders. Infections or infectious diseases are caused by the invasion of a foreign pathogen. The infection may be caused by, for instance, a bacteria, a fungus, or virus. Bacterial infections include, but are not limited to *streptococcus* infections, mycobacterial infections, *bacillus* infections, *Salmonella* infections, *Vibrio* infections, spirochete infections, and *Neisseria* infections. Viral infections include, but are not limited to herpes virus infections, hepatitis virus infections, west nile virus infections, flavivrus infections, influenza virus infections, rhinovirus infections, papillomavirus infections, paromyxovirus infections, parainfluenza virus infections, and retrovirus infections. In particular embodiments, the compounds of the present invention are useful for treating infections which result in an inflammatory cytokine burst. Nonlimiting examples of such infections include Ebola and othe viral hemorghagic fever-causing viruses, and Malaria.

Another therapeutic use of the compounds of the present invention is also to treat and/or prevent allergy and unwanted immune responses associated with allergy. A non-limiting list of allergies and related conditions includes, pollen allergy (e.g. Japanese Cedar Pollen), mold allergy, food allergies (including, but not limited to peanut, tree nut, milk, soy, gluten, and egg allergies), animal allergies (e.g. allergies to dogs, cats, rabbits), dust mite allergy, atopic dermatitis, allergic rhinitis, allergic otitis, allergic asthma, dry eye, ocular allergy, allergic urticaria, contact dermatitis, anaphalaxis, eosinophilic esophagitis.

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, non-alcoholic fatty liver disease and heart failure.

Yet another therapeutic use of the compounds of the present invention is also to treat hematologic disorders. Hematologic diseases primarily affect the blood. Hematologic disorders can include but are not limited to anemia, multiple myeloma, lymphoma, and leukemia.

Yet another therapeutic use of the compounds of the present invention is also to prevent and/or treat transplant rejection. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, and heart failure.

Another therapeutic use of the compounds of the present invention is for purging the reservoir of latently infected memory CD4+ T cells in HIV+ patients (Matalon, et al., Mol Med. 2011; 17(5-6): 466-472).

The disclosed compounds can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formula I and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present invention can inhibit HDACs such as HDAC8 by interacting with the zinc ($Zn^{2-}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present invention includes a number of unique features and advantages compared with other inhibitors of HDAC enzymes, in particular HDAC8. For instance, the present invention features a unique class of small molecule therapeutic agents of Formula I. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:
Ac$_2$O acetic anhydride
Boc tert-butoxycarbonyl
DCE 1,2-dichloroethane
DCM dichloromethane or methylene chloride
DIPEA N,N-diisopropylethyl amine
DMAP 4-(dimethylamino)pyridine
DMF N,N-dimethylformamide
DMSO dimethylsulfoxide
DPPA diphenylphosphoryl azide
dppf bis(diphenylphosphino)ferrocene
EDCI 1-Ethyl-3-(3-dimethylaminopropyl)carbodiimide
Et$_3$N triethylamine
EtOAc ethyl acetate
EtOH ethanol
h hours
HATU 2-(3H-[1,2,3]triazolo[4,5-b]pyridin-3-yl)-1,1,3,3-tetramethylisouronium hexafluorophosphate
HCl hydrogen chloride
HOBT Hydroxybenzotriazole
HPLC high performance liquid chromatography (i-Pr)$_2$NEt N,N-diisopropylethylamine
LC/MS liquid chromatography/mass spectrometry
K$_2$CO$_3$ potassium carbonate
MS mass spectrometry
NBS N-bromosuccinimide
Ph$_3$P triphenylphosphine
PhCHO benzaldehyde
Pd$_2$(dba)$_3$ tris(dibenzylideneacetone)dipalladium
p-TsOH para-toluenesulfonic acid
rt room temperature
TFAA trifluoroacetic anhydride
THF tetrahydrofuran
XPhos 2-dicyclohexylphosphino-2',4',6'-triisopropylbiphenyl Analytical Methods, Materials, and Instrumentation Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH Cis 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Example 1—Intermediate 1: Methyl 6-(methoxycarbonyl)-4-methyl-3,4-dihydro-2H-benzo[b][1,4]oxazine-2-carboxylic Acid

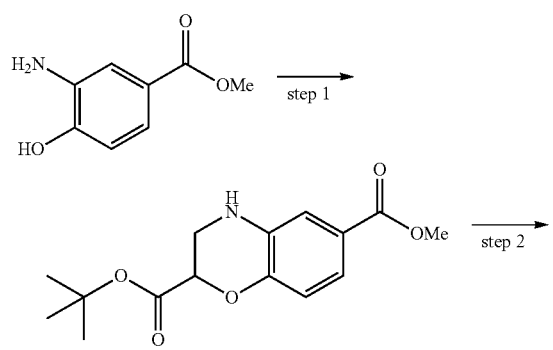

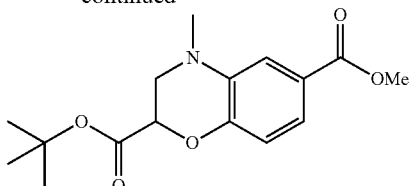

step 3

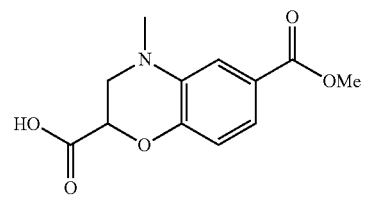

Step-1: 2-tert-butyl 6-methyl 3,4-dihydro-2H-benzo[b][1,4]oxazine-2,6-dicarboxylate Into a 500-mL 3-necked round-bottom flask was placed a solution of methyl 3-amino-4-hydroxybenzoate (10 g, 59.82 mmol) and potassium carbonate (25 g, 180.88 mmol) in N,N-dimethylformamide (150 mL). This was followed by the dropwise addition of tert-butyl 2,3-dibromopropanoate (19 g, 65.98 mmol) with stirring. The resulting solution was stirred for 4 h at room temperature and overnight at 70° C. The reaction was then quenched by the addition of 500 mL of water. The resulting solution was extracted with 3×200 mL of ethyl acetate, washed with 3×300 mL of brine, dried over anhydrous sodium sulfate, filtered, and concentrated under vacuum. The residue was purified via column chromatography on silica gel (eluting with 1:3, ethyl acetate/petroleum ether). The collected fractions were concentrated to give 2-tert-butyl 6-methyl 3,4-dihydro-2H-benzo[b][1,4]oxazine-2,6-dicarboxylate (9.4 g, 54%) as an off-white solid. MS: (ES, m/z): 294 [M+H]+.

Step-2: 2-tert-butyl 6-methyl 4-methyl-3,4-dihydro-2H-benzo[b][1,4]oxazine-2,6-dicarboxylate Into a 50-mL 3-necked round-bottom flask was placed a solution of 2-tert-butyl 6-methyl 3,4-dihydro-2H-1,4-benzoxazine-2,6-dicarboxylate (2 g, 6.82 mmol), potassium carbonate (2.83 g, 20.48 mmol) and methyl iodide (2.9 g, 20.42 mmol) in N,N-dimethylformamide (20 mL). The resulting mixture was stirred overnight at 70° C. The reaction was then quenched by the addition of 100 mL of water. The resulting solution was extracted with 3×50 mL of ethyl acetate, washed with 3×50 mL of brine, dried over anhydrous sodium sulfate, filtered, and concentrated under vacuum. The residue was purified via column chromatography on silica gel (eluting with 1:4, ethyl acetate/petroleum ether). The collected fractions were concentrated to give 2-tert-butyl 6-methyl 4-methyl-3,4-dihydro-2H-benzo[b][1,4]oxazine-2,6-dicarboxylate (1.7 g, 81%) as an off-white solid. MS: (ES, m/z): 308 [M+H]+.

Step-3: 6-(methoxycarbonyl)-4-methyl-3,4-dihydro-2H-benzo[b][1,4]oxazine-2-carboxylic Acid Into a 100-mL round-bottom flask was placed 2-tert-butyl 6-methyl 4-methyl-3,4-dihydro-2H-1,4-benzoxazine-2,6-dicarboxylate (1 g, 3.25 mmol), dichloromethane (25 mL) and trifluoroacetic acid (5 mL). The resulting solution was stirred overnight at room temperature and then concentrated under vacuum to give 6-(methoxycarbonyl)-4-methyl-3,4-dihydro-2H-benzo[b][1,4]oxazine-2-carboxylic acid (1.2 g) as a gray solid which was used without any purification. MS: (ES, m/z): 252 [M+H]⁺.

Example 2—Intermediate 2: 4-benzyl-6-(methoxycarbonyl)-3,4-dihydro-2H-benzo[b][1,4]oxazine-2-carboxylic Acid

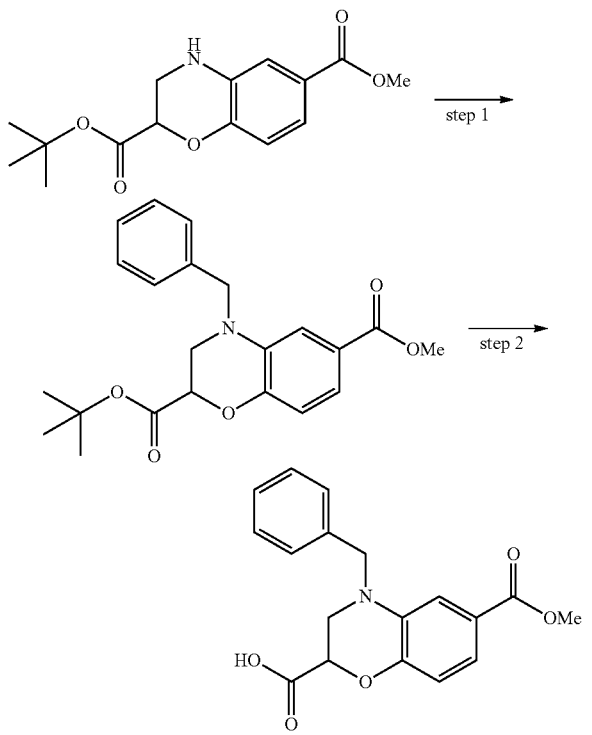

Step-1: 2-tert-butyl 6-methyl 4-benzyl-3,4-dihydro-2H-benzo[b][1,4]oxazine-2,6-dicarboxylate Into a 50-mL 3-necked round-bottom flask was placed a solution of 2-tert-butyl 6-methyl 3,4-dihydro-2H-1,4-benzoxazine-2,6-dicarboxylate (2 g, 6.82 mmol) and potassium carbonate (2.83 g, 20.48 mmol) in N,N-dimethylformamide (20 mL). This was followed by the dropwise addition of benzyl bromide (2.3 g, 13.45 mmol) with stirring at 0° C. The resulting solution was stirred overnight at 70° C. The reaction was then quenched by the addition of 100 mL of water. The resulting solution was extracted with 3×50 mL of ethyl acetate, washed with 3×50 mL of brine, dried over anhydrous sodium sulfate, filtered, and concentrated under vacuum. The residue was purified via column chromatography on silica gel, eluting with ethyl acetate/petroleum ether (1:4). The collected fractions were concentrated to give 2-tert-butyl 6-methyl 4-benzyl-3,4-dihydro-2H-benzo[b][1,4]oxazine-2,6-dicarboxylate (1.2 g, 46%) of title compound as an off-white solid. MS: (ES, m/z): 384[M+H]⁺.

Step-2: 4-benzyl-6-(methoxycarbonyl)-3,4-dihydro-2H-benzo[b][1,4]oxazine-2-carboxylic Acid Into a 100-mL round-bottom flask was placed 2-tert-butyl 6-methyl 4-benzyl-3,4-dihydro-2H-1,4-benzoxazine-2,6-dicarboxylate (1.2 g, 3.13 mmol), dichloromethane (25 mL) and trifluoroacetic acid (5 mL). The resulting solution was stirred overnight at room temperature and then concentrated under vacuum to give 4-benzyl-6-(methoxycarbonyl)-3,4-dihydro-2H-benzo[b][1,4]oxazine-2-carboxylic acid (1.5 g) as brown oil which was used without any purification. MS: (ES, m/z): 328[M+H]⁺.

Example 3—Intermediate 3: 7-(methoxycarbonyl)-4-methyl-3,4-dihydro-2H-benzo[b][1,4]oxazine-2-carboxylic Acid

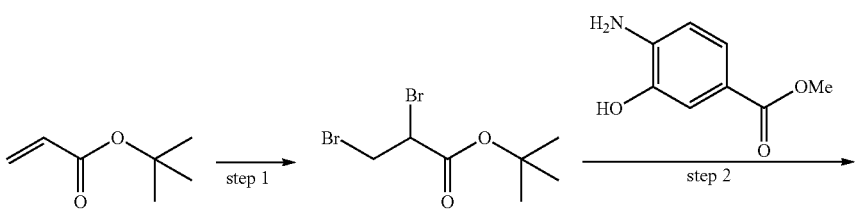

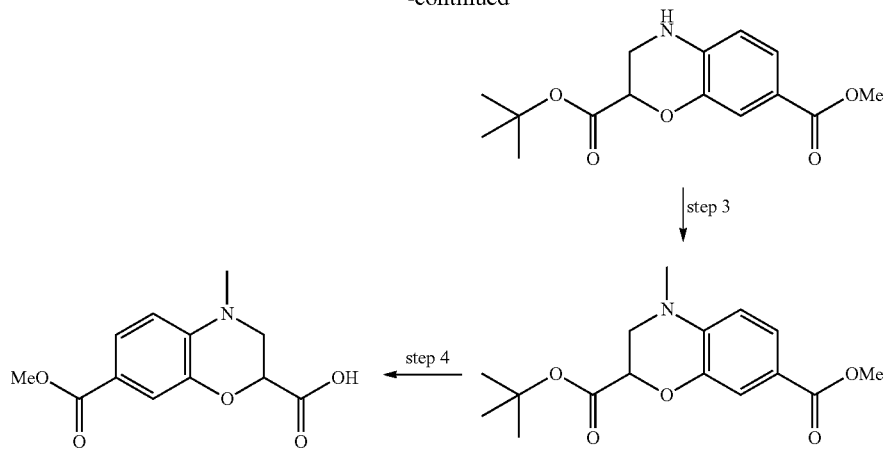

Step-1: Tert-butyl 2,3-dibromopropanoate

Into a 1000-mL, 3-necked round-bottom flask was placed a solution of tert-butyl prop-2-enoate (64 g, 499 mmol) in chloroform (200 mL). This was followed by the dropwise addition of a solution of bromine (80 g, 500 mmol) in chloroform (100 mL) with stirring. The resulting solution was stirred overnight at room temperature. The reaction was then quenched by the addition of sodium sulfite solution (1 M, 200 mL). The resulting solution was extracted with 2×200 mL of dichloromethane, washed with 400 mL of brine, dried over anhydrous sodium sulfate, filtered, and concentrated under vacuum to give tert-butyl 2,3-dibromopropanoate (130 g) as colorless oil which was used directly for the next step without any purification.

Step-2: 2-tert-butyl 7-methyl 3,4-dihydro-2H-benzo[b][1,4]oxazine-2,7-dicarboxylate Into a 250-mL 3-necked round-bottom flask was placed methyl 4-amino-3-hydroxybenzoate (10 g, 59.82 mmol), acetone (100 mL) and potassium carbonate (24.8 g, 179.44 mmol). This was followed by the dropwise addition of tert-butyl 2,3-dibromopropanoate (19.9 g, 69.10 mmol) with stirring. The resulting mixture was stirred overnight at 56° C. in an oil bath. The reaction was then quenched by the addition of 200 mL of water. The resulting solution was extracted with 3×300 mL of dichloromethane, washed with 100 mL of brine, dried over anhydrous sodium sulfate, filtered, and concentrated under vacuum. The residue purified via column chromatography on silica gel, eluting with ethyl acetate/petroleum ether (1:2). The collected fractions were concentrated to give 2-tert-butyl 7-methyl 3,4-dihydro-2H-benzo[b][1,4]oxazine-2,7-dicarboxylate (3.7 g, 21%) as a white solid. MS: (ES, m/z): 294 [m+h]$^+$.

Step-3: 2-tert-butyl 7-methyl 4-methyl-3,4-dihydro-2H-benzo[b][1,4]oxazine-2,7-dicarboxylate Into a 50-mL sealed tube was placed 2-tert-butyl 7-methyl 3,4-dihydro-2H-1,4-benzoxazine-2,7-dicarboxylate (1.0 g, 3.41 mmol), N,N-dimethylformamide (10 mL), potassium carbonate (1.41 g, 10.2 mmol) and methyl iodide (1.45 g, 310.2 mmol). The resulting solution was stirred overnight at 70° C. in an oil bath. The reaction was cooled to room temperature and then quenched by the addition of 100 mL of water. The resulting solution was extracted with 3×150 mL of ethyl acetate, washed with 2×100 mL of brine, dried over anhydrous sodium sulfate, filtered, and concentrated under vacuum. The residue was purified via column chromatography on silica gel, eluting with ethyl acetate/petroleum ether (1:5). The collected fractions were concentrated to give 2-tert-butyl 7-methyl 4-methyl-3,4-dihydro-2H-benzo[b][1,4]oxazine-2,7-dicarboxylate (400 mg, 38%) as a yellow solid. MS: (ES, m/z): 308 [M+H]$^+$.

Step-4: 7-(methoxycarbonyl)-4-methyl-3,4-dihydro-2H-benzo[b][1,4]oxazine-2-carboxylic Acid Into a 50-mL round-bottom flask, was placed 2-tert-butyl 7-methyl 4-methyl-3,4-dihydro-2H-1,4-benzoxazine-2,7-dicarboxylate (400 mg, 1.30 mmol), dichloromethane (5 mL) and trifluoroacetic acid (1 mL). The resulting solution was stirred overnight at room temperature, and then concentrated under vacuum to give 7-(methoxycarbonyl)-4-methyl-3,4-dihydro-2H-benzo[b][1,4]oxazine-2-carboxylic acid (380 mg) as a brown solid which was used without any purification. MS: (ES, m/z): 252 [M+H]$^+$.

Example 4—Intermediate 4: 4-benzyl-7-(methoxycarbonyl)-3,4-dihydro-2H-benzo[b][1,4]oxazine-2-carboxylic Acid

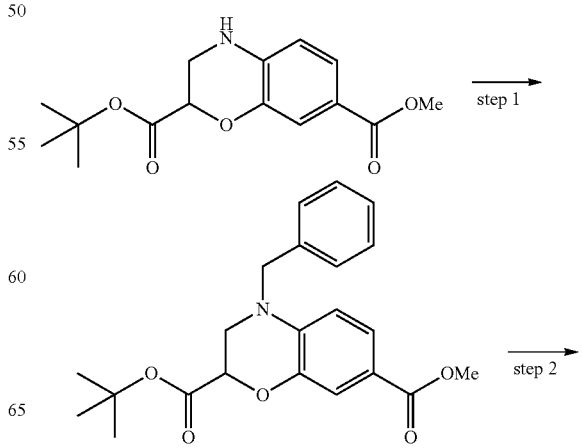

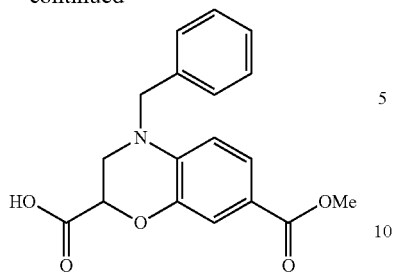

Step-1: 2-tert-butyl 7-methyl 4-benzyl-3,4-dihydro-2H-benzo[b][1,4]oxazine-2,7-dicarboxylate Into a 50-mL sealed tube was placed 2-tert-butyl 7-methyl 3,4-dihydro-2H-1,4-benzoxazine-2,7-dicarboxylate (1.0 g, 3.41 mmol), N,N-dimethylformamide (10 mL), potassium carbonate (1.41 g, 10.20 mmol) and benzyl bromide (1.17 g, 6.84 mmol). The resulting mixture was stirred overnight at 70° C. in an oil bath. The reaction was then cooled to room temperature and quenched by the addition of 100 mL of water. The resulting solution was extracted with 3×150 mL of ethyl acetate, washed with 2×100 mL of brine, dried over anhydrous sodium sulfate, filtered, and concentrated under vacuum. The residue was purified via column chromatography on silica gel, eluting with ethyl acetate/petroleum ether (1:5). The collected fractions were concentrated to give 2-tert-butyl 7-methyl 4-benzyl-3,4-dihydro-2H-benzo[b][1,4]oxazine-2,7-dicarboxylate (585 mg, 45%) as a white solid. MS: (ES, m/z): 384 [M+H]+.

Step-2: 4-benzyl-7-(methoxycarbonyl)-3,4-dihydro-2H-benzo[b][1,4]oxazine-2-carboxylic Acid Into a 50-mL round-bottom flask was placed 2-tert-butyl 7-methyl 4-benzyl-3,4-dihydro-2H-1,4-benzoxazine-2,7-dicarboxylate (585 mg, 1.53 mmol), dichloromethane (5 mL) and trifluoroacetic acid (1 mL). The resulting solution was stirred overnight at room temperature, and then concentrated under vacuum to give 4-benzyl-7-(methoxycarbonyl)-3,4-dihydro-2H-benzo[b][1,4]oxazine-2-carboxylic acid (510 mg) as a green solid which was used without any purification. MS: (ES, m/z): 328 [M+H]−.

Example 5—Intermediate 5: Methyl-3,4-dihydro-2H-benzo[b][1,4]thiazine-6-carboxylate-1,1-dioxide

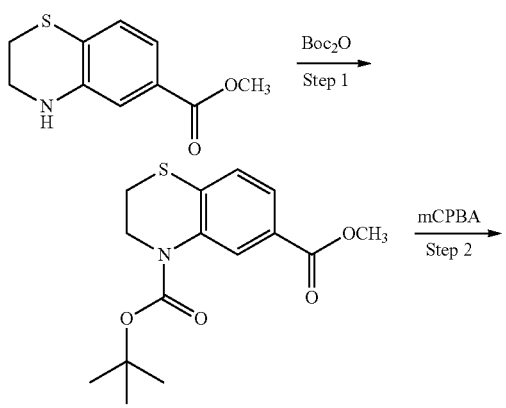

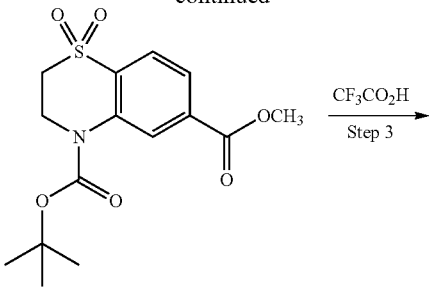

Step-1: 4-(tert-butyl)-6-methyl-2,3-dihydro-4H-benzo[b][1,4]thiazine-4,6-dicarboxylate Di-tert-butyl dicarbonate (0.78 g, 3.6 mmol), triethylamine (0.50 mL, 3.6 mmol), and 4-N,N-dimethylaminopyridine (0.44 g, 3.6, mmol) were added to a stirred solution of methyl-3,4-dihydro-2H-benzo[b][1,4]thiazine-6-carboxylate (0.50 g, 2.4 mmol) in 10 mL of acetonitrile. The reaction mixture was refluxed at 85° C. for 3 hours. The solvent was removed in vacuo, and the residue was dissolved in 50 mL of ethyl acetate. The mixture was washed with 1 M aqueous HCl (2×25 mL) and brine (1×25 mL), dried over sodium sulfate, filtered, and concentrated in vacuo to afford 4-(tert-butyl)-6-methyl-2,3-dihydro-4H-benzo[b][1,4]thiazine-4,6-dicarboxylate (780 mg, 95%) as an off-white solid, which was carried forward without further purification. MS (ESI-TOF) m/z: 331.9 [M+Na]+.

Step-2: 4-(tert-butyl)-6-methyl-2,3-dihydro-4H-benzo[b][1,4]thiazine-4,6-dicarboxylate-1,1-dioxide 4-(tert-Butyl)-6-methyl-2,3-dihydro-4H-benzo[b][1,4]thiazine-4,6-dicarboxylate (712 mg, 2.30 mmol) was dissolved in dichloromethane (10 mL) and cooled to 0° C. in an ice bath. 3-Chloroperoxybenzoic acid (794 mg, 4.60 mmol) was added in one portion. The reaction mixture stirred at 0° C. for 1 h, was warmed to room temperature, and then stirred for 1 h. The solvent was removed in vacuo and 50 mL of ethyl acetate was added. Then the mixture was washed with 10% aqueous potassium carbonate solution (2×25 mL) and brine (1×25 mL). The organic phase was dried with sodium sulfate and then filtered. The solvent was removed in vacuo to afford 4-(tert-butyl)-6-methyl-2,3-dihydro-4H-benzo[b][1,4]thiazine-4,6-dicarboxylate-1,1-dioxide (746 mg, 95%) as an off-white solid which was carried forward without further purification. MS (ESI-TOF) m/z: 363.9 [M+Na]+.

Step-3: Methyl-3,4-dihydro-2H-benzo[b][1,4]thiazine-6-carboxylate-1,1-dioxide 4-(tert-Butyl)-6-methyl-2,3-dihydro-4H-benzo[b][1,4]thiazine-4,6-dicarboxylate-1,1-dioxide (0.74 g, 2.2 mmol) was dissolved in dichloromethane (10 mL). Trifluoromethane acid (2 mL) was added, and the reaction mixture stirred for 2 h at room temperature. The reaction mixture was diluted with dichloromethane (25 mL) and washed with 10% aqueous potassium carbonate solution (2×20 mL) and brine (1×20 mL). The organic phase was dried with sodium sulfate and filtered. The solvent was removed in vacuo to afford methyl-3,4-dihydro-2H-benzo[b][1,4]thiazine-6-carboxylate-1,1-dioxide (0.50 g, 96%) as an off-white powder, which was used without further purification. $^1$H NMR (400 MHz, DMSO-d$_6$) δ 7.63 (d, J=8.0 Hz, 1H), 7.41 (d, J=1.5 Hz, 1H), 7.37 (bs, 1H), 7.17 (dd, J=8, 4 Hz, 1H), 3.84 (s, 3H), 3.75 (m, 2H), 3.44 (m, 2H); MS (ESI-TOF) m/z: 242 [M+H]+.

Example 6—Intermediate 6: 2-bromo-1-(2-methoxyethyl)-1H-benzo[d]imidazole

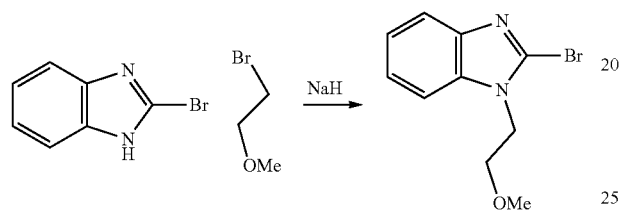

Sodium hydride (60% dispersion in mineral oil, 0.665 g, 16.63 mmol) was added to a solution of 2-bromo-1H-benzo[d]imidazole (2.73 g, 13.86 mmol) in DMF (30 mL), and the reaction stirred for 10 minutes at ambient temperature. 1-Bromo-2-methoxyethane (1.541 ml, 16.63 mmol) was added, and reaction stirred overnight at ambient temperature. The reaction was diluted with ethyl acetate and washed several times with brine. The organic layer was separated and dried over anhydrous magnesium sulfate, filtered and concentrated. The residue was purified via column chromatography on a 100 gram silica gel column eluting with 20-40% ethyl acetate-hexane. The desired fractions were combined and concentrated to afford 2-bromo-1-(2-methoxyethyl)-1H-benzo[d]imidazole (2.9 g, 82%) as an orange oil. $^1$H NMR (300 MHz, DMSO-d$_6$) δ ppm 7.54-7.67 (m, 2H) 7.14-7.34 (m, 2H) 4.42 (t, J=5.28 Hz, 2H) 3.67 (t, J=5.28 Hz, 2H) 3.20 (s, 3H).

Example 7—Intermediate 7: methyl 8-fluoro-3-oxo-3,4-dihydro-2H-benzo[b][1,4]oxazine-6-carboxylate

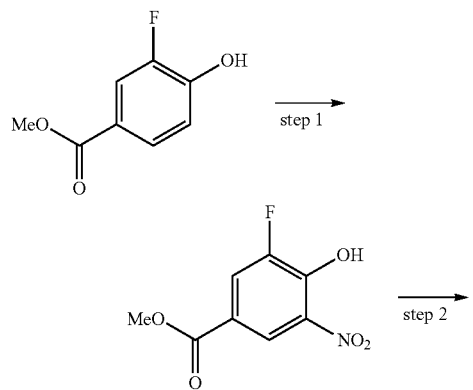

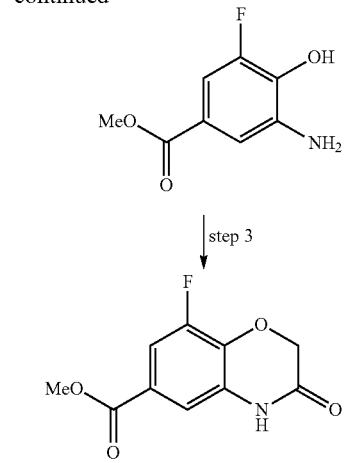

Step 1: Methyl 3-fluoro-4-hydroxy-5-nitrobenzoate

Into a 500-mL 3-necked round-bottom flask, was placed methyl 3-fluoro-4-hydroxybenzoate (4.27 g, 25.10 mmol, 1.00 equiv), ether (200 mL). This was followed by the addition of nitric acid (65%) (3.48 mL, 50.24 mmol, 2.00 equiv) dropwise with stirring at −10° C. To this was added fuming nitric acid (2.15 mL, 50.23 mmol, 2.00 equiv) dropwise with stirring at −10° C., The resulting solution was stirred for 2 h at room temperature (27° C.) and then slowly poured into 100 mL of water/ice. The mixture was extracted with 2×100 mL of dichloromethane, dried over anhydrous sodium sulfate and concentrated under vacuum. The residue was purified via column chromatography on silica gel (eluting with ethyl acetate/petroleum ether (1:1)) to afford methyl 3-fluoro-4-hydroxy-5-nitrobenzoate (4.3 g, 80% as a yellow solid. MS: (ESI, m/z): 214[M−H]$^+$.

Step 2: Methyl 3-amino-5-fluoro-4-hydroxybenzoate

Into a 250-mL round-bottom flask, was placed methyl 3-fluoro-4-hydroxy-5-nitrobenzoate (4.3 g, 19.99 mmol, 1.00 equiv), MeOH (100 mL) and 10% Pd/C (430 mg). To the above hydrogen was introduced in. The resulting solution was stirred for 1 h at room temperature (25° C.). The solids were filtered out. The filtrate was concentrated under vacuum. The residue was purified via column chromatography on silica gel (eluting with ethyl acetate/petroleum ether (1:3)) to afford methyl 3-amino-5-fluoro-4-hydroxybenzoate (3.1 g, 84%) as a yellow solid. MS: (ESI, m/z): 186[M+H]$^+$.

Step 3: Methyl 8-fluoro-3-oxo-3,4-dihydro-2H-benzo[b][1,4]oxazine-6-carboxylate

Into a 100-mL round-bottom flask, was placed methyl 3-amino-5-fluoro-4-hydroxybenzoate (1 g, 5.40 mmol, 1.00 equiv), dichloromethane (40 mL) and TEA (2.25 mL, 16.21 mmol, 3.00 equiv). This was followed by the addition of 2-chloroacetyl chloride (0.48 mL, 6.43 mmol, 1.20 equiv) dropwise with stirring at 0° C. The resulting solution was stirred for 2 hours at room temperature (25° C.) and additional overnight at 60° C. The resulting mixture was cooled to room temperature and then concentrated under vacuum. The crude product was washed with 5 mL of dichloromethane to afford methyl 8-fluoro-3-oxo-3,4-dihydro-2H-benzo[b][1,4]oxazine-6-carboxylate (980 mg, 81%) as a yellow solid. MS: (ESI, m/z): 226[M+H]$^+$.

Example 8—Intermediate 8: methyl 2-oxo-2,4-dihydro-1H-benzo[d][1,3]oxazine-7-carboxylate

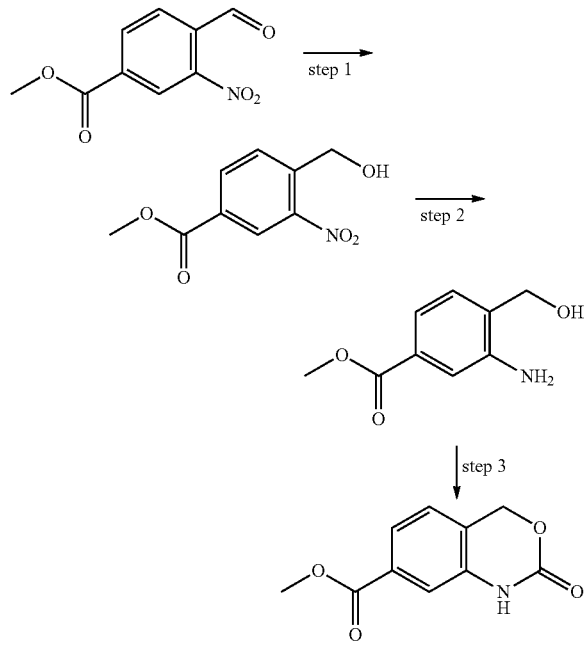

Step 1: Methyl 4-(hydroxymethyl)-3-nitrobenzoate

Into a 100-mL 3-necked round-bottom flask, was placed methyl 4-formyl-3-nitrobenzoate (2.09 g, 9.99 mmol, 1.00 equiv), methanol (30 mL). This was followed by the addition of NaBH$_4$ (760 mg, 20.09 mmol, 2.01 equiv), in portions at 0° C. The resulting solution was stirred for overnight at room temperature (25° C.). The reaction was quenched by the addition of 5 mL of water, and then concentrated under vacuum. The residue was diluted with 50 mL of water. The mixture was extracted with 2×50 mL of dichloromethane, dried over anhydrous sodium sulfate and concentrated under vacuum. The residue was purified via column chromatography on silica gel (eluting with ethyl acetate/petroleum ether (1:1)) to afford methyl 4-(hydroxymethyl)-3-nitrobenzoate (1.28 g, 61%) as a yellow solid. $^1$H-NMR: (DMSO 400 MHz, ppm): δ 8.51 (s, 1H), 8.32 (d, J=8 Hz, 1H), 8.03 (d, J=8 Hz, 1H), 5.76-5.74 (m, 1H), 4.91 (d, J=8 Hz, 2H), 3.92 (s, 3H).

Step 2: Methyl 3-amino-4-(hydroxymethyl)benzoate

Into a 100-mL round-bottom flask, was placed methyl 4-(hydroxymethyl)-3-nitrobenzoate (500 mg, 2.37 mmol, 1.00 equiv), methanol (20 mL), 10% Pd/C (300 mg). To the above hydrogen was introduced in. The resulting solution was stirred for 18 h at room temperature (25° C.). The solids were filtered out. The filtrate was concentrated under vacuum. The residue was purified via column chromatography on silica gel (eluting with ethyl acetate/petroleum ether (1:1)) to afford methyl 3-amino-4-(hydroxymethyl)benzoate (195 mg, 45%) as an off-white solid. MS: (ESI, m/z): 182[M+H]$^+$.

Step 3: Methyl 2-oxo-2,4-dihydro-1H-benzo[d][1,3]oxazine-7-carboxylate

Into a 25-mL round-bottom flask, was placed methyl 3-amino-4-(hydroxymethyl)benzoate (175 mg, 0.97 mmol, 1.00 equiv) in tetrahydrofuran (10 mL). This was followed by the addition of a solution of ditrichloromethyl carbonate (345 mg, 1.16 mmol, 1.20 equiv) in tetrahydrofuran (1 mL) dropwise with stirring at 0° C. The resulting mixture was stirred for 10 minutes at 0° C. To this was added TEA (0.47 mL, 3.38 mmol, 3.48 equiv) dropwise with stirring at 0° C. The resulting solution was stirred for 3 h at room temperature (27° C.). The reaction mixture was then diluted with 50 mL of dichloromethane, washed with 2×30 mL of water, dried over anhydrous magnesium sulfate and concentrated under vacuum. The residue was purified via column chromatography on silica gel (eluting with ethyl acetate/petroleum ether (1:3)) to afford methyl 2-oxo-2,4-dihydro-1H-benzo[d][1,3]oxazine-7-carboxylate (190 mg, 95%) as a off-white solid. MS: (ESI, m/z): 208[M+H]$^t$.

Example 9—Intermediate 9: methyl 3,3-dimethyl-3,4-dihydro-2H-benzo[b][1,4]oxazine-6-carboxylate)

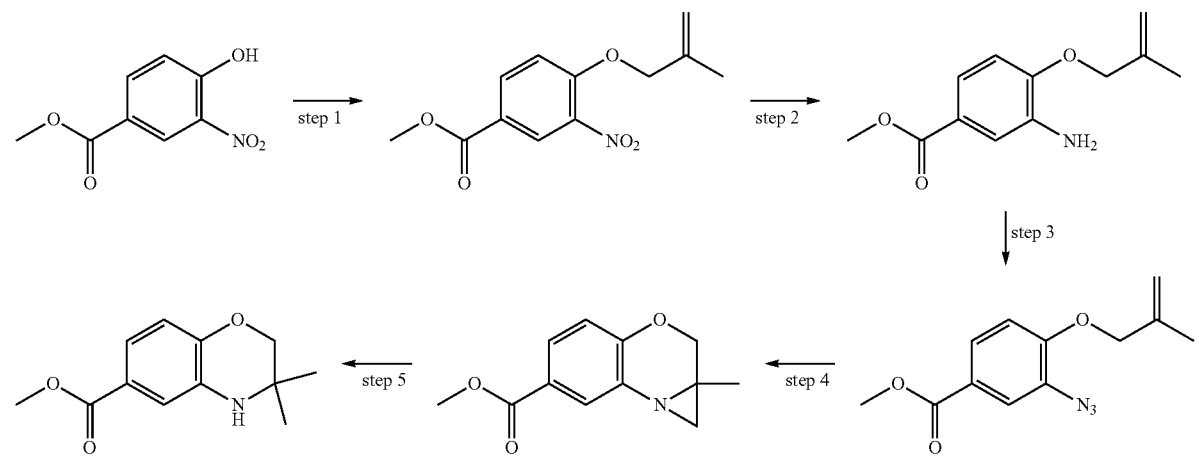

Step 1: Methyl 4-(2-methylallyloxy)-3-nitrobenzoate

Into a 250-mL 3-necked round-bottom flask, was placed methyl 4-hydroxy-3-nitrobenzoate (5 g, 25.36 mmol, 1.00 equiv), acetone (100 mL), potassium carbonate (10.5 g, 75.97 mmol, 3.00 equiv), and 3-bromo-2-methylprop-1-ene (3.79 mL, 37.04 mmol, 1.46 equiv). The resulting solution was stirred for overnight at 50° C. and then cooled to room temperature. The solids were filtered out. The filtrate was concentrated under vacuum. The residue was diluted with 100 mL of water. The resulting solution was extracted with 2×100 mL of ethyl acetate, washed with 100 mL of brine, dried over anhydrous sodium sulfate and concentrated under vacuum. The residue was purified via column chromatography on silica gel (eluting with ethyl acetate/petroleum ether (1:4)) to afford methyl 4-(2-methylallyloxy)-3-nitrobenzoate (5 g, 78%) as a yellow solid. GCMS: (EI): 251 [M].

Step 2: Methyl 3-amino-4-(2-methylallyloxy)benzoate

Into a 250-mL 3-necked round-bottom flask, was placed methyl 4-(2-methylallyloxy)-3-nitrobenzoate (2.51 g, 9.99 mmol, 1.00 equiv), ethanol (100 mL), water (30 mL) and NH$_4$Cl (1.59 g, 29.72 mmol, 3.00 equiv). This was followed by the addition of Fe (5.6 g, 100.28 mmol, 10.00 equiv) in portions at 60° C. The resulting solution was stirred for 4 h at 90° C. and then cooled to 50° C. The solids were filtered out. The filtrate was concentrated under vacuum. The residue was diluted with 100 mL of water. The resulting solution was extracted with 2×50 mL of ethyl acetate, washed with 100 mL of brine, dried over anhydrous sodium sulfate and concentrated under vacuum. The residue was purified via column chromatography on silica gel (eluting with ethyl acetate/petroleum ether (1:1)) to afford methyl 3-amino-4-(2-methylallyloxy)benzoate (2.2 g, 100%) as a white solid. MS: (ESI, m/z): 222[M+H]$^+$.

Step 3: Methyl 3-azido-4-(2-methylallyloxy)benzoate

Into a 50-mL 3-necked round-bottom flask, was placed HCl (6M) (6 mL), methyl 3-amino-4-(2-methylallyloxy)benzoate (442 mg, 2.00 mmol, 1.00 equiv). This was followed by the addition of a solution of NaNO$_2$ (166 mg, 2.40 mmol, 1.20 equiv) in water (1 mL) dropwise with stirring at 0° C. The mixture was stirred for 20 min at 0° C. The pH value of the solution was adjusted to 7 with sodium bicarbonate solid. To this was added a solution of NaN$_3$ (156 mg, 2.40 mmol, 1.20 equiv) in water (1 mL) dropwise with stirring at 0° C. The mixture was stirred for 30 min at 0° C. The solids were collected by filtration and dried to afford methyl 3-azido-4-(2-methylallyloxy)benzoate (440 mg, 89%) as a yellow solid. MS: (ESI, m/z): 248[M+H]$^+$.

Step 4: Methyl 1a-methyl-1a,2-dihydro-1H-azirino[1,2-d]benzo[b][1,4]oxazine-6-carboxylate Into a 50-mL round-bottom flask, was placed methyl 3-azido-4-(2-methylallyloxy)benzoate (440 mg, 1.78 mmol, 1.00 equiv), toluene (20 mL). The resulting solution was stirred for 4 h at 90° C. The reaction mixture was cooled to room temperature and concentrated under vacuum. The residue was purified via column chromatography on silica gel (eluting with ethyl acetate/petroleum ether (1:3)) to afford methyl 1a-methyl-1a,2-dihydro-1H-azirino[1,2-d]benzo[b][1,4]oxazine-6-carboxylate (280 mg, 65%) as yellow oil. MS: (ESI, m/z): 220[M+H]$^+$.

Step 5: Methyl 3,3-dimethyl-3,4-dihydro-2H-benzo[b][1,4]oxazine-6-carboxylate Into a 50-mL round-bottom flask, was placed methyl 1a-methyl-1a,2-dihydro-1H-azirino[1,2-d]benzo[b][1,4]oxazine-6-carboxylate (280 mg, 1.28 mmol, 1.00 equiv), methanol (10 mL), 10% Pd/C (100 mg). To the above hydrogen was introduced in. The resulting solution was stirred for overnight at room temperature (25° C.). The solids were filtered out, the filtrate was concentrated under vacuum to afford methyl 3,3-dimethyl-3,4-dihydro-2H-benzo[b][1,4]oxazine-6-carboxylate (240 mg, 85%) as colorless oil. MS: (ESI, m/z): 222[M+H]$^-$.

Example 10—Intermediate 10: 3-((6-(methoxycarbonyl)-3-oxo-2,3-dihydro-4H-benzo[b][1,4]oxazin-4-yl)methyl)benzoic Acid

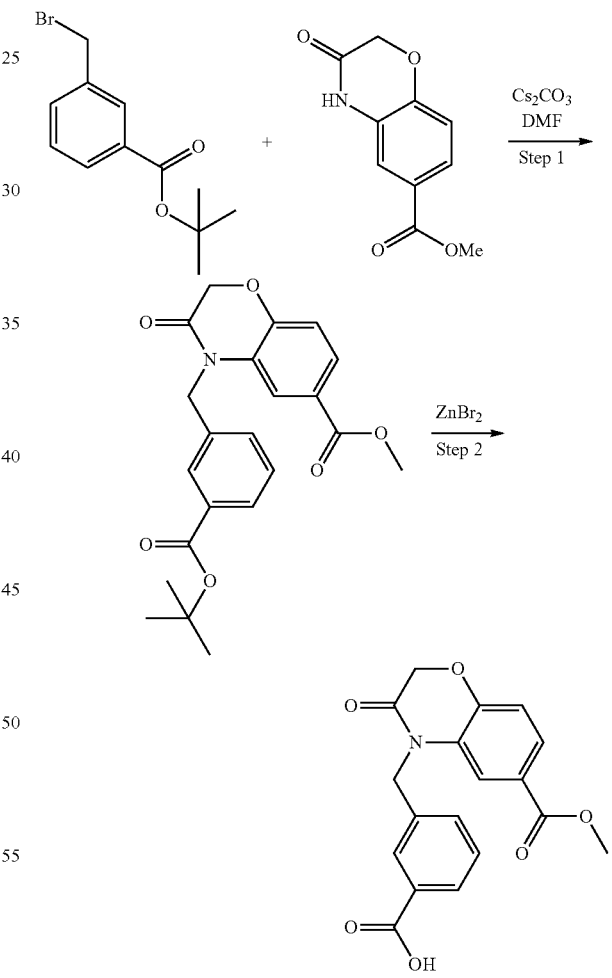

Step-1: Methyl 4-(3-(tert-butoxycarbonyl)benzyl)-3-oxo-3,4-dihydro-2H-benzo[b][1,4]oxazine-6-carboxylate tert-butyl 3-(bromomethyl)benzoate (1.31 g, 4.83 mmol) was added to a solution of methyl 3-oxo-3,4-dihydro-2H- benzo[b][1,4]oxazine-6-carboxylate (1.00 g, 4.83 mmol) and cesium carbonate (3.15 g, 9.65 mmol) in DMF (10 mL). The reaction was stirred overnight at ambient temperature. The reaction was diluted with ethyl acetate (50 mL) and washed with 1N aq. NaOH (5 mL). The organic phase was separated, dried over Na$_2$SO$_4$, filtered and concentrated. The residue was purified by normal phase column chromatography on silica gel (Biotage KP-SIL 50 g column, 15%-45% EtOAc/Hexanes gradient) to afford methyl 4-(3-(tert-butoxycarbonyl)benzyl)-3-oxo-3,4-dihydro-2H-benzo[b][1,4]oxazine-6-carboxylate (2.1 g, 5.28 mmol, 109%) as a white solid. MS: (ES, m/z): 398 [M+H]$^+$. $^1$H NMR (300 MHz, DMSO-d6) δ ppm 1.45-1.55 (m, 9H) 2.73 (s, 2H) 2.81-2.92 (m, 1H) 2.81-2.84 (m, 1H) 3.16 (s, 3H) 3.61-3.81 (m, 7H) 4.94 (s, 2H) 5.27 (s, 3H) 7.13 (d, J=8.50 Hz, 2H) 7.32-7.50 (m, 4H) 7.51-7.79 (m, 2H) 7.86 (d, J=8.21 Hz, 2H) 7.92-8.02 (m, 1H).

Step-2: 3-((6-(methoxycarbonyl)-3-oxo-2,3-dihydro-4H-benzo[b][1,4]oxazin-4-yl)methyl)benzoic Acid methyl 4-(3-(tert-butoxycarbonyl)benzyl)-3-oxo-3,4-dihydro-2H-benzo[b][1,4]oxazine-6-carboxylate (2.03 g, 5.11 mmol) was dissolved in CH$_2$Cl$_2$ (15 mL). Zinc (II) bromide (5.75 g, 25.2 mmol) was added. The resulting solution stirred for 16 hours at ambient temperature. The reaction mixture was washed with H$_2$O (10 mL). The organic layer was separated, dried over Na$_2$SO$_4$, filtered and concentrated to afford 3-((6-(methoxycarbonyl)-3-oxo-2,3-dihydro-4H-benzo[b][1,4]oxazin-4-yl)methyl)benzoic acid (3.5 mg, 0.009 mmol, 2.5%) as an off-white solid. MS: (ES, m/z): 342 [M+H]$^+$. $^1$H NMR (300 MHz, CHLOROFORM-d) δ ppm 3.76-3.85 (m, 4H) 4.73-4.84 (m, 3H) 5.14-5.34 (m, 4H) 6.80-7.11 (m, 2H) 7.14-7.42 (m, 4H) 7.51 (d, J=1.88 Hz, 1H) 7.57-7.90 (m, 2H) 7.91-7.98 (m, 2H).

Example 11—N$^6$-hydroxy-4-methyl-N$^2$-(tetrahydro-2H-pyran-4-yl)-3,4-dihydro-2H-benzo[b][1,4]oxazine-2,6-dicarboxamide Hydrochloride (I-1)

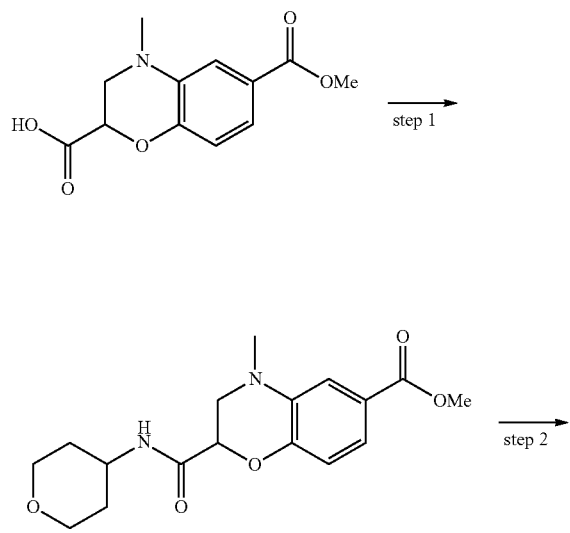

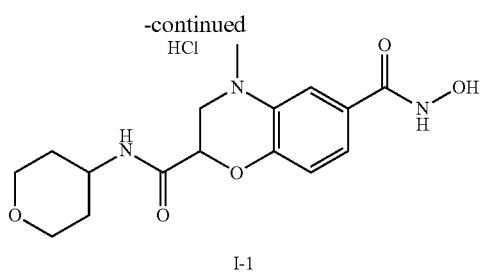

Step-1: Methyl 4-methyl-2-(tetrahydro-2H-pyran-4-ylcarbamoyl)-3,4-dihydro-2H-benzo[b][1,4]oxazine-6-carboxylate Into a 10-mL round-bottom flask was placed 6-(methoxycarbonyl)-4-methyl-3,4-dihydro-2H-1,4-benzoxazine-2-carboxylic acid (150 mg, 0.60 mmol), THF (5 mL), triethylamine (182 mg, 1.80 mmol), oxan-4-amine (90 mg, 0.89 mmol), HOBT (122 mg, 0.90 mmol) and EDCI (288 mg, 0.90 mmol). The resulting solution was stirred for 5 h at room temperature. The reaction was then quenched by the addition of 30 mL of water. The resulting solution was extracted with 3×30 mL of ethyl acetate washed with 50 mL of brine, dried over anhydrous sodium sulfate and concentrated under vacuum. The residue was purified via column chromatography on silica gel, eluting with ethyl acetate/petroleum ether (1:1). The collected fractions were concentrated to afford methyl 4-methyl-2-(tetrahydro-2H-pyran-4-ylcarbamoyl)-3,4-dihydro-2H-benzo[b][1,4]oxazine-6-carboxylate (100 mg, 50%) as a white solid. MS: (ES, m/z): 335 [M+H]$^+$.

Step-2: N$^6$-hydroxy-4-methyl-N$^2$-(tetrahydro-2H-pyran-4-yl)-3,4-dihydro-2H-benzo[b][1,4]oxazine-2,6-dicarboxamide Hydrochloride Into a 25-mL round-bottom flask was placed methyl 4-methyl-2-[(oxan-4-yl)carbamoyl]-3,4-dihydro-2H-1,4-benzoxazine-6-carboxylate (100 mg, 0.30 mmol), methanol/THF (1:4, 3 mL), hydroxylamine (50% in water, 1.15 g, 18 mmol), and aqueous sodium hydroxide solution (1 M, 0.6 mL, 0.60 mmol). The resulting solution was stirred for 2 h at room temperature. The crude product (4 mL) was purified by Prep-HPLC with the following conditions: Column: X Bridge C18, 19*150 mm, 5 um; Mobile Phase A: Water/0.05% FA, Mobile Phase B: ACN; Flow rate: 20 mL/min; Gradient: 5% B to 30% B in 7 min; 254 nm. 2 M HCl (0.2 mL, 0.60 mmol) was added to the collected fractions and the solution was lyophilized to give N$^6$-hydroxy-4-methyl-N$^2$-(tetrahydro-2H-pyran-4-yl)-3,4-dihydro-2H-benzo[b][1,4]oxazine-2,6-dicarboxamide hydrochloride (20.7 mg, 19%) as an off-white solid. $^1$H NMR (DMSO-d$_6$, 300 MHz): δ ppm 11.00 (s, 1H), 8.86-8.85 (d, J=1.5 Hz, 1H), 7.99-7.96 (d, J=7.8 Hz, 1H), 7.10-7.07 (t, J=4.8 Hz, 2H), 6.87-6.84 (d, J=8.4 Hz, 1H), 4.73-4.69 (m, 1H), 3.83-3.80 (m, 3H), 3.44-3.30 (m, 3H), 3.30-3.16 (m, 1H), 2.86 (s, 3H), 1.58-1.51 (m, 4H). MS: (ES, m/z): 336[M+H]$^+$.

The following compounds were prepared according to the procedures described above for Example 11.

| Compd. No. | Structure | IUPAC Name | ¹H NMR | MS (ES, m/z) [M + H]⁺ |
|---|---|---|---|---|
| I-2 | 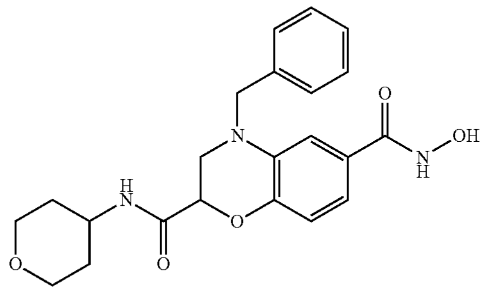 [SMILES: O=C(NO)c1ccc2c(c1)N(Cc1ccccc1)CC(C(=O)NC1CCOCC1)O2] | 4-benzyl-$N^6$-hydroxy-$N^2$-(tetrahydro-2H-pyran-4-yl)-3,4-dihydro-2H-benzo[b][1,4]oxazine-2,6-dicarboxamide | (DMSO, 400 MHz, ppm): 10.94 (s, 1H), 8.82 (s, 1H), 8.00-7.98 (d, J = 8 Hz, 1H), 7.36-7.25 (m, 5H), 7.14 (s, 1H), 7.06-7.04 (d, 8.4 Hz, 1H), 6.91-6.89 (d, J = 8.4 Hz, 1H), 4.72-4.69 (m, 1H), 4.58-4.46 (m, 2H), 3.81 (s, 3H), 3.52-3.49 (m, 1H), 3.37-3.34 (t, J = 19.2 Hz, 2H), 3.31 (s, 1H), 1.68-1.60 (t, J = 15.4 Hz, 2H), 1.54-1.45 (m, 2H). | 412 |
| I-3 | 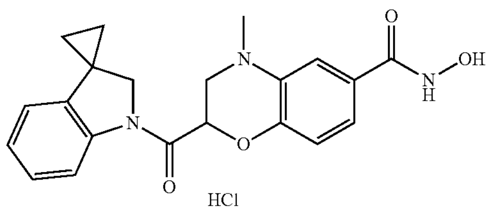 [SMILES: CN1CC(C(=O)N2CC3(CC3)c3ccccc32)Oc2ccc(C(=O)NO)cc21 ; Cl] | N-hydroxy-4-methyl-2-(spiro[cyclopropane-1,3'-indoline]-1'-carbonyl)-3,4-dihydro-2H-benzo[b][1,4]oxazine-6-carboxamide hydrochloride | (DMSO, 400 MHz, ppm): 11.02 (s, 1H), 8.05-8.03 (d, J = 8 Hz, 1H), 7.16-7.01 (m, 4H), 6.86-6.83 (t, J = 6.6 Hz, 2H), 5.14 (s, 1H), 4.39-4.27 (m, 2H), 3.53-3.41 (m, 2H), 2.91 (s, 3H), 1.15-1.06 (m, 4H) | 380 |
| I-4 | 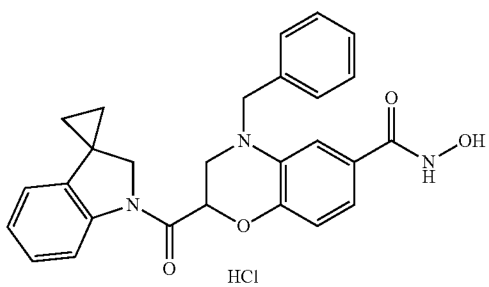 [SMILES: O=C(NO)c1ccc2c(c1)N(Cc1ccccc1)CC(C(=O)N1CC3(CC3)c3ccccc31)O2 ; Cl] | 4-benzyl-N-hydroxy-2-(spiro[cyclopropane-1,3'-indoline]-1'-carbonyl)-3,4-dihydro-2H-benzo[b][1,4]oxazine-6-carboxamide hydrochloride | (DMSO, 400 MHz, ppm): 11.30 (s, 1H), 8.82 (br, 1H), 8.05-8.04 (d, J = 7.6 Hz, 1H), 7.31-7.21 (m, 6H), 7.18-7.11 (m, 2H), 7.05-7.01 (t, J = 7.4 Hz, 2H), 6.94-6.84 (m, 2H), 5.14 (s, 1H), 4.64-4.50 (m, 2H), 4.34-4.32 (d, 10.4 Hz, 1H), 4.14-4.12 (d, J = 10 Hz, 1H), 3.57-3.56 (d, 4.4 Hz, 2H), 1.16-1.06 (m, 4H) | 456 |
| I-5 | 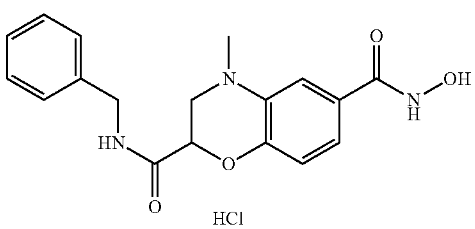 [SMILES: CN1CC(C(=O)NCc2ccccc2)Oc2ccc(C(=O)NO)cc21 ; Cl] | $N^2$-benzyl-$N^6$-hydroxy-4-methyl-3,4-dihydro-2H-benzo[b][1,4]oxazine-2,6-dicarboxamide hydrochloride | (DMSO, 300 MHz, ppm): 11.01 (s, 1H), 8.60-8.57 (t, J = 6 Hz, 1H), 7.31-7.27 (t, J = 7.2 Hz, 2H), 7.24-7.19 (m, 3H), 7.12-7.10 (t, J = 3.2 Hz, 2H), 6.87-6.85 (d, J = 8 HZ, 1H), 4.87-4.85 (t, J = 3.2 HZ, 1H), 4.38-4.28 (m, 2H), 3.44-3.40 (m, 1H), 3.32-3.29 (t, J = 5.6 Hz, 1H), 2.87 (s, 3H). | 342 |
| I-6 | 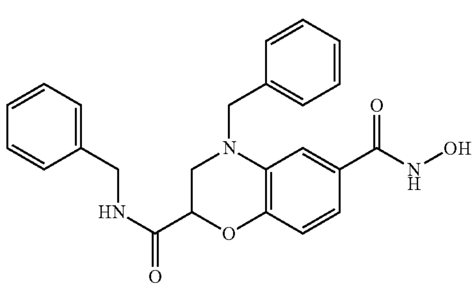 [SMILES: O=C(NO)c1ccc2c(c1)N(Cc1ccccc1)CC(C(=O)NCc1ccccc1)O2] | $N^{2,4}$-dibenzyl-$N^6$-hydroxy-3,4-dihydro-2H-benzo[b][1,4]oxazine-2,6-dicarboxamide | (DMSO, 300 MHz, ppm): 10.96 (s, 1H), 8.63-8.60 (t, J = 6.2 Hz, 1H), 7.34-7.16 (m, 11H), 7.09-7.04 (m, 1H), 6.91-6.89 (d, J = 8.4 Hz, 1H), 4.85-4.83 (m, 1H), 4.52 (s, 2H), 4.40-4.28 (m, 2H), 3.55-3.51 (m, 1H), 3.52-3.40 (m, 1H) | 418 |

Example 12—N⁷-hydroxy-4-methyl-N²-(tetrahydro-2H-pyran-4-yl)-3,4-dihydro-2H-benzo[b][1,4]oxazine-2,7-dicarboxamide (I-7)

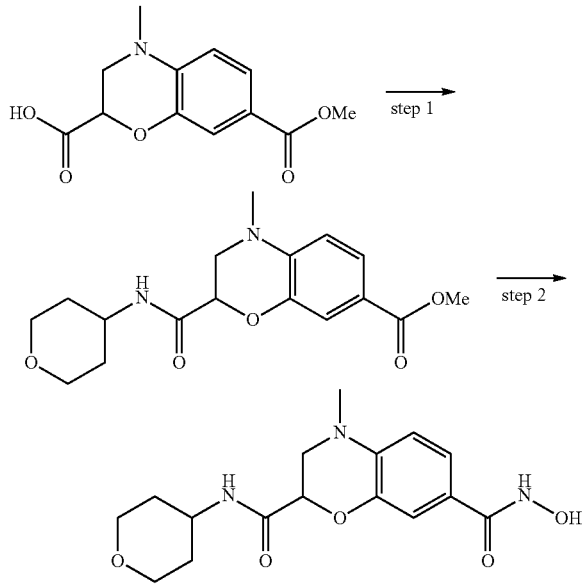

Step-1: Methyl 4-methyl-2-(tetrahydro-2H-pyran-4-ylcarbamoyl)-3,4-dihydro-2H-benzo[b][1,4]oxazine-7-carboxylate Into a 10-mL vial was placed 7-(methoxycarbonyl)-4-methyl-3,4-dihydro-2H-1,4-benzoxazine-2-carboxylic acid (100 mg, 0.40 mmol), THF (2 mL), EDCI (192 mg, 0.60 mmol), HOBT (81 mg, 0.60 mmol), triethylamine (121 mg, 1.20 mmol) and oxan-4-amine (60 mg, 0.59 mmol). The resulting mixture was stirred overnight at room temperature. The reaction was then quenched by the addition of 30 mL of water. The resulting solution was extracted with 3×50 mL of ethyl acetate, washed with 2×30 mL of brine, dried over anhydrous sodium sulfate, filtered, and concentrated under vacuum. The residue was purified via column chromatography on silica gel, eluting with ethyl acetate/petroleum ether (1:5). The collected fractions were concentrated to give methyl 4-methyl-2-(tetrahydro-2H-pyran-4-ylcarbamoyl)-3,4-dihydro-2H-benzo[b][1,4]oxazine-7-carboxylate (103 mg, 77%) as a brown solid. MS: (ES, m/z): 335[M+H]⁺.

Step-2: N⁷-hydroxy-4-methyl-N²-(tetrahydro-2H-pyran-4-yl)-3,4-dihydro-2H-benzo[b][1,4]oxazine-2,7-dicarboxamide Into a 25-mL round-bottom flask was placed methyl 4-methyl-2-(tetrahydro-2H-pyran-4-ylcarbamoyl)-3,4-dihydro-2H-benzo[b][1,4]oxazine-7-carboxylate (103 mg, 0.31 mmol), methanol/THF (1:4, 2 mL), hydroxylamine (50% in water, 0.62 mL, 18.6 mmol), and aqueous sodium hydroxide solution (1 M, 0.62 mL, 0.62 mmol). The resulting solution was stirred for 4 h at room temperature. The crude product was purified by Prep-HPLC with the following conditions (Waters III): Column, Sunfire C18 19*150 mm; mobile phase, water with 0.05% FA and $CH_3CN$ (5% up to 40% in 9 min); Detector, UV 220 & 254 nm. The collected fractions was lyophilized to give N⁷-hydroxy-4-methyl-N²-(tetrahydro-2H-pyran-4-yl)-3,4-dihydro-2H-benzo[b][1,4]oxazine-2,7-dicarboxamide (42.5 mg, 41%) as a pink solid. ¹H NMR (DMSO, 400 MHz) δ ppm: 10.89 (s, 1H), 8.78 (s, 1H), 8.00-7.98 (d, J=8.0 Hz, 1H), 7.31-7.28 (m, 2H), 6.72-6.70 (d, J=8.0 Hz, 1H), 4.67-4.64 (m, 1H), 3.89-3.80 (m, 3H), 3.50-3.46 (m, 1H), 3.37-3.31 (m, 2H), 3.27-3.22 (m, 1H), 2.89 (s, 3H), 1.69-1.45 (m, 4H). MS: (ES, m/z): 358 [M+23]⁺.

The following compounds were prepared according to the procedures described above for Example 12.

| Compd. No. | Structure | IUPAC Name | ¹H NMR | MS (ES, m/z) [M + H]⁺ |
|---|---|---|---|---|
| I-8 | 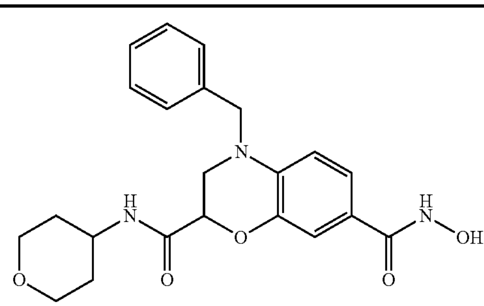 | 4-benzyl-N⁷-hydroxy-N²-(tetrahydro-2H-pyran-4-yl)-3,4-dihydro-2H-benzo[b][1,4]oxazine-2,7-dicarboxamide | (DMSO, 400 MHz, ppm): 10.86 (s, 1H), 8.77 (s, 1H), 8.02-8.00 (d, J = 8.0 Hz, 1H), 7.35-7.18 (m, 7H), 6.68-6.66 (d, J = 8.4 Hz, 1H), 4.69-4.66 (m, 1H), 4.62-4.50 (m, 2H), 3.87-3.79 (m, 3H), 3.62-3.58 (m, 1H), 3.45-3.40 (m, 2H), 3.37-3.33 (m, 1H), 1.68-1.47 (m, 4H) | [M + 23]⁺ 434 |
| I-9 | 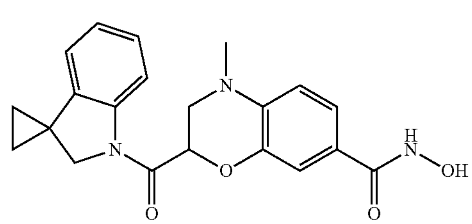 [SMILES: CN1CC(C(=O)N2CC3(CC3)c3ccccc32)Oc2cc(C(=O)NO)ccc21] | N-hydroxy-4-methyl-2-(spiro[cyclopropane-1,3'-indoline]-1'-carbonyl)-3,4-dihydro-2H-benzo[b][1,4]oxazine-7-carboxamide | (DMSO, 400 MHz, ppm): 10.89 (s, 1H), 8.77 (s, 1H), 8.06-8.03 (d, J = 8.8 Hz, 1H), 7.33-7.30 (m, 1H), 7.23 (s, 1H), 7.17-7.13 (t, J = 7.4 Hz, 1H), 7.05-7,02 (m, 1H), 6.87-6.85 (d, J = 7.6 Hz, 1H), 6.74-6.72 (d, J = 8.4 Hz, 1H), 5.07 (s, 1H), 4,40-4.38 (d, J = 10.0 Hz, 1H), 4.31-4.28 (d, J = 10.8 Hz, 1H), 3.57-3.48 (m, 2H), 2,95 (s, 3H), 1.16-1.09 (m, 2H), 1.07-1.00 (m, 2H) | 380 |

| Compd. No. | Structure | IUPAC Name | $^1$H NMR | MS (ES, m/z) [M + H]$^+$ |
|---|---|---|---|---|
| I-10 | 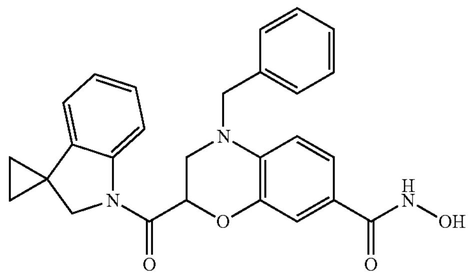 [SMILES: O=C(NO)c1ccc2c(c1)OC(C(=O)N1CC3(CC3)c3ccccc31)CN2Cc1ccccc1] | 4-benzyl-N-hydroxy-2-(spiro[cyclopropane-1,3'-indoline]-1'-carbonyl)-3,4-dihydro-2H-benzo[b][1,4]oxazine-7-carboxamide | (DMSO, 400 MHz, ppm): 10.86 (s, 1H), 8.78 (s, 1H), 8.06-8.04 (d, J = 7.6 Hz, 1H), 7.30-7.22 (m, 7H), 7.18-7.14 (m, 1H), 7.06-7.02 (t, J = 7.4 Hz, 1H), 6.87-6.85 (d, J = 6.8 Hz, 1H), 6.71-6.68 (d, J = 8.8 Hz, 1H), 5.10-5.09 (d, J = 4.8 Hz, 1H), 4.68-4.64 (d, J = 16.0 Hz, 1H), 4.58-4.54 (d, J = 16.4 Hz, 1H), 4.38-4.35 (d, J = 10.8 Hz, 1H), 4.22-4.19 (d, J = 10.4 Hz, 1H), 3.66-3.65 (d, J = 4.4 Hz, 2H), 1.15-1.05 (m, 4H) | 456 |
| I-11 | 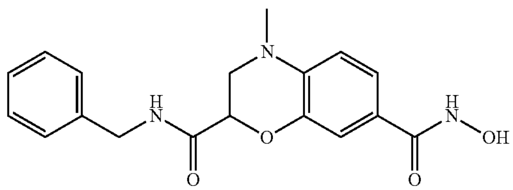 [SMILES: CN1CC(C(=O)NCc2ccccc2)Oc2cc(C(=O)NO)ccc21] | N$^2$-benzyl-N$^7$-hydroxy-4-methyl-3,4-dihydro-2H-benzo[b][1,4]oxazine-2,7-dicarboxamide | (DMSO, 400 MHz, ppm): 10.90 (s, 1H), 8.77 (s, 1H), 8.62-8.59 (t, J = 6.0 Hz, 1H), 7.31-7.27 (t, J = 8.4 Hz, 4H), 7.23-7.18 (m, 3H), 6.73-6.71 (d, J = 8.4 Hz, 1H), 4.82-4.80 (m, 1H), 4.39-4.27 (m, 2H), 3.49-3.46 (m, 1H), 3.38-3.33 (m, 1H), 2.90 (s, 3H) | 342 |
| I-12 | 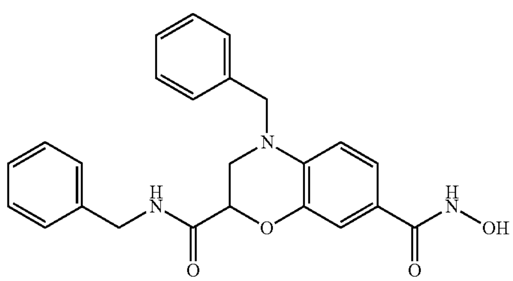 [SMILES: O=C(NO)c1ccc2c(c1)OC(C(=O)NCc1ccccc1)CN2Cc1ccccc1] | N$^{2,4}$-dibenzyl-N$^7$-hydroxy-3,4-dihydro-2H-benzo[b][1,4]oxazine-2,7-dicarboxamide | (DMSO, 400 MHz, ppm): 10.89 (s, 1H), 8.76 (s, 1H), 8.64 (s, 1H), 7.34-7.20 (m, 8H), 7.19-7.17 (m, 4H), 6.68-6.66 (d, J = 8.8 Hz, 1H), 4.83-4.81 (m, 1H), 4.55 (s, 2H), 4.37-4.30 (m, 2H), 3.63-3.60 (t, J = 6.2 Hz, 1H), 3.53-3.48 (m, 1H) | 417 |

Example 13—N-hydroxy-1-(1-(2-methoxyethyl)-1H-benzo[d]imidazol-2-yl)-1,2,3,4-tetrahydroquinoline-5-carboxamide (I-13)

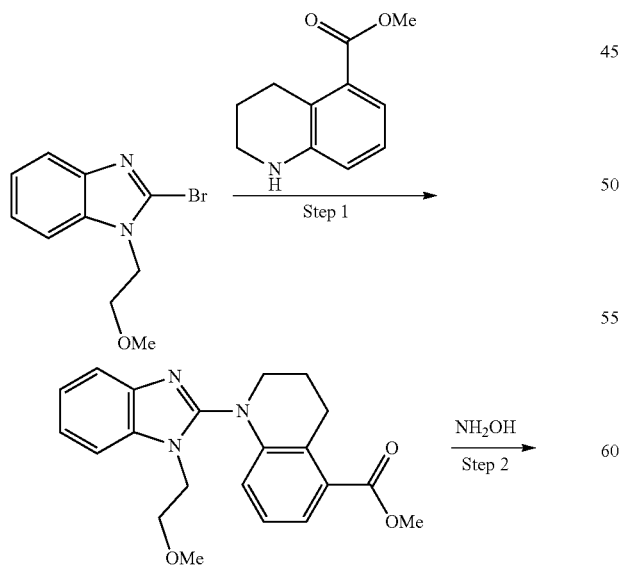

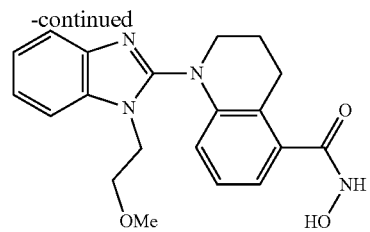

Step-1: Methyl 1-(1-(2-methoxyethyl)-1H-benzo[d]imidazol-2-yl)-1,2,3,4-tetrahydroquinoline-5-carboxylate A 10-mL microwave vial was equipped with stir bar and 2-bromo-1-(2-methoxyethyl)-1H-benzo[d]imidazole (0.050 g, 0.196 mmol), methyl 1,2,3,4-tetrahydroquinoline-5-carboxylate (0.075 g, 0.392 mmol), and concentrated HCl (0.0060 mL, 0.20 mmol) were combined in 2-propanol (2 mL). The resulting mixture was heated to 150° C. in the microwave for 2 hours. The reaction mixture was concentrated under vacuum to afford methyl 1-(1-(2-methoxyethyl)-1H-benzo[d]imidazol-2-yl)-1,2,3,4-tetrahydroquinoline-5-carboxylate (0.0152 g, 22%) as a yellow oil. MS (ESI, m/z): 366 [M+H]$^+$.

Step-2: N-hydroxy-1-(1-(2-methoxyethyl)-1H-benzo[d]imidazol-2-yl)-1,2,3,4-tetrahydroquinoline-5-carboxamide Methyl 1-(1-(2-methoxyethyl)-1H-benzo[d]imidazol-2-yl)-1,2,3,4-tetrahydroquinoline-5-carboxylate (0.0152 g, 0.041 mmol) was dissolved in tetrahydrofuran (1 mL) and methanol (0.25 mL). Hydroxylamine (0.112 g, 1.195 mmol, 50% in water), and aqueous sodium hydroxide solution (1 M, 0.239 mL) were added. The resulting solution stirred for 2 hours at room temperature. The crude product was purified by Prep-HPLC with the following conditions: Column Waters RP-HPLC XBridge Prep C18 5 uM OBD 19×50 mm; Mobile Phase A: Water/0.05% Formic Acid, Mobile Phase B: ACN/0.05% Formic Acid B: ACN; Flow rate: 23 mL/min; Gradient: 25% B to 65% B in 6.6 min, hold 0.9 min; 220 nm and 254 nm. The collected fractions were dried under vacuum to afford N-hydroxy-1-(1-(2-methoxyethyl)-1H-benzo[d]imidazol-2-yl)-1,2,3,4-tetrahydroquinoline-5-carboxamide (0.0025 g, 17%). MS (ESI, m/z): 367 [M+H]$^+$.

Example 14—1-(1H-1,3-benzodiazol-2-yl)-N-hydroxy-1,2,3,4-tetrahydroquinoline-5-carboxamide (I-14)

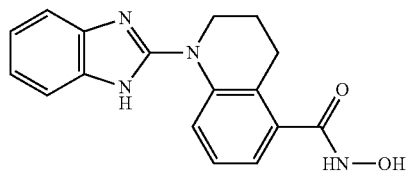 [SMILES: O=C(NO)c1cccc2c1CCCN2c1nc2ccccc2[nH]1]

1-(1H-1,3-benzodiazol-2-yl)-N-hydroxy-1,2,3,4-tetrahydroquinoline-5-carboxamide was synthesized according to the procedures outlined above for N-hydroxy-1-(1-(2-methoxyethyl)-1H-benzo[d]imidazol-2-yl)-1,2,3,4-tetrahydroquinoline-5-carboxamide (I-13; Example 13). MS (ESI, m/z): 309 [M+H]$^+$.

Example 15—N-hydroxy-4-(3-((trifluoromethyl)sulfonyl)benzyl)-3,4-dihydro-2H-benzo[b][1,4]thiazine-6-carboxamide-1,1-dioxide (I-15)

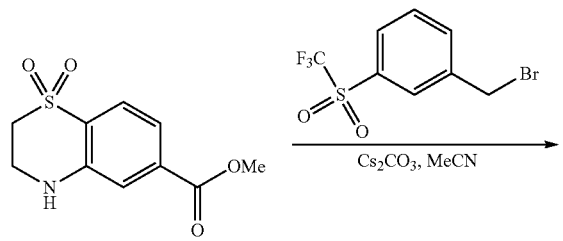

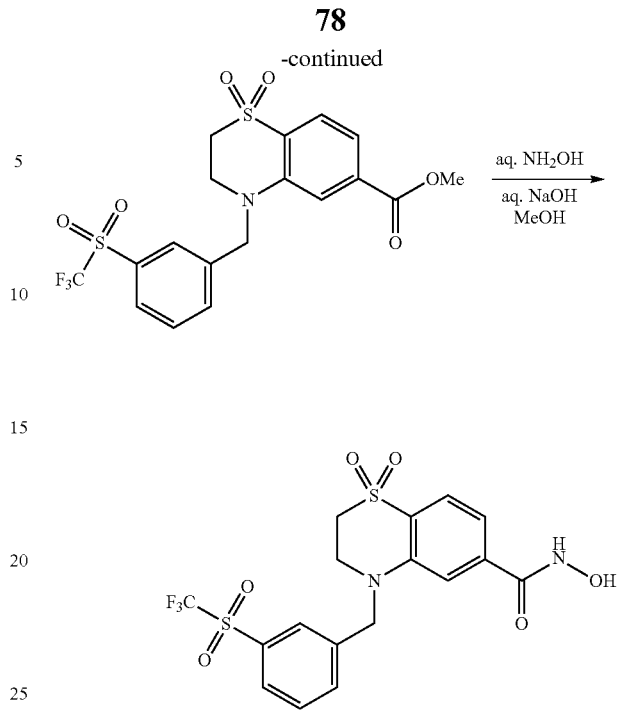

A 2 mL vial was charged methyl-3,4-dihydro-2H-benzo[b][1,4]thiazine-6-carboxylate-1,1-dioxide (0.2 M in acetonitrile, 150 µL, 30 µmol) and cesium carbonate (39 mg, 120 µmol). A solution of 1-(bromomethyl)-3-((trifluoromethyl)sulfonyl)benzene (0.2 M in acetonitrile, 300 µL, 60 mmol) was added, and the vial was sealed and shaken at 50° C. for 72 h. The solvent was removed under a stream of nitrogen. The residue was diluted with brine (500 µL) and extracted with ethyl acetate (2×500 ML). The combined organic layers were dried under a stream of nitrogen, and a solution of THF/methanol (3:1, 200 µL) was added to the residue. The vial was sealed and shaken at 50° C. for 15 minutes to dissolve the residue, then cooled to room temperature. Hydroxylamine (150 µL, 50% v/v solution in water) was added, followed by 1 N aqueous sodium hydroxide solution (100 ML). The mixture was sealed and then shaken at room temperature for 18 h. The reaction mixture was concentrated under a stream of nitrogen at room temperature, then dissolved in 500 µL of DMSO and purified by mass triggered preparative HPLC (Column: Waters Sunfire C18, 5 µm, 19×50 mm; Mobile Phase: water (0.1% formic acid) and acetonitrile (0.1% formic acid) (15% to 100% acetonitrile in 6 min; flow rate: 23 mL/min); Detector: UV 254/220 nm). The product-containing fractions were combined and concentrated in a Genevac to afford N-hydroxy-4-(3-((trifluoromethyl)sulfonyl)benzyl)-3,4-dihydro-2H-benzo[b][1,4]thiazine-6-carboxamide-1,1-dioxide (3.5 mg, 25% yield). (ESI, m/z) 464.03 [M]$^+$.

The following compounds were synthesized according to the procedure outlined above for Example 15.

| Compd. No. | Structure | IUPAC Name | LC-MS [M + H]+ | HPLC RT (min) |
|---|---|---|---|---|
| I-16 | 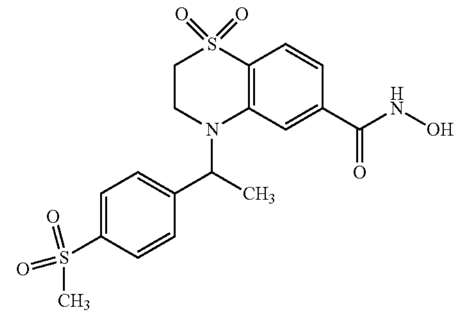 [SMILES: CC(c1ccc(S(C)(=O)=O)cc1)N1CCS(=O)(=O)c2ccc(C(=O)NO)cc21] | N-hydroxy-4-(1-(4-(methylsulfonyl)phenyl)ethyl)-3,4-dihydro-2H-benzo[b][1,4]thiazine-6-carboxamide-1,1-dioxide | 425 | 1.05 |
| I-17 | 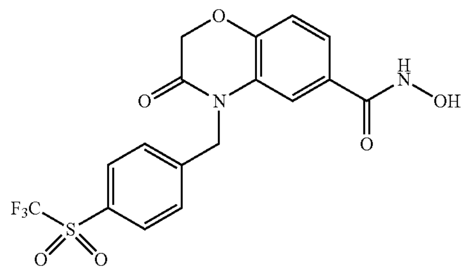 [SMILES: O=C(NO)c1ccc2c(c1)N(Cc1ccc(S(=O)(=O)C(F)(F)F)cc1)C(=O)CO2] | N-hydroxy-3-oxo-4-(4-((trifluoromethyl)sulfonyl)benzyl)-3,4-dihydro-2H-benzo[b][1,4]oxazine-6-carboxamide | 431 | 1.13 |
| I-18 | 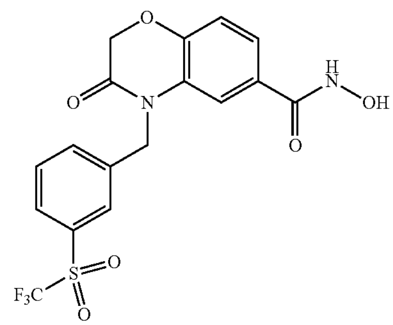 [SMILES: O=C(NO)c1ccc2c(c1)N(Cc1cccc(S(=O)(=O)C(F)(F)F)c1)C(=O)CO2] | N-hydroxy-3-oxo-4-(3-((trifluoromethyl)sulfonyl)benzyl)-3,4-dihydro-2H-benzo[b][1,4]oxazine-6-carboxamide | 431 | 1.11 |

Example 16—N-hydroxy-4-(4-(trifluoromethoxy)benzyl)-3,4-dihydro-2H-benzo[b][1,4]oxazine-6-carboxamide (I-19)

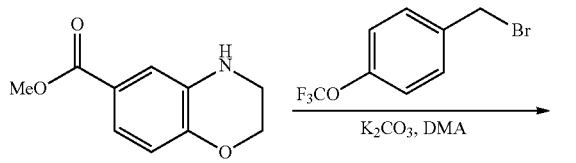

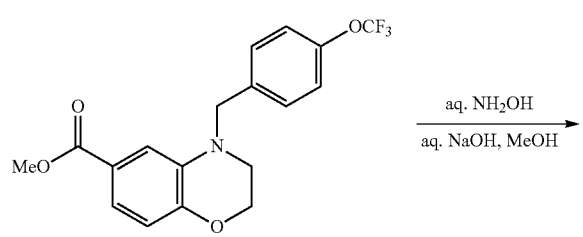

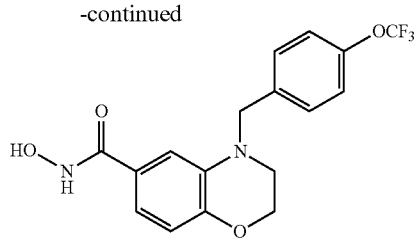

A half-dram vial was charged with methyl 3,4-dihydro-2H-benzo[b][1,4]oxazine-6-carboxylate (0.2 M in N,N-dimethylacetamide, 150 μL, 30 μmol) and potassium carbonate (20.7 mg, 150 μmol). Then a solution of 1-(bromomethyl)-4-(trifluoromethoxy)benzene (0.2 M in N,N-dimethylacetamide, 400 μL, 80 μmol) was added. The system was sealed and shaken at 50° C. for 16 h, and then the solvent was removed under a stream of nitrogen. The residue was diluted with ethyl acetate (0.6 mL) and brine (0.5 mL), and the mixture was shaken. The organic layer was separated, and the aqueous phase was extracted with ethyl acetate (0.6 mL). The combined organic layers were dried under a stream of nitrogen. THF/methanol (3:1, 200 μL) was added to the residue. The vial was sealed and shaken at 50°

C. for 15 min to dissolve the residue, then cooled to room temperature. Hydroxylamine (150 μL, 50% v/v solution in water) was added, followed by 1 N aqueous sodium hydroxide solution (100 μL). The mixture was sealed and then shaken at room temperature for 16 h. The reaction mixture was concentrated under a stream of nitrogen at room temperature, then dissolved in 500 μL of DMSO, and purified by mass triggered preparative HPLC (Column: Waters Sunfire C18, 5 μm, 19×50 mm; Mobile Phase: water (0.1% formic acid) and acetonitrile (0.1% formic acid) (15% to 100% acetonitrile in 6 min; flow rate: 23 mL/min); Detector: UV 254/220 nm). The product-containing fractions were combined and concentrated in a Genevac to afford N-hydroxy-4-(4-(trifluoromethoxy)benzyl)-3,4-dihydro-2H-benzo[b][1,4]oxazine-6-carboxamide (6.7 mg, 60.6%). (ES, m/z) 369 [M+H]$^+$, LC-MS R$_t$ 1.35 min.

The following compounds were synthesized according to the above protocol of Example 16.

| Compd. No. | Structure | IUPAC Name | LC-MS [M + H]$^+$ | HPLC RT (min) |
|---|---|---|---|---|
| I-20 | 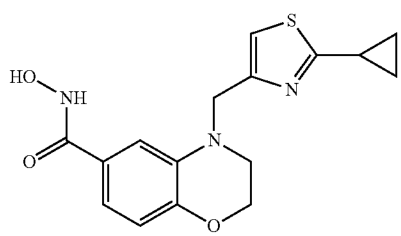 [SMILES: O=C(NO)c1ccc2c(c1)N(Cc1csc(C3CC3)n1)CCO2] | 4-((2-cyclopropylthiazol-4-yl)methyl)-N-hydroxy-3,4-dihydro-2H-benzo[b][1,4]oxazine-6-carboxamide | 332 | 1.00 |
| I-21 | 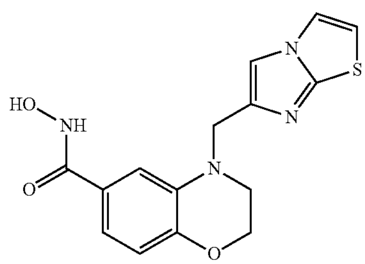 [SMILES: O=C(NO)c1ccc2c(c1)N(Cc1cn3ccsc3n1)CCO2] | N-hydroxy-4-(imidazo[2,1-b]thiazol-6-ylmethyl)-3,4-dihydro-2H-benzo[b][1,4]oxazine-6-carboxamide | 331 | 0.63 |
| I-22 | 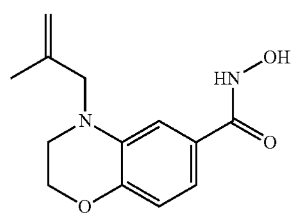 [SMILES: C=C(C)CN1CCOc2ccc(C(=O)NO)cc21] | N-hydroxy-4-(2-methylallyl)-3,4-dihydro-2H-benzo[b][1,4]oxazine-6-carboxamide | 249 | 0.98 |
| I-23 | 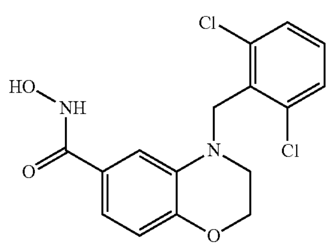 [SMILES: O=C(NO)c1ccc2c(c1)N(Cc1c(Cl)cccc1Cl)CCO2] | 4-(2,6-dichlorobenzyl)-N-hydroxy-3,4-dihydro-2H-benzo[b][1,4]oxazine-6-carboxamide | 353 | 1.27 |
| I-24 | 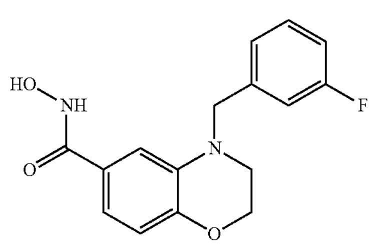 [SMILES: O=C(NO)c1ccc2c(c1)N(Cc1cccc(F)c1)CCO2] | 4-(3-fluorobenzyl)-N-hydroxy-3,4-dihydro-2H-benzo[b][1,4]oxazine-6-carboxamide | 303 | 1.11 |

-continued

| Compd. No. | Structure | IUPAC Name | LC-MS [M + H]+ | HPLC RT (min) |
|---|---|---|---|---|
| I-25 | 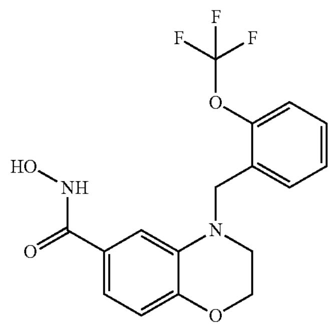 [SMILES: O=C(NO)c1ccc2c(c1)N(Cc1ccccc1OC(F)(F)F)CCO2] | N-hydroxy-4-(2-(trifluoromethoxy)benzyl)-3,4-dihydro-2H-benzo[b][1,4]oxazine-6-carboxamide | 369 | 1.31 |
| I-26 | 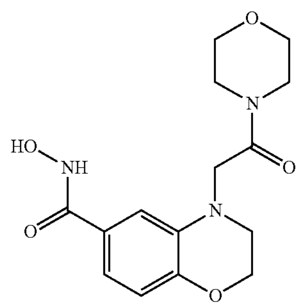 [SMILES: O=C(NO)c1ccc2c(c1)N(CC(=O)N1CCOCC1)CCO2] | N-hydroxy-4-(2-morpholino-2-oxoethyl)-3,4-dihydro-2H-benzo[b][1,4]oxazine-6-carboxamide | 322 | 0.58 |
| I-27 | 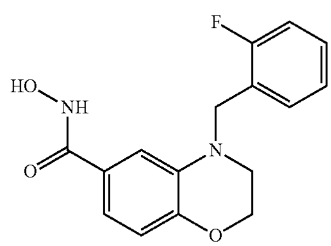 [SMILES: O=C(NO)c1ccc2c(c1)N(Cc1ccccc1F)CCO2] | 4-(2-fluorobenzyl)-N-hydroxy-3,4-dihydro-2H-benzo[b][1,4]oxazine-6-carboxamide | 303 | 1.11 |
| I-28 | 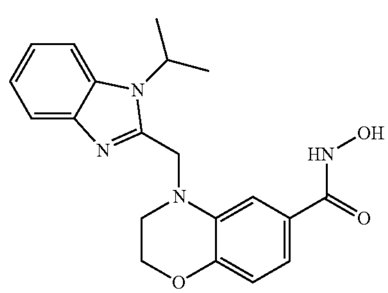 [SMILES: CC(C)n1c(CN2CCOc3ccc(C(=O)NO)cc32)nc2ccccc21] | N-hydroxy-4-((1-isopropyl-1H-benzo[d]imidazol-2-yl)methyl)-3,4-dihydro-2H-benzo[b][1,4]oxazine-6-carboxamide | 367 | 0.79 |
| I-29 | 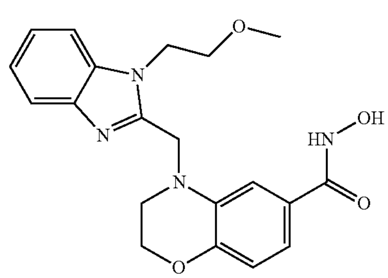 [SMILES: COCCn1c(CN2CCOc3ccc(C(=O)NO)cc32)nc2ccccc21] | N-hydroxy-4-((1-(2-methoxyethyl)-1H-benzo[d]imidazol-2-yl)methyl)-3,4-dihydro-2H-benzo[b][1,4]oxazine-6-carboxamide | 383 | 0.72 |

-continued

| Compd. No. | Structure | IUPAC Name | LC-MS [M + H]⁺ | HPLC RT (min) |
|---|---|---|---|---|
| I-30 | 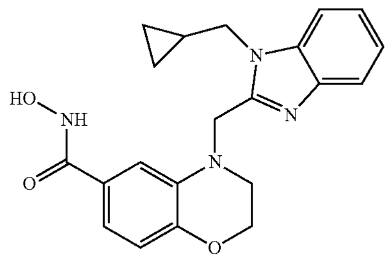 [SMILES: O=C(NO)c1ccc2c(c1)N(Cc1nc3ccccc3n1CC1CC1)CCO2] | 4-((1-(cyclopropylmethyl)-1H-benzo[d]imidazol-2-yl)methyl)-N-hydroxy-3,4-dihydro-2H-benzo[b][1,4]oxazine-6-carboxamide) | 379 | 0.84 |

Example 17—4-(cyclobutylmethyl)-N-hydroxy-3-oxo-3,4-dihydro-2H-benzo[b][1,4]oxazine-6-carboxamide (I-31)

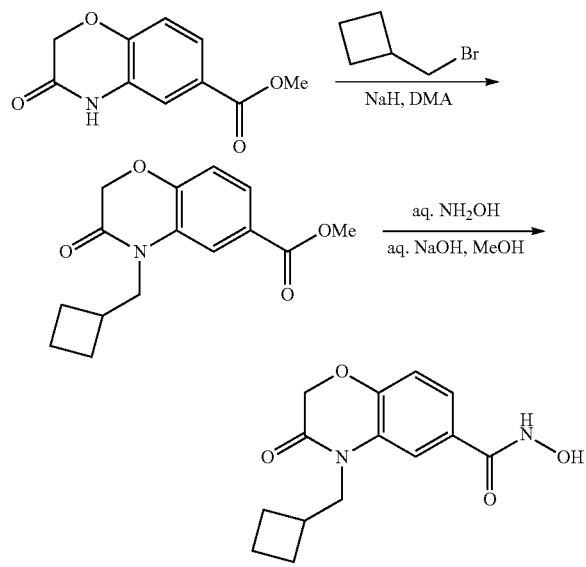

A half-dram vial was charged with methyl 3-oxo-3,4-dihydro-2H-benzo[b][1,4]oxazine-6-carboxylate (0.2 M in N,N-dimethylacetamide, 150 µL, 30 µmol) and sodium hydride (1.8 mg, 60% in mineral oil, 45 µmol), and the mixture was shaken for 10 minutes. A solution of (bromomethyl)cyclobutane (0.4 M in N,N-dimethylacetamide, 150 µL, 60 µmol) was added, and the system was sealed and shaken at room temperature for 16 h. The solvent was removed under a stream of nitrogen. The residue was diluted with ethyl acetate (0.6 mL) and brine (0.5 mL), and the mixture was shaken. The organic layer was separated and the aqueous phase was extracted with ethyl acetate (0.6 mL). The combined organic layers were dried under a stream of nitrogen. THF/methanol (3:1, 200 µL) was added to the residue. The vial was sealed and shaken at 50° C. for 15 minutes to dissolve the residue, then cooled to room temperature. Hydroxylamine (150 µL, 50% v/v solution in water) was added, followed by 1 N aqueous sodium hydroxide solution (100 µL). The mixture was sealed and then shaken at room temperature for 16 h. The reaction mixture was concentrated under a stream of nitrogen at room temperature, then dissolved in 500 µL of DMSO and purified by mass triggered preparative HPLC (Column: Waters Sunfire C18, 5 µm, 19×50 mm; Mobile Phase: water (0.1% formic acid) and acetonitrile (0.1% formic acid) (15% to 100% acetonitrile in 6 min; flow rate: 23 mL/min); Detector: UV 254/220 nm). The product-containing fractions were combined and concentrated in a Genevac to afford 4-(cyclobutylmethyl)-N-hydroxy-3-oxo-3,4-dihydro-2H-benzo[b][1,4]oxazine-6-carboxamide (1.0 mg, 12%). (ES, m/z) 277 [M+H]⁺, LC-MS $R_t$ 0.86 min.

The following compounds were synthesized according to the above protocol of Example 17.

| Compd. No. | Structure | IUPAC Name | LC-MS [M + H]⁺ | HPLC RT (min) |
|---|---|---|---|---|
| I-32 | 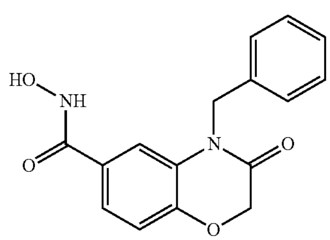 [SMILES: O=C(NO)c1ccc2c(c1)N(Cc1ccccc1)C(=O)CO2] | 4-benzyl-N-hydroxy-3-oxo-3,4-dihydro-2H-benzo[b][1,4]oxazine-6-carboxamide | 299 | 0.87 |

-continued

| Compd. No. | Structure | IUPAC Name | LC-MS [M + H]+ | HPLC RT (min) |
|---|---|---|---|---|
| I-33 | 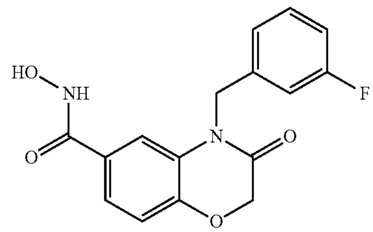 [SMILES: O=C(NO)c1ccc2c(c1)N(Cc1cccc(F)c1)C(=O)CO2] | 4-(3-fluorobenzyl)-N-hydroxy-3-oxo-3,4-dihydro-2H-benzo[b][1,4]oxazine-6-carboxamide | 317 | 0.91 |
| I-34 | 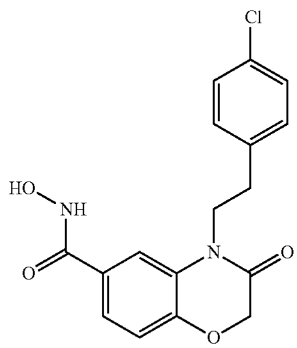 [SMILES: O=C(NO)c1ccc2c(c1)N(CCc1ccc(Cl)cc1)C(=O)CO2] | 4-(4-chlorophenethyl)-N-hydroxy-3-oxo-3,4-dihydro-2H-benzo[b][1,4]oxazine-6-carboxamide | 347 | 1.10 |
| I-35 | 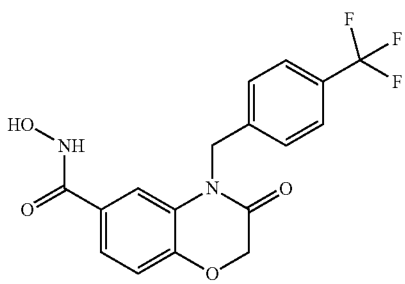 [SMILES: O=C(NO)c1ccc2c(c1)N(Cc1ccc(C(F)(F)F)cc1)C(=O)CO2] | N-hydroxy-3-oxo-4-(4-(trifluoromethyl)benzyl)-3,4-dihydro-2H-benzo[b][1,4]oxazine-6-carboxamide | 367 | 1.12 |
| I-36 | 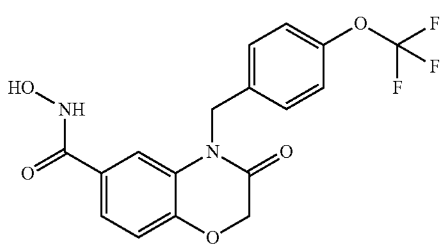 [SMILES: O=C(NO)c1ccc2c(c1)N(Cc1ccc(OC(F)(F)F)cc1)C(=O)CO2] | N-hydroxy-3-oxo-4-(4-(trifluoromethoxy)benzyl)-3,4-dihydro-2H-benzo[b][1,4]oxazine-6-carboxamide | 383 | 1.16 |
| I-37 | 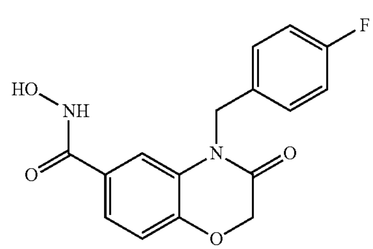 [SMILES: O=C(NO)c1ccc2c(c1)N(Cc1ccc(F)cc1)C(=O)CO2] | 4-(4-fluorobenzyl)-N-hydroxy-3-oxo-3,4-dihjydro-2H-benzo[b][1,4]oxazine-6-carboxamide | 317 | 0.92 |

-continued

| Compd. No. | Structure | IUPAC Name | LC-MS [M + H]⁺ | HPLC RT (min) |
|---|---|---|---|---|
| I-38 | 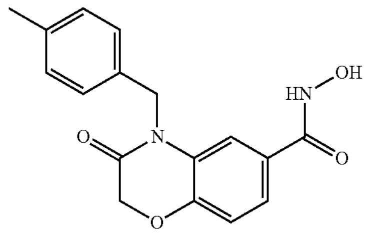 [SMILES: Cc1ccc(CN2C(=O)COc3ccc(C(=O)NO)cc32)cc1] | N-hydroxy-4-(4-methylbenzyl)-3-oxo-3,4-dihydro-2H-benzo[b][1,4]oxazine-6-carboxamide | 313 | 0.98 |
| I-39 | 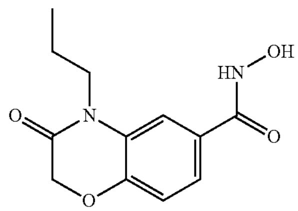 [SMILES: CCCN1C(=O)COc2ccc(C(=O)NO)cc21] | N-hydroxy-3-oxo-4-propyl-3,4-dihydro-2H-benzo[b][1,4]oxazine-6-carboxamide | 251 | 0.69 |
| I-40 | 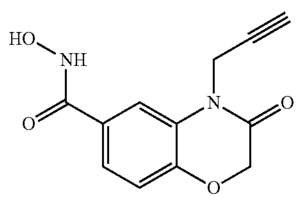 [SMILES: C#CCN1C(=O)COc2ccc(C(=O)NO)cc21] | N-hydroxy-3-oxo-4-(prop-2-yn-1-yl)-3,4-dihydro-2H-benzo[b][1,4]oxazine-6-carboxamide | 247 | 0.61 |
| I-41 | 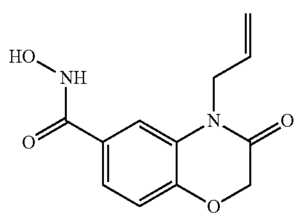 [SMILES: C=CCN1C(=O)COc2ccc(C(=O)NO)cc21] | 4-allyl-N-hydroxy-3-oxo-3,4-dihydro-2H-benzo[b][1,4]oxazine-6-carboxamide | 249 | 0.63 |
| I-42 | 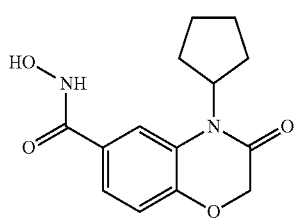 [SMILES: O=C(NO)c1ccc2c(c1)N(C1CCCC1)C(=O)CO2] | 4-cyclopentyl-N-hydroxy-3-oxo-3,4-dihydro-2H-benzo[b][1,4]oxazine-6-carboxamide | 277 | 0.85 |
| I-43 | 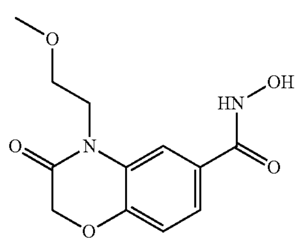 [SMILES: COCCN1C(=O)COc2ccc(C(=O)NO)cc21] | N-hydroxy-4-(2-methoxyethyl)-3-oxo-3,4-dihydro-2H-benzo[b][1,4]oxazine-6-carboxamide | 267 | 0.57 |

-continued

| Compd. No. | Structure | IUPAC Name | LC-MS [M + H]+ | HPLC RT (min) |
|---|---|---|---|---|
| I-44 | 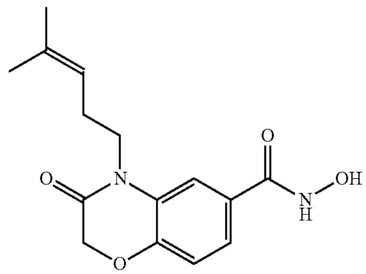 [SMILES: CC(C)=CCCN1C(=O)COc2ccc(C(=O)NO)cc21] | N-hydroxy-4-(4-methylpent-3-en-1-yl)-3-oxo-3,4-dihydro-2H-benzo[b][1,4]oxazine-6-carboxamide | 291 | 0.96 |
| I-45 | 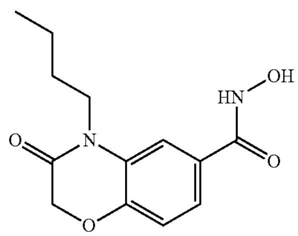 [SMILES: CCCCN1C(=O)COc2ccc(C(=O)NO)cc21] | 4-butyl-N-hydroxy-3-oxo-3,4-dihydro-2H-benzo[b][1,4]oxazine-6-carboxamide | 265 | 0.82 |
| I-46 | 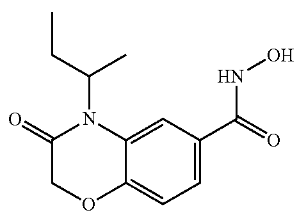 [SMILES: CCC(C)N1C(=O)COc2ccc(C(=O)NO)cc21] | 4-(sec-butyl)-N-hydroxy-3-oxo-3,4-dihydro-2H-benzo[b][1,4]oxazine-6-carboxamide | 265 | 0.79 |
| I-47 | 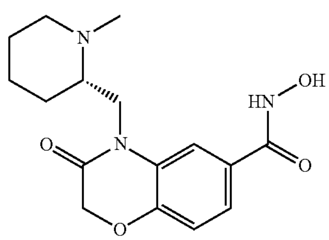 [SMILES: CN1CCCC[C@H]1CN1C(=O)COc2ccc(C(=O)NO)cc21] | N-hydroxy-4-((1-methylpiperidin-2-yl)methyl)-3-oxo-3,4-dihydro-2H-benzo[b][1,4]oxazine-6-carboxamide | 320 | 0.44 |
| I-48 | 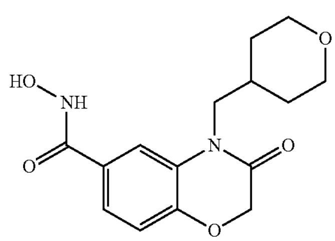 [SMILES: O=C(NO)c1ccc2c(c1)N(CC1CCOCC1)C(=O)CO2] | N-hydroxy-3-oxo-4-((tetrahydro-2H-pyran-4-yl)methyl)-3,4-dihydro-2H-benzo[b][1,4]oxazine-6-carboxamide | 307 | 0.64 |
| I-49 | 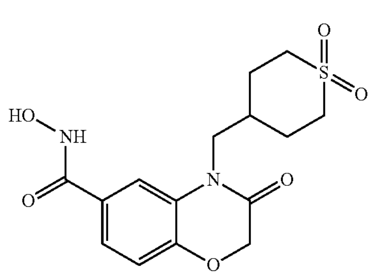 [SMILES: O=C(NO)c1ccc2c(c1)N(CC1CCS(=O)(=O)CC1)C(=O)CO2] | 4-((1,1-dioxidotetrahydro-2H-thiopyran-4-yl)methyl)-N-hydroxy-3-oxo-3,4-dihydro-2H-benzo[b][1,4]oxazine-6-carboxamide | 355 | 0.58 |

-continued

| Compd. No. | Structure | IUPAC Name | LC-MS [M + H]+ | HPLC RT (min) |
|---|---|---|---|---|
| I-50 | 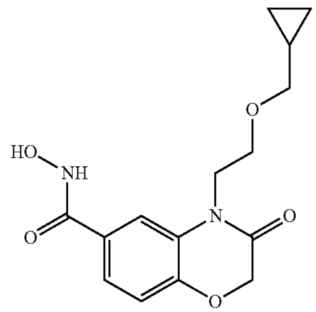 [SMILES: O=C(NO)c1ccc2c(c1)N(CCOCC1CC1)C(=O)CO2] | 4-(2-(cyclopropylmethoxy)ethyl)-N-hydroxy-3-oxo-3,4-dihydro-2H-benzo[b][1,4]oxazine-6-carboxamide | 307 | 0.79 |
| I-51 | 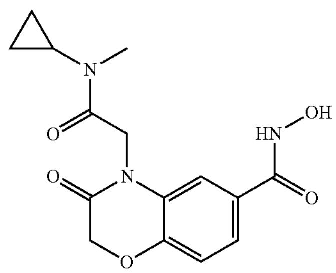 [SMILES: CN(C(=O)CN1C(=O)COc2ccc(C(=O)NO)cc21)C1CC1] | 4-(2-(cyclopropyl(methyl)amino)-2-oxoethyl)-N-hydroxy-3-oxo-3,4-dihydro-2H-benzo[b][1,4]oxazine-6-carboxamide | 320 | 0.62 |
| I-52 | 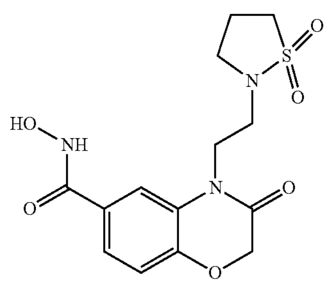 [SMILES: O=C(NO)c1ccc2c(c1)N(CCN1CCCS1(=O)=O)C(=O)CO2] | 4-(2-(1,1-dioxidoisothiazolidin-2-yl)ethyl)-N-hydroxy-3-oxo-3,4-dihydro-2H-benzo[b][1,4]oxazine-6-carboxamide | 356 | 0.56 |
| I-53 | 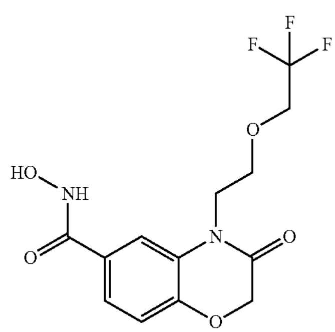 [SMILES: O=C(NO)c1ccc2c(c1)N(CCOCC(F)(F)F)C(=O)CO2] | N-hydroxy-3-oxo-4-(2-(2,2,2-trifluoroethoxy)ethyl)-3,4-dihydro-2H-benzo[b][1,4]oxazine-6-carboxamide | 335 | 0.81 |
| I-54 | 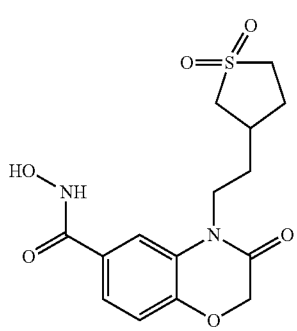 [SMILES: O=C(NO)c1ccc2c(c1)N(CCC1CCS(=O)(=O)C1)C(=O)CO2] | 4-(2-(1,1-dioxidotetrahydrothiophen-3-yl)ethyl)-N-hydroxy-3-oxo-3,4-dihydro-2H-benzo[b][1,4]oxazine-6-carboxamide | 355 | 0.61 |

-continued

| Compd. No. | Structure | IUPAC Name | LC-MS [M + H]⁺ | HPLC RT (min) |
|---|---|---|---|---|
| I-55 | 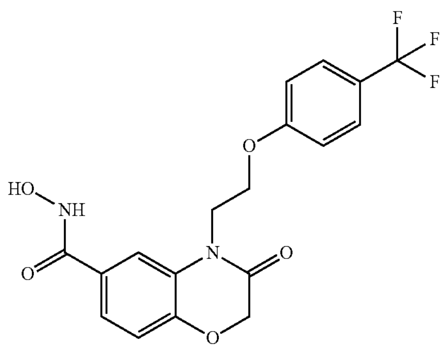 [SMILES: O=C(NO)c1ccc2c(c1)N(CCOc1ccc(C(F)(F)F)cc1)C(=O)CO2] | N-hydroxy-3-oxo-4-(2-(4-(trifluoromethyl)phenoxy)ethyl)-3,4-dihydro-2H-benzo[b][1,4]oxazine-6-carboxamide | 397 | 1.20 |
| I-56 | 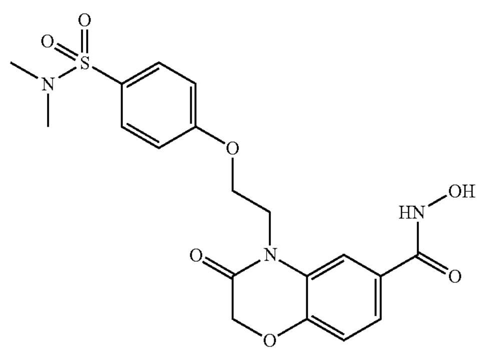 [SMILES: CN(C)S(=O)(=O)c1ccc(OCCN2C(=O)COc3ccc(C(=O)NO)cc32)cc1] | 4-(2-(4-(N,N-dimethylsulfamoyl)phenoxy)ethyl)-N-hydroxy-3-oxo-3,4-dihydro-2H-benzo[b][1,4]oxazine-6-carboxamide | 436 | 0.91 |
| I-57 | 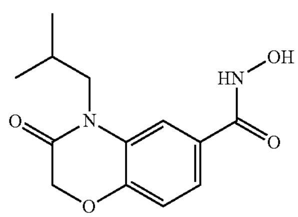 [SMILES: CC(C)CN1C(=O)COc2ccc(C(=O)NO)cc21] | N-hydroxy-4-isobutyl-3-oxo-3,4-dihydro-2H-benzo[b][1,4]oxazine-6-carboxamide | 265 | 0.80 |
| I-58 | 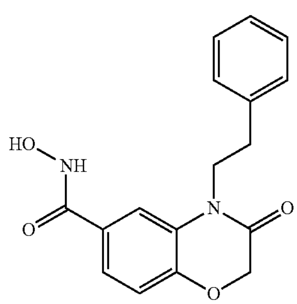 [SMILES: O=C(NO)c1ccc2c(c1)N(CCc1ccccc1)C(=O)CO2] | N-hydroxy-3-oxo-4-phenethyl-3,4-dihydro-2H-benzo[b][1,4]oxazine-6-carboxamide | 313 | 0.94 |
| I-59 | 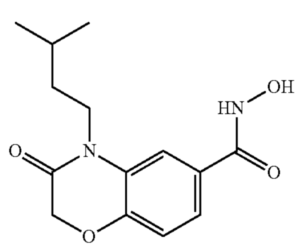 [SMILES: CC(C)CCN1C(=O)COc2ccc(C(=O)NO)cc21] | N-hydroxy-4-isopentyl-3-oxo-3,4-dihydro-2H-benzo[b][1,4]oxazine-6-carboxamide | 279 | 0.93 |

| Compd. No. | Structure | IUPAC Name | LC-MS [M + H]+ | HPLC RT (min) |
|---|---|---|---|---|
| I-60 | 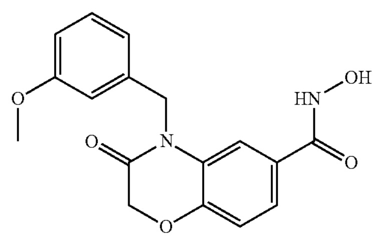 [SMILES: COc1cccc(CN2C(=O)COc3ccc(C(=O)NO)cc32)c1] | N-hydroxy-4-(3-methoxybenzyl)-3-oxo-3,4-dihydro-2H-benzo[b][1,4]oxazine-6-carboxamide | 329 | 0.89 |
| I-61 | 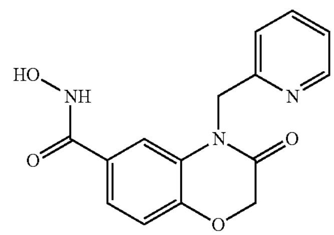 [SMILES: O=C(NO)c1ccc2c(c1)N(Cc1ccccn1)C(=O)CO2] | N-hydroxy-3-oxo-4-(pyridin-2-ylmethyl)-3,4-dihydro-2H-benzo[b][1,4]oxazine-6-carboxamide | 300 | 0.60 |
| I-62 | 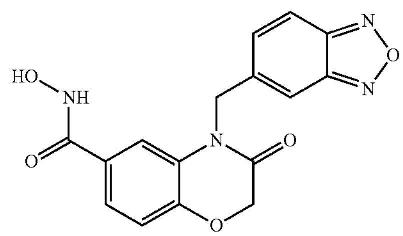 [SMILES: O=C(NO)c1ccc2c(c1)N(Cc1ccc3nonc3c1)C(=O)CO2] | 4-(benzo[c][1,2,5]oxadiazol-5-ylmethyl)-N-hydroxy-3-oxo-3,4-dihydro-2H-benzo[b][1,4]oxazine-6-carboxamide | 341 | 0.88 |
| I-63 | 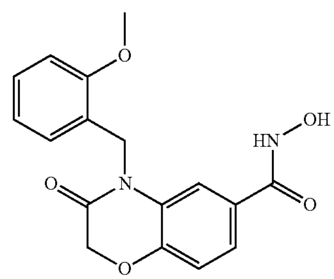 [SMILES: COc1ccccc1CN1C(=O)COc2ccc(C(=O)NO)cc21] | N-hydroxy-4-(2-methoxybenzyl)-3-oxo-3,4-dihydro-2H-benzo[b][1,4]oxazine-6-carboxamide | 329 | 0.92 |
| I-64 | 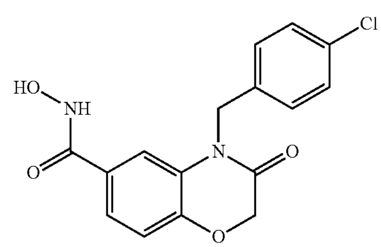 [SMILES: O=C(NO)c1ccc2c(c1)N(Cc1ccc(Cl)cc1)C(=O)CO2] | 4-(4-chlorobenzyl)-N-hydroxy-3-oxo-3,4-dihydro-2H-benzo[b][1,4]oxazine-6-carboxamide | 333 | 1.02 |
| I-65 | 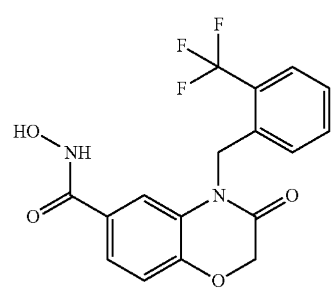 [SMILES: O=C(NO)c1ccc2c(c1)N(Cc1ccccc1C(F)(F)F)C(=O)CO2] | N-hydroxy-3-oxo-4-(2-(trifluoromethyl)benzyl)-3,4-dihydro-2H-benzo[b][1,4]oxazine-6-carboxamide | 367 | 1.06 |

-continued

| Compd. No. | Structure | IUPAC Name | LC-MS [M + H]+ | HPLC RT (min) |
|---|---|---|---|---|
| I-66 | 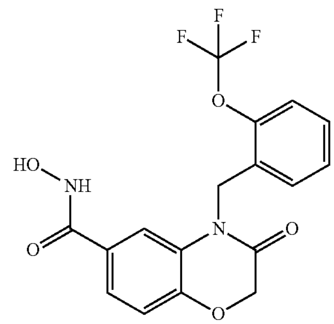 [SMILES: O=C(NO)c1ccc2c(c1)N(Cc1ccccc1OC(F)(F)F)C(=O)CO2] | N-hydroxy-3-oxo-4-(2-(trifluoromethoxy)benzyl)-3,4-dihydro-2H-benzo[b][1,4]oxazine-6-carboxamide | 383 | 1.10 |
| I-67 | 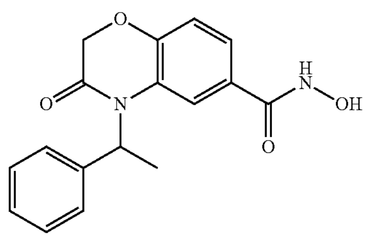 [SMILES: CC(c1ccccc1)N1C(=O)COc2ccc(C(=O)NO)cc21] | N-hydroxy-3-oxo-4-(1-phenylethyl)-3,4-dihydro-2H-benzo[b][1,4]oxazine-6-carboxamide | 313 | 0.93 |
| I-68 | 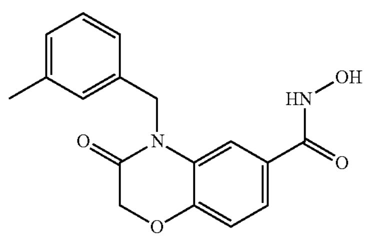 [SMILES: Cc1cccc(CN2C(=O)COc3ccc(C(=O)NO)cc32)c1] | N-hydroxy-4-(3-methylbenzyl)-3-oxo-3,4-dihydro-2H-benzo[b][1,4]oxazine-6-carboxamide | 313 | 0.97 |
| I-69 | 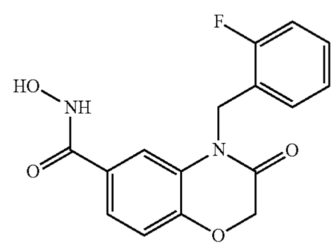 [SMILES: O=C(NO)c1ccc2c(c1)N(Cc1ccccc1F)C(=O)CO2] | 4-(2-fluorobenzyl)-N-hydroxy-3-oxo-3,4-dihydro-2H-benzo[b][1,4]oxazine-6-carboxamide | 317 | 0.89 |
| I-70 | 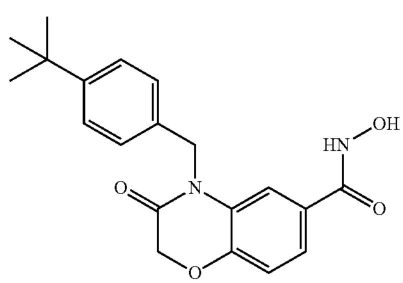 [SMILES: CC(C)(C)c1ccc(CN2C(=O)COc3ccc(C(=O)NO)cc32)cc1] | 4-(4-(tert-butyl)benzyl)-N-hydroxy-3-oxo-3,4-dihydro-2H-benzo[b][1,4]oxazine-6-carboxamide | 355 | 1.27 |
| I-71 | 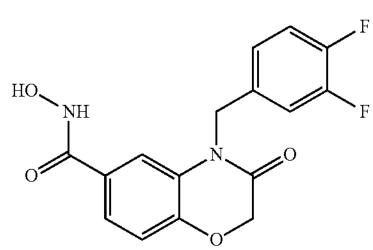 [SMILES: O=C(NO)c1ccc2c(c1)N(Cc1ccc(F)c(F)c1)C(=O)CO2] | 4-(3,4-difluorobenzyl)-N-hydroxy-3-oxo-3,4-dihydro-2H-benzo[b][1,4]oxazine-6-carboxamide | 335 | 0.97 |

-continued

| Compd. No. | Structure | IUPAC Name | LC-MS [M + H]+ | HPLC RT (min) |
|---|---|---|---|---|
| I-72 | 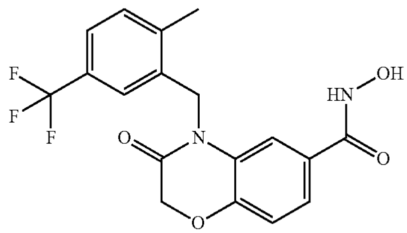 [SMILES: Cc1ccc(C(F)(F)F)cc1CN1C(=O)COc2ccc(C(=O)NO)cc21] | N-hydroxy-4-(2-methyl-5-(trifluoromethyl)benzyl)-3-oxo-3,4-dihydro-2H-benzo[b][1,4]oxazine-6-carboxamide | 380 | 1.14 |
| I-73 | 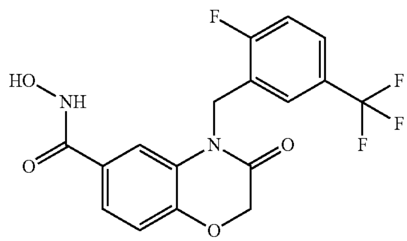 [SMILES: O=C(NO)c1ccc2c(c1)N(Cc1cc(C(F)(F)F)ccc1F)C(=O)CO2] | 4-(2-fluoro-5-(trifluoromethyl)benzyl)-N-hydroxy-3-oxo-3,4-dihydro-2H-benzo[b][1,4]oxazine-6-carboxamide | 385 | 1.10 |
| I-74 | 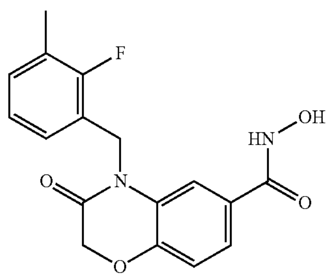 [SMILES: Cc1cccc(CN2C(=O)COc3ccc(C(=O)NO)cc32)c1F] | 4-(2-fluoro-3-methylbenzyl)-N-hydroxy-3-oxo-3,4-dihydro-2H-benzo[b][1,4]oxazine-6-carboxamide | 331 | 1.00 |
| I-75 | 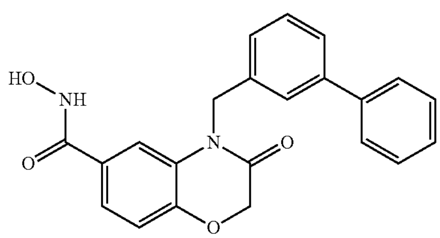 [SMILES: O=C(NO)c1ccc2c(c1)N(Cc1cccc(-c3ccccc3)c1)C(=O)CO2] | 4-([1,1'-biphenyl]-3-ylmethyl)-N-hydroxy-3-oxo-3,4-dihydro-2H-benzo[b][1,4]oxazine-6-carboxamide | 375 | 1.22 |
| I-76 | 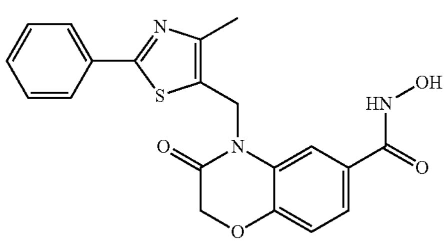 [SMILES: Cc1nc(-c2ccccc2)sc1CN1C(=O)COc2ccc(C(=O)NO)cc21] | N-hydroxy-4-((4-methyl-2-phenylthiazol-5-yl)methyl)-3-oxo-3,4-dihydro-2H-benzo[b][1,4]oxazine-6-carboxamide | 396 | 1.08 |
| I-77 | 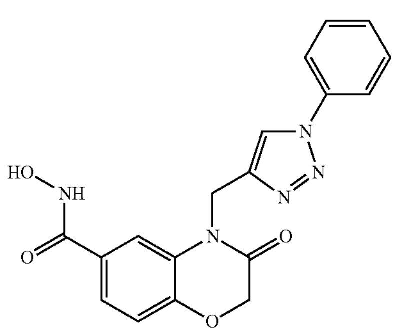 [SMILES: O=C(NO)c1ccc2c(c1)N(Cc1cn(-c3ccccc3)nn1)C(=O)CO2] | N-hydroxy-3-oxo-4-[(1-phenyl-1H-1,2,3-triazol-4-yl)methyl]-3,4-dihydro-2H-1,4-benzoxazine-6-carboxamide | 366 | 0.88 |

| Compd. No. | Structure | IUPAC Name | LC-MS [M + H]+ | HPLC RT (min) |
|---|---|---|---|---|
| I-214 | 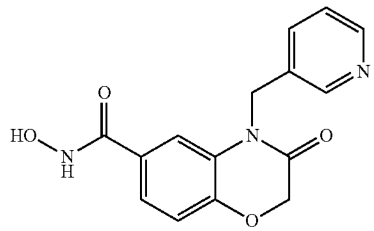 [SMILES: O=C(NO)c1ccc2c(c1)N(Cc1cccnc1)C(=O)CO2] | N-hydroxy-3-oxo-4-(pyridin-3-ylmethyl)-3,4-dihydro-2H-benzo[b][1,4]oxazine-6-carboxamide | 300 | 0.31 |
| I-215 | 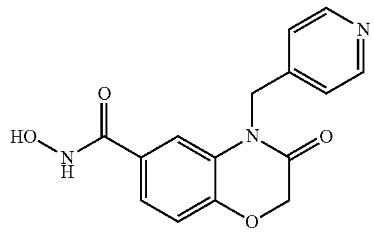 [SMILES: O=C(NO)c1ccc2c(c1)N(Cc1ccncc1)C(=O)CO2] | N-hydroxy-3-oxo-4-(pyridin-4-ylmethyl)-3,4-dihydro-2H-benzo[b][1,4]oxazine-6-carboxamide | 300 | 0.29 |
| I-216 | 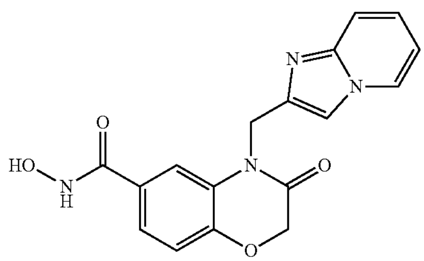 [SMILES: O=C(NO)c1ccc2c(c1)N(Cc1cn3ccccc3n1)C(=O)CO2] | N-hydroxy-4-(imidazo[1,2-a]pyridin-2-ylmethyl)-3-oxo-3,4-dihydro-2H-benzo[b][1,4]oxazine-6-carboxamide | 339 | 0.31 |
| I-217 | 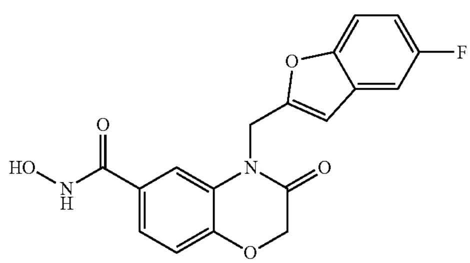 [SMILES: O=C(NO)c1ccc2c(c1)N(Cc1cc3cc(F)ccc3o1)C(=O)CO2] | 4-((5-fluorobenzo[d]oxazol-2-yl)methyl)-N-hydroxy-3-oxo-3,4-dihydro-2H-benzo[b][1,4]oxazine-6-carboxamide | 358 | 0.96 |
| I-218 | 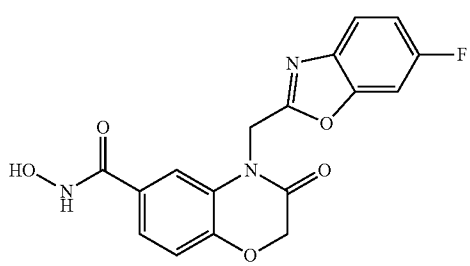 [SMILES: O=C(NO)c1ccc2c(c1)N(Cc1nc3ccc(F)cc3o1)C(=O)CO2] | 4-((6-fluorobenzo[d]oxazol-2-yl)methyl)-N-hydroxy-3-oxo-3,4-dihydro-2H-benzo[b][1,4]oxazine-6-carboxamide | 358 | 0.93 |
| I-219 | 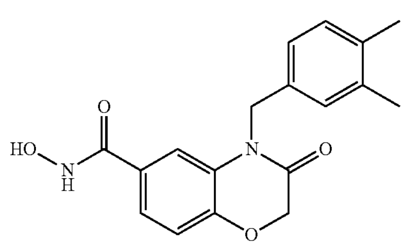 [SMILES: Cc1ccc(CN2C(=O)COc3ccc(C(=O)NO)cc32)cc1C] | 4-(3,4-dimethylbenzyl)-N-hydroxy-3-oxo-3,4-dihydro-2H-benzo[b][1,4]oxazine-6-carboxamide | 327 | 1.11 |

| Compd. No. | Structure | IUPAC Name | LC-MS [M + H]+ | HPLC RT (min) |
|---|---|---|---|---|
| I-220 | 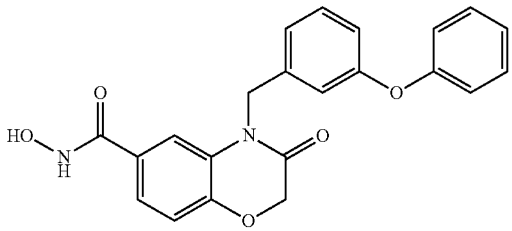 [SMILES: O=C(NO)c1ccc2c(c1)N(Cc1cccc(Oc3ccccc3)c1)C(=O)CO2] | N-hydroxy-3-oxo-4-(3-phenoxybenzyl)-3,4-dihydro-2H-benzo[b][1,4]oxazine-6-carboxamide | 391 | 1.26 |
| I-221 | 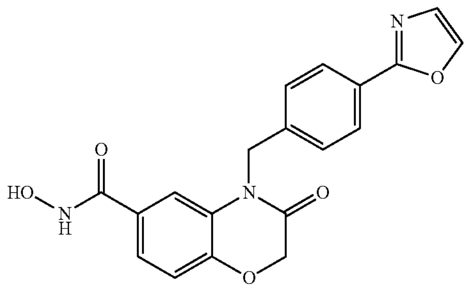 [SMILES: O=C(NO)c1ccc2c(c1)N(Cc1ccc(-c3ncco3)cc1)C(=O)CO2] | N-hydroxy-4-(4-(oxazol-2-yl)benzyl)-3-oxo-3,4-dihydro-2H-benzo[b][1,4]oxazine-6-carboxamide | 366 | 0.91 |
| I-222 | 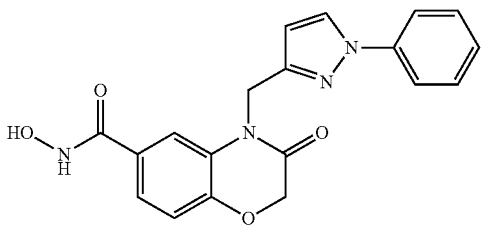 [SMILES: O=C(NO)c1ccc2c(c1)N(Cc1ccn(-c3ccccc3)n1)C(=O)CO2] | N-hydroxy-3-oxo-4-((1-phenyl-1H-pyrazol-3-yl)methyl)-3,4-dihydro-2H-benzo[b][1,4]oxazine-6-carboxamide | 365 | 1.01 |
| I-223 | 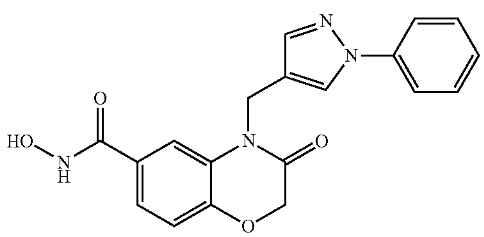 [SMILES: O=C(NO)c1ccc2c(c1)N(Cc1cnn(-c3ccccc3)c1)C(=O)CO2] | N-hydroxy-3-oxo-4-((1-phenyl-1H-pyrazol-4-yl)methyl)-3,4-dihydro-2H-benzo[b][1,4]oxazine-6-carboxamide | 365 | 0.97 |
| I-224 | 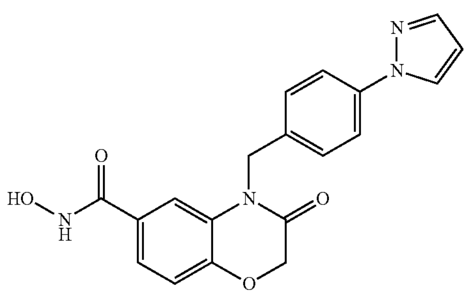 [SMILES: O=C(NO)c1ccc2c(c1)N(Cc1ccc(-n3cccn3)cc1)C(=O)CO2] | 4-(4-(1H-pyrazol-1-yl)benzyl)-N-hydroxy-3-oxo-3,4-dihydro-2H-benzo[b][1,4]oxazine-6-carboxamide | 365 | 0.92 |
| I-225 | 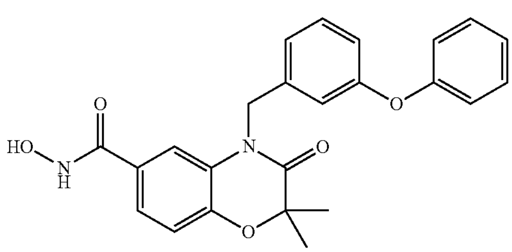 [SMILES: CC1(C)Oc2ccc(C(=O)NO)cc2N(Cc2cccc(Oc3ccccc3)c2)C1=O] | N-hydroxy-2,2-dimethyl-3-oxo-4-(3-phenoxybenzyl)-3,4-dihydro-2H-benzo[b][1,4]oxazine-6-carboxamide | 419 | 1.43 |

| Compd. No. | Structure | IUPAC Name | LC-MS [M + H]⁺ | HPLC RT (min) |
|---|---|---|---|---|
| I-266 | 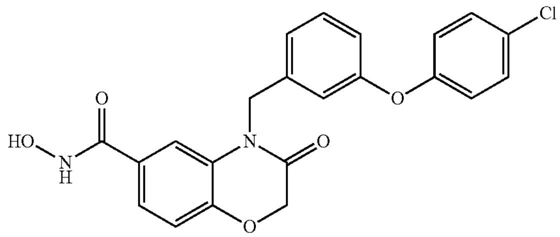 [SMILES: O=C(NO)c1ccc2c(c1)N(Cc1cccc(Oc3ccc(Cl)cc3)c1)C(=O)CO2] | 4-(3-(4-chlorophenoxy)benzyl)-N-hydroxy-3-oxo-3,4-dihydro-2H-benzo[b][1,4]oxazine-6-carboxamide | 425 | 1.40 |
| I-227 | 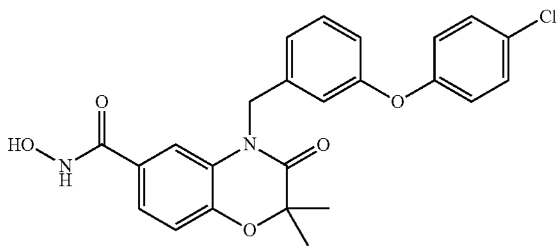 [SMILES: CC1(C)Oc2ccc(C(=O)NO)cc2N(Cc2cccc(Oc3ccc(Cl)cc3)c2)C1=O] | 4-(3-(4-chlorophenoxy)benzyl)-N-hydroxy-2,2-dimethyl-3-oxo-3,4-dihydro-2H-benzo[b][1,4]oxazine-6-carboxamide | 453 | 1.57 |
| I-228 | 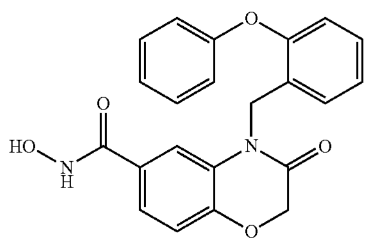 [SMILES: O=C(NO)c1ccc2c(c1)N(Cc1ccccc1Oc1ccccc1)C(=O)CO2] | N-hydroxy-3-oxo-4-(2-phenoxybenzyl)-3,4-dihydro-2H-benzo[b][1,4]oxazine-6-carboxamide | 391 | 1.25 |
| I-229 | 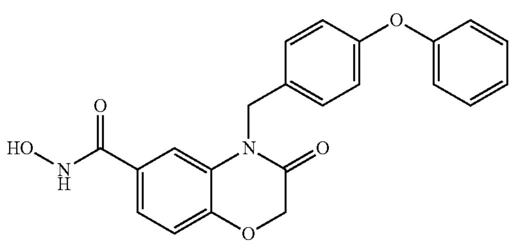 [SMILES: O=C(NO)c1ccc2c(c1)N(Cc1ccc(Oc3ccccc3)cc1)C(=O)CO2] | N-hydroxy-3-oxo-4-(4-phenoxybenzyl)-3,4-dihydro-2H-benzo[b][1,4]oxazine-6-carboxamide | 391 | 1.27 |
| I-230 | 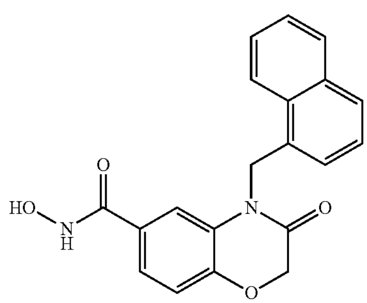 [SMILES: O=C(NO)c1ccc2c(c1)N(Cc1cccc3ccccc13)C(=O)CO2] | N-hydroxy-4-(naphthalen-1-ylmethyl)-3-oxo-3,4-dihydro-2H-benzo[b][1,4]oxazine-6-carboxamide | 349 | 1.11 |
| I-231 | 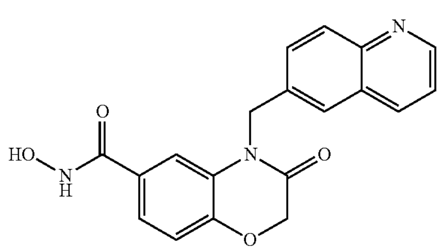 [SMILES: O=C(NO)c1ccc2c(c1)N(Cc1ccc3ncccc3c1)C(=O)CO2] | N-hydroxy-3-oxo-4-(quinolin-6-ylmethyl)-3,4-dihydro-2H-benzo[b][1,4]oxazine-6-carboxamide | 350 | 0.48 |

-continued

| Compd. No. | Structure | IUPAC Name | LC-MS [M + H]+ | HPLC RT (min) |
|---|---|---|---|---|
| I-232 | 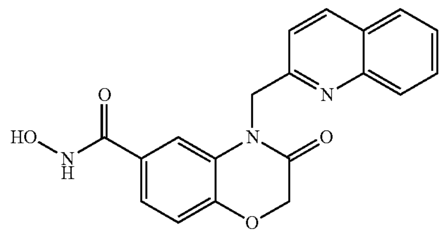 [SMILES: O=C(NO)c1ccc2c(c1)N(Cc1ccc3ccccc3n1)C(=O)CO2] | N-hydroxy-3-oxo-4-(quinolin-2-ylmethyl)-3,4-dihydro-2H-benzo[b][1,4]oxazine-6-carboxamide | 350 | 0.87 |
| I-233 | 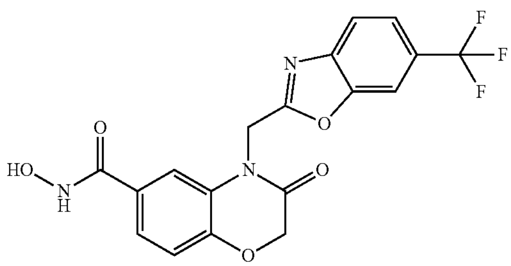 [SMILES: O=C(NO)c1ccc2c(c1)N(Cc1nc3ccc(C(F)(F)F)cc3o1)C(=O)CO2] | N-hydroxy-3-oxo-4-((6-(trifluoromethyl)benzo[d]oxazol-2-yl)methyl)-3,4-dihydro-2H-benzo[b][1,4]oxazine-6-carboxamide | 408 | 1.13 |
| I-234 | 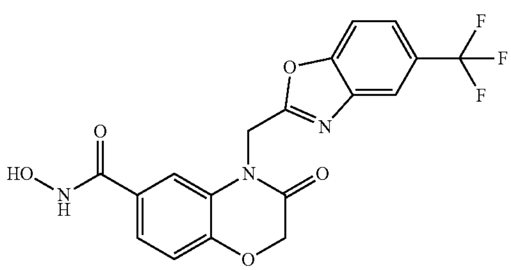 [SMILES: O=C(NO)c1ccc2c(c1)N(Cc1nc3cc(C(F)(F)F)ccc3o1)C(=O)CO2] | N-hydroxy-3-oxo-4-((5-(trifluoromethyl)benzo[d]oxazol-2-yl)methyl)-3,4-dihydro-2H-benzo[b][1,4]oxazine-6-carboxamide | 408 | 1.12 |
| I-235 | 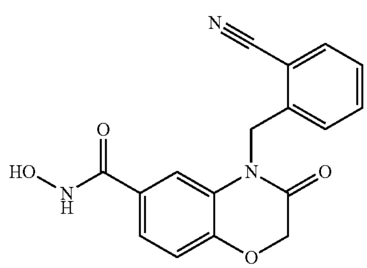 [SMILES: N#Cc1ccccc1CN1C(=O)COc2ccc(C(=O)NO)cc21] | 4-(2-cyanobenzyl)-N-hydroxy-3-oxo-3,4-dihydro-2H-benzo[b][1,4]oxazine-6-carboxamide | 324 | 0.85 |
| I-236 | 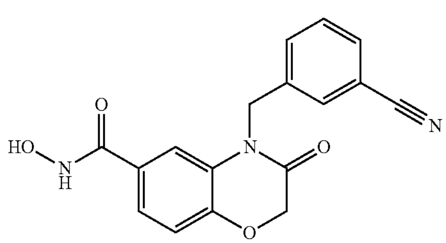 [SMILES: N#Cc1cccc(CN2C(=O)COc3ccc(C(=O)NO)cc32)c1] | 4-(3-cyanobenzyl)-N-hydroxy-3-oxo-3,4-dihydro-2H-benzo[b][1,4]oxazine-6-carboxamide | 324 | 0.86 |
| I-237 | 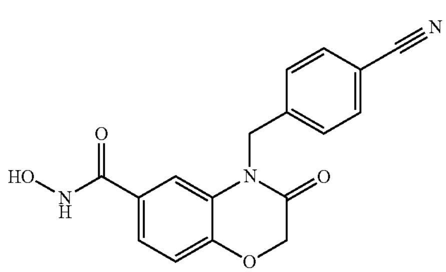 [SMILES: N#Cc1ccc(CN2C(=O)COc3ccc(C(=O)NO)cc32)cc1] | 4-(4-cyanobenzyl)-N-hydroxy-3-oxo-3,4-dihydro-2H-benzo[b][1,4]oxazine-6-carboxamide | 324 | 0.87 |

| Compd. No. | Structure | IUPAC Name | LC-MS [M + H]+ | HPLC RT (min) |
|---|---|---|---|---|
| I-238 | 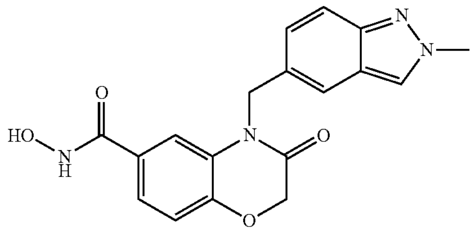 [SMILES: Cn1cc2cc(CN3C(=O)COc4ccc(C(=O)NO)cc43)ccc2n1] | N-hydroxy-4-((2-methyl-2H-indazol-5-yl)methyl)-3-oxo-3,4-dihydro-2H-benzo[b][1,4]oxazine-6-carboxamide | 353 | .074 |
| I-239 | 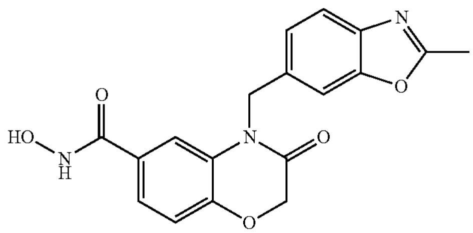 [SMILES: Cc1nc2ccc(CN3C(=O)COc4ccc(C(=O)NO)cc43)cc2o1] | N-hydroxy-4-((2-methylbenzo[d]oxazol-6-yl)methyl)-3-oxo-3,4-dihydro-2H-benzo[b][1,4]oxazine-6-carboxamide | 354 | 0.82 |
| I-240 | 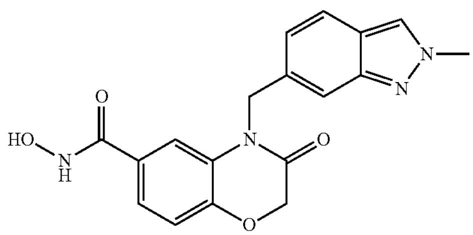 [SMILES: Cn1cc2ccc(CN3C(=O)COc4ccc(C(=O)NO)cc43)cc2n1] | N-hydroxy-4-((2-methyl-2H-indazol-6-yl)methyl)-3-oxo-3,4-dihydro-2H-benzo[b][1,4]oxazine-6-carboxamide | 353 | 0.77 |
| I-241 | 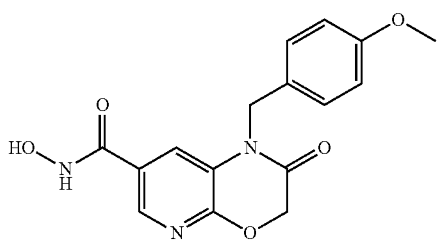 [SMILES: COc1ccc(CN2C(=O)COc3ncc(C(=O)NO)cc32)cc1] | N-hydroxy-1-(4-methoxybenzyl)-2-oxo-2,3-dihydro-1H-pyrido[2,3-b][1,4]oxazine-7-carboxamide | 330 | 0.79 |
| I-242 | 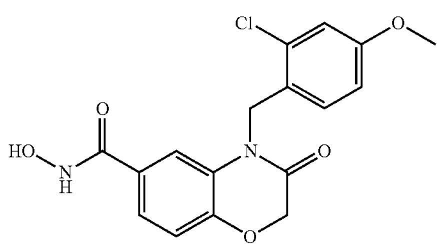 [SMILES: COc1ccc(CN2C(=O)COc3ccc(C(=O)NO)cc32)c(Cl)c1] | 4-(2-chloro-4-methoxybenzyl)-N-hydroxy-3-oxo-3,4-dihydro-2H-benzo[b][1,4]oxazine-6-carboxamide | 363 | 1.06 |
| I-243 | 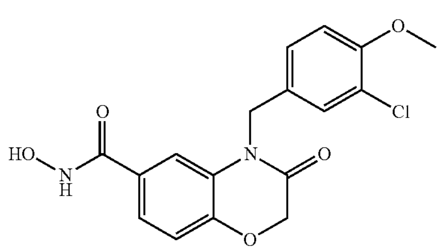 [SMILES: COc1ccc(CN2C(=O)COc3ccc(C(=O)NO)cc32)cc1Cl] | 4-(3-chloro-4-methoxybenzyl)-N-hydroxy-3-oxo-3,4-dihydro-2H-benzo[b][1,4]oxazine-6-carboxamide | 363 | 1.04 |

-continued

| Compd. No. | Structure | IUPAC Name | LC-MS [M + H]+ | HPLC RT (min) |
|---|---|---|---|---|
| I-244 | 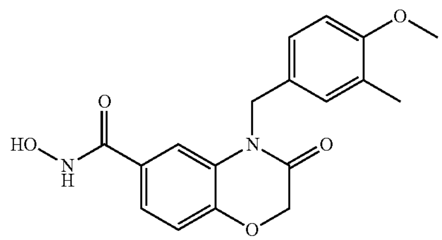 [SMILES: COc1ccc(CN2C(=O)COc3ccc(C(=O)NO)cc32)cc1C] | N-hydroxy-4-(4-methoxy-3-methylbenzyl)-3-oxo-3,4-dihydro-2H-benzo[b][1,4]oxazine-6-carboxamide | 343 | 1.05 |
| I-245 | 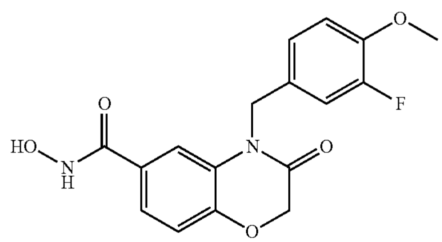 [SMILES: COc1ccc(CN2C(=O)COc3ccc(C(=O)NO)cc32)cc1F] | 4-(3-fluoro-4-methoxybenzyl)-N-hydroxy-3-oxo-3,4-dihydro-2H-benzo[b][1,4]oxazine-6-carboxamide | 347 | 0.97 |
| I-246 | 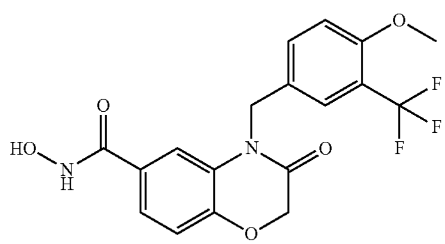 [SMILES: COc1ccc(CN2C(=O)COc3ccc(C(=O)NO)cc32)cc1C(F)(F)F] | N-hydroxy-4-(4-methoxy-3-(trifluoromethyl)benzyl)-3-oxo-3,4-dihydro-2H-benzo[b][1,4]oxazine-6-carboxamide | 397 | 1.15 |
| I-247 | 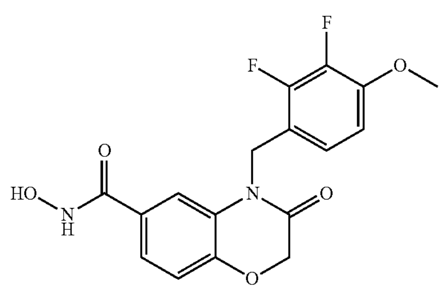 [SMILES: COc1ccc(CN2C(=O)COc3ccc(C(=O)NO)cc32)c(F)c1F] | 4-(2,3-difluoro-4-methoxybenzyl)-N-hydroxy-3-oxo-3,4-dihydro-2H-benzo[b][1,4]oxazine-6-carboxamide | 365 | 1.02 |
| I-248 | 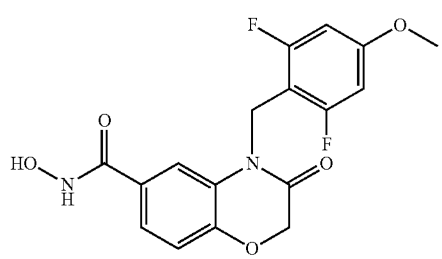 [SMILES: COc1cc(F)c(CN2C(=O)COc3ccc(C(=O)NO)cc32)c(F)c1] | 4-(2,6-difluoro-4-methoxybenzyl)-N-hydroxy-3-oxo-3,4-dihydro-2H-benzo[b][1,4]oxazine-6-carboxamide | 365 | 1.00 |
| I-249 | 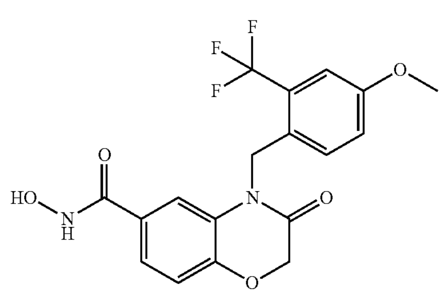 [SMILES: COc1ccc(CN2C(=O)COc3ccc(C(=O)NO)cc32)c(C(F)(F)F)c1] | N-hydroxy-4-(4-methoxy-2-(trifluoromethyl)benzyl)-3-oxo-3,4-dihydro-2H-benzo[b][1,4]oxazine-6-carboxamide | 397 | 1.16 |

-continued

| Compd. No. | Structure | IUPAC Name | LC-MS [M + H]+ | HPLC RT (min) |
|---|---|---|---|---|
| I-250 | 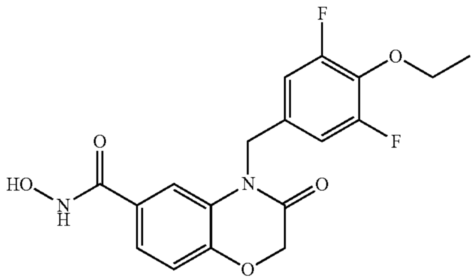 [SMILES: CCOc1c(F)cc(CN2C(=O)COc3ccc(C(=O)NO)cc32)cc1F] | 4-(4-ethoxy-3,5-difluorobenzyl)-N-hydroxy-3-oxo-3,4-dihydro-2H-benzo[b][1,4]oxazine-6-carboxamide | 379 | 1.14 |
| I-251 | 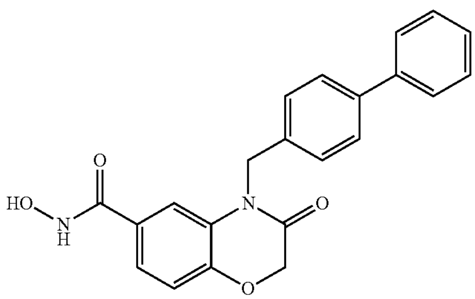 [SMILES: O=C(NO)c1ccc2c(c1)N(Cc1ccc(-c3ccccc3)cc1)C(=O)CO2] | 4-([1,1'-biphenyl]-4-ylmethyl)-N-hydroxy-3-oxo-3,4-dihydro-2H-benzo[b][1,4]oxazine-6-carboxamide | 375 | 1.27 |
| I-252 | 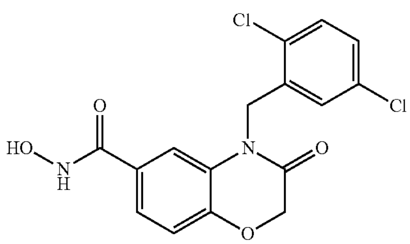 [SMILES: O=C(NO)c1ccc2c(c1)N(Cc1cc(Cl)ccc1Cl)C(=O)CO2] | 4-(2,5-dichlorobenzyl)-N-hydroxy-3-oxo-3,4-dihydro-2H-benzo[b][1,4]oxazine-6-carboxamide | 367 | 1.13 |
| I-253 | 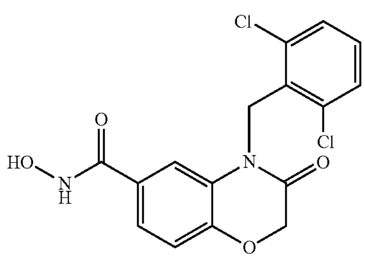 | 4-(2,6-dichlorobenzyl)-N-hydroxy-3-oxo-3,4-dihydro-2H-benzo[b][1,4]oxazine-6-carboxamide | 367 | 1.04 |
| I-254 | 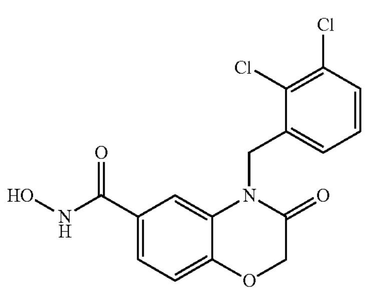 [SMILES: O=C(NO)c1ccc2c(c1)N(Cc1cccc(Cl)c1Cl)C(=O)CO2] | 4-(2,3-dichlorobenzyl)-N-hydroxy-3-oxo-3,4-dihydro-2H-benzo[b][1,4]oxazine-6-carboxamide | 367 | 1.15 |

-continued

| Compd. No. | Structure | IUPAC Name | LC-MS [M + H]+ | HPLC RT (min) |
|---|---|---|---|---|
| I-255 | 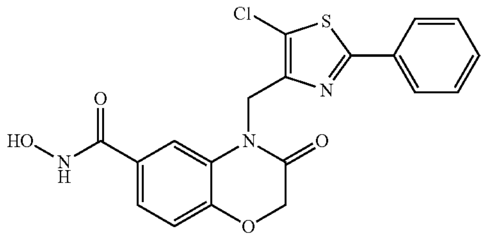 [SMILES: O=C(NO)c1ccc2c(c1)N(Cc1nc(-c3ccccc3)sc1Cl)C(=O)CO2] | 4-((5-chloro-2-phenylthiazol-4-yl)methyl)-N-hydroxy-3-oxo-3,4-dihydro-2H-benzo[b][1,4]oxazine-6-carboxamide | 416 | 1.27 |
| I-256 | 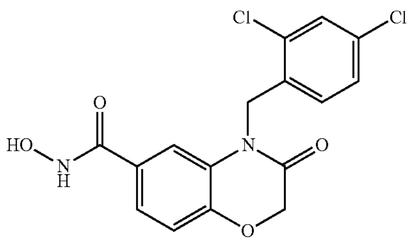 [SMILES: O=C(NO)c1ccc2c(c1)N(Cc1ccc(Cl)cc1Cl)C(=O)CO2] | 4-(2,4-dichlorobenzyl)-N-hydroxy-3-oxo-3,4-dihydro-2H-benzo[b][1,4]oxazine-6-carboxamide | 367 | 1.17 |
| I-257 | 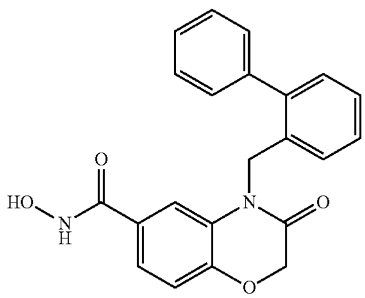 [SMILES: O=C(NO)c1ccc2c(c1)N(Cc1ccccc1-c1ccccc1)C(=O)CO2] | 4-([1,1'-biphenyl]-2-ylmethyl)-N-hydroxy-3-oxo-3,4-dihydro-2H-benzo[b][1,4]oxazine-6-carboxamide | 375 | 1.23 |
| I-258 | 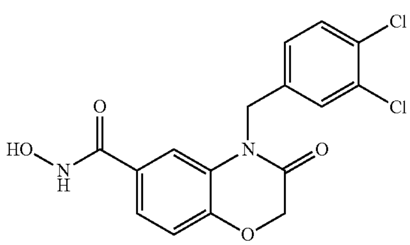 [SMILES: O=C(NO)c1ccc2c(c1)N(Cc1ccc(Cl)c(Cl)c1)C(=O)CO2] | 4-(3,4-dichlorobenzyl)-N-hydroxy-3-oxo-3,4-dihydro-2H-benzo[b][1,4]oxazine-6-carboxamide | 367 | 1.18 |
| I-259 | 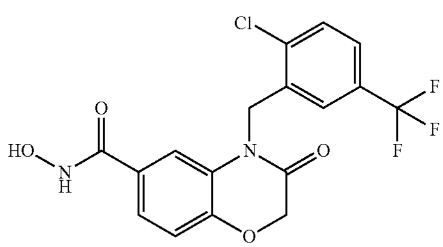 [SMILES: O=C(NO)c1ccc2c(c1)N(Cc1cc(C(F)(F)F)ccc1Cl)C(=O)CO2] | 4-(2-chloro-5-(trifluoromethyl)benzyl)-N-hydroxy-3-oxo-3,4-dihydro-2H-benzo[b][1,4]oxazine-6-carboxamide | 401 | 1.21 |
| I-260 | 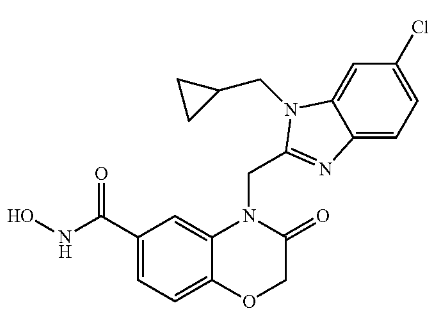 [SMILES: O=C(NO)c1ccc2c(c1)N(Cc1nc3ccc(Cl)cc3n1CC1CC1)C(=O)CO2] | 4-((6-chloro-1-(cyclopropylmethyl)-1H-benzo[d]imidazol-2-yl)methyl)-N-hydroxy-3-oxo-3,4-dihydro-2H-benzo[b][1,4]oxazine-6-carboxamide | 427 | 1.13 |

-continued

| Compd. No. | Structure | IUPAC Name | LC-MS [M + H]+ | HPLC RT (min) |
|---|---|---|---|---|
| I-261 | 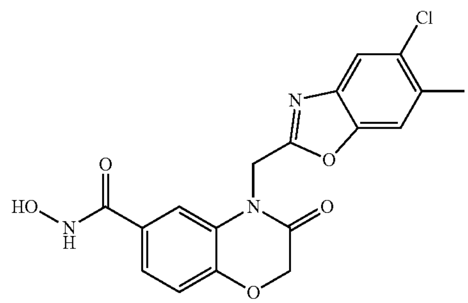 [SMILES: Cc1cc2oc(CN3C(=O)COc4ccc(C(=O)NO)cc43)nc2cc1Cl] | 4-((5-chloro-6-methylbenzo[d]oxazol-2-yl)methyl)-N-hydroxy-3-oxo-3,4-dihydro-2H-benzo[b][1,4]oxazine-6-carboxamide | 388 | 1.13 |
| I-262 | 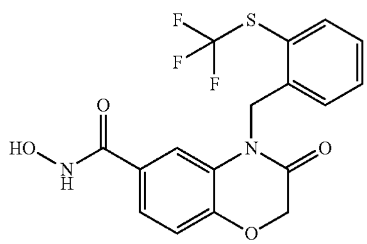 [SMILES: O=C(NO)c1ccc2c(c1)N(Cc1ccccc1SC(F)(F)F)C(=O)CO2] | N-hydroxy-3-oxo-4-(2-((trifluoromethyl)thio)benzyl)-3,4-dihydro-2H-benzo[b][1,4]oxazine-6-carboxamide | 399 | 1.22 |
| I-263 | 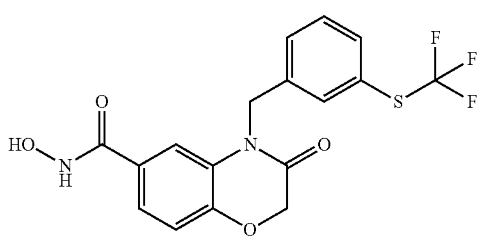 [SMILES: O=C(NO)c1ccc2c(c1)N(Cc1cccc(SC(F)(F)F)c1)C(=O)CO2] | N-hydroxy-3-oxo-4-(3-((trifluoromethyl)thio)benzyl)-3,4-dihydro-2H-benzo[b][1,4]oxazine-6-carboxamide | 399 | 1.25 |
| I-264 | 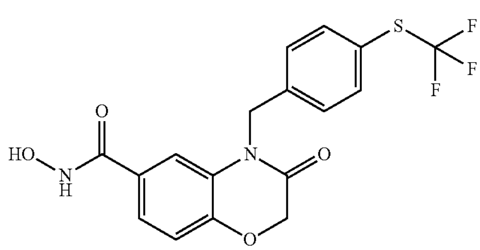 [SMILES: O=C(NO)c1ccc2c(c1)N(Cc1ccc(SC(F)(F)F)cc1)C(=O)CO2] | N-hydroxy-3-oxo-4-(4-((trifluoromethyl)thio)benzyl)-3,4-dihydro-2H-benzo[b][1,4]oxazine-6-carboxamide | 399 | 1.28 |
| I-265 | 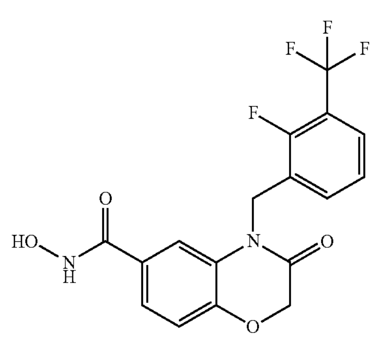 | 4-(2-fluoro-3-(trifluoromethyl)benzyl)-N-hydroxy-3-oxo-3,4-dihydro-2H-benzo[b][1,4]oxazine-6-carboxamide | 385 | 1.16 |

-continued

| Compd. No. | Structure | IUPAC Name | LC-MS [M + H]+ | HPLC RT (min) |
|---|---|---|---|---|
| I-266 | 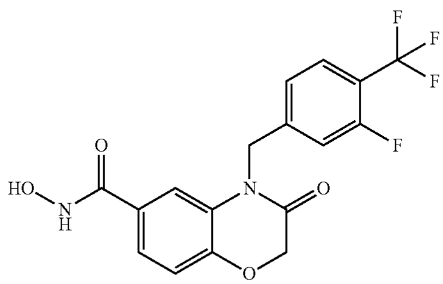 [SMILES: O=C(NO)c1ccc2c(c1)N(Cc1ccc(C(F)(F)F)c(F)c1)C(=O)CO2] | 4-(3-fluoro-4-(trifluoromethyl)benzyl)-N-hydroxy-3-oxo-3,4-dihydro-2H-benzo[b][1,4]oxazine-6-carboxamide | 385 | 1.19 |
| I-267 | 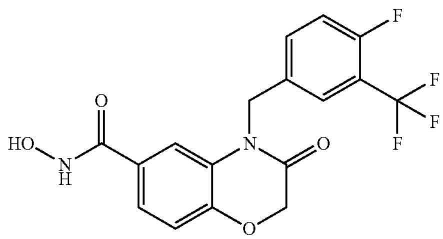 [SMILES: O=C(NO)c1ccc2c(c1)N(Cc1ccc(F)c(C(F)(F)F)c1)C(=O)CO2] | 4-(4-fluoro-3-(trifluoromethyl)benzyl)-N-hydroxy-3-oxo-3,4-dihydro-2H-benzo[b][1,4]oxazine-6-carboxamide | 385 | 1.17 |
| I-268 | 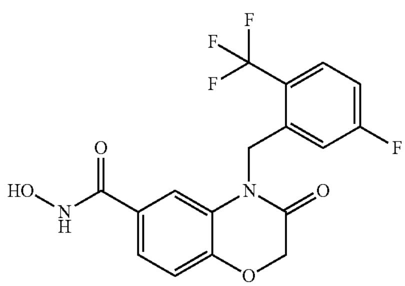 [SMILES: O=C(NO)c1ccc2c(c1)N(Cc1cc(F)ccc1C(F)(F)F)C(=O)CO2] | 4-(5-fluoro-2-(trifluoromethyl)benzyl)-N-hydroxy-3-oxo-3,4-dihydro-2H-benzo[b][1,4]oxazine-6-carboxamide | 385 | 1.14 |
| I-269 | 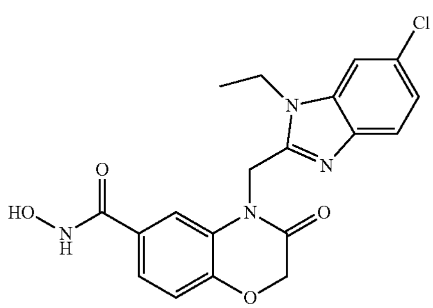 [SMILES: CCn1c(CN2C(=O)COc3ccc(C(=O)NO)cc32)nc2ccc(Cl)cc21] | 4-((6-chloro-1-ethyl-1H-benzo[d]imidazol-2-yl)methyl)-N-hydroxy-3-oxo-3,4-dihydro-2H-benzo[b][1,4]oxazine-6-carboxamide | 401 | 1.02 |
| I-270 | 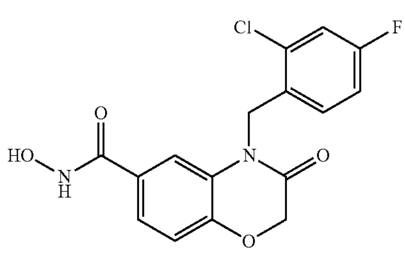 [SMILES: O=C(NO)c1ccc2c(c1)N(Cc1ccc(F)cc1Cl)C(=O)CO2] | 4-(2-chloro-4-fluorobenzyl)-N-hydroxy-3-oxo-3,4-dihydro-2H-benzo[b][1,4]oxazine-6-carboxamide | 351 | 1.06 |

-continued

| Compd. No. | Structure | IUPAC Name | LC-MS [M + H]+ | HPLC RT (min) |
|---|---|---|---|---|
| I-271 | 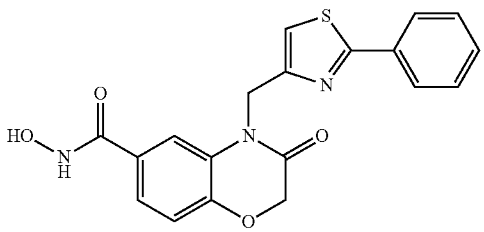 [SMILES: O=C(NO)c1ccc2c(c1)N(Cc1csc(-c3ccccc3)n1)C(=O)CO2] | N-hydroxy-3-oxo-4-((2-phenylthiazol-4-yl)methyl)-3,4-dihydro-2H-benzo[b][1,4]oxazine-6-carboxamide | 382 | 1.13 |
| I-272 | 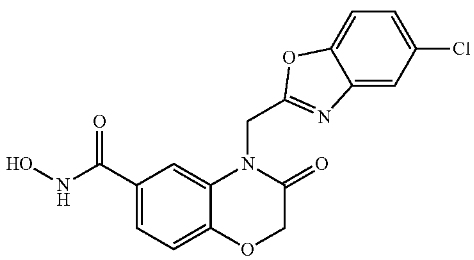 | 4-((5-chlorobenzo[d]oxazol-2-yl)methyl)-N-hydroxy-3-oxo-3,4-dihydro-2H-benzo[b][1,4]oxazine-6-carboxamide | 374 | 1.04 |
| I-273 | 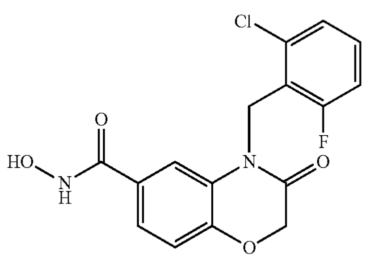 [SMILES: O=C(NO)c1ccc2c(c1)N(Cc1c(F)cccc1Cl)C(=O)CO2] | 4-(2-chloro-6-fluorobenzyl)-N-hydroxy-3-oxo-3,4-dihydro-2H-benzo[b][1,4]oxazine-6-carboxamide | 351 | 0.98 |
| I-274 | 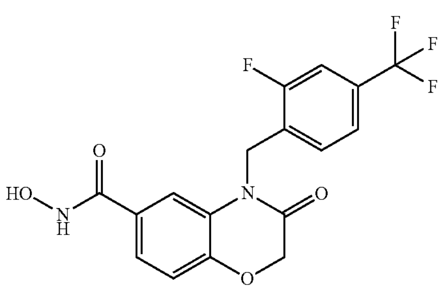 [SMILES: O=C(NO)c1ccc2c(c1)N(Cc1ccc(C(F)(F)F)cc1F)C(=O)CO2] | 4-(2-fluoro-4-(trifluoromethyl)benzyl)-N-hydroxy-3-oxo-3,4-dihydro-2H-benzo[b][1,4]oxazine-6-carboxamide | 385 | 1.18 |
| I-275 | 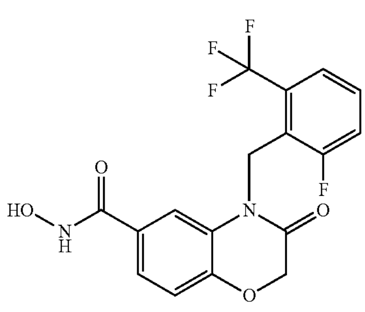 [SMILES: O=C(NO)c1ccc2c(c1)N(Cc1c(F)cccc1C(F)(F)F)C(=O)CO2] | 4-(2-fluoro-6-(trifluoromethyl)benzyl)-N-hydroxy-3-oxo-3,4-dihydro-2H-benzo[b][1,4]oxazine-6-carboxamide | 385 | 1.07 |

-continued

| Compd. No. | Structure | IUPAC Name | LC-MS [M + H]+ | HPLC RT (min) |
|---|---|---|---|---|
| I-276 | 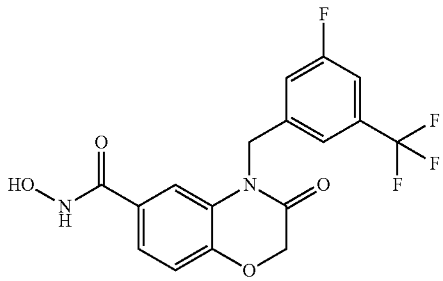 [SMILES: O=C(NO)c1ccc2c(c1)N(Cc1cc(F)cc(C(F)(F)F)c1)C(=O)CO2] | 4-(3-fluoro-5-(trifluoromethyl)benzyl)-N-hydroxy-3-oxo-3,4-dihydro-2H-benzo[b][1,4]oxazine-6-carboxamide | 385 | 1.19 |
| I-277 | 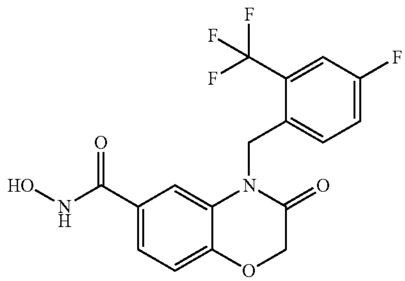 [SMILES: O=C(NO)c1ccc2c(c1)N(Cc1ccc(F)cc1C(F)(F)F)C(=O)CO2] | 4-(4-fluoro-2-(trifluoromethyl)benzyl)-N-hydroxy-3-oxo-3,4-dihydro-2H-benzo[b][1,4]oxazine-6-carboxamide | 385 | 1.15 |
| I-278 | 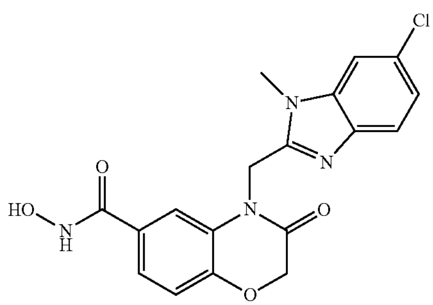 [SMILES: Cn1c(CN2C(=O)COc3ccc(C(=O)NO)cc32)nc2ccc(Cl)cc21] | 4-((6-chloro-1-methyl-1H-benzo[d]imidazol-2-yl)methyl)-N-hydroxy-3-oxo-3,4-dihydro-2H-benzo[b][1,4]oxazine-6-carboxamide | 387 | 0.91 |
| I-279 | 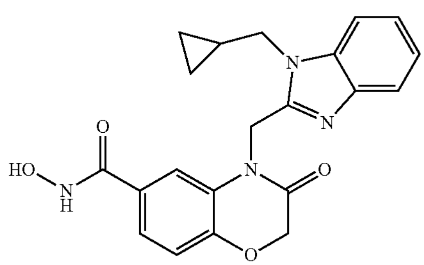 [SMILES: O=C(NO)c1ccc2c(c1)N(Cc1nc3ccccc3n1CC1CC1)C(=O)CO2] | 4-((1-(cyclopropylmethyl)-1H-benzo[d]imidazol-2-yl)methyl)-N-hydroxy-3-oxo-3,4-dihydro-2H-benzo[b][1,4]oxazine-6-carboxamide | 393 | 0.79 |
| I-280 | 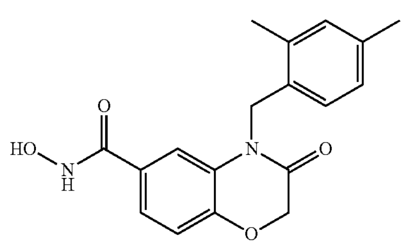 [SMILES: Cc1ccc(CN2C(=O)COc3ccc(C(=O)NO)cc32)c(C)c1] | 4-(2,4-dimethylbenzyl)-N-hydroxy-3-oxo-3,4-dihydro-2H-benzo[b][1,4]oxazine-6-carboxamide | 327 | 1.10 |

-continued

| Compd. No. | Structure | IUPAC Name | LC-MS [M + H]+ | HPLC RT (min) |
|---|---|---|---|---|
| I-281 | 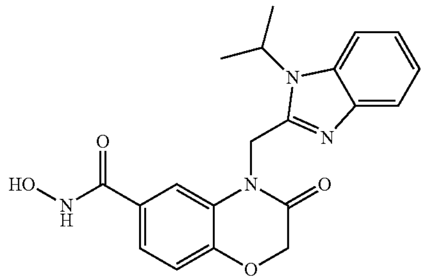 [SMILES: CC(C)n1c(CN2C(=O)COc3ccc(C(=O)NO)cc32)nc2ccccc21] | N-hydroxy-4-((1-isopropyl-1H-benzo[d]imidazol-2-yl)methyl)-3-oxo-3,4-dihydro-2H-benzo[b][1,4]oxazine-6-carboxamide | 381 | 0.71 |
| I-282 | 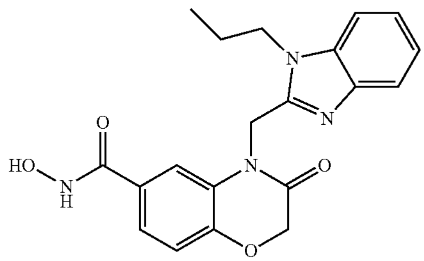 [SMILES: CCCn1c(CN2C(=O)COc3ccc(C(=O)NO)cc32)nc2ccccc21] | N-hydroxy-3-oxo-4-((1-propyl-1H-benzo[d]imidazol-2-yl)methyl)-3,4-dihydro-2H-benzo[b][1,4]oxazine-6-carboxamide | 381 | 0.77 |
| I-283 | 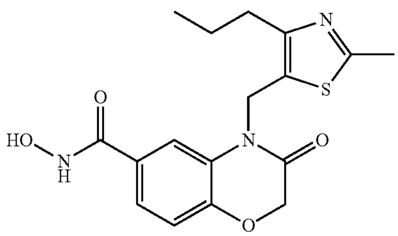 [SMILES: CCCc1nc(C)sc1CN1C(=O)COc2ccc(C(=O)NO)cc21] | N-hydroxy-4-((2-methyl-4-propylthiazol-5-yl)methyl)-3-oxo-3,4-dihydro-2H-benzo[b][1,4]oxazine-6-carboxamide | 362 | 0.86 |
| I-284 | 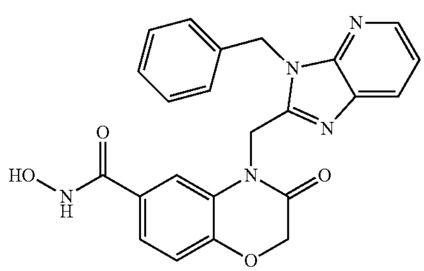 [SMILES: O=C(NO)c1ccc2c(c1)N(Cc1nc3cccnc3n1Cc1ccccc1)C(=O)CO2] | 4-((3-benzyl-3H-imidazo[4,5-b]pyridin-2-yl)methyl)-N-hydroxy-3-oxo-3,4-dihydro-2H-benzo[b][1,4]oxazine-6-carboxamide | 430 | 0.98 |
| I-285 | 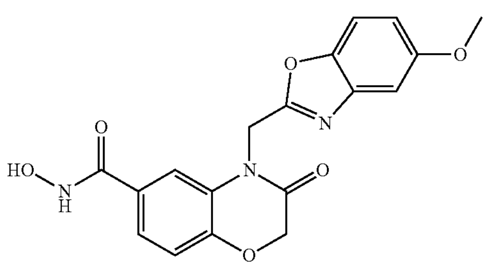 [SMILES: COc1ccc2oc(CN3C(=O)COc4ccc(C(=O)NO)cc43)nc2c1] | N-hydroxy-4-((5-methoxybenzo[d]oxazol-2-yl)methyl)-3-oxo-3,4-dihydro-2H-benzo[b][1,4]oxazine-6-carboxamide | 370 | 0.96 |
| I-286 | 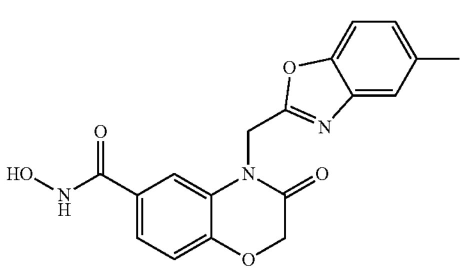 [SMILES: Cc1ccc2oc(CN3C(=O)COc4ccc(C(=O)NO)cc43)nc2c1] | N-hydroxy-4-((5-methylbenzo[d]oxazol-2-yl)methyl)-3-oxo-3,4-dihydro-2H-benzo[b][1,4]oxazine-6-carboxamide | 354 | 1.03 |

| Compd. No. | Structure | IUPAC Name | LC-MS [M + H]+ | HPLC RT (min) |
|---|---|---|---|---|
| I-287 | 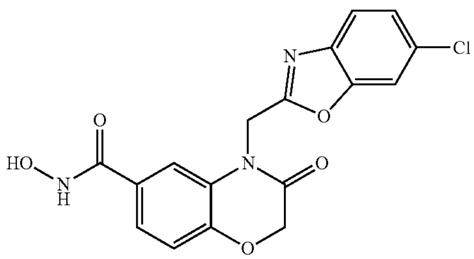 [SMILES: O=C(NO)c1ccc2c(c1)N(Cc1nc3ccc(Cl)cc3o1)C(=O)CO2] | 4-((6-chlorobenzo[d]oxazol-2-yl)methyl)-N-hydroxy-3-oxo-3,4-dihydro-2H-benzo[b][1,4]oxazine-6-carboxamide | 374 | 1.04 |
| I-288 | 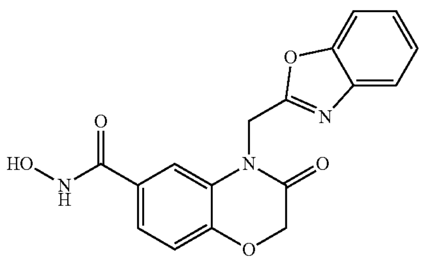 [SMILES: O=C(NO)c1ccc2c(c1)N(Cc1nc3ccccc3o1)C(=O)CO2] | 4-(benzo[d]oxazol-2-ylmethyl)-N-hydroxy-3-oxo-3,4-dihydro-2H-benzo[b][1,4]oxazine-6-carboxamide | 340 | 0.88 |
| I-289 | 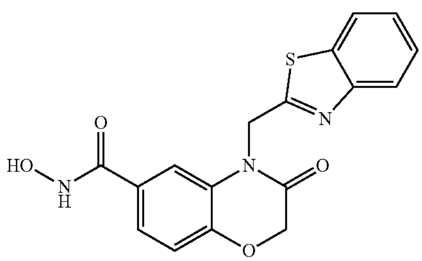 [SMILES: O=C(NO)c1ccc2c(c1)N(Cc1nc3ccccc3s1)C(=O)CO2] | 4-(benzo[d]thiazol-2-ylmethyl)-N-hydroxy-3-oxo-3,4-dihydro-2H-benzo[b][1,4]oxazine-6-carboxamide | 356 | 1.51 |
| I-290 | 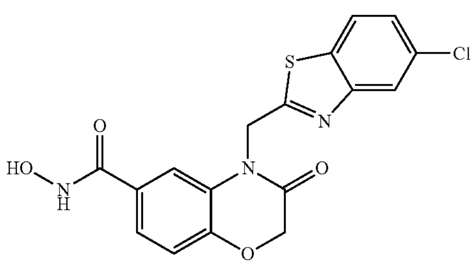 [SMILES: O=C(NO)c1ccc2c(c1)N(Cc1nc3cc(Cl)ccc3s1)C(=O)CO2] | 4-((5-chlorobenzo[d]thiazol-2-yl)methyl)-N-hydroxy-3-oxo-3,4-dihydro-2H-benzo[b][1,4]oxazine-6-carboxamide | 390 | 1.13 |
| I-291 | 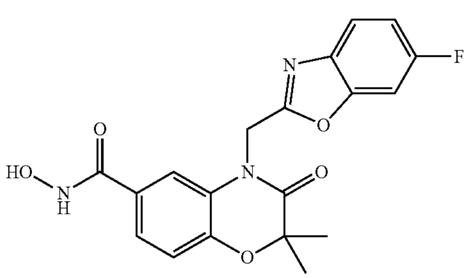 [SMILES: CC1(C)Oc2ccc(C(=O)NO)cc2N(Cc2nc3ccc(F)cc3o2)C1=O] | 4-((6-fluorobenzo[d]oxazol-2-yl)methyl)-N-hydroxy-2,2-dimethyl-3-oxo-3,4-dihydro-2H-benzo[b][1,4]oxazine-6-carboxamide | 386 | 1.14 |

-continued

| Compd. No. | Structure | IUPAC Name | LC-MS [M + H]+ | HPLC RT (min) |
|---|---|---|---|---|
| I-292 | 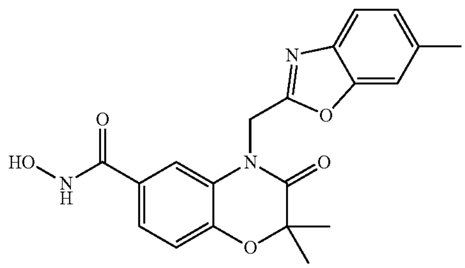 [SMILES: Cc1ccc2nc(CN3C(=O)C(C)(C)Oc4ccc(C(=O)NO)cc43)oc2c1] | N-hydroxy-2,2-dimethyl-4-((6-methylbenzo[d]oxazol-2-yl)methyl)-3-oxo-3,4-dihydro-2H-benzo[b][1,4]oxazine-6-carboxamide | 382 | 1.20 |
| I-293 | 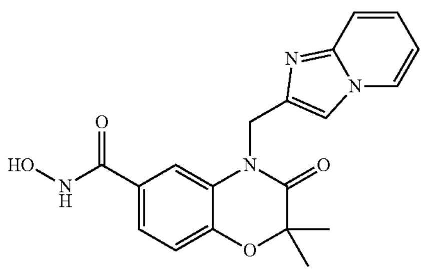 [SMILES: CC1(C)Oc2ccc(C(=O)NO)cc2N(Cc2cn3ccccc3n2)C1=O] | N-hydroxy-4-(imidazo[1,2-a]pyridin-2-ylmethyl)-2,2-dimethyl-3-oxo-3,4-dihydro-2H-benzo[b][1,4]oxazine-6-carboxamide | 367 | 0.51 |
| I-294 | 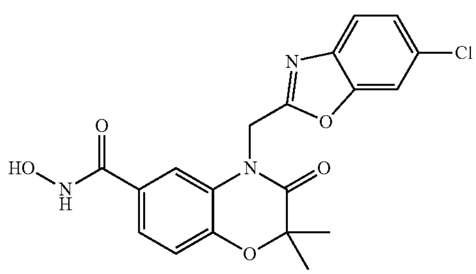 [SMILES: CC1(C)Oc2ccc(C(=O)NO)cc2N(Cc2nc3ccc(Cl)cc3o2)C1=O] | 4-((6-chlorobenzo[d]oxazol-2-yl)methyl)-N-hydroxy-2,2-dimethyl-3-oxo-3,4-dihydro-2H-benzo[b][1,4]oxazine-6-carboxamide | 402 | 1.25 |
| I-295 | 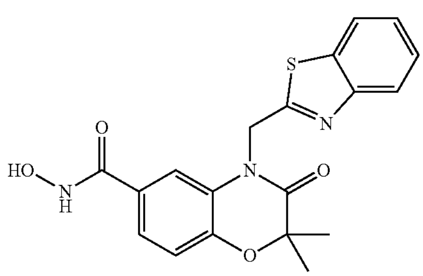 [SMILES: CC1(C)Oc2ccc(C(=O)NO)cc2N(Cc2nc3ccccc3s2)C1=O] | 4-(benzo[d]thiazol-2-ylmethyl)-N-hydroxy-2,2-dimethyl-3-oxo-3,4-dihydro-2H-benzo[b][1,4]oxazine-6-carboxamide | 384 | 1.19 |
| I-296 | 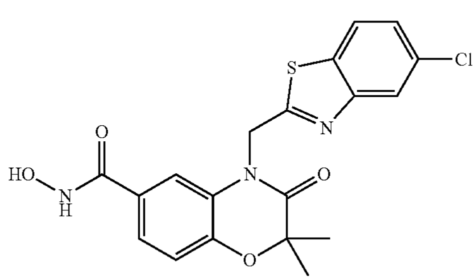 [SMILES: CC1(C)Oc2ccc(C(=O)NO)cc2N(Cc2nc3cc(Cl)ccc3s2)C1=O] | 4-((5-chlorobenzo[d]thiazol-2-yl)methyl)-N-hydroxy-2,2-dimethyl-3-oxo-3,4-dihydro-2H-benzo[b][1,4]oxazine-6-carboxamide | 418 | 1.33 |

| Compd. No. | Structure | IUPAC Name | LC-MS [M + H]+ | HPLC RT (min) |
|---|---|---|---|---|
| I-297 | 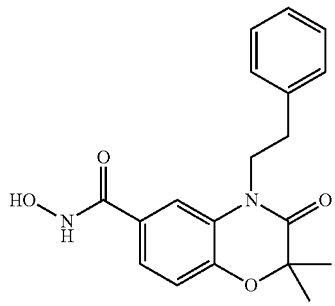 [SMILES: CC1(C)Oc2ccc(C(=O)NO)cc2N(CCc2ccccc2)C1=O] | N-hydroxy-2,2-dimethyl-3-oxo-4-phenethyl-3,4-dihydro-2H-benzo[b][1,4]oxazine-6-carboxamide | 341 | 1.18 |
| I-298 | 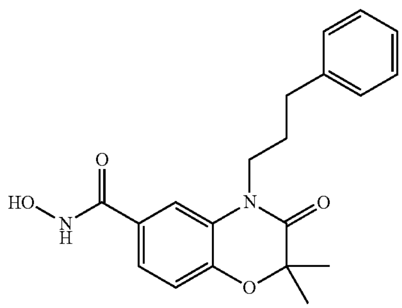 [SMILES: CC1(C)Oc2ccc(C(=O)NO)cc2N(CCCc2ccccc2)C1=O] | N-hydroxy-2,2-dimethyl-3-oxo-4-(3-phenylpropyl)-3,4-dihydro-2H-benzo[b][1,4]oxazine-6-carboxamide | 355 | 1.29 |
| I-299 | 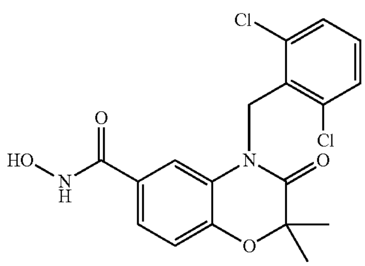 [SMILES: CC1(C)Oc2ccc(C(=O)NO)cc2N(Cc2c(Cl)cccc2Cl)C1=O] | 4-(2,6-dichlorobenzyl)-N-hydroxy-2,2-dimethyl-3-oxo-3,4-dihydro-2H-benzo[b][1,4]oxazine-6-carboxamide | 395 | 1.22 |
| I-300 | 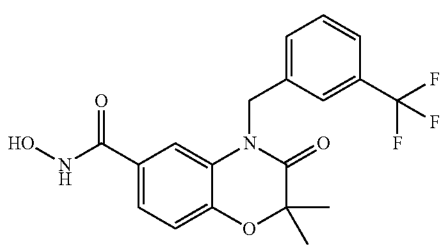 [SMILES: CC1(C)Oc2ccc(C(=O)NO)cc2N(Cc2cccc(C(F)(F)F)c2)C1=O] | N-hydroxy-2,2-dimethyl-3-oxo-4-(3-(trifluoromethyl)benzyl)-3,4-dihydro-2H-benzo[b][1,4]oxazine-6-carboxamide | 395 | 1.32 |
| I-301 | 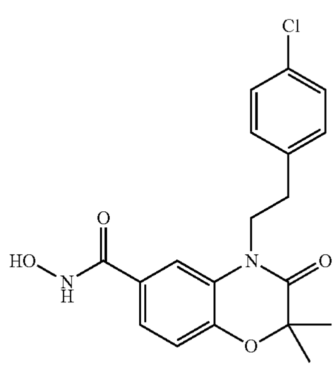 [SMILES: CC1(C)Oc2ccc(C(=O)NO)cc2N(CCc2ccc(Cl)cc2)C1=O] | 4-(4-chlorophenethyl)-N-hydroxy-2,2-dimethyl-3-oxo-3,4-dihydro-2H-benzo[b][1,4]oxazine-6-carboxamide | 375 | 1.31 |

| Compd. No. | Structure | IUPAC Name | LC-MS [M + H]+ | HPLC RT (min) |
|---|---|---|---|---|
| I-302 | 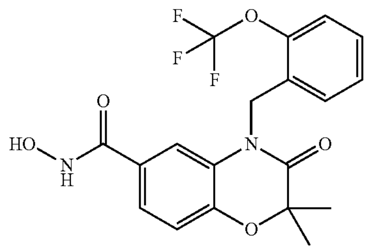 [SMILES: CC1(C)Oc2ccc(C(=O)NO)cc2N(Cc2ccccc2OC(F)(F)F)C1=O] | N-hydroxy-2,2-dimethyl-3-oxo-4-(2-(trifluoromethoxy)benzyl)-3,4-dihydro-2H-benzo[b][1,4]oxazine-6-carboxamide | 411 | 1.33 |
| I-303 | 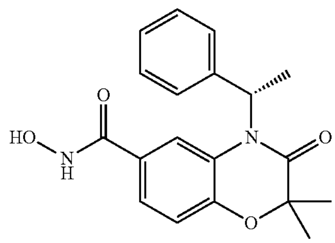 [SMILES: C[C@@H](c1ccccc1)N1C(=O)C(C)(C)Oc2ccc(C(=O)NO)cc21] | (S)-N-hydroxy-2,2-dimethyl-3-oxo-4-(1-phenylethyl)-3,4-dihydro-2H-benzo[b][1,4]oxazine-6-carboxamide | 341 | 1.17 |
| I-304 | 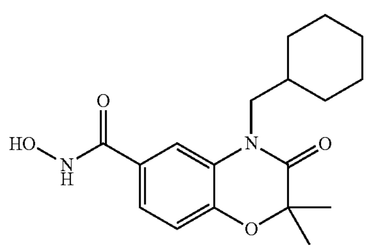 [SMILES: CC1(C)Oc2ccc(C(=O)NO)cc2N(CC2CCCCC2)C1=O] | 4-(cyclohexylmethyl)-N-hydroxy-2,2-dimethyl-3-oxo-3,4-dihydro-2H-benzo[b][1,4]oxazine-6-carboxamide | 333 | 1.30 |
| I-305 | 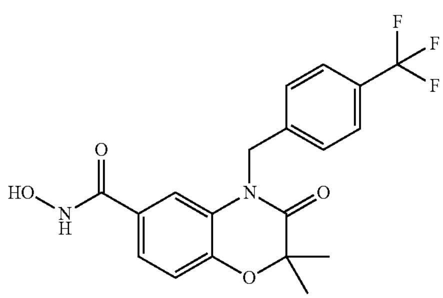 [SMILES: CC1(C)Oc2ccc(C(=O)NO)cc2N(Cc2ccc(C(F)(F)F)cc2)C1=O] | N-hydroxy-2,2-dimethyl-3-oxo-4-(4-(trifluoromethyl)benzyl)-3,4-dihydro-2H-benzo[b][1,4]oxazine-6-carboxamide | 395 | 1.34 |
| I-306 | 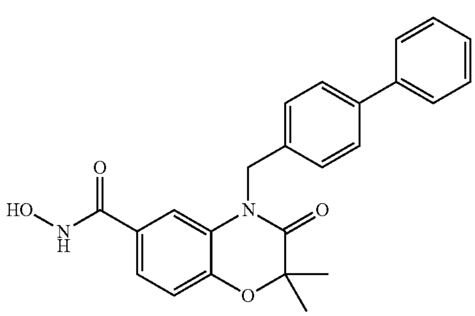 [SMILES: CC1(C)Oc2ccc(C(=O)NO)cc2N(Cc2ccc(-c3ccccc3)cc2)C1=O] | 4-([1,1'-biphenyl]-4-ylmethyl)-N-hydroxy-2,2-dimethyl-3-oxo-3,4-dihydro-2H-benzo[b][1,4]oxazine-6-carboxamide | 403 | 1.45 |

-continued

| Compd. No. | Structure | IUPAC Name | LC-MS [M + H]+ | HPLC RT (min) |
|---|---|---|---|---|
| I-307 | 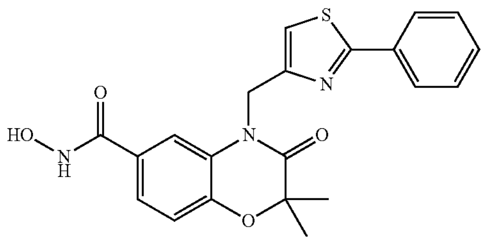 [SMILES: CC1(C)Oc2ccc(C(=O)NO)cc2N(Cc2csc(-c3ccccc3)n2)C1=O] | N-hydroxy-2,2-dimethyl-3-oxo-4-((2-phenylthiazol-4-yl)methyl)-3,4-dihydro-2H-benzo[b][1,4]oxazine-6-carboxamide | 410 | 1.31 |
| I-308 | 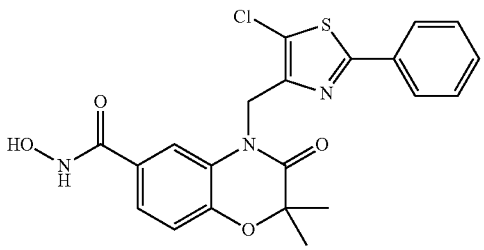 [SMILES: CC1(C)Oc2ccc(C(=O)NO)cc2N(Cc2nc(-c3ccccc3)sc2Cl)C1=O] | 4-((5-chloro-2-phenylthiazol-4-yl)methyl)-N-hydroxy-2,2-dimethyl-3-oxo-3,4-dihydro-2H-benzo[b][1,4]oxazine-6-carboxamide | 444 | 1.47 |
| I-309 | 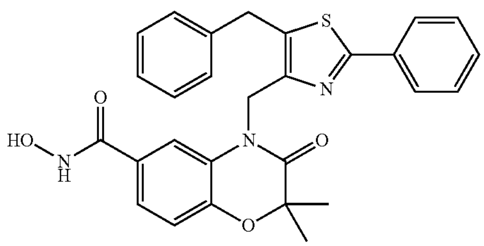 [SMILES: CC1(C)Oc2ccc(C(=O)NO)cc2N(Cc2nc(-c3ccccc3)sc2Cc2ccccc2)C1=O] | 4-((5-benzyl-2-phenylthiazol-4-yl)methyl)-N-hydroxy-2,2-dimethyl-3-oxo-3,4-dihydro-2H-benzo[b][1,4]oxazine-6-carboxamide | 500 | 1.71 |
| I-310 | 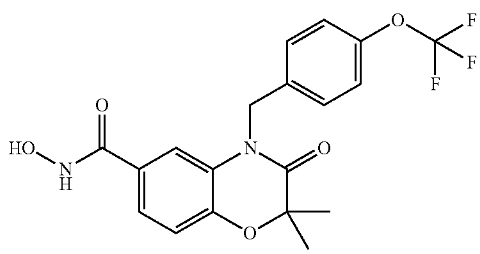 [SMILES: CC1(C)Oc2ccc(C(=O)NO)cc2N(Cc2ccc(OC(F)(F)F)cc2)C1=O] | N-hydroxy-2,2-dimethyl-3-oxo-4-(4-(trifluoromethoxy)benzyl)-3,4-dihydro-2H-benzo[b][1,4]oxazine-6-carboxamide | 411 | 1.37 |
| I-311 | 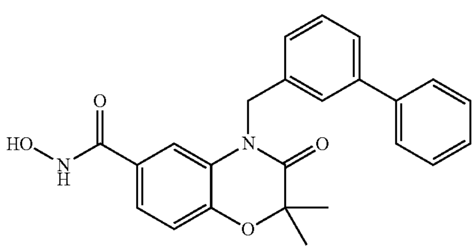 [SMILES: CC1(C)Oc2ccc(C(=O)NO)cc2N(Cc2cccc(-c3ccccc3)c2)C1=O] | 4-([1,1'-biphenyl]-3-ylmethyl)-N-hydroxy-2,2-dimethyl-3-oxo-3,4-dihydro-2H-benzo[b][1,4]oxazine-6-carboxamide | 403 | 1.44 |
| I-312 | 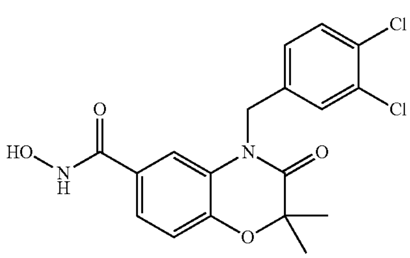 [SMILES: CC1(C)Oc2ccc(C(=O)NO)cc2N(Cc2ccc(Cl)c(Cl)c2)C1=O] | 4-(3,4-dichlorobenzyl)-N-hydroxy-2,2-dimethyl-3-oxo-3,4-dihydro-2H-benzo[b][1,4]oxazine-6-carboxamide | 395 | 1.38 |

-continued

| Compd. No. | Structure | IUPAC Name | LC-MS [M + H]+ | HPLC RT (min) |
|---|---|---|---|---|
| I-313 | 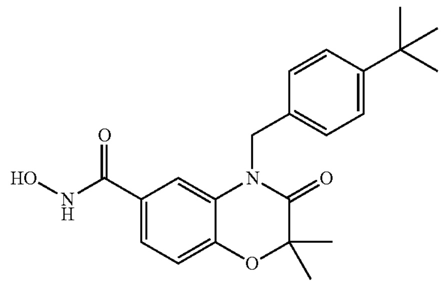 [SMILES: CC1(C)Oc2ccc(C(=O)NO)cc2N(Cc2ccc(C(C)(C)C)cc2)C1=O] | 4-(4-(tert-butyl)benzyl)-N-hydroxy-2,2-dimethyl-3-oxo-3,4-dihydro-2H-benzo[b][1,4]oxazine-6-carboxamide | 383 | 1.49 |
| I-314 | 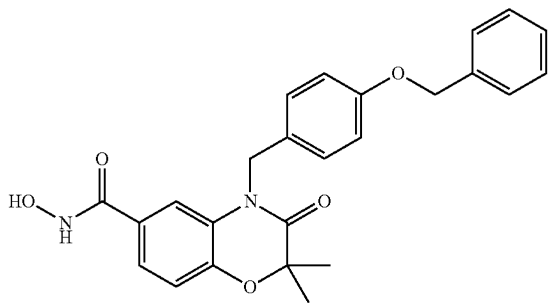 [SMILES: CC1(C)Oc2ccc(C(=O)NO)cc2N(Cc2ccc(OCc3ccccc3)cc2)C1=O] | 4-(4-(benzyloxy)benzyl)-N-hydroxy-2,2-dimethyl-3-oxo-3,4-dihydro-2H-benzo[b][1,4]oxazine-6-carboxamide | 433 | 1.46 |
| I-315 | 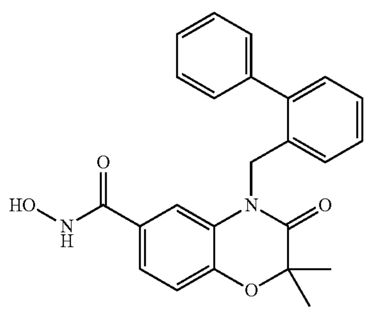 [SMILES: CC1(C)Oc2ccc(C(=O)NO)cc2N(Cc2ccccc2-c2ccccc2)C1=O] | 4-([1,1'-biphenyl]-2-ylmethyl)-N-hydroxy-2,2-dimethyl-3-oxo-3,4-dihydro-2H-benzo[b][1,4]oxazine-6-carboxamide | 403 | 1.41 |
| I-316 | 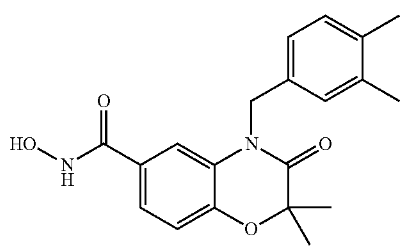 [SMILES: Cc1ccc(CN2C(=O)C(C)(C)Oc3ccc(C(=O)NO)cc32)cc1C] | 4-(3,4-dimethylbenzyl)-N-hydroxy-2,2-dimethyl-3-oxo-3,4-dihydro-2H-benzo[b][1,4]oxazine-6-carboxamide | 355 | 1.29 |
| I-317 | 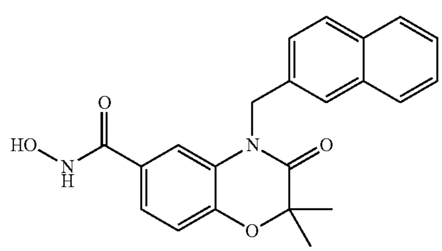 [SMILES: CC1(C)Oc2ccc(C(=O)NO)cc2N(Cc2ccc3ccccc3c2)C1=O] | N-hydroxy-2,2-dimethyl-4-(naphthalen-2-ylmethyl)-3-oxo-3,4-dihydro-2H-benzo[b][1,4]oxazine-6-carboxamide | 377 | 1.32 |

| Compd. No. | Structure | IUPAC Name | LC-MS [M + H]+ | HPLC RT (min) |
|---|---|---|---|---|
| I-318 | 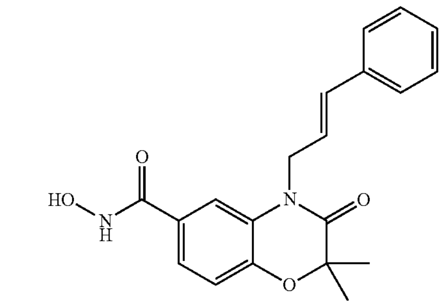 [SMILES: CC1(C)Oc2ccc(C(=O)NO)cc2N(C/C=C/c2ccccc2)C1=O] | 4-cinnamyl-N-hydroxy-2,2-dimethyl-3-oxo-3,4-dihydro-2H-benzo[b][1,4]oxazine-6-carboxamide | 353 | 1.25 |
| I-319 | 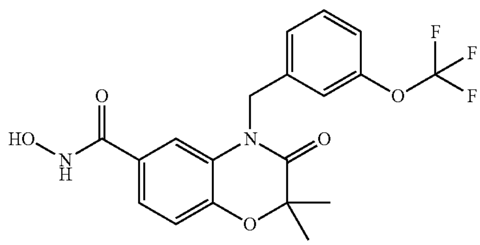 [SMILES: CC1(C)Oc2ccc(C(=O)NO)cc2N(Cc2cccc(OC(F)(F)F)c2)C1=O] | N-hydroxy-2,2-dimethyl-3-oxo-4-(3-(trifluoromethoxy)benzyl)-3,4-dihydro-2H-benzo[b][1,4]oxazine-6-carboxamide | 411 | 1.35 |
| I-320 | 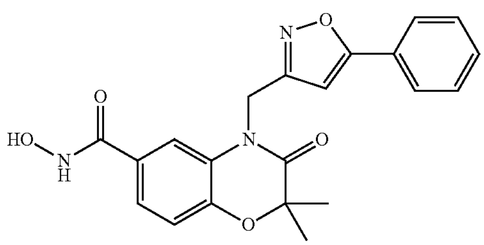 [SMILES: CC1(C)Oc2ccc(C(=O)NO)cc2N(Cc2cc(-c3ccccc3)on2)C1=O] | N-hydroxy-2,2-dimethyl-3-oxo-4-((5-phenylisoxazol-3-yl)methyl)-3,4-dihydro-2H-benzo[b][1,4]oxazine-6-carboxamide | 394 | 1.27 |
| I-321 | 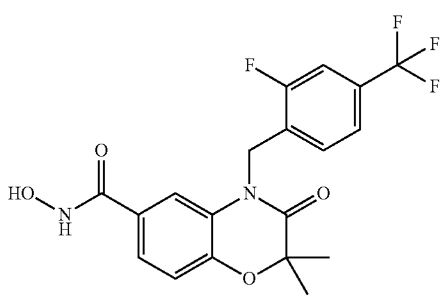 [SMILES: CC1(C)Oc2ccc(C(=O)NO)cc2N(Cc2ccc(C(F)(F)F)cc2F)C1=O] | 4-(2-fluoro-4-(trifluoromethyl)benzyl)-N-hydroxy-2,2-dimethyl-3-oxo-3,4-dihydro-2H-benzo[b][1,4]oxazine-6-carboxamide | 413 | 1.37 |
| I-322 | 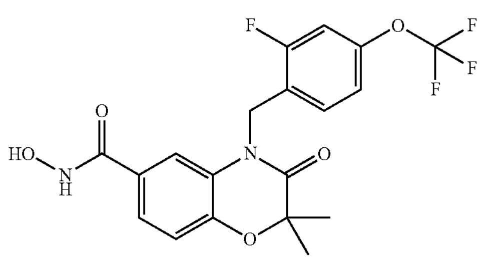 [SMILES: CC1(C)Oc2ccc(C(=O)NO)cc2N(Cc2ccc(OC(F)(F)F)cc2F)C1=O] | 4-(2-fluoro-4-(trifluoromethoxy)benzyl)-N-hydroxy-2,2-dimethyl-3-oxo-3,4-dihydro-2H-benzo[b][1,4]oxazine-6-carboxamide | 429 | 1.40 |
| I-323 | 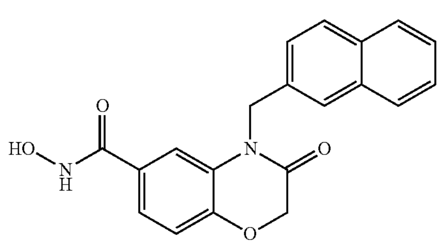 [SMILES: O=C(NO)c1ccc2c(c1)N(Cc1ccc3ccccc3c1)C(=O)CO2] | N-hydroxy-4-(naphthalen-2-ylmethyl)-3-oxo-3,4-dihydro-2H-benzo[b][1,4]oxazine-6-carboxamide | 349 | 1.12 |

| Compd. No. | Structure | IUPAC Name | LC-MS [M + H]+ | HPLC RT (min) |
|---|---|---|---|---|
| I-324 | 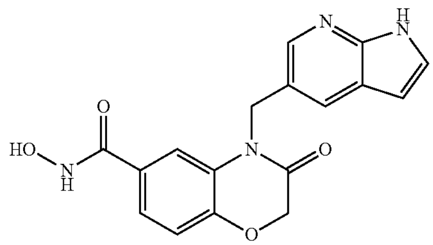 [SMILES: O=C(NO)c1ccc2c(c1)N(Cc1cnc3[nH]ccc3c1)C(=O)CO2] | 4-((1H-pyrrolo[2,3-b]pyridin-5-yl)methyl)-N-hydroxy-3-oxo-3,4-dihydro-2H-benzo[b][1,4]oxazine-6-carboxamide | 339 | 0.61 |
| I-325 | 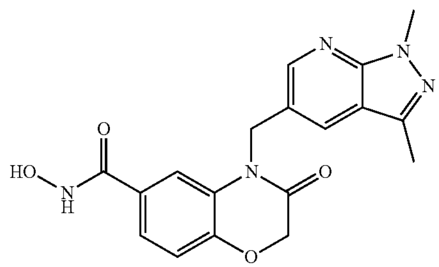 [SMILES: Cc1nn(C)c2ncc(CN3C(=O)COc4ccc(C(=O)NO)cc43)cc12] | 4-((1,3-dimethyl-1H-pyrazolo[3,4-b]pyridin-5-yl)methyl)-N-hydroxy-3-oxo-3,4-dihydro-2H-benzo[b][1,4]oxazine-6-carboxamide | 368 | 0.77 |
| I-326 | 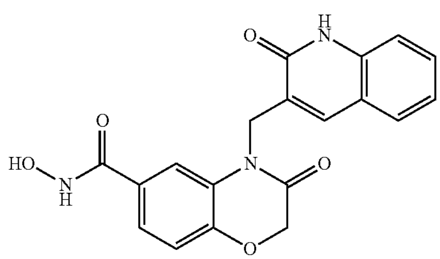 [SMILES: O=C(NO)c1ccc2c(c1)N(Cc1cc3ccccc3[nH]c1=O)C(=O)CO2] | N-hydroxy-3-oxo-4-((2-oxo-1,2-dihydroquinolin-3-yl)methyl)-3,4-dihydro-2H-benzo[b][1,4]oxazine-6-carboxamide | 366 | 0.81 |
| I-327 | 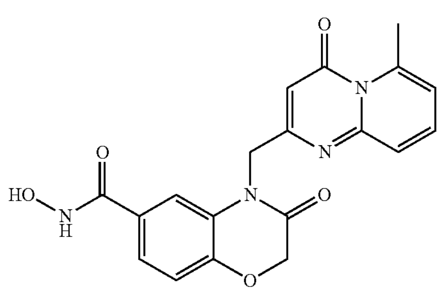 [SMILES: Cc1cccc2nc(CN3C(=O)COc4ccc(C(=O)NO)cc43)cc(=O)n12] | N-hydroxy-4-((6-methyl-4-oxo-4H-pyrido[1,2-a]pyrimidin-2-yl)methyl)-3-oxo-3,4-dihydro-2H-benzo[b][1,4]oxazine-6-carboxamide | 381 | 0.71 |
| I-328 | 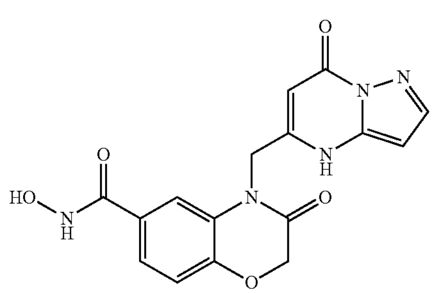 [SMILES: O=C(NO)c1ccc2c(c1)N(Cc1cc(=O)n3nccc3[nH]1)C(=O)CO2] | N-hydroxy-3-oxo-4-((7-oxo-4,7-dihydropyrazolo[1,5-a]pyrimidin-5-yl)methyl)-3,4-dihydro-2H-benzo[b][1,4]oxazine-6-carboxamide | 356 | 0.51 |

-continued

| Compd. No. | Structure | IUPAC Name | LC-MS [M + H]+ | HPLC RT (min) |
|---|---|---|---|---|
| I-329 | 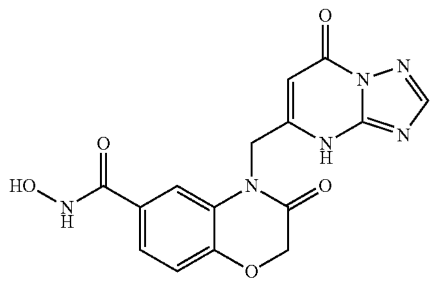 [SMILES: O=C(NO)c1ccc2c(c1)N(Cc1cc(=O)n3ncnc3[nH]1)C(=O)CO2] | N-hydroxy-3-oxo-4-((7-oxo-4,7-dihydro-[1,2,4]triazolo[1,5-a]pyrimidin-5-yl)methyl)-3,4-dihydro-2H-benzo[b][1,4]oxazine-6-carboxamide | 357 | 0.50 |
| I-330 | 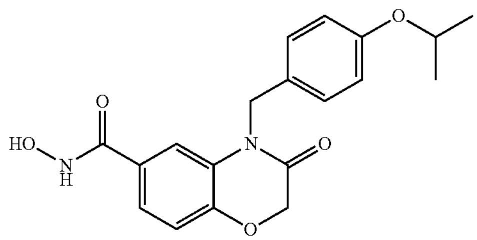 [SMILES: CC(C)Oc1ccc(CN2C(=O)COc3ccc(C(=O)NO)cc32)cc1] | N-hydroxy-4-(4-isopropoxybenzyl)-3-oxo-3,4-dihydro-2H-benzo[b][1,4]oxazine-6-carboxamide | 357 | 1.12 |
| I-331 | 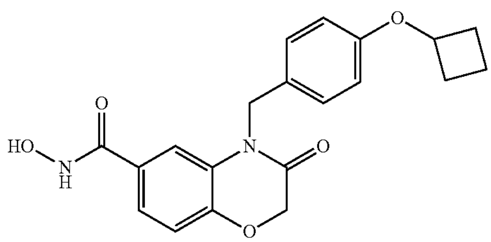 [SMILES: O=C(NO)c1ccc2c(c1)N(Cc1ccc(OC3CCC3)cc1)C(=O)CO2] | 4-(4-cyclobutoxybenzyl)-N-hydroxy-3-oxo-3,4-dihydro-2H-benzo[b][1,4]oxazine-6-carboxamide | 369 | 1.19 |
| I-332 | 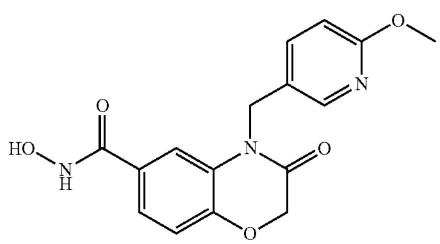 [SMILES: COc1ccc(CN2C(=O)COc3ccc(C(=O)NO)cc32)cn1] | N-hydroxy-4-((6-methoxypyridin-3-yl)methyl)-3-oxo-3,4-dihydro-2H-benzo[b][1,4]oxazine-6-carboxamide | 330 | .078 |
| I-333 | 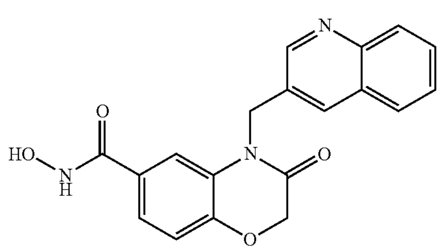 [SMILES: O=C(NO)c1ccc2c(c1)N(Cc1cnc3ccccc3c1)C(=O)CO2] | N-hydroxy-3-oxo-4-(quinolin-3-ylmethyl)-3,4-dihydro-2H-benzo[b][1,4]oxazine-6-carboxamide | 350 | 0.65 |
| I-334 | 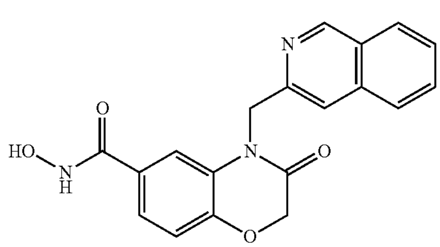 [SMILES: O=C(NO)c1ccc2c(c1)N(Cc1cc3ccccc3cn1)C(=O)CO2] | N-hydroxy-4-(isoquinolin-3-ylmethyl)-3-oxo-3,4-dihydro-2H-benzo[b][1,4]oxazine-6-carboxamide | 350 | 0.78 |

-continued

| Compd. No. | Structure | IUPAC Name | LC-MS [M + H]+ | HPLC RT (min) |
|---|---|---|---|---|
| I-335 | 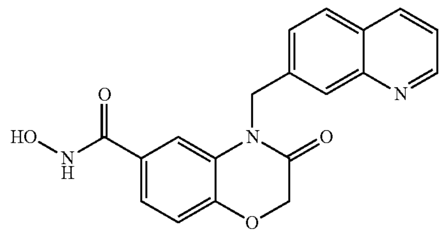 [SMILES: O=C(NO)c1ccc2c(c1)N(Cc1ccc3cccnc3c1)C(=O)CO2] | N-hydroxy-3-oxo-4-(quinolin-7-ylmethyl)-3,4-dihydro-2H-benzo[b][1,4]oxazine-6-carboxamide | 350 | 0.51 |
| I-336 | 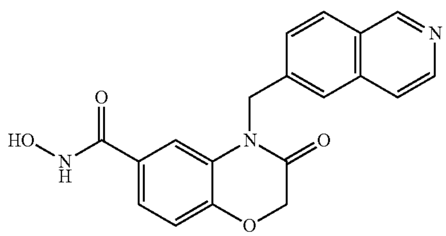 [SMILES: O=C(NO)c1ccc2c(c1)N(Cc1ccc3cnccc3c1)C(=O)CO2] | N-hydroxy-4-(isoquinolin-6-ylmethyl)-3-oxo-3,4-dihydro-2H-benzo[b][1,4]oxazine-6-carboxamide | 350 | 0.39 |
| I-337 | 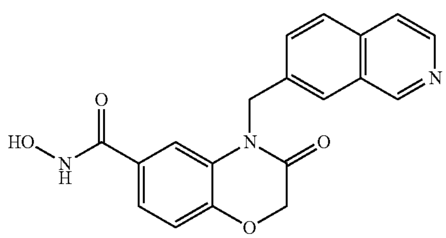 [SMILES: O=C(NO)c1ccc2c(c1)N(Cc1ccc3ccncc3c1)C(=O)CO2] | N-hydroxy-4-(isoquinolin-7-ylmethyl)-3-oxo-3,4-dihydro-2H-benzo[b][1,4]oxazine-6-carboxamide | 350 | 0.43 |
| I-338 | 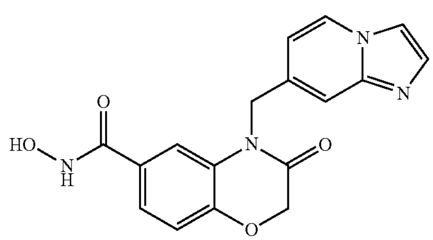 [SMILES: O=C(NO)c1ccc2c(c1)N(Cc1ccn3ccnc3c1)C(=O)CO2] | N-hydroxy-4-(imidazo[1,2-a]pyridin-7-ylmethyl)-3-oxo-3,4-dihydro-2H-benzo[b][1,4]oxazine-6-carboxamide | 339 | 0.30 |
| I-339 | 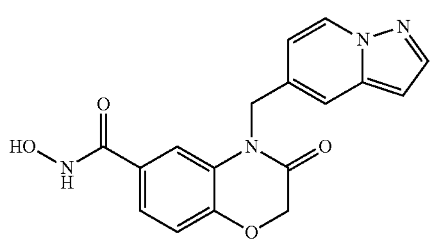 [SMILES: O=C(NO)c1ccc2c(c1)N(Cc1ccn3nccc3c1)C(=O)CO2] | N-hydroxy-3-oxo-4-(pyrazolo[1,5-a]pyridin-5-ylmethyl)-3,4-dihydro-2H-benzo[b][1,4]oxazine-6-carboxamide | 339 | 0.77 |
| I-340 | 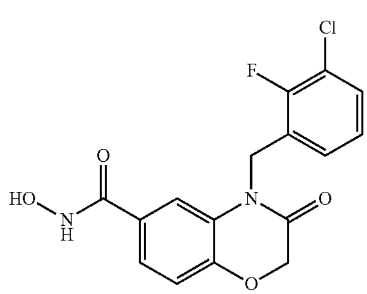 [SMILES: O=C(NO)c1ccc2c(c1)N(Cc1cccc(Cl)c1F)C(=O)CO2] | 4-(3-chloro-2-fluorobenzyl)-N-hydroxy-3-oxo-3,4-dihydro-2H-benzo[b][1,4]oxazine-6-carboxamide | 351 | 1.08 |

-continued

| Compd. No. | Structure | IUPAC Name | LC-MS [M + H]+ | HPLC RT (min) |
|---|---|---|---|---|
| I-341 | 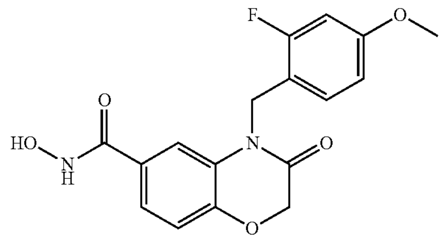 [SMILES: COc1ccc(CN2C(=O)COc3ccc(C(=O)NO)cc32)c(F)c1] | 4-(2-fluoro-4-methoxybenzyl)-N-hydroxy-3-oxo-3,4-dihydro-2H-benzo[b][1,4]oxazine-6-carboxamide | 347 | 0.98 |
| I-342 | 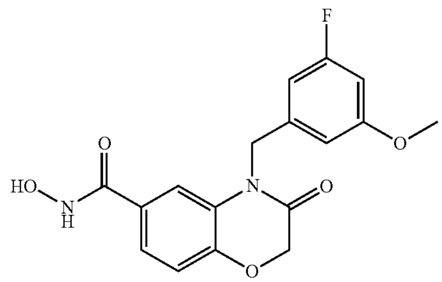 [SMILES: COc1cc(F)cc(CN2C(=O)COc3ccc(C(=O)NO)cc32)c1] | 4-(3-fluoro-5-methoxybenzyl)-N-hydroxy-3-oxo-3,4-dihydro-2H-benzo[b][1,4]oxazine-6-carboxamide | 347 | 1.02 |
| I-343 | 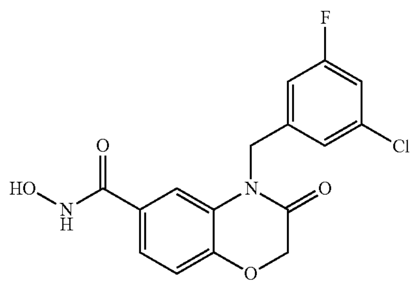 [SMILES: O=C(NO)c1ccc2c(c1)N(Cc1cc(F)cc(Cl)c1)C(=O)CO2] | 4-(3-chloro-5-fluorobenzyl)-N-hydroxy-3-oxo-3,4-dihydro-2H-benzo[b][1,4]oxazine-6-carboxamide | 351 | 1.10 |
| I-344 | 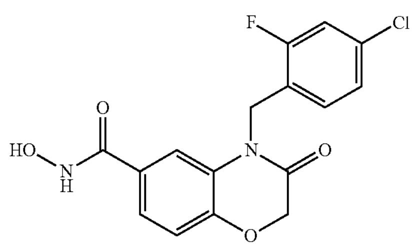 [SMILES: O=C(NO)c1ccc2c(c1)N(Cc1ccc(Cl)cc1F)C(=O)CO2] | 4-(4-chloro-2-fluorobenzyl)-N-hydroxy-3-oxo-3,4-dihydro-2H-benzo[b][1,4]oxazine-6-carboxamide | 351 | 1.10 |
| I-345 | 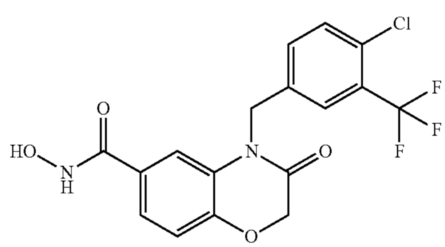 [SMILES: O=C(NO)c1ccc2c(c1)N(Cc1ccc(Cl)c(C(F)(F)F)c1)C(=O)CO2] | 4-(4-chloro-3-(trifluoromethyl)benzyl)-N-hydroxy-3-oxo-3,4-dihydro-2H-benzo[b][1,4]oxazine-6-carboxamide | 401 | 1.25 |
| I-346 | 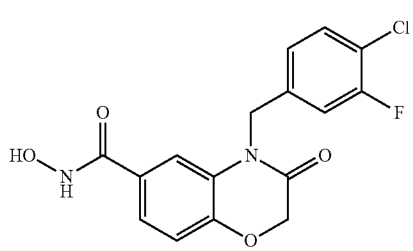 [SMILES: O=C(NO)c1ccc2c(c1)N(Cc1ccc(Cl)c(F)c1)C(=O)CO2] | 4-(4-chloro-3-fluorobenzyl)-N-hydroxy-3-oxo-3,4-dihydro-2H-benzo[b][1,4]oxazine-6-carboxamide | 351 | 1.11 |

| Compd. No. | Structure | IUPAC Name | LC-MS [M + H]+ | HPLC RT (min) |
|---|---|---|---|---|
| I-347 | 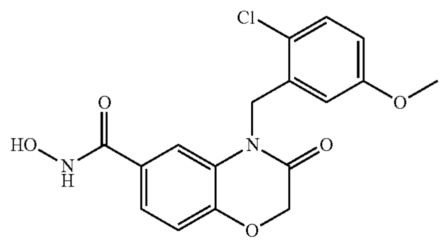 [SMILES: COc1ccc(Cl)c(CN2C(=O)COc3ccc(C(=O)NO)cc32)c1] | 4-(2-chloro-5-methoxybenzyl)-N-hydroxy-3-oxo-3,4-dihydro-2H-benzo[b][1,4]oxazine-6-carboxamide | 363 | 1.06 |
| I-348 | 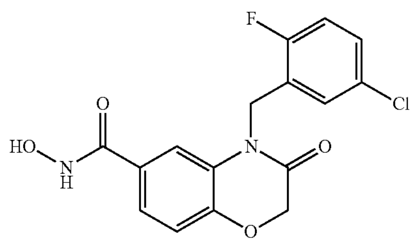 [SMILES: O=C(NO)c1ccc2c(c1)N(Cc1cc(Cl)ccc1F)C(=O)CO2] | 4-(5-chloro-2-fluorobenzyl)-N-hydroxy-3-oxo-3,4-dihydro-2H-benzo[b][1,4]oxazine-6-carboxamide | 351 | 1.07 |
| I-349 | 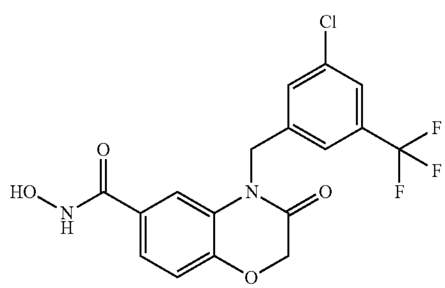 | 4-(3-chloro-5-(trifluoromethyl)benzyl)-N-hydroxy-3-oxo-3,4-dihydro-2H-benzo[b][1,4]oxazine-6-carboxamide | 401 | 1.27 |
| I-350 | 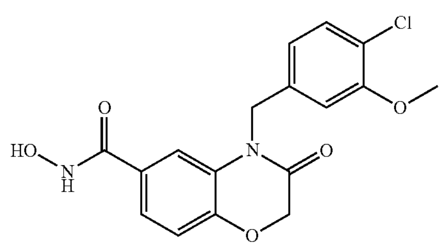 | 4-(4-chloro-3-methoxybenzyl)-N-hydroxy-3-oxo-3,4-dihydro-2H-benzo[b][1,4]oxazine-6-carboxamide | 363 | 1.08 |
| I-351 | 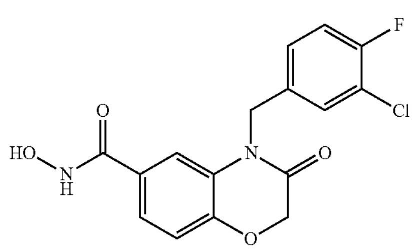 [SMILES: O=C(NO)c1ccc2c(c1)N(Cc1ccc(F)c(Cl)c1)C(=O)CO2] | 4-(3-chloro-4-fluorobenzyl)-N-hydroxy-3-oxo-3,4-dihydro-2H-benzo[b][1,4]oxazine-6-carboxamide | 351 | 1.09 |
| I-352 | 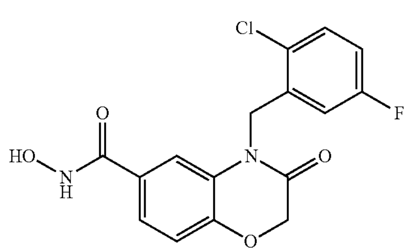 [SMILES: O=C(NO)c1ccc2c(c1)N(Cc1cc(F)ccc1Cl)C(=O)CO2] | 4-(2-chloro-5-fluorobenzyl)-N-hydroxy-3-oxo-3,4-dihydro-2H-benzo[b][1,4]oxazine-6-carboxamide | 351 | 1.05 |

-continued

| Compd. No. | Structure | IUPAC Name | LC-MS [M + H]+ | HPLC RT (min) |
|---|---|---|---|---|
| I-353 | 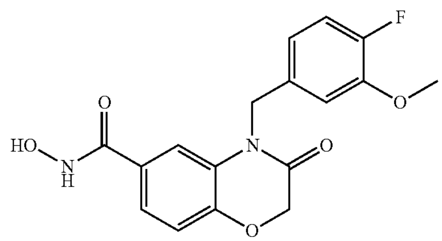 [SMILES: COc1cc(CN2C(=O)COc3ccc(C(=O)NO)cc32)ccc1F] | 4-(4-fluoro-3-methoxybenzyl)-N-hydroxy-3-oxo-3,4-dihydro-2H-benzo[b][1,4]oxazine-6-carboxamide | 347 | 0.97 |
| I-354 | 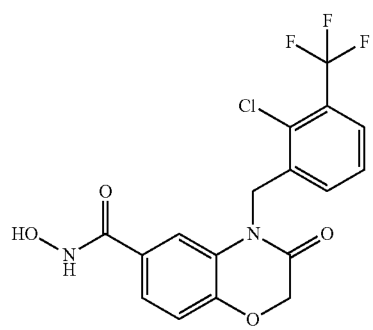 [SMILES: O=C(NO)c1ccc2c(c1)N(Cc1cccc(C(F)(F)F)c1Cl)C(=O)CO2] | 4-(2-chloro-3-(trifluoromethyl)benzyl)-N-hydroxy-3-oxo-3,4-dihydro-2H-benzo[b][1,4]oxazine-6-carboxamide | 401 | 1.23 |
| I-355 | 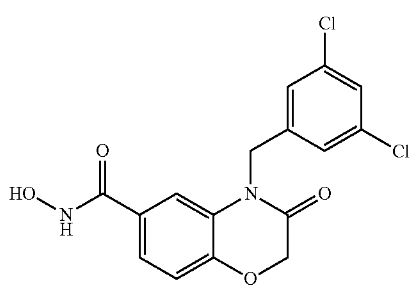 [SMILES: O=C(NO)c1ccc2c(c1)N(Cc1cc(Cl)cc(Cl)c1)C(=O)CO2] | 4-(3,5-dichlorobenzyl)-N-hydroxy-3-oxo-3,4-dihydro-2H-benzo[b][1,4]oxazine-6-carboxamide | 367 | 1.20 |
| I-356 | 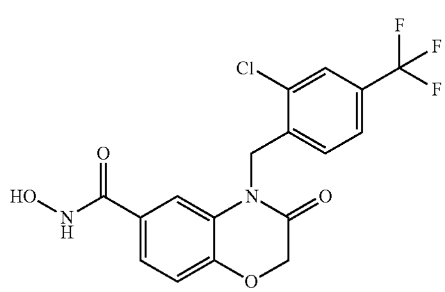 [SMILES: O=C(NO)c1ccc2c(c1)N(Cc1ccc(C(F)(F)F)cc1Cl)C(=O)CO2] | 4-(2-chloro-4-(trifluoromethyl)benzyl)-N-hydroxy-3-oxo-3,4-dihydro-2H-benzo[b][1,4]oxazine-6-carboxamide | 401 | 1.25 |

Example 18—N-hydroxy-4-pentyl-3,4-dihydro-2H-benzo[b][1,4]oxazine-6-carboxamide (I-78)

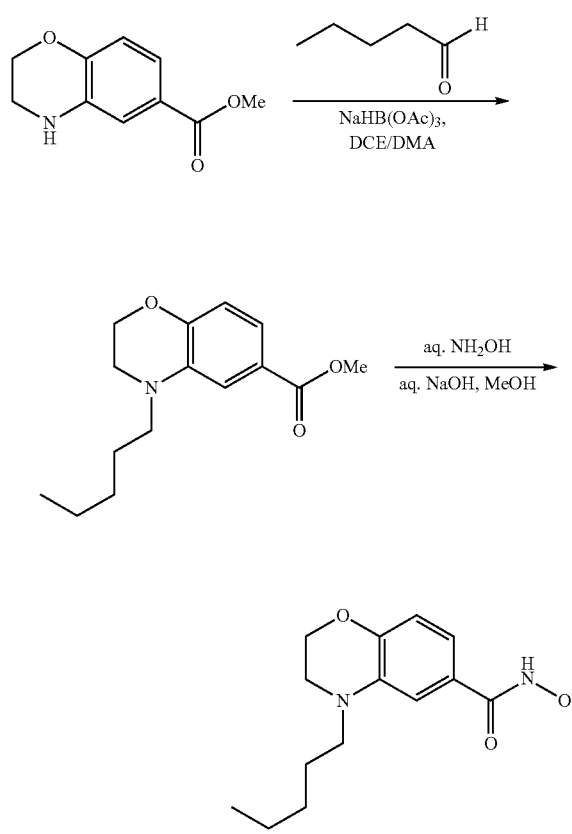

A half-dram vial was charged with methyl 3,4-dihydro-2H-benzo[b][1,4]oxazine-6-carboxylate (0.2 M in N,N-dimethylacetamide, 150 µL, 30 µmol) and pentanal (0.2M in 1,2-dichloroethane, 300 µL, 60 µmol). A solution of sodium triacetoxyborohydride (0.2 M in 1,2-dichloroethane, 450 µL, 90 µmol) was added, and the system was sealed and shaken at room temperature for 16 h. The solvent was removed under a stream of nitrogen, the residue was diluted with ethyl acetate (0.6 mL) and a solution of 1 N sodium hydroxide in brine (0.5 mL), and the mixture was shaken. The organic layer was separated and the aqueous phase was extracted with ethyl acetate (0.6 mL). The combined organic layers were dried under a stream of nitrogen. THF/methanol (3:1, 200 µL) was added to the residue. The vial was sealed and shaken at 50° C. for 15 minutes to dissolve the residue, then cooled to room temperature. Hydroxylamine (150 µL, 50% v/v solution in water) was added, followed by 1 N aqueous sodium hydroxide solution (100 µL). The mixture was sealed and then shaken at room temperature for 16 h. The reaction mixture was concentrated under a stream of nitrogen at room temperature, dissolved in 500 µL of DMSO, and purified by mass triggered preparative HPLC (Column: Waters Sunfire C18, 5 µm, 19×50 mm; Mobile Phase: water (0.1% formic acid) and acetonitrile (0.1% formic acid) (15% to 100% acetonitrile in 6 min; flow rate: 23 mL/min); Detector: UV 254/220 nm). The product-containing fractions were combined and concentrated in a Genevac to afford N-hydroxy-4-pentyl-3,4-dihydro-2H-benzo[b][1,4]oxazine-6-carboxamide (1.3 mg, 16%). (ES, m/z) 265 [M+H]$^+$, LC-MS R$_t$ 1.20 min.

Example 19—N-hydroxy-4-(4-(trifluoromethyl)benzyl)-3,4-dihydro-2H-benzo[b][1,4]thiazine-6-carboxamide 1,1-dioxide (I-79)

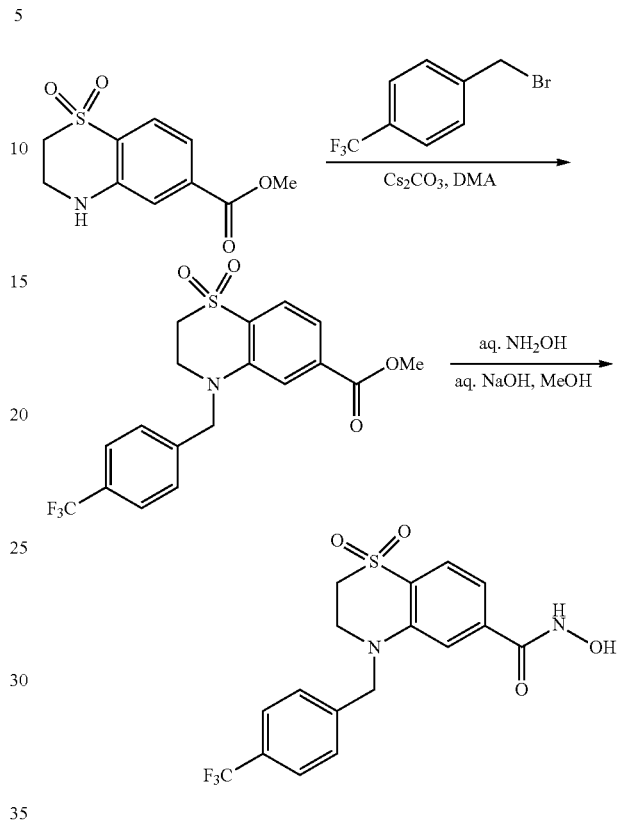

A half-dram vial was charged with methyl 3,4-dihydro-2H-benzo[b][1,4]thiazine-6-carboxylate 1,1-dioxide (0.2 M in N,N-dimethylacetamide, 250 µL, 50 µmol) and cesium carbonate (65 mg, 200 µmol). Then a solution of 1-(bromomethyl)-4-(trifluoromethyl)benzene (0.2 M in N,N-dimethylacetamide, 500 µL, 100 mmol) was added. The vial was sealed and shaken at 50° C. for 16 h, then the solvent was removed under a stream of nitrogen. The residue was diluted with brine (500 µL) and extracted with ethyl acetate (2×500 µL). The combined organic layers were dried under a stream of nitrogen. THF/methanol (3:1, 200 µL) was added to the residue. The vial was sealed and shaken at 50° C. for 15 min to dissolve the residue, then cooled to room temperature. Hydroxylamine (150 µL, 50% v/v solution in water) was added, followed by 1 N aqueous sodium hydroxide (100 µL). The mixture was sealed and then shaken at room temperature for 16 h. The reaction mixture was concentrated under a stream of nitrogen at room temperature, then dissolved in 500 µL of DMSO and purified by mass triggered preparative HPLC (Column: Waters Sunfire C18, 5 µm, 19×50 mm; Mobile Phase: water (0.1% formic acid) and acetonitrile (0.1% formic acid) (15% to 100% acetonitrile in 6 min; flow rate: 23 mL/min); Detector: UV 254/220 nm). The product-containing fractions were combined and concentrated in a Genevac to afford N-hydroxy-4-(4-(trifluoromethyl)benzyl)-3,4-dihydro-2H-benzo[b][1,4]thiazine-6-carboxamide 1,1-dioxide (8.0 mg, 40% yield). (ES, m/z) 401 [M+H]$^+$.

The following compounds were synthesized according to the above protocol of Example 19.

| Compd. No. | Structure | IUPAC Name | LC-MS [M + H]+ | HPLC RT (min) |
|---|---|---|---|---|
| I-80 | 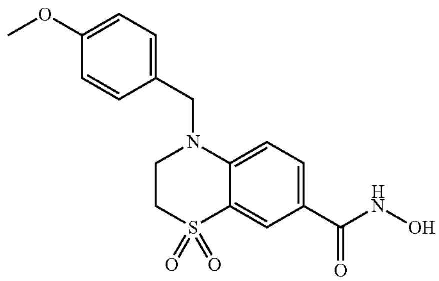 [SMILES: COc1ccc(CN2CCS(=O)(=O)c3cc(C(=O)NO)ccc32)cc1] | N-hydroxy-4-(4-methoxybenzyl)-3,4-dihydro-2H-benzo[b][1,4]thiazine-7-carboxamide-1,1-dioxide | 363 | 0.92 |
| I-81 | 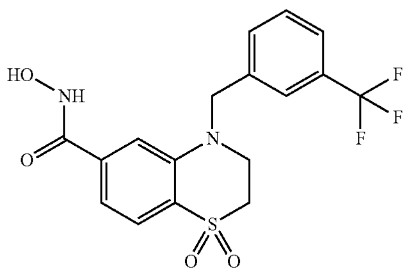 [SMILES: O=C(NO)c1ccc2c(c1)N(Cc1cccc(C(F)(F)F)c1)CCS2(=O)=O] | N-hydroxy-4-(3-(trifluoromethyl)benzyl)-3,4-dihydro-2H-benzo[b][1,4]thiazine-6-carboxamide-1,1-dioxide | 401 | 1.09 |
| I-82 | 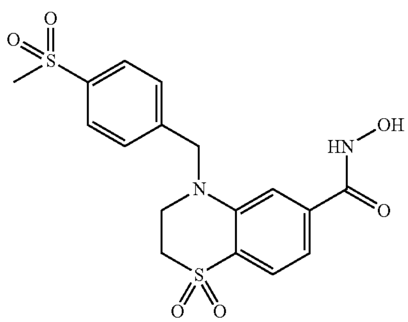 [SMILES: CS(=O)(=O)c1ccc(CN2CCS(=O)(=O)c3ccc(C(=O)NO)cc32)cc1] | N-hydroxy-4-(4-(methylsulfonyl)benzyl)-3,4-dihydro-2H-benzo[b][1,4]thiazine-6-carboxamide-1,1-dioxide | 411 | 0.66 |

Example 20—4-benzyl-N-hydroxy-2-methyl-3,4-dihydro-2H-benzo[b][1,4]oxazine-6-carboxamide (I-83)

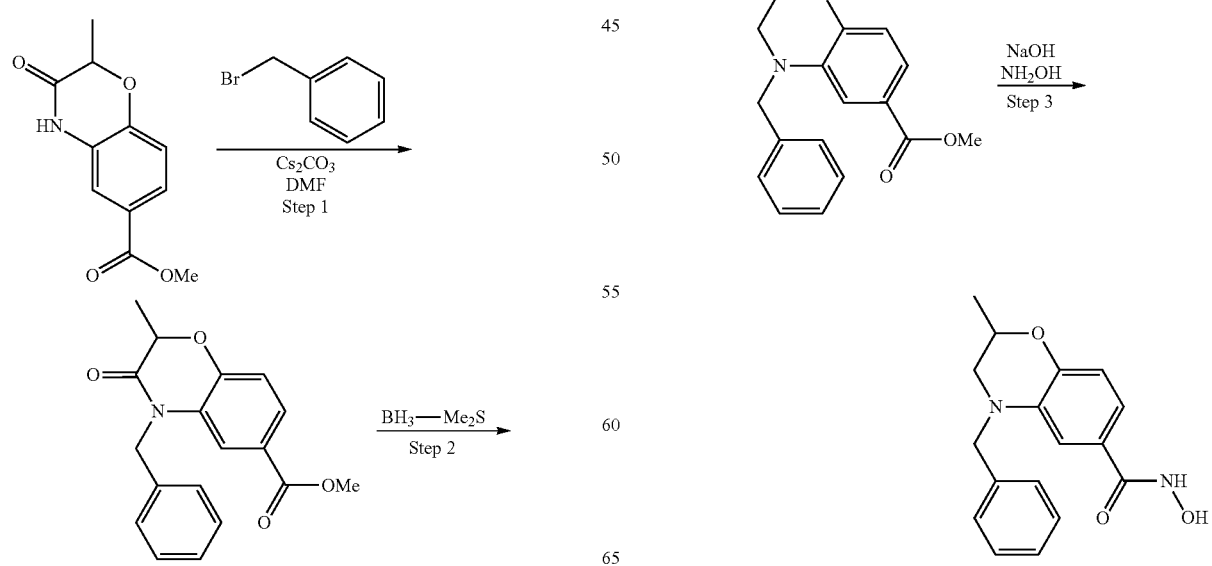

Step-1: Methyl 4-benzyl-2-methyl-3-oxo-3,4-dihydro-2H-benzo[b][1,4]oxazine-6-carboxylate 1-(Chloromethyl)-4-methoxybenzene (0.035 ml, 0.249 mmol) was added to a solution of methyl 2-methyl-3-oxo-3,4-dihydro-2H-benzo[b][1,4]oxazine-6-carboxylate (50 mg, 0.226 mmol) and cesium carbonate (221 mg, 0.678 mmol) in DMF (2 mL), and the reaction stirred overnight at ambient temperature. The reaction was diluted with ethyl acetate and washed with brine. The organic layer was separated and concentrated to give methyl 4-benzyl-2-methyl-3-oxo-3,4-dihydro-2H-benzo[b][1,4]oxazine-6-carboxylate which was used directly in the next step without further purification. MS: (ES, m/z): 212 [M+H]$^+$.

Step-2: Methyl 4-benzyl-2-methyl-3,4-dihydro-2H-benzo[b][1,4]oxazine-6-carboxylate Borane-methyl sulfide complex in 2-methyltetrahydrofuran (0.675 mL, 0.675 mmol) was added to a solution of methyl 4-benzyl-2-methyl-3-oxo-3,4-dihydro-2H-benzo[b][1,4]oxazine-6-carboxylate (70 mg, 0.225 mmol) in THF (5 mL), and the reaction was placed on a heater/shaker at 50° C. for 3 hours. The reaction was cooled to room temperature and 2.5 mL of methanol was added and stirred overnight at ambient temperature. The reaction mixture was concentrated to dryness to give methyl 4-benzyl-2-methyl-3,4-dihydro-2H-benzo[b][1,4]oxazine-6-carboxylate as an orange residue which was used directly in the next step without further purification. MS: (ES, m/z): 298 [M+H]$^+$.

Step-3: 4-benzyl-N-hydroxy-2-methyl-3,4-dihydro-2H-benzo[b][1,4]oxazine-6-carboxamide Methyl 4-benzyl-2-methyl-3,4-dihydro-2H-benzo[b][1,4]oxazine-6-carboxylate (66 mg, 0.222 mmol) was dissolved in MeOH/THF (1/1) (2 mL), and 50% aqueous hydroxyl amine (0.75 mL, 11.4 mmol) and 1 N aqueous sodium hydroxide solution (0.75 mL, 0.75 mmol) were added. The resulting solution stirred for 2 hours at ambient temperature, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column. The collected fractions were combined and lyophilized to afford N-hydroxy-2-methyl-4-(4-(methylsulfonyl)benzyl)-3,4-dihydro-2H-benzo[b][1,4]oxazine-6-carboxamide (12.8 mg, 0.034 mmol, 15%) as a grey solid. $^1$H NMR (300 MHz, DMSO-d$_6$) δ ppm 10.92 (s, 1H) 8.81 (s, 1H) 7.20-7.42 (m, 5H) 7.12 (d, J=1.76 Hz, 1H) 6.97 (dd, J=8.21, 1.76 Hz, 1H) 6.73 (d, J=8.21 Hz, 1H) 4.43-4.62 (m, 2H) 4.22-4.32 (m, 1H) 3.39 (dd, J=12.02, 2.35 Hz, 1H) 3.08 (dd, J=12.17, 8.06 Hz, 1H) 1.29 (d, J=6.16 Hz, 3H). MS: (ES, m/z): 299 [M+H]$^+$.

The compounds below were synthesized according to the procedures outlined above for Example 20.

| Compd. No. | Structure | IUPAC Name | $^1$H NMR | MS (ES, m/z) [M + H]$^+$ |
|---|---|---|---|---|
| I-84 | 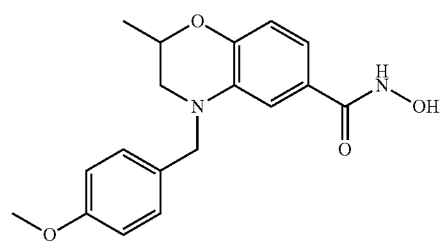 [SMILES: COc1ccc(CN2CC(C)Oc3ccc(C(=O)NO)cc32)cc1] | N-hydroxy-4-(4-methoxybenzyl)-2-methyl-3,4-dihydro-2H-benzo[b][1,4]oxazine-6-carboxamide | $^1$H NMR (300 MHz, DMSO-d$_6$) δ ppm 10.93 (br s, 1 H) 8.81 (s, 1 H) 7.12-7.27 (m, 3 H) 6.97 (dd, J = 8.21, 1.76 Hz, 1 H) 6.85-6.94 (m, 2 H) 6.72 (d, J = 8.21 Hz, 1 H) 4.34-4.54 (m, 2 H) 4.19-4.29 (m, 1 H) 3.37 (br d, J = 2.35 Hz, 1 H) 3.01 (dd, J = 11.87, 8.06 Hz, 1 H) 1.27 (d, J = 6.16 Hz, 3 H) | 329 |
| I-85 | 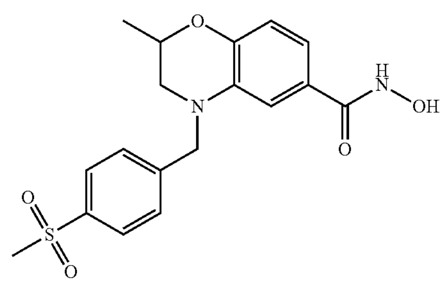 [SMILES: CC1CN(Cc2ccc(S(C)(=O)=O)cc2)c2cc(C(=O)NO)ccc2O1] | N-hydroxy-2-methyl-4-(4-(methylsulfonyl)benzyl)-3,4-dihydro-2H-benzo[b][1,4]oxazine-6-carboxamide | $^1$H NMR (300 MHz, DMSO-d$_6$) δ ppm 10.91 (br s, 1 H) 8.81 (s, 1 H) 7.90 (d, J = 8.21 Hz, 2 H) 7.55 (d, J = 8.50 Hz, 2 H) 6.91-7.14 (m, 2 H) 6.76 (d, J = 7.92 Hz, 1 H) 4.51-4.78 (m, 2 H) 4.31 (br d, J = 6.16 Hz, 1 H) 3.44 (br d, J = 9.67 Hz, 1 H) 3.21 (s, 3 H) 3.12-3.19 (m, 1 H) 1.31 (d, J = 6.45 Hz, 3 H) | 377 |

Example 21—N-hydroxy-4-(phenylsulfonyl)-3,4-dihydro-2H-benzo[b][1,4]oxazine-6-carboxamide (I-86)

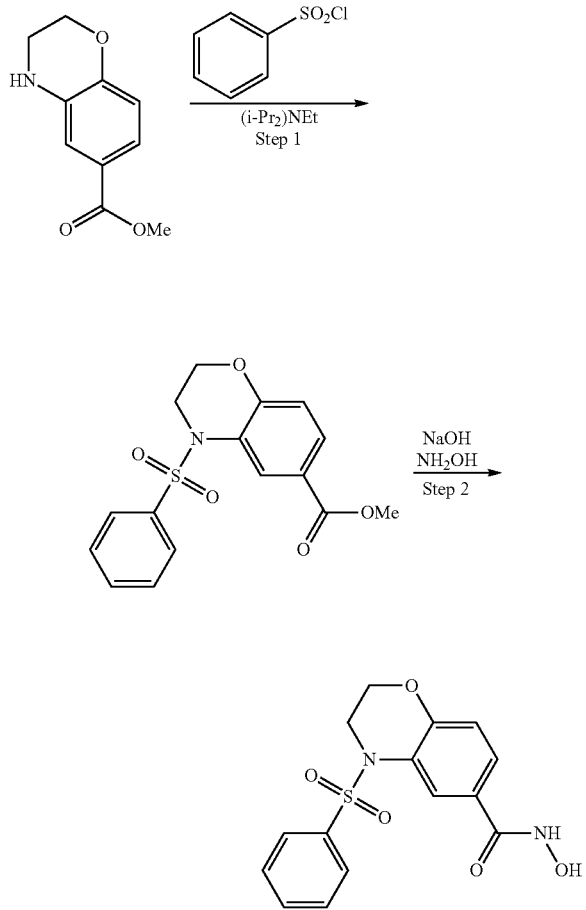

Step-1: Methyl 4-(phenylsulfonyl)-3,4-dihydro-2H-benzo[b][1,4]oxazine-6-carboxylate Benzenesulfonyl chloride (43.9 mg, 0.248 mmol) and N,N-diisopropylethylamine (0.108 mL, 0.621 mmol) were added to a solution of methyl 3,4-dihydro-2H-benzo[b][1,4]oxazine-6-carboxylate (40 mg, 0.207 mmol) in acetonitrile (2 mL), and the reaction stirred at ambient temperature overnight. The reaction was diluted with ethyl acetate and washed with brine. The organic phase was separated and concentrated to afford methyl 4-(phenyl sulfonyl)-3,4-dihydro-2H-benzo[b][1,4]oxazine-6-carboxylate which was used directly in the next step without further purification. MS: (ES, m/z): 366 [M+S+H]$^+$.

Step-2: N-hydroxy-4-(phenylsulfonyl)-3,4-dihydro-2H-benzo[b][1,4]oxazine-6-carboxamide Methyl 4-(phenylsulfonyl)-3,4-dihydro-2H-benzo[b][1,4]oxazine-6-carboxylate (60 mg, 0.180 mmol) was dissolved in MeOH/THF (1/1) (2 mL), and 50% aqueous hydroxyl amine (0.5 mL, 7.57 mmol), and 1 N aqueous sodium hydroxide solution (0.5 mL, 0.55 mmol) were added. The resulting solution stirred for 2 hours at ambient temperature, and was then concentrated to dryness. The crude product was purified by Prep-HPLC with the following conditions: Waters reversed phase HPLC: 23 mL/min, 8 min gradient 0%-35% Acetonitrile, 0.1% formic acid on a Waters XBridge Prep C18 OBD 5 μm, 19×50 mm column. The collected fraction was lyophilized to afford N-hydroxy-4-(phenylsulfonyl)-3,4-dihydro-2H-benzo[b][1,4]oxazine-6-carboxamide (23 mg, 0.069 mmol, 38%) as an off-white solid. $^1$H NMR (300 MHz, DMSO-d$_6$) δ ppm 11.16 (br s, 1H) 9.00 (s, 1H) 8.19 (d, J=2.05 Hz, 1H) 7.55-7.76 (m, 5H) 7.47 (dd, J=8.50, 2.05 Hz, 1H) 6.88 (d, J=8.50 Hz, 1H) 3.91 (t, J=4.40 Hz, 2H) 3.65-3.77 (m, 2H). MS: (ES, m/z): 335[M+H]$^+$.

The compounds below were synthesized according to the procedures outlined above for Example 21.

| Compd. No. | Structure | IUPAC Name | $^1$H NMR | MS (ES, m/z) [M + H]$^+$ |
|---|---|---|---|---|
| I-87 | 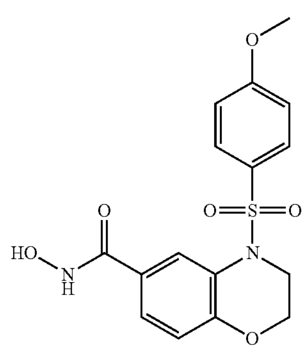 [SMILES: COc1ccc(S(=O)(=O)N2CCOc3ccc(C(=O)NO)cc32)cc1] | N-hydroxy-4-((4-methoxyphenyl)sulfonyl)-3,4-dihydro-2H-benzo[b][1,4]oxazine-6-carboxamide | $^1$H NMR (300 MHz, DMSO-d$_6$) δ ppm 11.14 (br s, 1 H) 8.98 (br s, 1 H) 8.20 (d, J = 2.05 Hz, 1 H) 7.54-7.64 (m, 2 H) 7.46 (dd, J = 8.50, 2.05 Hz, 1 H) 7.04-7.14 (m, 2 H) 6.87 (d, J = 8.79 Hz, 1 H) 3.83-3.92 (m, 2 H) 3.80-3.83 (m, 3 H) 3.70-3.77 (m, 2 H) | 365 |

Example 22—4-(4-((difluoromethyl)sulfonyl)benzyl)-N-hydroxy-3-oxo-3,4-dihydro-2H-benzo[b][1,4]oxazine-6-carboxamide (I-88)

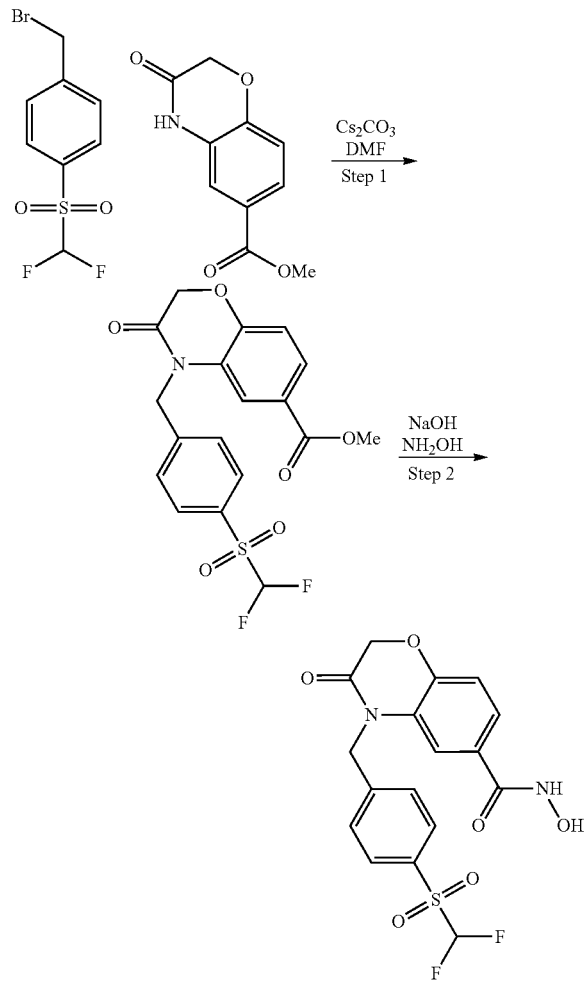

Step-1: Methyl 4-(4-((difluoromethyl)sulfonyl)benzyl)-3-oxo-3,4-dihydro-2H-benzo[b][1,4]oxazine-6-carboxylate 1-(Bromomethyl)-4-((difluoromethyl)sulfonyl)benzene (68.8 mg, 0.241 mmol) was added to a solution of methyl 3-oxo-3,4-dihydro-2H-benzo[b][1,4]oxazine-6-carboxylate (50 mg, 0.241 mmol) and cesium carbonate (236 mg, 0.724 mmol) in DMF (2 mL), and the reaction stirred overnight at ambient temperature. The reaction was diluted with ethyl acetate and washed with brine. The organic phase was separated and concentrated to afford methyl 4-(4-((difluoromethyl)sulfonyl)benzyl)-3-oxo-3,4-dihydro-2H-benzo[b][1,4]oxazine-6-carboxylate as a residue which was used directly in the next step without further purification. MS: (ES, m/z): 434 $[M+Na+H]^+$.

Step-2: 4-(4-((difluoromethyl)sulfonyl)benzyl)-N-hydroxy-3-oxo-3,4-dihydro-2H-benzo[b][1,4]oxazine-6-carboxamide Methyl 4-(4-((difluoromethyl)sulfonyl)benzyl)-3-oxo-3,4-dihydro-2H-benzo[b][1,4]oxazine-6-carboxylate (90 mg, 0.219 mmol) was dissolved in MeOH/THF (1/1) (3 mL) and 50% aqueous hydroxyl amine (1 mL, 15.14 mmol) and 1 N aqueous sodium hydroxide solution (1 mL, 1 mmol) were added. The resulting solution stirred for 2 hours at ambient temperature, and was then concentrated to dryness. The crude product was purified by Prep-HPLC with the following conditions: Waters reversed phase HPLC (23 mL/min, 8 min gradient 15%-65% Acetonitrile, 0.1% formic acid on a Waters XBridge Prep C18 OBD 5 μm, 19×50 mm column). The collected fractions were combined and lyophilized to afford 4-(4-((difluoromethyl)sulfonyl)benzyl)-N-hydroxy-3-oxo-3,4-dihydro-2H-benzo[b][1,4]oxazine-6-carboxamide (37.7 mg, 0.091 mmol, 42%) as a fluffy white solid. $^1$H NMR (300 MHz, DMSO-$d_6$) δ ppm 11.11 (br s, 1H) 8.98 (s, 1H) 7.96 (d, J=8.21 Hz, 2H) 7.68 (d, J=8.21 Hz, 2H) 7.40-7.50 (m, 1H) 7.28-7.35 (m, 1H) 7.11 (d, J=8.21 Hz, 1H) 5.34 (s, 2H) 4.90 (s, 2H) 3.30 (s, 1H). MS: (ES, m/z): 413 $[M+H]^+$.

The compounds below were synthesized according to the procedures outlined above for Example 22.

| Compd. No. | Structure | IUPAC Name | $^1$H NMR | MS (ES, m/z) $[M + H]^+$ |
|---|---|---|---|---|
| I-89 | (structure) | N-hydroxy-4-(4-methoxybenzyl)-3-oxo-3,4-dihydro-2H-benzo[b][1,4]oxazine-7-carboxamide | $^1$H NMR (300 MHz, DMSO-$d_6$) δ ppm 11.14 (br s, 1 H) 9.03 (br s, 1 H) 7.30-7.43 (m, 2 H) 7.11-7.25 (m, 3 H) 6.88 (d, J = 8.79 Hz, 2 H) 5.11 (s, 2 H) 4.83 (s, 2 H) 3.71 (s, 3 H) | 329 |

| Compd. No. | Structure | IUPAC Name | ¹H NMR | MS (ES, m/z) [M + H]⁺ |
|---|---|---|---|---|
| I-90 | 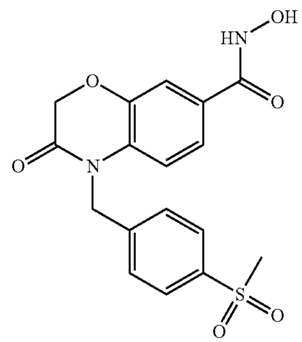 [SMILES: CS(=O)(=O)c1ccc(CN2C(=O)COc3cc(C(=O)NO)ccc32)cc1] | N-hydroxy-4-(4-(methylsulfonyl)benzyl)-3-oxo-3,4-dihydro-2H-benzo[b][1,4]oxazine-7-carboxamide | N/A | 377⁺ |
| I-91 | 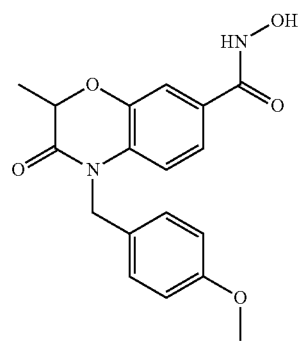 [SMILES: COc1ccc(CN2C(=O)C(C)Oc3cc(C(=O)NO)ccc32)cc1] | N-hydroxy-4-(4-methoxybenzyl)-2-methyl-3-oxo-3,4-dihydro-2H-benzo[b][1,4]oxazine-7-carboxamide | ¹H NMR (300 MHz, DMSO-d₆) δ ppm 11.14 (s, 1 H) 9.03 (s, 1 H) 7.05-7.40 (m, 5 H) 6.79-6.97 (m, 2 H) 5.10 (s, 2 H) 4.80-5.01 (m, 1 H) 3.71 (s, 3 H) 1.51 (d, J = 6.74 Hz, 3 H) | 343 |
| I-92 | 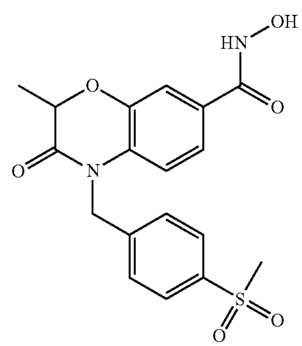 [SMILES: CC1Oc2cc(C(=O)NO)ccc2N(Cc2ccc(S(C)(=O)=O)cc2)C1=O] | N-hydroxy-2-methyl-4-(4-(methylsulfonyl)benzyl)-3-oxo-3,4-dihydro-2H-benzo[b][1,4]oxazine-7-carboxamide | ¹H NMR (300 MHz, DMSO-d₆) δ ppm 11.15 (br s, 1 H) 9.04 (s, 1 H) 7.89 (d, J = 8.50 Hz, 2 H) 7.52 (d, J = 8.21 Hz, 2 H) 7.34-7.45 (m, 2 H) 6.99-7.18 (m, 1 H) 5.18-5.39 (m, 2 H) 4.98 (q, J = 6.64 Hz, 1 H) 3.20 (s, 3 H) 1.53 (d, J = 6.74 Hz, 3 H) | 391 |
| I-93 | 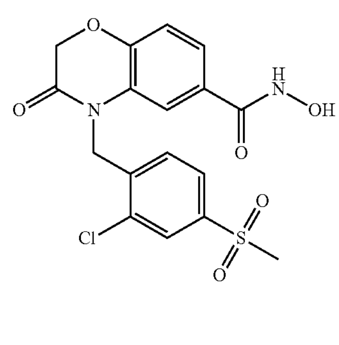 [SMILES: CS(=O)(=O)c1ccc(CN2C(=O)COc3ccc(C(=O)NO)cc32)c(Cl)c1] | 4-(2-chloro-4-(methylsulfonyl)benzyl)-N-hydroxy-3-oxo-3,4-dihydro-2H-benzo[b][1,4]oxazine-6-carboxamide | ¹H NMR (300 MHz, DMSO-d₆) δ ppm 8.08 (d, J = 1.76 Hz, 1 H) 7.80 (dd, J = 8.21, 1.76 Hz, 1 H) 7.29-7.45 (m, 2 H) 7.15 (d, J = 1.47 Hz, 1 H) 6.95 (d, J = 8.21 Hz, 1 H) 5.16 (s, 2 H) 4.84 (s, 2 H) 3.34 (s, 4 H) | 411 |

-continued

| Compd. No. | Structure | IUPAC Name | ¹H NMR | MS (ES, m/z) [M + H]⁺ |
|---|---|---|---|---|
| I-94 | 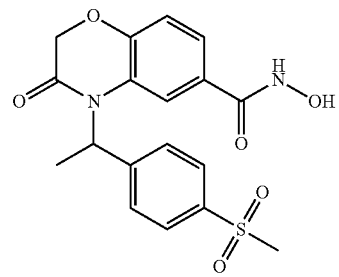 [SMILES: CC(c1ccc(S(C)(=O)=O)cc1)N1C(=O)COc2ccc(C(=O)NO)cc21] | N-hydroxy-4-(1-(4-(methylsulfonyl)phenyl)ethyl)-3-oxo-3,4-dihydro-2H-benzo[b][1,4]oxazine-6-carboxamide | | 411 |
| I-95 | 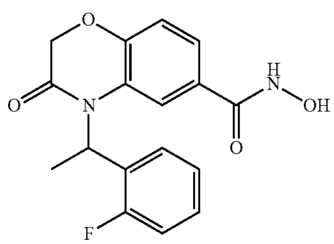 [SMILES: CC(c1ccccc1F)N1C(=O)COc2ccc(C(=O)NO)cc21] | 4-(1-(2-fluorophenyl)ethyl)-N-hydroxy-3-oxo-3,4-dihydro-2H-benzo[b][1,4]oxazine-6-carboxamide | ¹H NMR (300 MHz, DMSO-d₆) δ ppm 11.16 (s, 1 H) 9.00 (s, 1 H) 7.60 (t, J = 7.62 Hz, 1 H) 7.51 (d, J = 1.76 Hz, 1 H) 7.26-7.41 (m, 2 H) 7.18-7.26 (m, 1 H) 7.01-7.15 (m, 2 H) 6.01 (q, J = 7.13 Hz, 1 H) 4.66 (d, J = 2.35 Hz, 2 H) 1.86 (d, J = 7.33 Hz, 3 H) | 331 |
| I-96 | 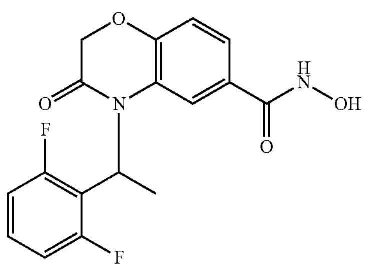 [SMILES: CC(c1c(F)cccc1F)N1C(=O)COc2ccc(C(=O)NO)cc21] | 4-(1-(2,6-difluorophenyl)ethyl)-N-hydroxy-3-oxo-3,4-dihydro-2H-benzo[b][1,4]oxazine-6-carboxamide | ¹H NMR (300 MHz, DMSO-d₆) δ ppm 11,21 (br s, 1 H) 9.06 (s, 1 H) 7.73 (d, J = 1.76 Hz, 1 H) 7.41 (dd, J = 8.35, 1.91 Hz, 1 H) 7.27-7.38 (m, 1 H) 7.07 (d, J = 8.50 Hz, 1 H) 7.01 (t, J = 8.79 Hz, 2 H) 5.88-6.12 (m, 1 H) 4.56-4.68 (m, 2 H) 1.84-1.94 (m, 3 H) | 349 |

Example 23—N-hydroxy-4-(piperidine-1-carbonyl)-3,4-dihydro-2H-benzo[b][1,4]oxazine-6-carboxamide (I-97)

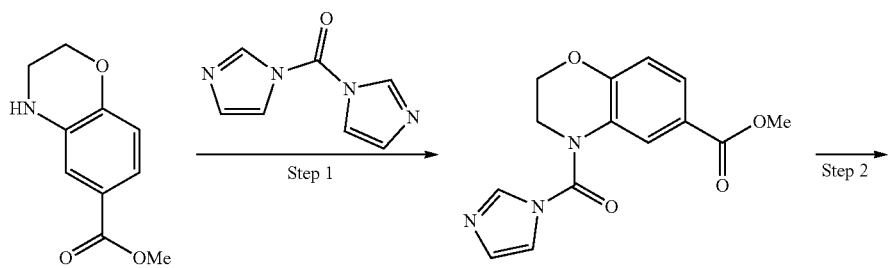

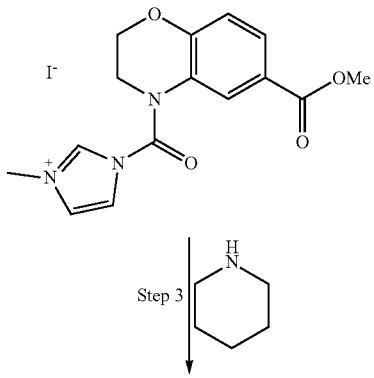

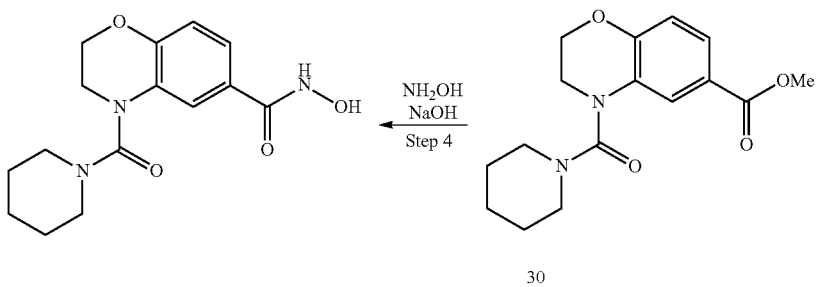

Step-1: Methyl 4-(1H-imidazole-1-carbonyl)-3,4-dihydro-2H-benzo[b][1,4]oxazine-6-carboxylate A solution of methyl 3,4-dihydro-2H-benzo[b][1,4]oxazine-6-carboxylate (300 mg, 1.55 mmol) and carbonyl diimidazole (277 mg, 1.708 mmol) in THF (10 mL) was heated at 80° C. for 8 days. The reaction was cooled to ambient temperature and then concentrated to dryness. The residue was diluted with dichloromethane and washed with brine. The organic layer was passed through an Isolute© phase separator and then concentrated to afford methyl 4-(1H-imidazole-1-carbonyl)-3,4-dihydro-2H-benzo[b][1,4]oxazine-6-carboxylate which was used directly in the next step without further purification. MS: (ES, m/z): 288 [M+H]$^+$.

Step-2: 1-(6-(Methoxycarbonyl)-3,4-dihydro-2H-benzo[b][1,4]oxazine-4-carbonyl)-3-methyl-1H-imidazol-3-ium Iodide Methyl iodide (0.9 mL, 14 mmol) was added to a solution of methyl 4-(1H-imidazole-1-carbonyl)-3,4-dihydro-2H-benzo[b][1,4]oxazine-6-carboxylate (400 mg, 1.392 mmol) in acetonitrile (5 mL), and the reaction stirred at ambient temperature for 48 hours. The reaction was concentrated to afford 1-(6-(methoxycarbonyl)-3,4-dihydro-2H-benzo[b][1,4]oxazine-4-carbonyl)-3-methyl-1H-imidazol-3-ium iodide as a yellow-brown solid which was used directly in the next step without further purification. MS: (ES, m/z): 302 [M-I+H]$^+$.

Step-3: Methyl 4-(piperidine-1-carbonyl)-3,4-dihydro-2H-benzo[b][1,4]oxazine-6-carboxylate Piperidine (0.013 mL, 0.128 mmol) and triethylamine (0.049 mL, 0.349 mmol) were added to a solution of 1-(6-(methoxycarbonyl)-3,4-dihydro-2H-benzo[b][1,4]oxazine-4-carbonyl)-3-methyl-1H-imidazol-3-ium iodide (50 mg, 0.116 mmol) in chloroform (3 mL), and the reaction mixture stirred at ambient temperature overnight. The reaction was diluted with dichloromethane and washed with aqueous brine. The organic layer was separated, passed through an Isolute© phase separator, and concentrated to afford methyl 4-(piperidine-1-carbonyl)-3,4-dihydro-2H-benzo[b][1,4]oxazine-6-carboxylate which was used directly in the next step without further purification. MS: (ES, m/z): 305 [M+H]$^+$.

Step-4: N-hydroxy-4-(piperidine-1-carbonyl)-3,4-dihydro-2H-benzo[b][1,4]oxazine-6-carboxamide (I-97)

Hydroxyl amine (50% aqueous solution, 0.3 mL, 4.54 mmol) and 1 N aqueous sodium hydroxide solution (0.3 mL, 0.300 mmol) were added to a solution of methyl 4-(piperidine-1-carbonyl)-3,4-dihydro-2H-benzo[b][1,4]oxazine-6-carboxylate (30 mg, 0.099 mmol) in methanol (1.0 mL) and THF (1.0 mL). The reaction mixture stirred at ambient temperature for 2 hours, and was then concentrated to dryness. The crude product was purified by Prep-HPLC with the following conditions: Waters reversed phase HPLC: 23 mL/min, 8 min gradient 0%-35% Acetonitrile, 0.1% formic acid on a Waters XBridge Prep C18 OBD 5 µm, 19×50 mm column. The collected fraction was lyophilized to afford N-hydroxy-4-(piperidine-1-carbonyl)-3,4-dihydro-2H-benzo[b][1,4]oxazine-6-carboxamide (10 mg, 0.033 mmol, 33%) as a white solid. $^1$H NMR (300 MHz, DMSO-d$_6$) δ ppm 11.00 (s, 1H) 8.93 (s, 1H) 7.53 (d, J=2.05 Hz, 1H) 7.27 (dd, J=8.50, 2.05 Hz, 1H) 6.86 (d, J=8.50 Hz, 1H) 4.00-4.40 (m, 2H) 3.45-3.66 (m, 2H) 3.30 (br d, J=5.57 Hz, 5H) 1.55 (br s, 6H). MS: (ES, m/z): 306[M+H]$^+$.

The compounds below were synthesized according to the procedures outlined above for Example 23:

| Compd. No. | Structure | IUPAC Name | LC-MS [M + H]+ | HPLC RT (min) |
|---|---|---|---|---|
| I-156 | 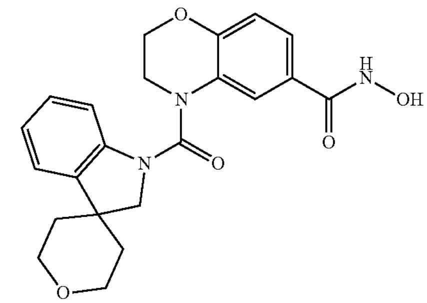 [SMILES: O=C(NO)c1ccc2c(c1)N(C(=O)N1CC3(CCOCC3)c3ccccc31)CCO2] | N-hydroxy-4-(2',3',5',6'-tetrahydrospiro[indoline-3,4'-pyran]-1-carbonyl)-3,4-dihydro-2H-benzo[b][1,4]oxazine-6-carboxamide | 410 | 0.97 |

Example 24—N-hydroxy-4-(4-methoxybenzyl)-2,2-dimethyl-3-oxo-3,4-dihydro-2H-benzo[b][1,4]oxazine-6-carboxamide (I-98)

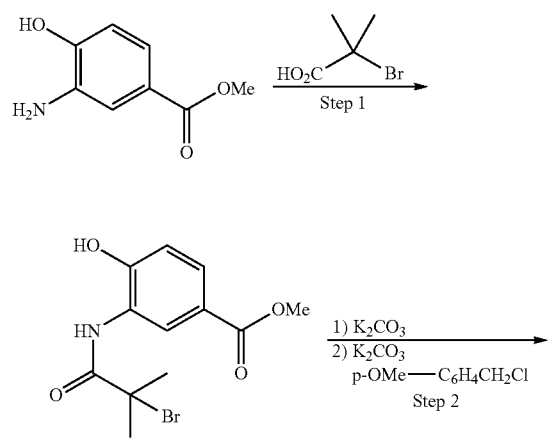

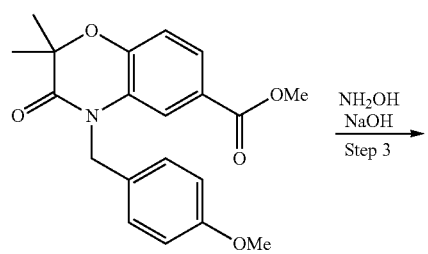

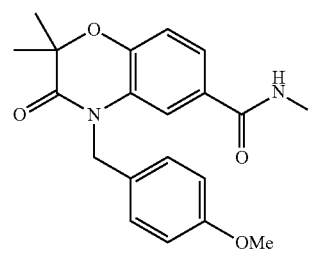

Step-1: Methyl 3-(2-bromo-2-methylpropanamido)-4-hydroxybenzoate

2-Bromo-2-methylpropanoic acid (100 mg, 0.598 mmol) and N,N-diisopropylamine (0.313 mL, 1.795 mmol) were added to a solution of methyl 3-amino-4-hydroxybenzoate (100 mg, 0.598 mmol) in chloroform (5 mL). 2-Chloro-1,3-dimethylimidazolinium chloride (DMC) (111 mg, 0.658 mmol) was added, and the reaction stirred at ambient temperature overnight. The reaction was diluted with dichloromethane and washed with brine. The organic layer was passed through an Isolute© phase separator and then concentrated to afford methyl 3-(2-bromo-2-methylpropanamido)-4-hydroxybenzoate as semi solid which was used directly in the next step without further purification. MS (ESI, m/z): 316, 318 [M+H]+.

Step-2: methyl 4-(4-methoxybenzyl)-2,2-dimethyl-3-oxo-3,4-dihydro-2H-benzo[b][1,4]oxazine-6-carboxylate Potassium carbonate (79 mg, 0.569 mmol) was added to a solution of methyl 3-(2-bromo-2-methylpropanamido)-4-hydroxybenzoate (60 mg, 0.190 mmol) in DMF (5 mL) and the reaction mixture was placed on a heater shaker at 50° C. for 2 hours. The reaction was cooled to ambient temperature, and 1-(chloromethyl)-4-methoxybenzene (0.027 ml, 0.190 mmol) was added. The reaction stirred at room temperature overnight. The reaction was diluted with ethyl acetate and washed with brine. The organic layer was separated and concentrated, and the residue was purified by column chromatography on silica gel (Biotage 25 g column, eluting with 20-60% ethyl acetate-hexane) to afford methyl 4-(4-methoxybenzyl)-2,2-dimethyl-3-oxo-3,4-dihydro-2H-benzo[b][1,4]oxazine-6-carboxylate (50 mg, 0.141 mmol, 74%). $^1$H NMR (300 MHz, DMSO-$d_6$) δ ppm 7.50-7.69 (m, 2H) 7.14 (dd, J=18.47, 8.50 Hz, 3H) 6.83-7.02 (m, 2H) 5.12 (s, 2H) 3.78 (s, 3H) 3.72 (s, 3H) 1.51 (s, 6H). MS: (ES, m/z): 378 [M+Na+H]+.

Step-3: N-hydroxy-4-(4-methoxybenzyl)-2,2-dimethyl-3-oxo-3,4-dihydro-2H-benzo[b][1,4]oxazine-6-carboxamide (I-98)

Methyl 4-(4-methoxybenzyl)-2,2-dimethyl-3-oxo-3,4-dihydro-2H-benzo[b][1,4]oxazine-6-carboxylate (50 mg, 0.141 mmol) was dissolved in methanol (1 mL) and THF (1 mL). 50% aqueous hydroxylamine (0.5 mL, 7.6 mmol) and 1N aqueous sodium hydroxide solution (0.5 mL, 0.500 mmol) were added, and the reaction stirred at ambient temperature for 2 hours. The reaction mixture was concentrated, and the crude product was purified by prep-HPLC with the following conditions: Waters reversed phase HPLC: (23 mL/min, 8 min gradient 15%-65% Acetonitrile, 0.1% formic acid on a Waters XBridge Prep C18 OBD 5 μm, 19×50 mm column. The collected fractions were lyophilized to afford N-hydroxy-4-(4-methoxybenzyl)-2,2-dimethyl-3-oxo-3,4-dihydro-2H-benzo[b][1,4]oxazine-6-carboxamide (24.8 mg, 0.070 mmol, 50%) as a white solid. $^1$H NMR (300 MHz, DMSO-d$_6$) δ ppm 11.12 (br s, 1H) 8.99 (s, 1H) 7.28-7.56 (m, 2H) 7.16 (d, J=8.79 Hz, 2H) 7.04 (d, J=8.21 Hz, 1H) 6.90 (d, J=8.79 Hz, 2H) 5.10 (s, 2H) 3.71 (s, 3H) 1.49 (s, 6H). MS: (ES, m/z): 357[M+H]$^-$.

Example 25—2-ethyl-N-hydroxy-4-(4-methoxybenzyl)-3-oxo-3,4-dihydro-2H-benzo[b][1,4]oxazine-6-carboxamide (I-99)

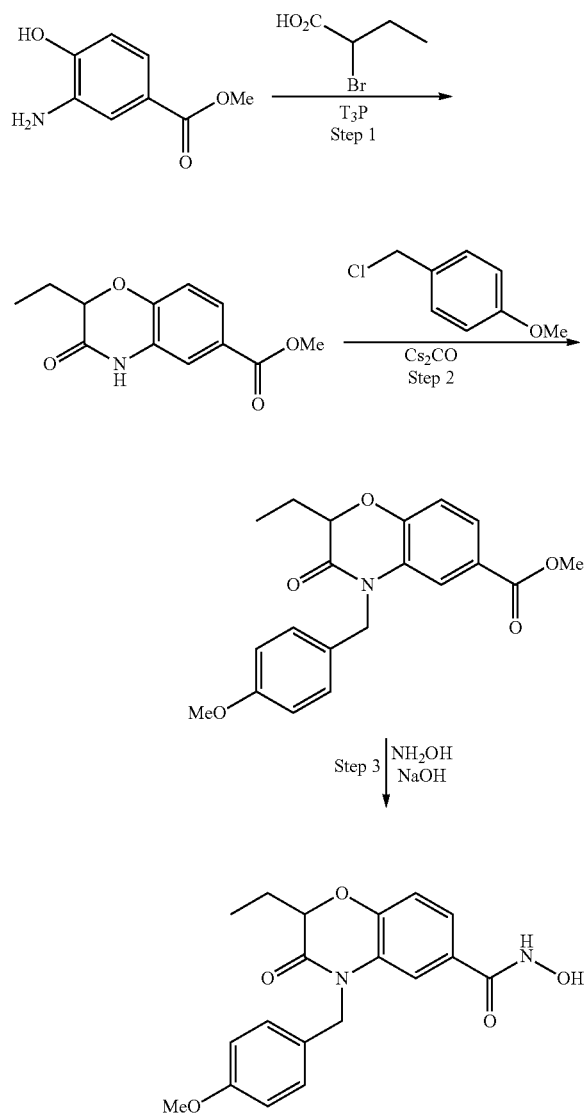

Step-1: methyl 2-ethyl-3-oxo-3,4-dihydro-2H-benzo[b][1,4]oxazine-6-carboxylate

2-Bromobutanoic acid (0.032 mL, 0.299 mmol), N,N-diisopropylethylamine (0.157 mL, 0.897 mmol) and 2,4,6-tripropyl-1,3,5,2,4,6-trioxatriphosphinane 2,4,6-trioxide (T$_3$P) (0.231 mL, 0.389 mmol) were added to a solution of methyl 3-amino-4-hydroxybenzoate (50 mg, 0.299 mmol) in acetonitrile (2 mL), and the reaction stirred at ambient temperature overnight. The reaction was diluted with ethyl acetate and washed with brine. The organic layer was separated and concentrated, and the residue was purified via column chromatography on silica gel (Biotage 10 gram column, eluting with 5-60% ethyl acetate-hexane) to afford methyl 2-ethyl-3-oxo-3,4-dihydro-2H-benzo[b][1,4]oxazine-6-carboxylate (13 mg, 0.055 mmol, 18%) which was used directly in the next step. MS (ESI, r/z): 236 [M+H]$^+$.

Step-2: methyl 2-ethyl-4-(4-methoxybenzyl)-3-oxo-3,4-dihydro-2H-benzo[b][1,4]oxazine-6-carboxylate 1-(Chloromethyl)-4-methoxybenzene (7.49 μL, 0.055 mmol) and cesium carbonate (54.0 mg, 0.166 mmol) were added to a solution of methyl 2-ethyl-3-oxo-3,4-dihydro-2H-benzo[b][1,4]oxazine-6-carboxylate (13 mg, 0.055 mmol) in DMF (2 mL), and the reaction stirred at ambient temperature overnight. The reaction mixture was diluted with ethyl acetate and washed with brine. The organic layer was separated and concentrated to afford methyl 2-ethyl-4-(4-methoxybenzyl)-3-oxo-3,4-dihydro-2H-benzo[b][1,4]oxazine-6-carboxylate as semi solid which was used directly in the next step without further purification. MS (ESI, m/z): 356 [M+H]$^+$.

Step-3: 2-ethyl-N-hydroxy-4-(4-methoxybenzyl)-3-oxo-3,4-dihydro-2H-benzo[b][1,4]oxazine-6-carboxamide (I-99)

Methyl 2-ethyl-4-(4-methoxybenzyl)-3-oxo-3,4-dihydro-2H-benzo[b][1,4]oxazine-6-carboxylate (20 mg, 0.056 mmol) was dissolved in methanol (0.5 mL) and THF (0.5 mL), and 50% aqueous hydroxyl amine (0.25 ml, 3.78 mmol) and 1N aqueous sodium hydroxide solution (0.25 mL, 0.250 mmol) were added. The reaction mixture stirred at ambient temperature for 2 hours and was then concentrated to dryness. The crude product was purified by Prep-HPLC with the following conditions: Waters reversed phase HPLC: (23 mL/min, 8 min gradient 15%-65% Acetonitrile, 0.1% formic acid on a Waters XBridge Prep C18 OBD 5 μm, 19×50 mm column. The collected fractions were lyophilized to afford 2-ethyl-N-hydroxy-4-(4-methoxybenzyl)-3-oxo-3,4-dihydro-2H-benzo[b][1,4]oxazine-6-carboxamide (11.6 mg, 0.033 mmol, 57.8% yield) as a white solid. 1H NMR (300 MHz, DMSO-d6) δ ppm 11.13 (br s, 1H) 9.00 (br s, 1H) 7.33-7.47 (m, 2H) 7.18 (d, J=8.50 Hz, 2H) 7.08 (d, J=8.21 Hz, 1H) 6.89 (d, J=8.50 Hz, 2H) 5.11 (d, J=5.57 Hz, 2H) 4.79 (dd, J=7.62, 4.69 Hz, 1H) 3.71 (s, 3H) 1.77-1.95 (m, 2H) 1.02 (t, J=7.48 Hz, 3H). MS: (ES, m/z): 357[M+H]+.

Example 26—N-hydroxy-2-isopropyl-4-(4-methoxybenzyl)-3-oxo-3,4-dihydro-2H-benzo[b][1,4]oxazine-6-carboxamide (I-100)

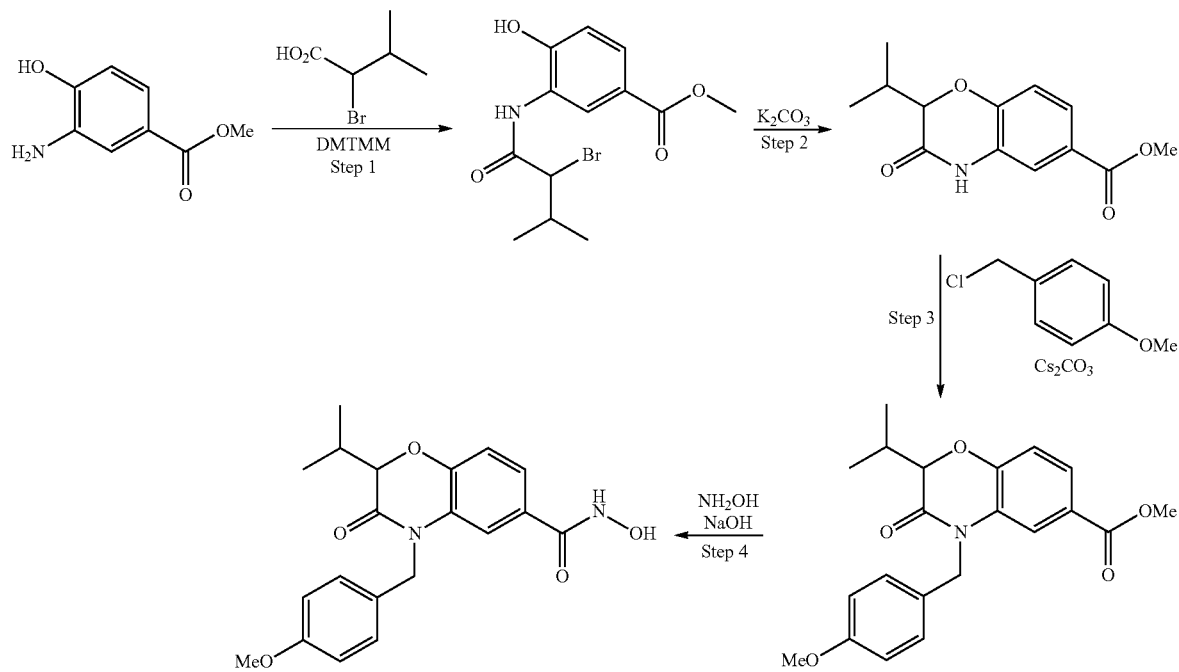

Step-1: Methyl 3-(2-bromo-3-methylbutanamido)-4-hydroxybenzoate 4-(4,6-Dimethoxy-1,3,5-triazin-2-yl)-4-methylmorpholin-4-ium chloride (DMTMM) (83 mg, 0.299 mmol) was added to a solution of methyl 3-amino-4-hydroxybenzoate (50 mg, 0.299 mmol) and 2-bromo-3-methylbutanoic acid (54.1 mg, 0.299 mmol) in dichloromethane (2 mL), and the reaction stirred at ambient temperature overnight. The reaction was diluted with dichloromethane and washed with brine. The organic layer was separated and filtered through an Isolute© phase separator. The filtrate was concentrated to afford methyl 3-(2-bromo-3-methylbutanamido)-4-hydroxybenzoate which was used directly in the next step without further purification. MS (ESI, m/z): 330, 332 [M+H]⁻.

Step-2: Methyl 2-isopropyl-3-oxo-3,4-dihydro-2H-benzo[b][1,4]oxazine-6-carboxylate Potassium carbonate (124 mg, 0.900 mmol) was added to a solution of methyl 3-(2-bromo-3-methylbutanamido)-4-hydroxybenzoate (99 mg, 0.300 mmol) in DMF (3 mL), and the reaction was placed on a heater/shaker at 80° C. overnight. The reaction was diluted with ethyl acetate and washed with brine. The organic layer was separated and concentrated. The residue purified by column chromatography on silica gel (Biotage 10 gram column, eluting with 0-10% methanol-dichloromethane) to afford methyl 2-isopropyl-3-oxo-3,4-dihydro-2H-benzo[b][1,4]oxazine-6-carboxylate (30 mg, 0.120 mmol, 40% yield) as a colorless film. $^1$H NMR (300 MHz, DMSO-d$_6$) δ ppm 10.89 (s, 1H) 7.50-7.59 (m, 1H) 7.49 (s, 1H) 7.07 (d, J=8.21 Hz, 1H) 4.53 (d, J=4.98 Hz, 1H) 3.81 (s, 3H) 2.20 (dd, J=12, 02, 6.74 Hz, 1H) 1.03 (d, J=6.74 Hz, 3H) 0.92 (d, J=6.74 Hz, 3H). MS: (ES, m/z): 250 [M+H]⁺.

Step-3: Methyl 2-isopropyl-4-(4-methoxybenzyl)-3-oxo-3,4-dihydro-2H-benzo[b][1,4]oxazine-6-carboxylate 1-(Chloromethyl)-4-methoxybenzene (0.016 ml, 0.120 mmol) and potassium carbonate (49.9 mg, 0.361 mmol) were added to a solution of methyl 2-isopropyl-3-oxo-3,4-dihydro-2H-benzo[b][1,4]oxazine-6-carboxylate (30 mg, 0.120 mmol) in DMF (2 mL), and the reaction stirred at ambient temperature overnight. The reaction mixture was diluted with ethyl acetate and washed with brine. The organic layer was separated and concentrated to afford methyl 2-isopropyl-4-(4-methoxybenzyl)-3-oxo-3,4-dihydro-2H-benzo[b][1,4]oxazine-6-carboxylate which was used directly in the next step without further purification. MS (ESI, m/z): 370 [M+H]⁺.

Step-4: N-hydroxy-2-isopropyl-4-(4-methoxybenzyl)-3-oxo-3,4-dihydro-2H-benzo[b][1,4]oxazine-6-carboxamide (I-100)

Methyl 2-isopropyl-4-(4-methoxybenzyl)-3-oxo-3,4-dihydro-2H-benzo[b][1,4]oxazine-6-carboxylate (40 mg, 0.108 mmol) was dissolved in methanol (1 mL) and THF (1 mL), and 50% aqueous hydroxyl amine (0.5 ml, 7.57 mmol) and 1 N aqueous sodium hydroxide solution (0.5 mL, 0.500 mmol) were added. The reaction stirred at ambient temperature for 2 hours and was then concentrated to dryness. The crude product was purified by Prep-HPLC with the following conditions: Waters reversed phase HPLC: (23 mL/min, 8 min gradient 15%-65% Acetonitrile, 0.1% formic acid on a Waters XBridge Prep C18 OBD 5 μm, 19×50 mm column. The collected fractions were lyophilized to afford N-hydroxy-2-isopropyl-4-(4-methoxybenzyl)-3-oxo-3,4-dihydro-2H-benzo[b][1,4]oxazine-6-carboxamide (15.4 mg, 0.042 mmol, 38%) as a fluffy white solid. $^1$H NMR (300 MHz, DMSO-d$_6$) δ ppm 11.12 (br s, 1H) 8.99 (s, 1H) 7.35-7.49 (m, 2H) 7.19 (d, J=8.50 Hz, 2H) 7.08 (d, J=8.21 Hz, 1H) 6.90 (d, J=8.79 Hz, 2H) 5.00-5.22 (m, 2H) 4.60 (d, J=6.45 Hz, 1H) 3.71 (s, 3H) 2.13-2.26 (m, 1H) 1.00 (dd, J=15.68, 6.89 Hz, 6H). MS: (ES, m/z): 371[M+H]$^+$.

The compounds below were synthesized according to the procedures outlined above for Example 26.

| Compd. No. | Structure | IUPAC Name | $^1$H NMR | MS (ES, m/z) [M + H]$^+$ |
|---|---|---|---|---|
| I-101 | 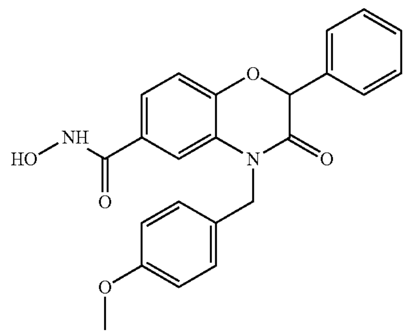 [SMILES: COc1ccc(CN2C(=O)C(c3ccccc3)Oc3ccc(C(=O)NO)cc32)cc1] | N-hydroxy-4-(4-methoxybenzyl)-3-oxo-2-phenyl-3,4-dihydro-2H-benzo[b][1,4]oxazine-6-carboxamide | $^1$H NMR (300 MHz, DMSO-d$_6$) δ ppm 11.13 (s, 1 H) 9.01 (br s, 1 H) 7.39 (s, 6 H) 7.17 (dd, J = 18.32, 8.35 Hz, 4 H) 6.84-6.92 (m, 2 H) 6.08 (s, 1 H) 5.18 (s, 2 H) 3.71 (s, 3 H) | 405 |
| I-102 | 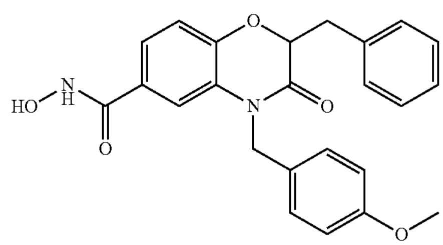 [SMILES: COc1ccc(CN2C(=O)C(Cc3ccccc3)Oc3ccc(C(=O)NO)cc32)cc1] | 2-benzyl-N-hydroxy-4-(4-methoxybenzyl)-3-oxo-3,4-dihydro-2H-benzo[b][1,4]oxazine-6-carboxamide | $^1$H NMR (300 MHz, DMSO-d$_6$) δ ppm 11.13 (br s, 1 H) 8.99 (s, 1 H) 7.44 (d, J = 1.76 Hz, 1 H) 7.39 (dd, J = 8.50, 1.76 Hz, 1 H) 7.20-7.35 (m, 5 H) 7.15 (d, J = 8.79 Hz, 2 H) 6.97 (d, J = 8.21 Hz, 1 H) 6.85-6.92 (m, 2 H) 5.02-5.21 (m, 3 H) 3.71 (s, 3 H) 3.20-3.28 (m, 1 H) 3.06-3.17 (m, 1 H) | 419 |
| I-103 | 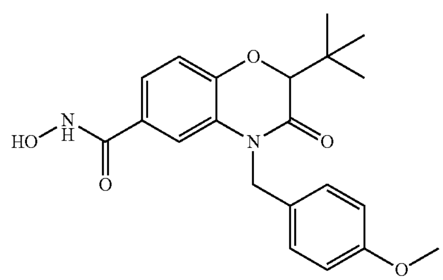 [SMILES: COc1ccc(CN2C(=O)C(C(C)(C)C)Oc3ccc(C(=O)NO)cc32)cc1] | 2-(tert-butyl)-N-hydroxy-4-(4-methoxybenzyl)-3-oxo-3,4-dihydro-2H-benzo[b][1,4]oxazine-6-carboxamide | $^1$H NMR (300 MHz, DMSO-d$_6$) δ ppm 11.11 (br s, 1 H) 8.99 (br s, 1 H) 7.46 (d, J = 1.76 Hz, 1 H) 7.39 (dd, J = 8.21, 1.76 Hz, 1 H) 7.24 (d, J = 8.79 Hz, 2 H) 7.06 (d, J = 8.50 Hz, 1 H) 6.91 (d, J = 8.79 Hz, 2 H) 5.02-5.23 (m, 2 H) 4.59 (s, 1 H) 3.71 (s, 3 H) 0.99 (s, 9 H) | 385 |
| I-157 | 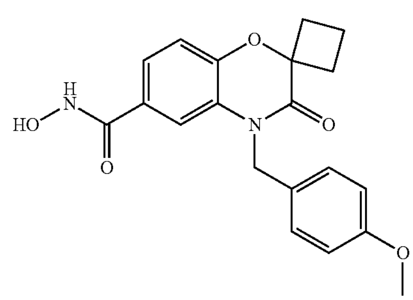 [SMILES: COc1ccc(CN2C(=O)C3(CCC3)Oc3ccc(C(=O)NO)cc32)cc1] | N-hydroxy-4-(4-methoxybenzyl)-3-oxo-3,4-dihydrospiro[benzo[b][1,4]oxazine-2,1'-cyclobutane]-6-carboxamide | 1H NMR (300 MHz, DMSO-d$_6$) δ ppm 11.12 (br s, 1 H) 9.01 (br s, 1 H) 7.34-7.51 (m, 2 H) 7.14 (dd, J = 14.66, 8.50 Hz, 3 H) 6.90 (d, J = 8.79 Hz, 2H) 5.11 (s, 2 H) 3.71 (s, 3 H) 2.13-2.39 (m, 3H) 1.91-2.10 (m, 1 H) 1.57-1.91 (m, 2 H) | 369 |

| Compd. No. | Structure | IUPAC Name | ¹H NMR | MS (ES, m/z) [M + H]⁺ |
|---|---|---|---|---|
| I-158 | 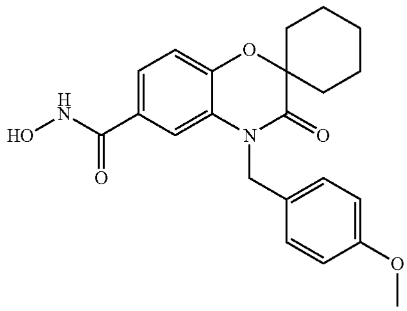 [SMILES: COc1ccc(CN2C(=O)C3(CCCCC3)Oc3ccc(C(=O)NO)cc32)cc1] | N-hydroxy-4-(4-methoxybenzyl)-3-oxo-3,4-dihydrospiro[benzo[b][1,4]oxazine-2,1'-cyclohexane]-6-carboxamide | None taken | 397 |
| I-159 | 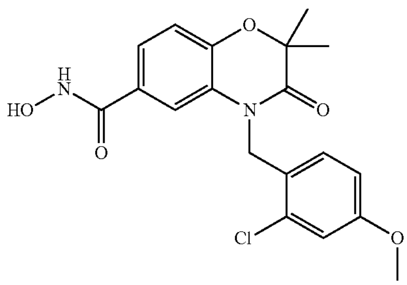 [SMILES: COc1ccc(CN2C(=O)C(C)(C)Oc3ccc(C(=O)NO)cc32)c(Cl)c1] | 4-(2-chloro-4-methoxybenzyl)-N-hydroxy-2,2-dimethyl-3-oxo-3,4-dihydro-2H-benzo[b][1,4]oxazine-6-carboxamide | 1H NMR (300 MHz, DMSO-d$_6$) δ ppm 8.45-9.12 (m, 1 H) 7.41 (dd, J = 8.50, 1.76 Hz, 1 H) 7.24 (d, J = 1.76 Hz, 1 H) 7.13 (d, J = 2.35 Hz, 1 H) 7.01 (d, J = 8.50 Hz, 1 H) 6.77-6.92 (m, 2 H) 5.07 (s, 2 H) 3.75 (s, 3 H) 1.50 (s, 7 H) | 391 |
| I-160 | 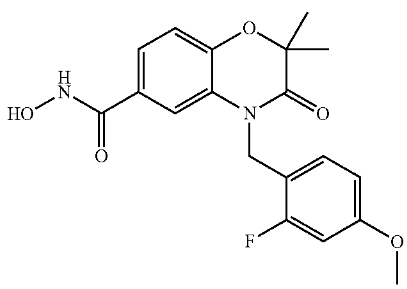 [SMILES: COc1ccc(CN2C(=O)C(C)(C)Oc3ccc(C(=O)NO)cc32)c(F)c1] | 4-(2-fluoro-4-methoxybenzyl)-N-hydroxy-2,2-dimethyl-3-oxo-3,4-dihydro-2H-benzo[b][1,4]oxazine-6-carboxamide | 1HNMR (300 MHz, DMSO-d$_6$) δ ppm 1.48 (s, 6 H) 3.73 (s, 3 H) 5,12 (s, 2 H) 6.73 (dd, J = 8.65, 2.49 Hz, 1 H) 6.87 (dd, J = 12.46, 2.49 Hz, 1 H) 6.97 (t, J = 8.79 Hz, 1 H) 7.06 (d, J = 8.79 Hz, 1 H) 7.42 (dd, J = 4.25, 2.49 Hz, 2 H) 9.00 (br s, 1 H) 11.13 (br s, 1 H) | 375 |
| I-161 | 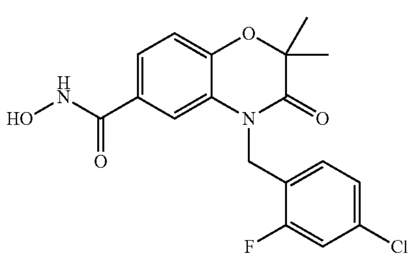 [SMILES: CC1(C)Oc2ccc(C(=O)NO)cc2N(Cc2ccc(Cl)cc2F)C1=O] | 4-(4-chloro-2-fluorobenzyl)-N-hydroxy-2,2-dimethyl-3-oxo-3,4-dihydro-2H-benzo[b][1,4]oxazine-6-carboxamide | 1H NMR (300 MHz, DMSO-d$_6$) δ ppm 1.49 (s, 6 H) 5.17 (s, 2 H) 6.98-7.14 (m, 2 H) 7.25 (dd, J = 8.79, 1.76 Hz, 1 H) 7.31-7.41 (m, 1 H) 7.41-7.56 (m, 2 H) 9.00 (s, 1 H) 11.13 (br s, 1 H) | 379⁺ |

Example 27—2-(2-aminoethyl)-N-hydroxy-4-(4-methoxybenzyl)-3-oxo-3,4-dihydro-2H-benzo[b][1,4]oxazine-6-carboxamide (I-104)

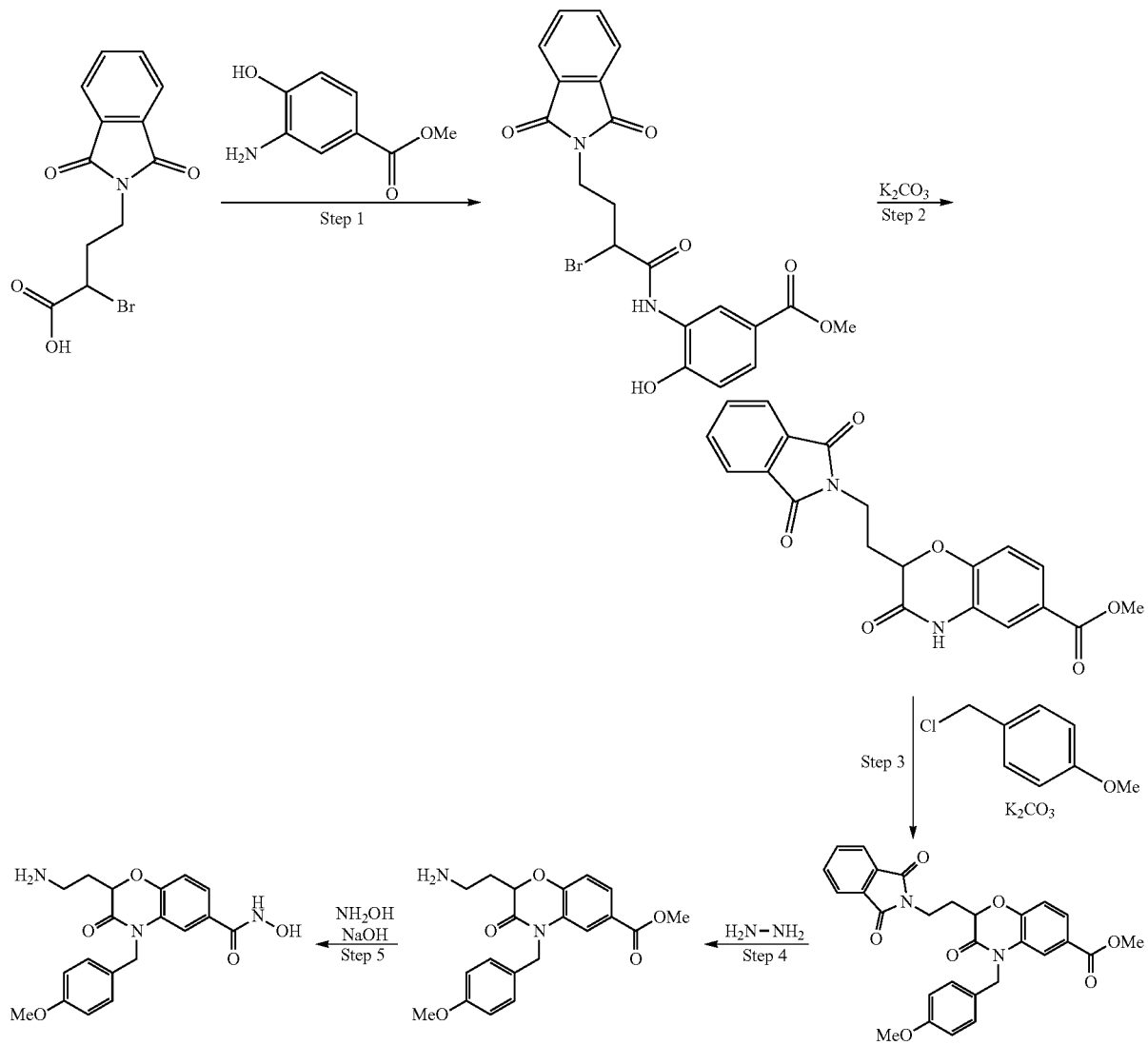

Step-1: Methyl 3-(2-bromo-4-(1,3-dioxoisoindolin-2-yl)butanamido)-4-hydroxybenzoate 4-(4,6-d4-(4,6-Dimethoxy-1,3,5-triazin-2-yl)-4-methylmorpholin-4-ium chloride (166 mg, 0.598 mmol) was added to a solution of methyl 3-amino-4-hydroxybenzoate (100 mg, 0.598 mmol) and 2-bromo-4-(1,3-dioxoisoindolin-2-yl)butanoic acid (187 mg, 0.598 mmol) in DMF (5 mL), and the reaction stirred overnight at ambient temperature. The reaction mixture was diluted with ethyl acetate and washed with brine. The organic layer was separated and concentrated to afford methyl 3-(2-bromo-4-(1,3-dioxoisoindolin-2-yl)butanamido)-4-hydroxybenzoate as a thin film which was used directly in the next step without further purification. MS (ESI, m/z): 461, 463 [M+H]+.

Step-2: Methyl 2-(2-(1,3-dioxoisoindolin-2-yl)ethyl)-3-oxo-3,4-dihydro-2H-benzo[b][1,4]oxazine-6-carboxylate Potassium carbonate (243 mg, 1.756 mmol) was added to a solution of methyl 3-(2-bromo-4-(1,3-dioxoisoindolin-2-yl)butanamido)-4-hydroxybenzoate (270 mg, 0.585 mmol) in DMF (5 mL), and the reaction was placed on heater/shaker at 50° C. overnight. The reaction mixture was diluted with ethyl acetate and washed with brine. The resulting precipitate was collected by suction filtration, rinsed with ethyl acetate, and dried to afford crude 2-(2-(1,3-dioxoisoindolin-2-yl)ethyl)-3-oxo-3,4-dihydro-2H-benzo[b][1,4]oxazine-6-carboxylate (240 mg). $^1$H NMR (300 MHz, DMSO-$d_6$) δ ppm 10.91 (br s, 1H) 7.74-7.94 (m, 4H) 7.41-7.56 (m, 2H) 6.89 (d, J=8.21 Hz, 1H) 4.79 (dd, J=8.21, 3.81 Hz, 1H) 3.74-3.87 (m, 5H) 2.07-2.34 (m, 2H). MS: (ES, m/z): 381 [M+H]+.

Step-3: Methyl 2-(2-(1,3-dioxoisoindolin-2-yl) ethyl)-4-(4-methoxybenzyl)-3-oxo-3,4-dihydro-2H-benzo[b][1,4]oxazine-6-carboxylate 1-(Chloromethyl)-4-methoxybenzene (0.089 mL, 0.631 mmol) and potassium carbonate (262 mg, 1.893 mmol) were added to a solution of methyl 2-(2-(1,3-dioxoisoindolin-2-yl)ethyl)-3-oxo-3,4-dihydro-2H-benzo[b][1,4]oxazine-6-carboxylate (240 mg, 0.631 mmol) in DMF (5 mL), and the reaction stirred at ambient temperature overnight. The reaction mixture was diluted with ethyl acetate and washed with brine. The organic layer was separated and concentrated to afford methyl 2-(2-(1,3-dioxoisoindolin-2-yl)ethyl)-4-(4-methoxybenzyl)-3-oxo-3,4-dihydro-2H-benzo[b][1,4]oxazine-6-carboxylate as a white solid which was used directly in the next step without further purification. MS (ESI, m/z): 501 [M+H]$^+$.

Step-4: Methyl 2-(2-aminoethyl)-4-(4-methoxybenzyl)-3-oxo-3,4-dihydro-2H-benzo[b][1,4]oxazine-6-carboxylate Hydrazine hydrate (0.046 mL, 0.799 mmol) was added to a solution of methyl 2-(2-(1,3-dioxoisoindolin-2-yl)ethyl)-4-(4-methoxybenzyl)-3-oxo-3,4-dihydro-2H-benzo[b][1,4]oxazine-6-carboxylate (200 mg, 0.400 mmol) in ethanol (2 mL). The reaction mixture was heated at 50° C. for 3 hours, and then cooled to room temperature. Ethyl acetate was added, and the mixture was washed with brine. The organic layer was separated and concentrated to afford methyl 2-(2-aminoethyl)-4-(4-methoxybenzyl)-3-oxo-3,4-dihydro-2H-benzo[b][1,4]oxazine-6-carboxylate which was used directly in the next step without further purification. MS (ESI, m/z): 371 [M+H]$^+$.

Step-5: 2-(2-aminoethyl)-N-hydroxy-4-(4-methoxybenzyl)-3-oxo-3,4-dihydro-2H-benzo[b][1,4]oxazine-6-carboxamide (I-104)

Methyl 2-(2-aminoethyl)-4-(4-methoxybenzyl)-3-oxo-3,4-dihydro-2H-benzo[b][1,4]oxazine-6-carboxylate (30 mg, 0.081 mmol) was dissolved in methanol (1 mL) and THF (1 mL), and 50% aqueous hydroxyl amine solution (0.268 mL, 4.05 mmol) and 1N aqueous sodium hydroxide solution (0.243 ml, 0.243 mmol) were added. The reaction stirred at ambient temperature for 2 hours, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 m, 19×50 mm column. The collected fractions were lyophilized to afford 2-(2-aminoethyl)-N-hydroxy-4-(4-methoxybenzyl)-3-oxo-3,4-dihydro-2H-benzo[b][1,4]oxazine-6-carboxamide (13.4 mg, 0.036 mmol, 44%) as the formic acid salt (peach colored solid). $^1$H NMR (300 MHz, DMSO-d$_6$) δ ppm 8.35 (s, 1H) 7.36-7.49 (m, 2H) 7.18 (d, J=8.50 Hz, 2H) 7.10 (d, J=8.21 Hz, 1H) 6.89 (d, J=8.79 Hz, 2H) 5.11 (s, 2H) 4.97 (dd, J=8.79, 4.10 Hz, 1H) 3.71 (s, 3H) 3.33 (br s, 2H) 2.89 (t, J=7.18 Hz, 2H) 1.93-2.18 (m, 2H). MS: (ES, m/z): 372[M+H]$^+$.

Example 28—2-(2-(dimethylamino)ethyl)-N-hydroxy-4-(4-methoxybenzyl)-3-oxo-3,4-dihydro-2H-benzo[b][1,4]oxazine-6-carboxamide (I-105)

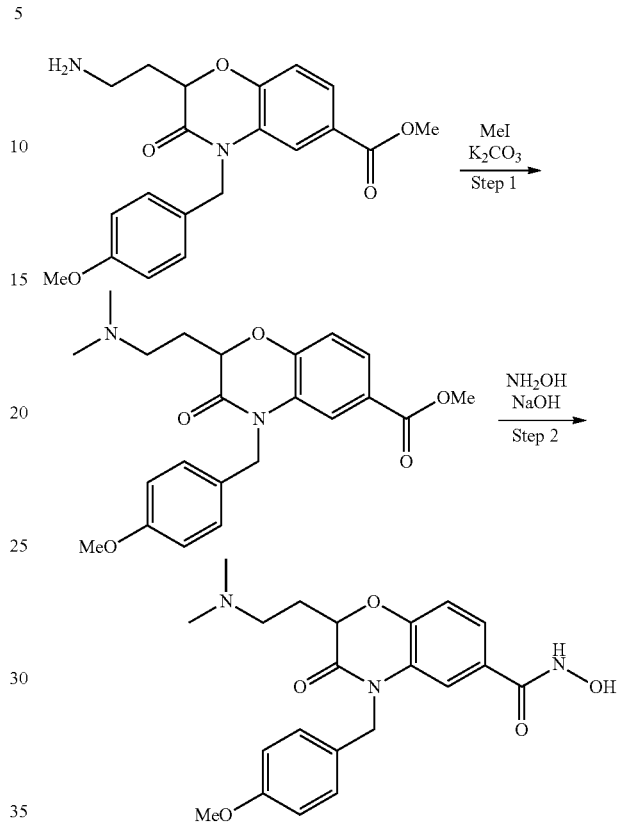

Step-1: Methyl 2-(2-(dimethylamino)ethyl)-4-(4-methoxybenzyl)-3-oxo-3,4-dihydro-2H-benzo[b][1,4]oxazine-6-carboxylate Potassium carbonate (56.0 mg, 0.405 mmol) and methyl iodide (0.017 mL, 0.270 mmol) were added to a solution of methyl 2-(2-aminoethyl)-4-(4-methoxybenzyl)-3-oxo-3,4-dihydro-2H-benzo[b][1,4]oxazine-6-carboxylate (50 mg, 0.135 mmol) in DMF (2 mL), and the reaction stirred overnight at ambient temperature. The reaction was diluted with ethyl acetate and washed with brine. The organic layer was separated and concentrated to afford methyl 2-(2-(dimethylamino)ethyl)-4-(4-methoxybenzyl)-3-oxo-3,4-dihydro-2H-benzo[b][1,4]oxazine-6-carboxylate as a thin film which was used directly in the next step without further purification. MS (ESI, m/z): 399 [M+H]$^+$.

Step-2: 2-(2-(dimethylamino)ethyl)-N-hydroxy-4-(4-methoxybenzyl)-3-oxo-3,4-dihydro-2H-benzo[b][1,4]oxazine-6-carboxamide (I-105)

Methyl 2-(2-(dimethylamino)ethyl)-4-(4-methoxybenzyl)-3-oxo-3,4-dihydro-2H-benzo[b][1,4]oxazine-6-carboxylate (51.8 mg, 0.130 mmol) was dissolved in methanol (1 mL) and THF (1 mL), and 50% aqueous hydroxyl amine solution (0.5 mL, 7.57 mmol) and 1N aqueous sodium hydroxide solution (0.5 mL, 0.5 mmol) were added. The reaction stirred at ambient temperature for 2 hours and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 m, 19×50 mm column. The collected fractions were lyophilized to afford 2-(2-(dimethylamino)ethyl)-N-hydroxy-4-(4-methoxybenzyl)-3-oxo-3,4-dihydro-2H-benzo[b][1,4]oxazine-6-carboxamide (1 mg, 2.504 μmol, 2% yield) as a white solid. MS: (ES, m/z): 400[M+H]$^+$.

Example 29—1-(1H-benzo[d]imidazol-2-yl)-N-hydroxy-1,2,3,4-tetrahydroquinoline-7-carboxamide (I-106)

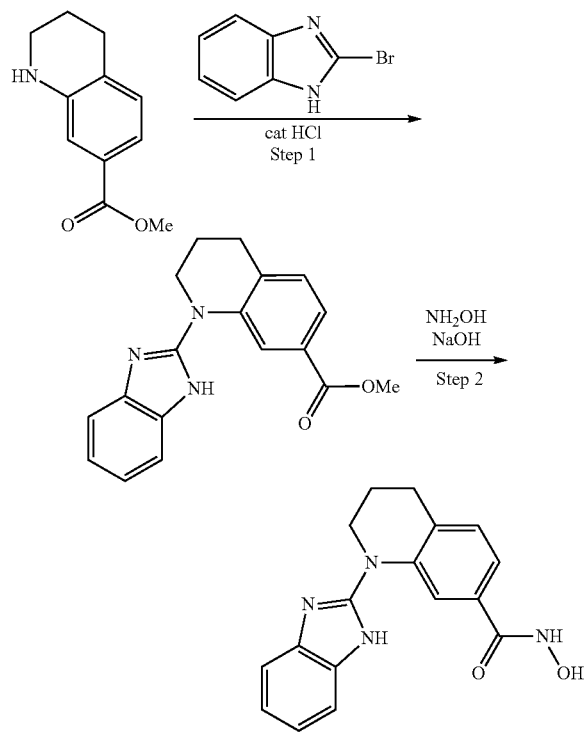

Step-1. Methyl 1-(1H-benzo[d]imidazol-2-yl)-1,2,3,4-tetrahydroquinoline-7-carboxylate Concentrated hydrochloric acid (1 drop) was added to a solution of 2-bromo-1H-benzo[d]imidazole (50 mg, 0.254 mmol) and methyl 1,2,3,4-tetrahydroquinoline-7-carboxylate (48.5 mg, 0.254 mmol) in ethanol (2 mL). The reaction vessel was sealed and the mixture was heated at 150° C. in the microwave for 3 hours. The reaction mixture was concentrated to afford methyl 1-(1H-benzo[d]imidazol-2-yl)-1,2,3,4-tetrahydroquinoline-7-carboxylate which was used directly in the next step without further purification. MS: (ES, m/z): 308 [M+H]$^+$.

Step-2. 1-(1H-benzo[d]imidazol-2-yl)-N-hydroxy-1,2,3,4-tetrahydroquinoline-7-carboxamide (I-106)

Methyl 1-(1H-benzo[d]imidazol-2-yl)-1,2,3,4-tetrahydroquinoline-7-carboxylate (78 mg, 0.25 mmol) was dissolved in methanol/THF (1/2, 3 mL), and 50% aqueous hydroxyl amine solution (0.5 mL, 7.57 mmol) and 1N aqueous sodium hydroxide solution (0.5 mL, 0.55 mmol) were added. The resulting solution was stirred for 2 hours at ambient temperature and then concentrated to dryness. Ethyl acetate and 1 N aqueous HCl solution were added and the solution was stirred for 30 minutes. The resulting solid was collected by suction filtration, washed with ethyl acetate, and dried to afford 1-(1H-benzo[d]imidazol-2-yl)-N-hydroxy-1,2,3,4-tetrahydroquinoline-7-carboxamide (0.024 g, 31%). $^1$H NMR (300 MHz, DMSO-d$_6$) δ ppm 13.45 (br s, 1H) 11.22 (s, 1H) 9.11 (s, 1H) 8.02 (s, 1H) 7.59 (d, J=7.62 Hz, 1H) 7.50 (dd, J=5.86, 3.22 Hz, 2H) 7.39 (d, J=7.92 Hz, 1H) 7.33 (dd, J=5.72, 3.08 Hz, 2H) 3.94 (t, J=6.30 Hz, 2H) 2.83 (br t, J=6.45 Hz, 2H) 2.04 (br t, J=6.30 Hz, 2H). MS (ESI, m/z): MS: (ES, m/z): 309 [M+H]$^+$.

The compounds below were synthesized according to the procedures outlined above for Example 29.

| Compd. No. | Structure | IUPAC Name | MS (ES, m/z) [M + H]$^+$ |
|---|---|---|---|
| I-107 | 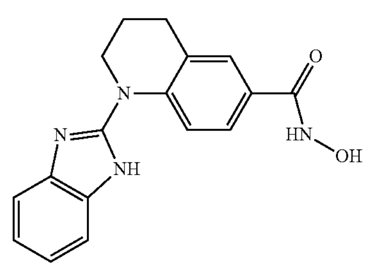 [SMILES: O=C(NO)c1ccc2c(c1)CCCN2c1nc2ccccc2[nH]1] | 1-(1H-benzo[d]imidazol-2-yl)-N-hydroxy-1,2,3,4-tetrahydroquinoline-6-carboxamide | 309 |

-continued

| Compd. No. | Structure | IUPAC Name | MS (ES, m/z) [M + H]⁺ |
|---|---|---|---|
| I-108 | 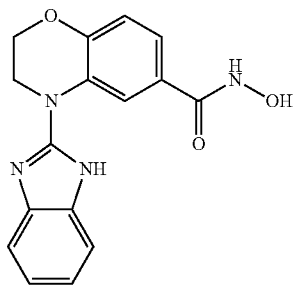 [SMILES: O=C(NO)c1ccc2c(c1)N(c1nc3ccccc3[nH]1)CCO2] | 4-(1H-benzo[d]imidazol-2-yl)-N-hydroxy-3,4-dihydro-2H-benzo[b][1,4]oxazine-6-carboxamide | 311 |
| I-109 | 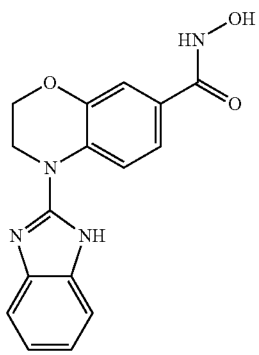 [SMILES: O=C(NO)c1ccc2c(c1)OCCN2c1nc2ccccc2[nH]1] | 4-(1H-benzo[d]imidazol-2-yl)-N-hydroxy-3,4-dihydro-2H-benzo[b][1,4]oxazine-7-carboxamide | 311 |

Example 30—N-hydroxy-1-(1-(2-methoxyethyl)-1H-benzo[d]imidazol-2-yl)-1,2,3,4-tetrahydroquinoline-7-carboxylate

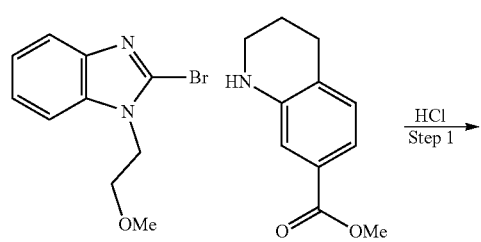

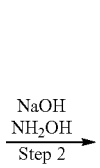

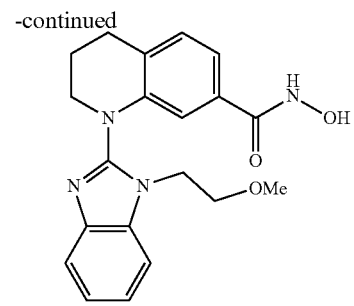

Step-1: Methyl 1-(1-(2-methoxyethyl)-1H-benzo[d]imidazol-2-yl)-1,2,3,4-tetrahydroquinoline-7-carboxylate Concentrated hydrochloric acid (1 drop) was added to a solution of 2-bromo-1-(2-methoxyethyl)-1H-benzo[d]imidazole (100 mg, 0.392 mmol) and methyl 1,2,3,4-tetrahydroquinoline-7-carboxylate (75 mg, 0.392 mmol) in ethanol (2 mL). The reaction vessel was sealed and the mixture was heated at 155° C. in the microwave for 3 hours. The reaction mixture was concentrated to dryness, and the residue was purified via column chromatography on silica gel (Biotage 10 gram column, eluting with 10-60% ethyl acetate-hexane) to afford methyl 1-(1-(2-methoxyethyl)-1H-benzo[d]imidazol-2-yl)-1,2,3,4-tetrahydroquinoline-7-carboxylate which was used directly in the next step without further purification. MS: (ES, m/z): 366 [M+H]⁺.

Step-2: N-hydroxy-1-(1-(2-methoxyethyl)-1H-benzo[d]imidazol-2-yl)-1,2,3,4-tetrahydroquinoline-7-carboxamide Methyl 1-(1-(2-methoxyethyl)-1H-benzo[d]imidazol-2-yl)-1,2,3,4-tetrahydroquinoline-7-carboxylate (10 mg, 0.027 mmol) was dissolved in methanol/THF (1/2, 1.5 mL), and 50% aqueous hydroxyl amine solution (0.25 mL, 3.78 mmol) and 1N aqueous sodium hydroxide solution (0.25 mL, 0.25 mmol) were added. The resulting solution was stirred for 2 hours at ambient temperature and then concentrated to dryness. The residue was purified via preparative-HPLC (eluting with acetonitrile and water) to afford N-hydroxy-1-(1-(2-methoxyethyl)-1H-benzo[d]imidazol-2-yl)-1,2,3,4-tetrahydroquinoline-7-carboxamide (0.0015 g, 10%) as a white solid. MS (ESI, m/z): 367 [M+H]$^+$.

The compounds below were synthesized according to the procedures outlined above for Example 30.

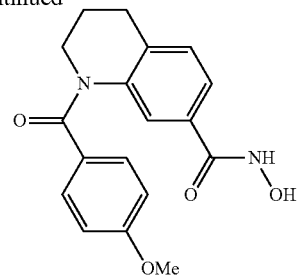

Step-1: Methyl 1-(1H-benzo[d]imidazol-2-yl)-1,2,3,4-tetrahydroquinoline-7-carboxylate N,N-Diisopropylethyl amine (114 uL, 0.654 mmol) and 2-chloro-1,3-dimethylimidazolinium chloride (DMC) (66.4

| Compd. No. | Structure | IUPAC Name | MS (ES, m/z) [M + H]$^+$ |
|---|---|---|---|
| I-111 | 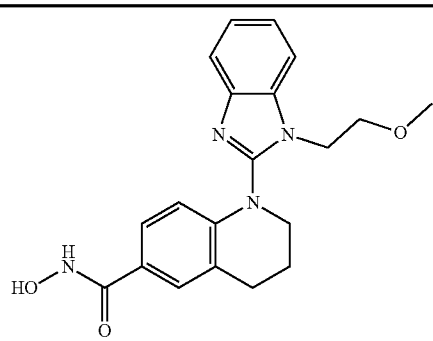 | N-hydroxy-1-(1-(2-methoxyethyl)-1H-benzo[d]imidazol-2-yl)-1,2,3,4-tetrahydroquinoline-6-carboxamide | 367 |

Example 31—N-hydroxy-1-(4-methoxybenzoyl)-1,2,3,4-tetrahydroquinoline-7-carboxamide (I-112)

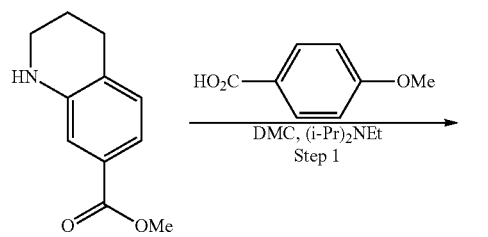

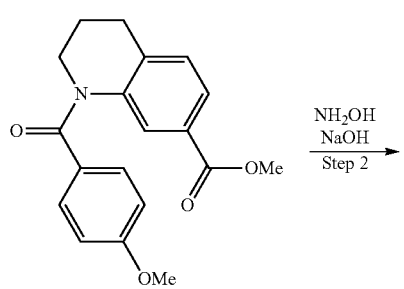

mg, 0.392 mmol) were added to a solution of methyl 1,2,3,4-tetrahydroquinoline-7-carboxylate (50 mg, 0.261 mmol) and 4-methoxybenzoic acid (40 mg, 0.261 mmol) in chloroform (2 mL), and the reaction stirred at ambient temperature overnight. The reaction was diluted with dichloromethane and washed with brine. The organic layer was separated and filtered through an Isolute© phase separator. The filtrate was concentrated to afford methyl 1-(1H-benzo[d]imidazol-2-yl)-1,2,3,4-tetrahydroquinoline-7-carboxylate which was used directly in the next step without further purification. MS: (ES, m/z): 326 [M+H]$^+$.

Step-2: N-hydroxy-1-(4-methoxybenzoyl)-1,2,3,4-tetrahydroquinoline-7-carboxamide Methyl 1-(1H-benzo[d]imidazol-2-yl)-1,2,3,4-tetrahydroquinoline-7-carboxylate (50 mg, 0.154 mmol) was dissolved in methanol/THF (1/4, 2.5 mL), and 50% aqueous hydroxyl amine solution (0.5 mL, 7.57 mmol) and 1N aqueous sodium hydroxide solution (0.5 mL, 0.5 mmol) were added. The resulting solution was stirred for 2 hours at ambient temperature and then concentrated to dryness. The residue was purified by preparative-HPLC with the following conditions: Waters reversed phase HPLC: 25 mL/min, 6 min gradient 25%-65% Acetonitrile, 0.1% formic acid on a Waters Sunfire C18, 5 μm, 19×50 mm column to afford N-hydroxy-1-(4-methoxybenzoyl)-1,2,3,4-tetrahydroquinoline-7-carboxamide. MS: (ES, m/z): 327 [M+H]$^+$.

The compounds below were synthesized according to the procedures outlined above for Example 31.

| Compd. No. | Structure | IUPAC Name | ¹H NMR | MS (ES, m/z [M + H]) |
|---|---|---|---|---|
| I-113 | 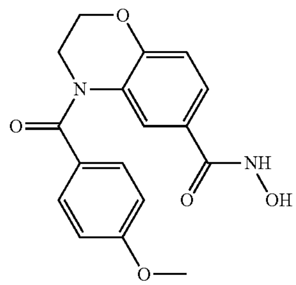 [SMILES: COc1ccc(C(=O)N2CCOc3ccc(C(=O)NO)cc32)cc1] | N-hydroxy-4-(4-methoxybenzoyl)-3,4-dihydro-2H-benzo[b][1,4]oxazine-6-carboxamide | ¹H NMR (300 MHz, DMSO-$d_6$) δ ppm 11.01 (br s, 1 H) 8.89 (s, 1H) 7.80 (s, 1 H) 7.54 (d, J = 8.79 Hz, 2 H) 7.39 (dd, J = 8.50, 2.05 Hz, 1 H) 6.97 (dd, J = 17.15, 8.65 Hz, 3 H) 4.32 (t, J = 4.40 Hz, 2 H) 3.85-3.94 (m, 2 H) 3.81 (s, 3 H) | 329 |
| I-114 | 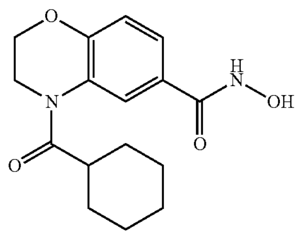 [SMILES: O=C(NO)c1ccc2c(c1)N(C(=O)C1CCCCC1)CCO2] | 4-(cyclohexanecarbonyl)-N-hydroxy-3,4-dihydro-2H-benzo[b][1,4]oxazine-6-carboxamide | ¹H NMR (300 MHz, DMSO-$d_6$) δ ppm 11.08 (br s, 1H) 8.93 (br s, 1 H) 8.12 (br s, 1H) 7.44 (br d, J = 7.92 Hz, 1H) 6.92 (d, J = 8.50 Hz, 1 H) 4.29 (t, J = 4.54 Hz, 2 H) 3.90 (t, J = 4.40 Hz, 2 H) 2.77-2.93 (m, 1 H) 1.60-1.83 (m, 5 H) 1.09-1.52 (m, 5 H) | 305 |

Example 32—N-hydroxy-4-(4-methoxybenzyl)-3,4-dihydro-2H-benzo[b][1,4]oxazine-6-carboxamide (I-115)

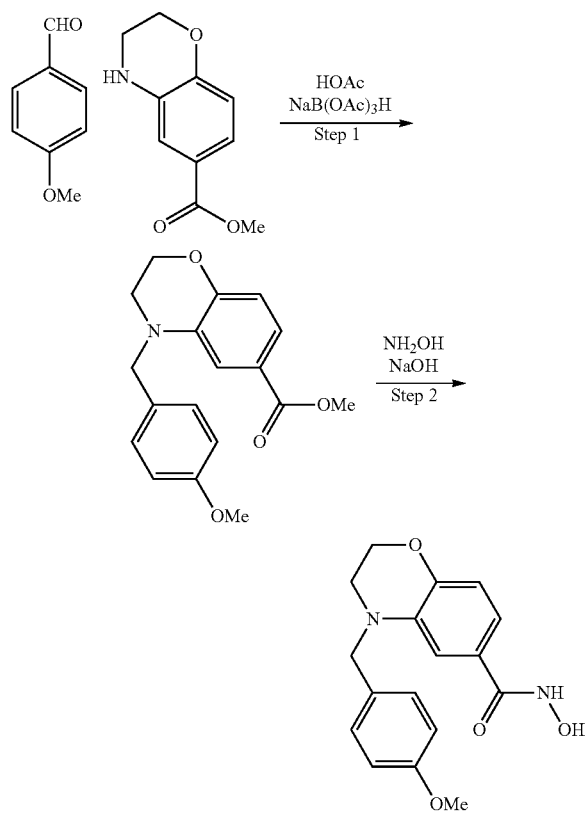

Step-1: Methyl 4-(4-methoxybenzyl)-3,4-dihydro-2H-benzo[b][1,4]oxazine-6-carboxylate 4-Methoxybenzaldehyde (31.5 μL, 0.259 mmol) and acetic acid (50 μL, 0.873 mmol) were added to a solution of methyl 3,4-dihydro-2H-benzo[b][1,4]oxazine-6-carboxylate (50.0 mg, 0.259 mmol) in 1,2-dichloroethane (2 mL), and the reaction mixture was placed on a heater/shaker at 50° C. for 2 hours. Sodium triacetoxyborohydride (137 mg, 0.647 mmol) was added, and the reaction was placed on the heater/shaker at 50° C. overnight. The reaction was diluted with dichloromethane, washed with brine, and passed through an Isolute© phase separator. The filtrate was concentrated and purified by column chromatography on silica gel (Biotage 10 gram column, eluting with 10-60% ethyl acetate-hexanes) to afford methyl 4-(4-methoxybenzyl)-3,4-dihydro-2H-benzo[b][1,4]oxazine-6-carboxylate which was used directly in the next step MS: (ES, m/z): 314 [M+H]⁺.

Step-2: N-hydroxy-4-(4-methoxybenzyl)-3,4-dihydro-2H-benzo[b][1,4]oxazine-6-carboxamide Methyl 4-(4-methoxybenzyl)-3,4-dihydro-2H-benzo[b][1,4]oxazine-6-carboxylate (25 mg, 0.154 mmol) was dissolved in methanol/THF (1/4, 2.5 mL), and 50% aqueous hydroxyl amine solution (0.25 mL, 3.78 mmol) and 1N aqueous sodium hydroxide solution (0.25 mL, 0.275 mmol) were added. The resulting solution stirred for 2 hours at ambient temperature, and was then concentrated to dryness. The crude product was purified by preparative-HPLC with the following conditions: Waters reversed phase HPLC: 25 mL/min, 6 min gradient 25%-65% Acetonitrile, 0.1% formic acid on a Waters Sunfire C18, 5 m, 19×50 mm column to afford N-hydroxy-4-(4-methoxybenzyl)-3,4-dihydro-2H-benzo[b][1,4]oxazine-6-carboxamide. MS: (ES, m/z): 315 [M+H]⁺.

Example 33—4-benzyl-N-hydroxy-3,4-dihydro-2H-benzo[b][1,4]oxazine-6-carboxamide (I-116)

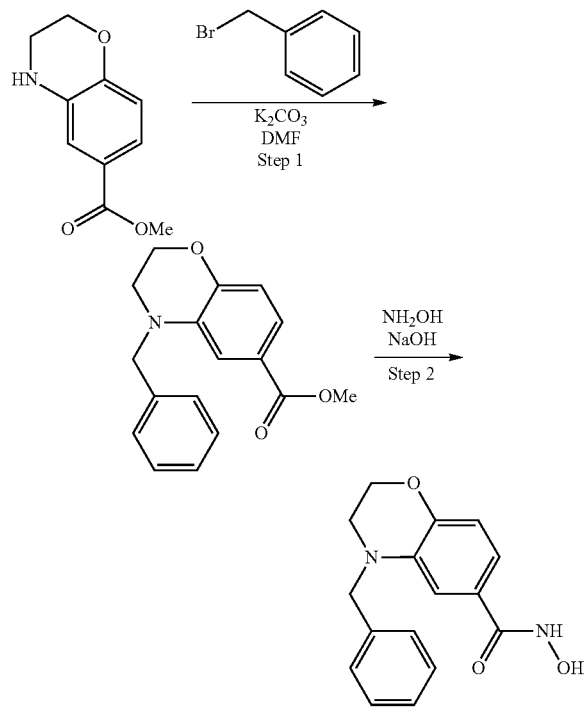

Step-1: Methyl 4-benzyl-3,4-dihydro-2H-benzo[b][1,4]oxazine-6-carboxylate

Potassium carbonate (86 mg, 0.621 mmol) was added to a solution of methyl 3,4-dihydro-2H-benzo[b][1,4]oxazine-6-carboxylate (30 mg, 0.155 mmol) in DMF (2 mL). (Bromomethyl)benzene (0.028 mL, 0.233 mmol) was added, and the reaction was placed on a heater/shaker at 80° C. overnight. The reaction mixture was cooled to room temperature, diluted with ethyl acetate, and washed with brine. The organic layer was separated and concentrated to afford methyl 4-benzyl-3,4-dihydro-2H-benzo[b][1,4]oxazine-6-carboxylate which was used directly in the next step without further purification. MS: (ES, m/z): 284 [M+H]+.

Step-2: 4-benzyl-N-hydroxy-3,4-dihydro-2H-benzo[b][1,4]oxazine-6-carboxamide

Methyl 4-benzyl-3,4-dihydro-2H-benzo[b][1,4]oxazine-6-carboxylate (45 mg, 0.159 mmol) was dissolved in methanol/THF (1/1, 2 mL), and 50% aqueous hydroxyl amine solution (0.5 mL, 7.57 mmol) and 1N aqueous sodium hydroxide solution (0.5 mL, 0.55 mmol) were added. The resulting solution stirred for 2 hours at ambient temperature, and was then concentrated to dryness. The crude product was purified by preparative-HPLC with the following conditions: Waters reversed phase HPLC (23 mL/min, 8 min gradient 15%-65% Acetonitrile, 0.1% formic acid on a Waters XBridge Prep C18 OBD 5 µm, 19×50 mm column. The desired fractions were lyophilized to afford 4-benzyl-N-hydroxy-3,4-dihydro-2H-benzo[b][1,4]oxazine-6-carboxamide (10 mg, 22%). $^1$H NMR (300 MHz, DMSO-$d_6$) δ ppm 10.91 (br s, 1H) 8.80 (br s, 1H) 7.20-7.40 (m, 5H) 7.12 (d, J=2.05 Hz, 1H) 6.97 (dd, J=8.21, 2.05 Hz, 1H) 6.73 (d, J=8.21 Hz, 1H) 4.53 (s, 2H) 4.16-4.30 (m, 2H) 3.35-3.40 (m, 2H). MS: (ES, m/z): 285 [M+H]+.

The compounds below were synthesized according to the procedures outlined above for Example 33.

| Compd. No. | Structure | IUPAC Name | $^1$H NMR | MS (ES, m/z) [M + H] |
|---|---|---|---|---|
| I-117 | 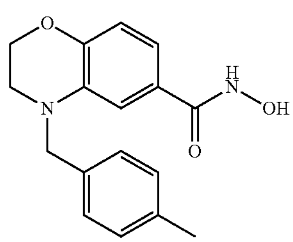 [SMILES: Cc1ccc(CN2CCOc3ccc(C(=O)NO)cc32)cc1] | N-hydroxy-4-(4-methylbenzyl)-3,4-dihydro-2H-benzo[b][1,4]oxazine-6-carboxamide | $^1$H NMR (300 MHz, DMSO-$d_6$) δ ppm 10.92 (br s, 1 H) 8.81 (br s, 1 H) 7.10-7.23 (m, 5 H) 6.97 (dd, J = 8.21, 1.47 Hz, 1 H) 6.72 (d, J = 8.21 Hz, 1H) 4.47 (s, 2 H) 4.19-4.25 (m, 2 H) 3.36 (br s, 2 H) 2.27 (s, 3 H) | 299 |
| I-118 | 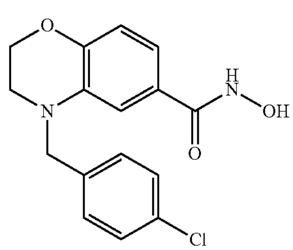 [SMILES: O=C(NO)c1ccc2c(c1)N(Cc1ccc(Cl)cc1)CCO2] | 4-(4-chlorobenzyl)-N-hydroxy-3,4-dihydro-2H-benzo[b][1,4]oxazine-6-carboxamide | N/A | 319 |

| Compd. No. | Structure | IUPAC Name | $^1$H NMR | MS (ES, m/z) [M + H] |
|---|---|---|---|---|
| I-119 | 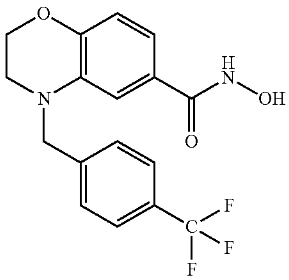 [SMILES: O=C(NO)c1ccc2c(c1)N(Cc1ccc(C(F)(F)F)cc1)CCO2] | N-hydroxy-4-(4-(trifluoromethyl)benzyl)-3,4-dihydro-2H-benzo[b][1,4]oxazine-6-carboxamide | $^1$H NMR (300 MHz, DMSO-d$_6$) δ ppm 10.91 (br s, 1 H) 8.80 (s, 1 H) 7.72 (d, J = 8.50 Hz, 2 H) 7.51 (d, J = 8.21 Hz, 2 H) 6.93-7.08 (m, 2 H) 6.75 (d, J = 8.21 Hz, 1 H) 4.63 (s, 2 H) 4.21-4.34 (m, 2 H) 3.37-3.50 (m, 2 H) | 353 |
| I-120 | 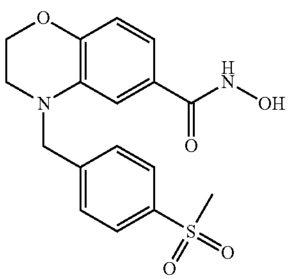 [SMILES: CS(=O)(=O)c1ccc(CN2CCOc3ccc(C(=O)NO)cc32)cc1] | N-hydroxy-4-(4-(methylsulfonyl)benzyl)-3,4-dihydro-2H-benzo[b][1,4]oxazine-6-carboxamide | $^1$H NMR (300 MHz, DMSO-d$_6$) δ ppm 10.91 (s, 1 H) 8.81 (s, 1 H) 7.90 (d, J = 8.50 Hz, 2 H) 7.55 (d, J = 8.50 Hz, 2 H) 6.94-7.05 (m, 2 H) 6.76 (d, J = 7.92 Hz, 1 H) 4.65 (s, 2 H) 4.18-4.36 (m, 2 H) 3.43 (br s, 2 H) 3.21 (s, 3 H) | 363 |
| I-121 | 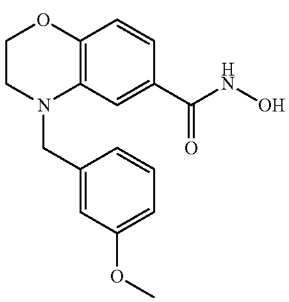 [SMILES: COc1cccc(CN2CCOc3ccc(C(=O)NO)cc32)c1] | N-hydroxy-4-(3-methoxybenzyl)-3,4-dihydro-2H-benzo[b][1,4]oxazine-6-carboxamide | $^1$H NMR (300 MHz, DMSO-d$_6$) δ ppm 10.92 (s, 1 H) 8.79 (s, 1 H) 7.26 (t, J = 7.92 Hz, 1 H) 7.12 (d, J = 2.05 Hz, 1 H) 6.98 (dd, J = 8.21, 1.47 Hz, 1 H) 6.79-6.91 (m, 3 H) 6.73 (d, J = 8.21 Hz, 1 H) 4.49 (s, 2 H) 4.23 (br d, J = 4.40 Hz, 2 H) 3.70-3.74 (m, 3 H) 3.38 (br d, J = 4.69 Hz, 2 H) | 315 |
| I-122 | 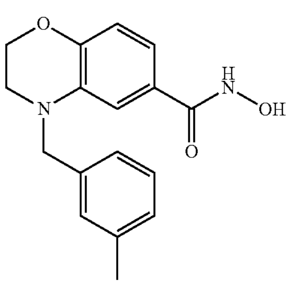 [SMILES: Cc1cccc(CN2CCOc3ccc(C(=O)NO)cc32)c1] | N-hydroxy-4-(3-methylbenzyl)-3,4-dihydro-2H-benzo[b][1,4]oxazine-6-carboxamide | $^1$H NMR (300 MHz, DMSO-d$_6$) δ ppm 10.92 (s, 1 H) 8.79 (s, 1 H) 7.18-7.25 (m, 1H) 7.05-7.14 (m, 4 H) 6.97 (dd, J = 8.21, 2.05 Hz, 1 H) 6.73 (d, J = 8.21 Hz, 1 H) 4.48 (s, 2 H) 4.17-4.28 (m, 2 H) 3.33-3.38 (m, 2 H) 2.27-2.31 (m, 3 H) | 299 |
| I-123 | 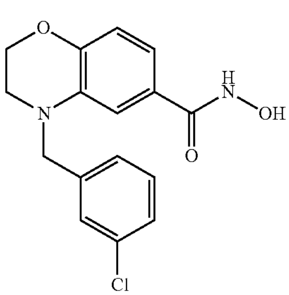 [SMILES: O=C(NO)c1ccc2c(c1)N(Cc1cccc(Cl)c1)CCO2] | 4-(3-chlorobenzyl)-N-hydroxy-3,4-dihydro-2H-benzo[b][1,4]oxazine-6-carboxamide | $^1$H NMR (300 MHz, DMSO-d$_6$) δ ppm 10.92 (s, 1 H) 8.80 (s, 1 H) 7.21-7.45 (m, 4 H) 7.06 (d, J = 1.76 Hz, 1 H) 7.00 (dd, J = 8.21, 1.76 Hz, 1 H) 6.74 (d, J = 7.92 Hz, 1 H) 4.53 (s, 2 H) 4.17-4.31 (m, 2 H) 3.36-3.46 (m, 2 H) | 319 |

| Compd. No. | Structure | IUPAC Name | ¹H NMR | MS (ES, m/z) [M + H] |
|---|---|---|---|---|
| I-124 | 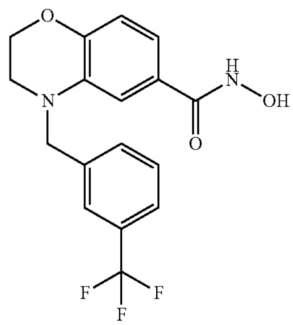 [SMILES: O=C(NO)c1ccc2c(c1)N(Cc1cccc(C(F)(F)F)c1)CCO2] | N-hydroxy-4-(3-(trifluoromethyl)benzyl)-3,4-dihydro-2H-benzo[b][1,4]oxazine-6-carboxamide | ¹H NMR (300 MHz, DMSO-d$_6$) δ ppm 10.91 (s, 1H) 8.80 (d, J = 1.76 Hz, 1 H) 7.54-7.70 (m, 4 H) 7.09 (d, J = 1.47 Hz, 1 H) 7,01 (dd, J = 8.21, 1.17 Hz, 1 H) 6.75 (dd, J = 8.21, 0.88 Hz, 1 H) 4.62 (s, 2 H) 4.20-4.32 (m, 2 H) 3.40 (t, J = 4.40 Hz, 2 H) | 353 |
| I-125 | 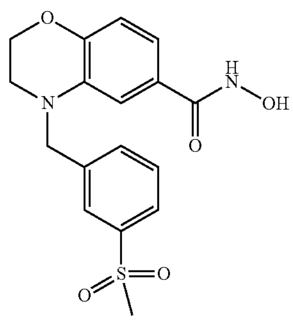 [SMILES: CS(=O)(=O)c1cccc(CN2CCOc3ccc(C(=O)NO)cc32)c1] | N-hydroxy-4-(3-(methylsulfonyl)benzyl)-3,4-dihydro-2H-benzo[b][1,4]oxazine-6-carboxamide | ¹H NMR (300 MHz, DMSO-d$_6$) δ ppm 10.92 (s, 1 H) 8.80 (s, 1 H) 7.76-7.92 (m, 2 H) 7.63 (d, J = 4.98 Hz, 2 H) 7.08 (d, J = 1.76 Hz, 1 H) 7.01 (dd, J = 8.06, 1.91 Hz, 1 H) 6.76 (d, J = 8.21 Hz, 1 H) 4.64 (s, 2 H) 4.26 (br d, J = 4.98 Hz, 2 H) 3.43 (br d, J = 4.40 Hz, 2 H) 3.16- 3.25 (m, 3 H) | 363 |
| I-126 | 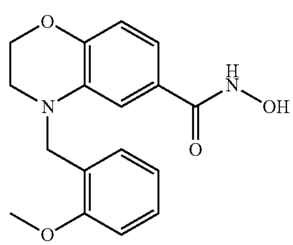 [SMILES: COc1ccccc1CN1CCOc2ccc(C(=O)NO)cc21] | N-hydroxy-4-(2-methoxybenzyl)-3,4-dihydro-2H-benzo[b][1,4]oxazine-6-carboxamide | ¹H NMR (300 MHz, DMSO-d$_6$) δ ppm 10.90 (br s, 1 H) 8.76 (d, J = 2.05 Hz, 1 H) 7.22-7.44 (m, 2 H) 6.87-7.05 (m, 4 H) 6.72 (d, J = 8.21 Hz, 1 H) 4.46 (s, 2 H) 4.14-4.27 (m, 2 H) 3.82-3.85 (m, 3 H) 3.36-3.45 (m, 2 H) | 315 |
| I-127 | 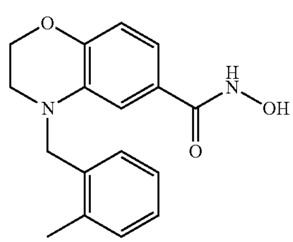 [SMILES: Cc1ccccc1CN1CCOc2ccc(C(=O)NO)cc21] | N-hydroxy-4-(2-methylbenzyl)-3,4-dihydro-2H-benzo[b][1,4]oxazine-6-carboxamide | ¹H NMR (300 MHz, DMSO-d$_6$) δ ppm 10.90 (s, 1 H) 8.79 (br s, 1 H) 7.06-7.24 (m, 4 H) 6.94-7.01 (m, 2 H) 6.75 (d, J = 8.79 Hz, 1 H) 4.46 (s, 2 H) 4.20-4.29 (m, 2 H) 3.24-3.33 (m, 3 H) 2.32 (s, 3 H) | 299 |
| I-128 | 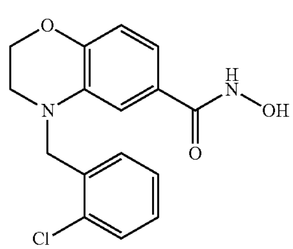 [SMILES: O=C(NO)c1ccc2c(c1)N(Cc1ccccc1Cl)CCO2] | 4-(2-chlorobenzyl)-N-hydroxy-3,4-dihydro-2H-benzo[b][1,4]oxazine-6-carboxamide | ¹H NMR (300 MHz, DMSO-d$_6$) δ ppm 10.92 (s, 1 H) 8.78 (d, J = 1.47 Hz, 1 H) 7.44-7.57 (m, 1 H) 7.33 (s, 1 H) 7.18-7.37 (m, 3 H) 6.86-7.04 (m, 2 H) 6.77 (d, J = 8.21 Hz, 1 H) 4.58 (s, 2 H) 4.17-4.35 (m, 2 H) 3.43 (t, J = 4.25 Hz, 2 H) | 319 |

| Compd. No. | Structure | IUPAC Name | ¹H NMR | MS (ES, m/z) [M + H] |
|---|---|---|---|---|
| I-129 | 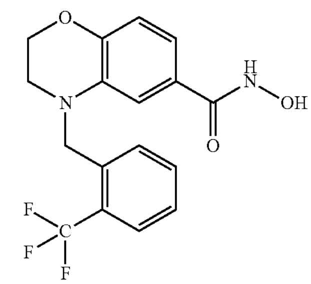 [SMILES: O=C(NO)c1ccc2c(c1)N(Cc1ccccc1C(F)(F)F)CCO2] | N-hydroxy-4-(2-(trifluoromethyl)benzyl)-3,4-dihydro-2H-benzo[b][1,4]oxazine-6-carboxamide | ¹H NMR (300 MHz, DMSO-d$_6$) δ ppm 10.90 (br s, 1 H) 8.81 (br s, 1 H) 7.42-7.87 (m, 4 H) 6.68-7.06 (m, 3 H) 4.61-4.73 (m, 2 H) 4.23-4.34 (m, 2 H) 3.40-3.47 (m, 2 H) | 353 |
| I-130 | 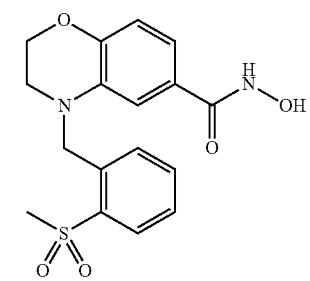 [SMILES: CS(=O)(=O)c1ccccc1CN1CCOc2ccc(C(=O)NO)cc21] | N-hydroxy-4-(2-(methylsulfonyl)benzyl)-3,4-dihydro-2H-benzo[b][1,4]oxazine-6-carboxamide | ¹H NMR (300 MHz, DMSO-d$_6$) δ ppm 10.88 (s, 1 H) 8.75 (d, J = 1.76 Hz, 1 H) 7.99 (dd, J = 7.77, 1.32 Hz, 1 H) 7.41-7.73 (m, 3 H) 6.69-7.05 (m, 3 H) 4.80-4.99 (m, 2 H) 4.14-4.35 (m, 2 H) 3.35-3.48 (m, 2 H) 3.31 (s, 3 H) | 363 |
| I-131 | 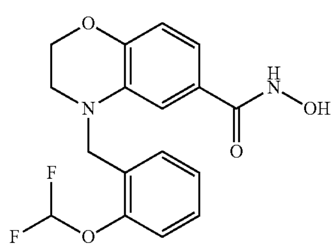 [SMILES: O=C(NO)c1ccc2c(c1)N(Cc1ccccc1OC(F)F)CCO2] | 4-(2-(difluoromethoxy)benzyl)-N-hydroxy-3,4-dihydro-2H-benzo[b][1,4]oxazine-6-carboxamide | ¹H NMR (300 MHz, DMSO-d$_6$) δ ppm 10.91 (s, 1 H) 8.78 (d, J = 1.47 Hz, 1 H) 7.31-7.39 (m, 1 H) 7.12-7.31 (m, 4 H) 6.93-7.06 (m, 2 H) 6.75 (d, J = 7.92 Hz, 1 H) 4.54 (s, 2 H) 4.21-4.31 (m, 2 H) 3.39 (t, J = 4.40 Hz, 2 H) | 351 |
| I-132 | 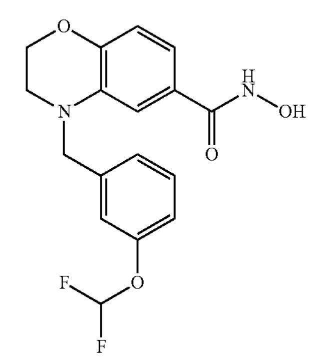 [SMILES: O=C(NO)c1ccc2c(c1)N(Cc1cccc(OC(F)F)c1)CCO2] | 4-(3-(difluoromethoxy)benzyl)-N-hydroxy-3,4-dihydro-2H-benzo[b][1,4]oxazine-6-carboxamide | ¹H NMR (300 MHz, DMSO-d$_6$) δ ppm 10.92 (s, 1 H) 8.80 (d, J = 2.05 Hz, 1 H) 7.36-7.49 (m, 1 H) 6.92-7.25 (m, 6 H) 6.74 (d, J = 8.21 Hz, 1 H) 4.54 (s, 2 H) 4.25 (dd, J = 4.98, 3.81 Hz, 2 H) 3.34-3.43 (m, 2 H) | 351 |
| I-133 | 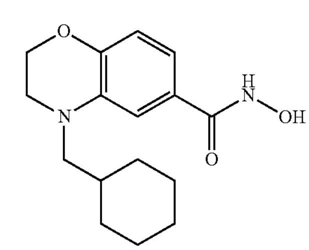 [SMILES: O=C(NO)c1ccc2c(c1)N(CC1CCCCC1)CCO2] | 4-(cyclohexylmethyl)-N-hydroxy-3,4-dihydro-2H-benzo[b][1,4]oxazine-6-carboxamide | ¹H NMR (300 MHz, DMSO-d$_6$) δ ppm 10.98 (br s, 1 H) 8.84 (s, 1 H) 7.02 (d, J = 1.76 Hz, 1 H) 6.92 (dd, J = 8.21, 1.76 Hz, 1 H) 6.68 (d, J = 8.21 Hz, 1 H) 4.13-4.19 (m, 2 H) 3.31 (s, 2 H) 3.08 (d, J = 6.74 Hz, 2 H) 1.70 (br d, J = 10.55 Hz, 6 H) 1.08-1.30 (m, 3 H) 0.96 (br d, J = 10.85 Hz, 2 H) | 291 |

| Compd. No. | Structure | IUPAC Name | ¹H NMR | MS (ES, m/z) [M + H] |
|---|---|---|---|---|
| I-134 | 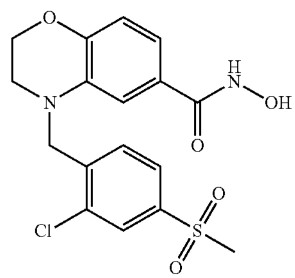 [SMILES: CS(=O)(=O)c1ccc(CN2CCOc3ccc(C(=O)NO)cc32)c(Cl)c1] | 4-(2-chloro-4-(methylsulfonyl)benzyl)-N-hydroxy-3,4-dihydro-2H-benzo[b][1,4]oxazine-6-carboxamide | ¹H NMR (300 MHz, DMSO-$d_6$) δ ppm 10.93 (br s, 1 H) 8.81 (s, 1 H) 8.05 (d, J = 1.76 Hz, 1 H) 7.84 (dd, J = 8.06, 1.91 Hz, 1 H) 7.49 (d, J = 8.21 Hz, 1 H) 7.03 (dd, J = 8.35, 1.91 Hz, 1 H) 6.85 (d, J = 2.05 Hz, 1 H) 6.79 (d, J = 8.21 Hz, 1 H) 4.67 (s, 2 H) 4.25-4.35 (m, 2 H) 3.49 (br d, J = 3.81 Hz, 2 H) 3.34 (s, 3 H) | 397 |
| I-135 | 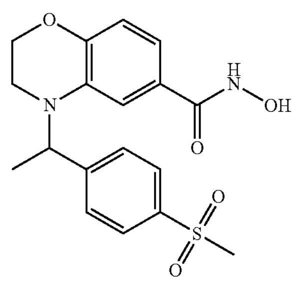 [SMILES: CC(c1ccc(S(C)(=O)=O)cc1)N1CCOc2ccc(C(=O)NO)cc21] | N-hydroxy-4-(1-(4-(methylsulfonyl)phenyl)ethyl)-3,4-dihydro-2H-benzo[b][1,4]oxazine-6-carboxamide | ¹H NMR (300 MHz, DMSO-$d_6$) δ ppm 10.94 (s, 1 H) 8.84 (s, 1 H) 7.91 (d, J = 8.50 Hz, 2 H) 7.64 (d, J = 8.50 Hz, 2 H) 6.50-7.34 (m, 3 H) 5.27 (br d, J = 7.33 Hz, 1 H) 4.09-4.24 (m, 2 H) 3.31 (br s, 2 H) 3.21 (s, 3 H) 1.56 (br d, J = 6.74 Hz, 3 H) | 377 |
| I-136 | 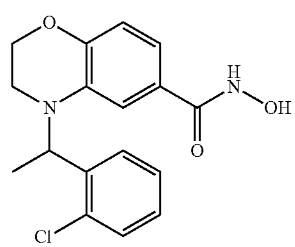 [SMILES: CC(c1ccccc1Cl)N1CCOc2ccc(C(=O)NO)cc21] | 4-(1-(2-chlorophenyl)ethyl)-N-hydroxy-3,4-dihydro-2H-benzo[b][1,4]oxazine-6-carboxamide | ¹H NMR (300 MHz, DMSO-$d_6$) δ ppm 10.94 (br s, 1 H) 8.81 (s, 1 H) 7.44-7.56 (m, 2 H) 7.29-7.41 (m, 2 H) 7.18 (d, J = 1.76 Hz, 1 H) 6.94 (dd, J = 8.21, 1.76 Hz, 1 H) 6.71 (d, J = 8.21 Hz, 1 H) 5.26 (q, J = 6.94 Hz, 1 H) 4.00-4.21 (m, 2 H) 3.30 (s, 1 H) 3.31 (br s, 1H) 2.97-3.14 (m, 1 H) 1.51 (d, J = 7.04 Hz, 3 H) | 333 |
| I-137 | 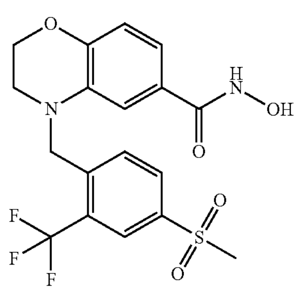 [SMILES: CS(=O)(=O)c1ccc(CN2CCOc3ccc(C(=O)NO)cc32)c(C(F)(F)F)c1] | N-hydroxy-4-(4-(methylsulfonyl)-2-(trifluoromethyl)benzyl)-3,4-dihydro-2H-benzo[b][1,4]oxazine-6-carboxamide | ¹H NMR (300 MHz, DMSO-$d_6$) δ ppm 10.91 (br s, 1 H) 8.79 (s, 1 H) 8.06-8.34 (m, 2 H) 7.74 (d, J = 8.35 Hz, 1 H) 7.02 (dd, J = 8.35, 1.76 Hz, 1 H) 6.72-6.89 (m, 2 H) 4.78 (s, 2 H) 4.33 (br d, J = 3.52 Hz, 2 H) 3.49 (br s, 2 H) 3.31 (s, 3 H) | 431 |
| I-138 | 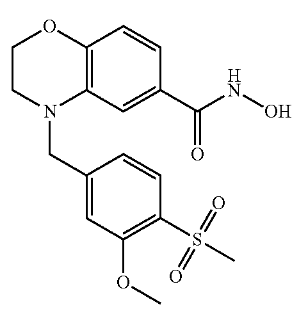 [SMILES: COc1cc(CN2CCOc3ccc(C(=O)NO)cc32)ccc1S(C)(=O)=O] | N-hydroxy-4-(3-methoxy-4-(methylsulfonyl)benzyl)-3,4-dihydro-2H-benzo[b][1,4]oxazine-6-carboxamide | ¹H NMR (300 MHz, DMSO-$d_6$) δ ppm 10.93 (br s, 1 H) 8.82 (s, 1 H) 7.65-7,88 (m, 1 H) 7.17-7.29 (m, 1 H) 6.85-7.12 (m, 2 H) 6.75 (d, J = 8.21 Hz, 1 H) 4.45-4.67 (m, 2 H) 4.28 (br s, 2 H) 3.94 (s, 3 H) 3.43 (br s, 2 H) 3.22 (s, 3 H) | 393 |

| Compd. No. | Structure | IUPAC Name | ¹H NMR | MS (ES, m/z) [M + H] |
|---|---|---|---|---|
| I-139 | 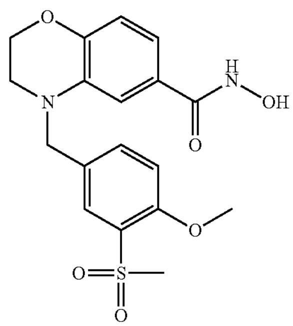 [SMILES: COc1ccc(CN2CCOc3ccc(C(=O)NO)cc32)cc1S(C)(=O)=O] | N-hydroxy-4-(4-methoxy-3-(methylsulfonyl)benzyl)-3,4-dihydro-2H-benzo[b][1,4]oxazine-6-carboxamide | ¹H NMR (300 MHz, DMSO-d$_6$) δ ppm 10.94 (br s, 1 H) 8.83 (br s, 1 H) 7.76 (d, J = 2.05 Hz, 1 H) 7.59 (dd, J = 8.50, 2.05 Hz, 1 H) 7.28 (d, J = 8.50 Hz, 1 H) 7.12 (d, J = 1.76 Hz, 1 H) 7.00 (dd, J = 8.21, 1.76 Hz, 1 H) 6.74 (d, J = 8.21 Hz, 1 H) 4.54 (s, 2 H) 4.23 (br d, J = 4.10 Hz, 2 H) 3.86-3.97 (m, 3 H) 3.36 (br s, 2 H) 3.24 (s, 3 H) | 393 |

Example 34—4-benzoyl-N-hydroxy-3,4-dihydro-2H-benzo[b][1,4]oxazine-6-carboxamide

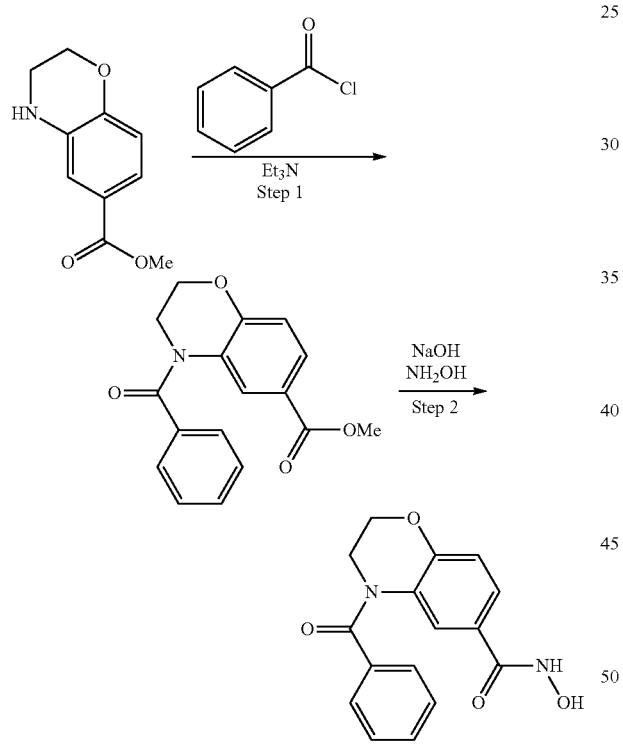

Step-1: Methyl 4-benzoyl-3,4-dihydro-2H-benzo[b][1,4]oxazine-6-carboxylate

Triethylamine (0.065 mL, 0.466 mmol) and benzoyl chloride (0.022 mL, 0.186 mmol) were added to a solution of methyl 3,4-dihydro-2H-benzo[b][1,4]oxazine-6-carboxylate (30 mg, 0.155 mmol) in 1,2-dichloroethane (2 mL), and the reaction stirred at ambient temperature overnight. The reaction was diluted with dichloromethane and washed with brine. The organic layer was passed through an Isolute© phase separator, and then concentrated to afford a quantitative yield of methyl 4-benzoyl-3,4-dihydro-2H-benzo[b][1,4]oxazine-6-carboxylate which was used directly in the next step without further purification. MS: (ES, m/z): 298 [M+H]⁺.

Step-2: 4-benzoyl-N-hydroxy-3,4-dihydro-2H-benzo[b][1,4]oxazine-6-carboxamide

Methyl 4-benzoyl-3,4-dihydro-2H-benzo[b][1,4]oxazine-6-carboxylate (45 mg, 0.151 mmol) was dissolved in methanol/THF (1/1, 3 mL), 50% aqueous hydroxyl amine solution (0.5 mL, 7.57 mmol) and 1N aqueous sodium hydroxide solution (0.5 mL, 0.55 mmol) were added, and the resulting solution stirred for 2 hours at ambient temperature; The reaction mixture was concentrated, and the crude product was purified by preparative-HPLC with the following conditions: Waters reversed phase HPLC: 23 mL/min, 8 min gradient 0%-35% Acetonitrile, 0.1% formic acid on a Waters XBridge Prep C18 OBD 5 µm, 19×50 mm column. The collected fraction was lyophilized to afford 4-benzoyl-N-hydroxy-3,4-dihydro-2H-benzo[b][1,4]oxazine-6-carboxamide (13.5 mg, 30%) as an off-white solid. ¹H NMR (300 MHz, DMSO-d$_6$) δ ppm 11.00 (br s, 1H) 8.88 (s, 1H) 7.80-8.01 (m, 2H) 7.35-7.66 (m, 7H) 6.95 (d, J=8.79 Hz, 1H) 4.28-4.38 (m, 2H) 3.80-3.93 (m, 2H). MS: (ES, m/z): 299 [M+H]⁻.

Example 35—N-hydroxy-4-(4-methoxybenzyl)-3-oxo-3,4-dihydro-2H-benzo[b][1,4]oxazine-6-carboxamide (I-141)

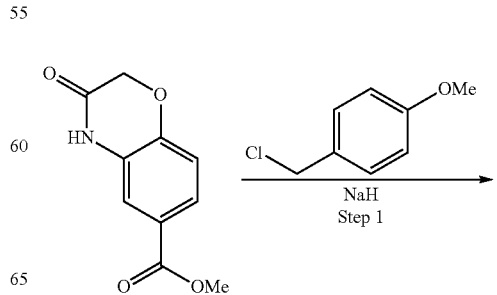

205

-continued

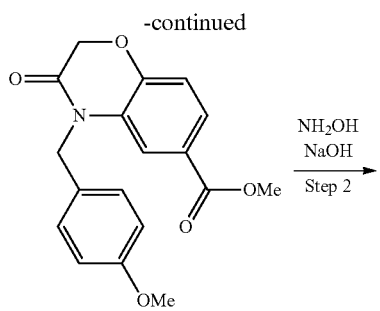

NH₂OH
NaOH
Step 2 →

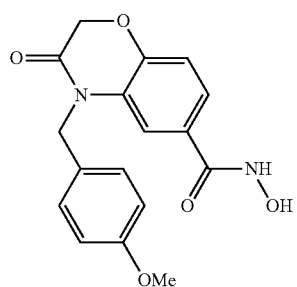

Step-1: Methyl 4-(4-methoxybenzyl)-3-oxo-3,4-dihydro-2H-benzo[b][1,4]oxazine-6-carboxylate Sodium hydride (23.17 mg, 0.579 mmol) was added to a solution of methyl 3-oxo-3,4-dihydro-2H-benzo[b][1,4]oxazine-6-carboxylate (100 mg, 0.483 mmol) in DMF (3 mL), and the reaction stirred for 5 minutes. 1-(Chloromethyl)-4-methoxybenzene (0.068 mL, 0.483 mmol) was added, and the reaction stirred at ambient temperature overnight. The reaction mixture was diluted with ethyl acetate and washed with brine. The organic layer was separated and concentrated to afford a quantitative yield of methyl 4-(4-methoxybenzyl)-3-oxo-3,4-dihydro-2H-benzo[b][1,4]oxazine-6-carboxylate which was used directly in the next step without further purification. MS: (ES, r/z): 328 [M+H]⁺.

Step2: N-hydroxy-4-(4-methoxybenzyl)-3-oxo-3,4-dihydro-2H-benzo[b][1,4]oxazine-6-carboxamide Methyl 4-(4-methoxybenzyl)-3-oxo-3,4-dihydro-2H-benzo[b][1,4]oxazine-6-carboxylate (150 mg, 0.458 mmol) was dissolved in methanol/THF (1/1, 4 mL), 50% aqueous hydroxyl amine solution (1.5 mL, 22.7 mmol) and 1N aqueous sodium hydroxide solution (1.5 mL, 1.5 mmol) were added, and the resulting solution stirred for 2 hours at ambient temperature. The reaction mixture was concentrated, and the crude product was purified by preparative-HPLC with the following conditions: Waters reversed phase HPLC: 23 mL/min, 8 min gradient 0%-35% Acetonitrile, 0.1% formic acid on a Waters XBridge Prep C18 OBD 5 µm, 19×50 mm column. The collected fraction was lyophilized to afford N-hydroxy-4-(4-methoxybenzyl)-3-oxo-3,4-dihydro-2H-benzo[b][1,4]oxazine-6-carboxamide (6.7 mg, 4%) as an off-white solid. ¹H NMR (300 MHz, DMSO-d₆) δ ppm 11.13 (s, 1H) 8.99 (s, 1H) 7.33-7.51 (m, 2H) 7.21 (d, J=8.50 Hz, 2H) 7.06 (d, J=8.50 Hz, 1H) 6.89 (d, J=8.79 Hz, 2H) 5.11 (s, 2H) 4.85 (s, 2H) 3.71 (s, 3H). MS: (ES, m/z): 329 [M+H]⁺.

The compounds below were synthesized according to the procedures outlined above for Example 35.

| Compd. No. | Structure | IUPAC Name | ¹H NMR | MS (ES, m/z) [M + H] |
|---|---|---|---|---|
| I-142 | 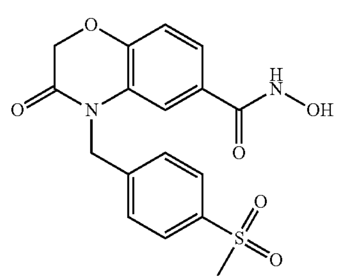 [SMILES: CS(=O)(=O)c1ccc(CN2C(=O)COc3ccc(C(=O)NO)cc32)cc1] | N-hydroxy-4-(4-(methylsulfonyl)benzyl)-3-oxo-3,4-dihydro-2H-benzo[b][1,4]oxazine-6-carboxamide | ¹H NMR (300 MHz, DMSO-d₆) δ ppm 11.13 (s, 1 H) 8.98 (s, 1 H) 7.90 (d, J = 8.21 Hz, 2 H) 7.56 (d, J = 8.50 Hz, 2 H) 7.28-7.46 (m, 2 H) 7.10 (d, J = 8.21 Hz, 1 H) 5.29 (s, 2 H) 4.83-4.91 (m, 2 H) 3.21 (s, 3 H) | 377 |
| I-143 | 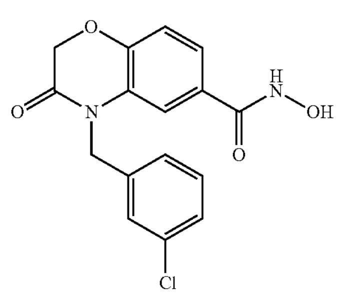 [SMILES: O=C(NO)c1ccc2c(c1)N(Cc1cccc(Cl)c1)C(=O)CO2] | 4-(3-chlorobenzyl)-N-hydroxy-3-oxo-3,4-dihydro-2H-benzo[b][1,4]oxazine-6-carboxamide | ¹H NMR (300 MHz, DMSO-d₆) δ ppm 11.13 (br s, 1 H) 8.99 (br s, 1 H) 7.52-7.72 (m, 4 H) 7.42 (dd, J = 8.35, 1.91 Hz, 1 H) 7.37 (d, J = 1.76 Hz, 1 H) 7.09 (d, J = 8.21 Hz, 1 H) 5.28 (s, 2 H) 4.90 (s, 2 H) | 333 |

| Compd. No. | Structure | IUPAC Name | ¹H NMR | MS (ES, m/z) [M + H] |
|---|---|---|---|---|
| I-144 | 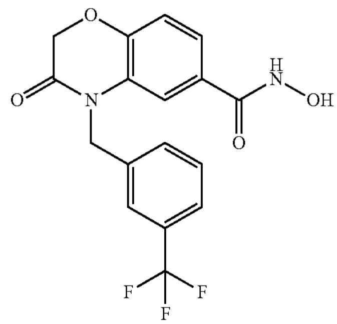 [SMILES: O=C(NO)c1ccc2c(c1)N(Cc1cccc(C(F)(F)F)c1)C(=O)CO2] | N-hydroxy-3-oxo-4-(3-(trifluoromethyl)benzyl)-3,4-dihydro-2H-benzo[b][1,4]oxazine-6-carboxamide | ¹H NMR (300 MHz, DMSO-d$_6$) δ ppm 11.13 (br s, 1 H) 8.99 (br s, 1 H) 7.51-7.72 (m, 4 H) 7.42 (dd, J = 8.35, 1.91 Hz, 1 H) 7.37 (d, J = 1.76 Hz, 1 H) 7.09 (d, J = 8.21 Hz, 1 H) 5.28 (s, 2 H) 4.90 (s, 2 H) | 367 |
| I-145 | 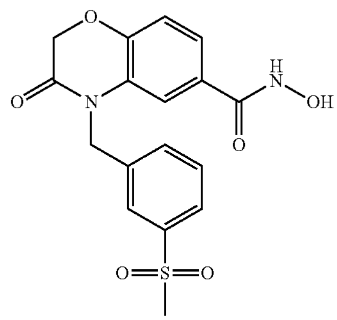 [SMILES: CS(=O)(=O)c1cccc(CN2C(=O)COc3ccc(C(=O)NO)cc32)c1] | N-hydroxy-4-(3-(methylsulfonyl)benzyl)-3-oxo-3,4-dihydro-2H-benzo[b][1,4]oxazine-6-carboxamide | ¹H NMR (300 MHz, DMSO-d$_6$) δ ppm 11.12 (br s, 1 H) 8.98 (br s, 1 H) 7.95 (s, 1 H) 7.84 (dt, J = 7.33, 1.76 Hz, 1 H) 7.54-7.68 (m, 2 H) 7.40-7.46 (m, 1 H) 7.39 (d, J = 2.05 Hz, 1 H) 7.09 (d, J = 8.21 Hz, 1 H) 5.30 (s, 2 H) 4.90 (s, 2 H) 3.22 (s, 3 H) | 377 |
| I-146 | 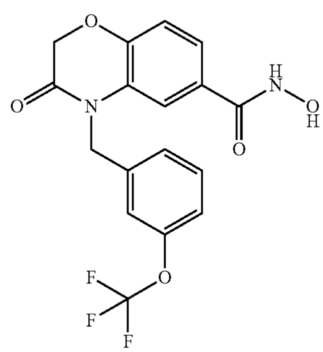 [SMILES: O=C(NO)c1ccc2c(c1)N(Cc1cccc(OC(F)(F)F)c1)C(=O)CO2] | N-hydroxy-3-oxo-4-(3-(trifluoromethoxy)benzyl)-3,4-dihydro-2H-benzo[b][1,4]oxazine-6-carboxamide | ¹H NMR (300 MHz, DMSO-d$_6$) δ ppm 11.11 (br s, 1 H) 8.98 (br s, 1 H) 7.45-7.52 (m, 1 H) 7.42 (dd, J = 8.35, 1.91 Hz, 1 H) 7.37 (d, J = 1.76 Hz, 1 H) 7.23-7.33 (m, 3 H) 7.09 (d, J = 8.21 Hz, 1 H) 5.23 (s, 2 H) 4.89 (s, 2 H) | 383 |
| I-147 | 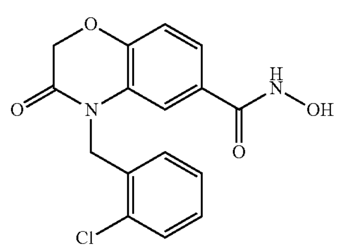 [SMILES: O=C(NO)c1ccc2c(c1)N(Cc1ccccc1Cl)C(=O)CO2] | 4-(2-chlorobenzyl)-N-hydroxy-3-oxo-3,4-dihydro-2H-benzo[b][1,4]oxazine-6-carboxamide | ¹H NMR (300 MHz, DMSO-d$_6$) δ ppm 11.15 (br s, 1 H) 8.97 (br s, 1 H) 7.55 (dd, J = 7.92, 1.47 Hz, 1 H) 7.44 (dd, J = 8.35, 1.91 Hz, 1 H) 7.17-7.39 (m, 3 H) 7.04-7.14 (m, 2 H) 5.17 (s, 2 H) 4.85-4.96 (m, 2 H) | 333 |
| I-148 | 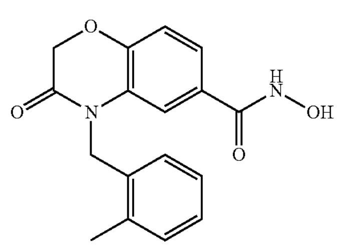 [SMILES: Cc1ccccc1CN1C(=O)COc2ccc(C(=O)NO)cc21] | N-hydroxy-4-(2-methylbenzyl)-3-oxo-3,4-dihydro-2H-benzo[b][1,4]oxazine-6-carboxamide | ¹H NMR (300 MHz, DMSO-d$_6$) δ ppm 11.10 (br s, 1 H) 8.95 (s, 1 H) 7.41 (dd, J = 8.35, 1.91 Hz, 1 H) 7.04-7.29 (m, 5 H) 6.89 (d, J = 6.74 Hz, 1 H) 5.09 (s, 2 H) 4.90 (s, 2 H) 3.33 (s, 3H) | 313 |

| Compd. No. | Structure | IUPAC Name | ¹H NMR | MS (ES, m/z) [M + H] |
|---|---|---|---|---|
| I-149 | 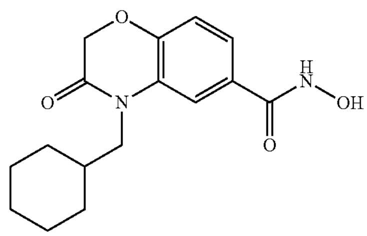 [SMILES: O=C(NO)c1ccc2c(c1)N(CC1CCCCC1)C(=O)CO2] | 4-(cyclohexylmethyl)-N-hydroxy-3-oxo-3,4-dihydro-2H-benzo[b][1,4]oxazine-6-carboxamide | ¹H NMR (300 MHz, DMSO-d$_6$) δ ppm 11.25 (br s, 1 H) 9.06 (br s, 1 H) 7.53 (d, J = 2.05 Hz, 1 H) 7.44 (dd, J = 8.50, 1.76 Hz, 1H) 7.07 (d, J = 8.21 Hz, 1 H) 4.70 (s, 2 H) 3.83 (d, J = 7.33 Hz, 2 H) 1.61 (br d, J = 14.07 Hz, 6H) 0.94-1.18 (m, 5 H) | 305 |
| I-150 | 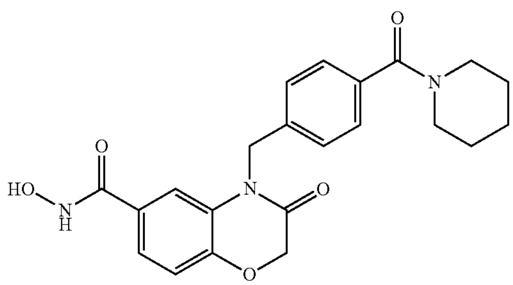 [SMILES: O=C(NO)c1ccc2c(c1)N(Cc1ccc(C(=O)N3CCCCC3)cc1)C(=O)CO2] | N-hydroxy-3-oxo-4-(4-(piperidine-1-carbonyl)benzyl)-3,4-dihydro-2H-benzo[b][1,4]oxazine-6-carboxamide | N/A | 409 |
| I-151 | 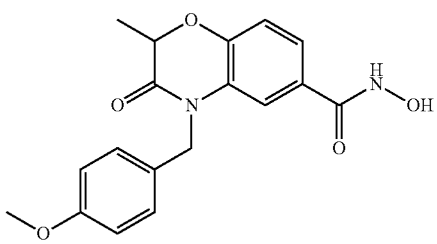 [SMILES: COc1ccc(CN2C(=O)C(C)Oc3ccc(C(=O)NO)cc32)cc1] | N-hydroxy-4-(4-methoxybenzyl)-2-methyl-3-oxo-3,4-dihydro-2H-benzo[b][1,4]oxazine-6-carboxamide | ¹H NMR (300 MHz, DMSO-d$_6$) δ ppm 11.13 (br s, 1 H) 8.99 (br s, 1 H) 7.45 (d, J = 2.05 Hz, 1 H) 7.39 (dd, J = 8.35, 1.91 Hz, 1 H) 7.19 (d, J = 8.79 Hz, 2 H) 7.07 (d, J = 8.21 Hz, 1 H) 6.85-6.93 (m, 2 H) 5.10 (s, 2 H) 4.85-5.02 (m, 1 H) 3.71 (s, 3 H) 1.51 (d, J = 6.74 Hz, 3 H) | 343 |
| I-152 | 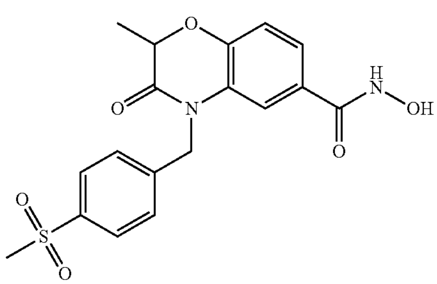 [SMILES: CC1Oc2ccc(C(=O)NO)cc2N(Cc2ccc(S(C)(=O)=O)cc2)C1=O] | N-hydroxy-2-methyl-4-(4-(methylsulfonyl)benzyl)-3-oxo-3,4-dihydro-2H-benzo[b][1,4]oxazine-6-carboxamide | ¹H NMR (300 MHz, DMSO-d$_6$) δ ppm 11.13 (s, 1 H) 8.99 (s, 1 H) 7.90 (d, J = 8.50 Hz, 2 H) 7.52 (d, J = 8.50 Hz, 2 H) 7.43 (dd, J = 8.35, 1.91 Hz, 1 H) 7.37 (d, J = 1.76 Hz, 1 H) 7.12 (d, J = 8.21 Hz, 1 H) 5.17-5.39 (m, 2 H) 4.95-5.06 (m, 1 H) 3.21 (s, 3 H) 1.53 (d, J = 6.74 Hz, 3 H) | 391 |
| I-153 | 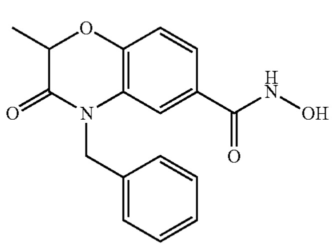 [SMILES: CC1Oc2ccc(C(=O)NO)cc2N(Cc2ccccc2)C1=O] | 4-benzyl-N-hydroxy-2-methyl-3-oxo-3,4-dihydro-2H-benzo[b][1,4]oxazine-6-carboxamide | ¹H NMR (300 MHz, DMSO-d$_6$) δ ppm 11.13 (br s, 1 H) 9.00 (br s, 1 H) 7.20-7.43 (m, 7 H) 7.09 (d, J = 8.79 Hz, 1 H) 5.09-5.26 (m, 2 H) 4.92-5.02 (m, 1 H) 1.52 (d, J = 6.74 Hz, 3 H) | 313 |

Example 36—4-benzyl-N-hydroxy-3-methyl-3,4-dihydro-2H-benzo[b][1,4]oxazine-6-carboxamide (I-154)

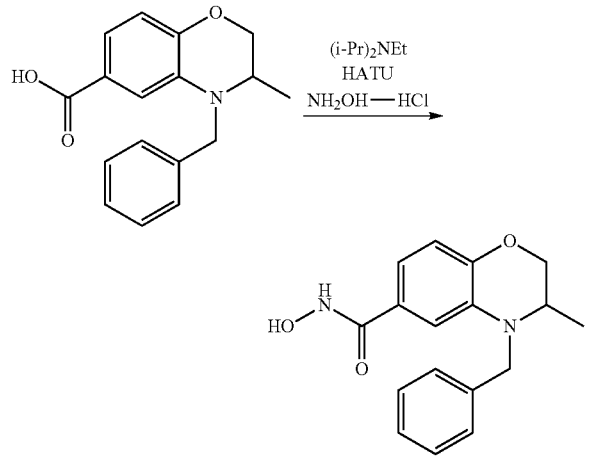

Hydroxylamine hydrochloride (14.72 mg, 0.212 mmol), N,N-diisopropylethylamine (0.074 mL, 0.424 mmol) and HATU (48.3 mg, 0.127 mmol) were added to a solution of 4-benzyl-3-methyl-3,4-dihydro-2H-benzo[b][1,4]oxazine-6-carboxylic acid (30 mg, 0.106 mmol) in DMF (2 mL), and the reaction mixture stirred at ambient temperature overnight. The reaction was diluted with ethyl acetate and washed with brine. The organic layer was separated and concentrated. The residue was purified with the following conditions: Waters reversed phase HPLC: 23 mL/min, 8 min gradient 35%-85% Acetonitrile, 0.1% formic acid on a Waters XBridge Prep C18 OBD 5 μm, 19×50 mm column. The collected fraction was lyophilized to afford 4-benzyl-N-hydroxy-3-methyl-3,4-dihydro-2H-benzo[b][1,4]oxazine-6-carboxamide (6 mg, 19%) as a light pink solid. $^1$H NMR (300 MHz, DMSO-d$_6$) δ ppm 10.87 (br s, 1H) 8.77 (s, 1H) 7.23-7.35 (m, 5H) 6.90-7.00 (m, 2H) 6.75 (d, J=8.21 Hz, 1H) 4.37-4.63 (m, 2H) 4.02-4.18 (m, 2H) 3.58 (br d, J=6.45 Hz, 1H) 1.12 (d, J=6.45 Hz, 3H). MS: (ES, m/z): 299[M+H]$^+$.

The compounds below were synthesized according to the procedures outlined above for Example 36.

| Compd. No. | Structure | IUPAC Name | $^1$H NMR | MS (ES, m/z) [M + H]$^+$ |
|---|---|---|---|---|
| I-155 | 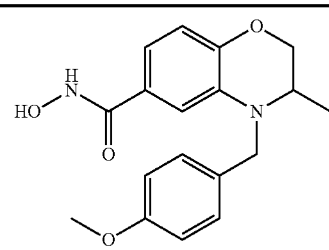 | N-hydroxy-4-(4-methoxybenzyl)-3-methyl-3,4-dihydro-2H-benzo[b][1,4]oxazine-6-carboxamide | $^1$H NMR (300 MHz, DMSO-d$_6$) δ ppm 10.89 (br s, 1 H) 8.78 (s, 1 H) 7.09-7.28 (m, 2 H) 6.82-7.07 (m, 4 H) 6.74 (d, J = 8.21 Hz, 1 H) 4.18-4.66 (m, 2 H) 4.08 (d, J = 2.35 Hz, 2 H) 3.69-3.76 (m, 3 H) 3.54 (br d, J = 6.45 Hz, 1 H) 1.10 (d, J = 6.74 Hz, 3 H) | 329 |

Example 37. (R)—N-hydroxy-4-(4-methoxybenzyl)-2-methyl-3-oxo-3,4-dihydro-2H-benzo[b][1,4]oxazine-6-carboxamide (I-162)

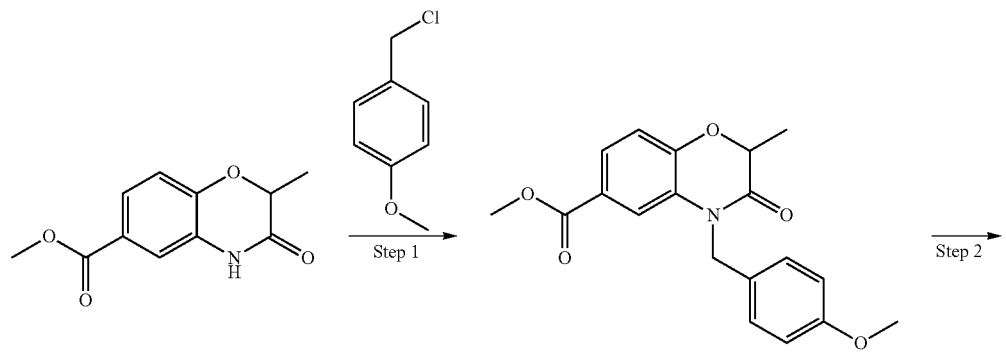

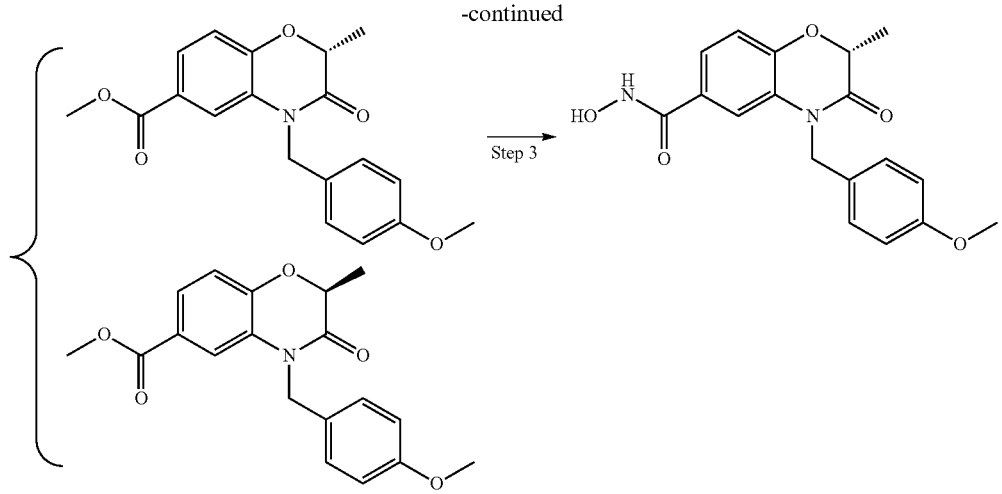

Step 1. Synthesis of Methyl 4-(4-methoxybenzyl)-2-methyl-3-oxo-3,4-dihydro-2H-benzo[b][1,4]oxazine-6-carboxylate 4-methoxybenzyl chloride (0.135 ml, 0.995 mmol) was added to a solution of methyl 2-methyl-3-oxo-3,4-dihydro-2H-benzo[b][1,4]oxazine-6-carboxylate (200 mg, 0.904 mmol) and cesium carbonate (884 mg, 2.71 mmol) in N,N-Dimethylformamide (5 ml), and the reaction stirred overnight at ambient temperature. The reaction was diluted with ethyl acetate and washed with brine. The organic layer was separated and concentrated then purified via column chromatography on a 25 gram silica gel column eluting with 10-50% ethyl acetate-hexane. The desired fractions were combined and concentrated to afford methyl 4-benzyl-2-methyl-3-oxo-3,4-dihydro-2H-benzo[b][1,4]oxazine-6-carboxylate (275 mg, 89%). MS: (ES, m/z): 342 [M+H]+.

Step 2. Synthesis of Methyl (R)-4-(4-methoxybenzyl)-2-methyl-3-oxo-3,4-dihydro-2H-benzo[b][1,4]oxazine-6-carboxylate The racemate of methyl 4-(4-methoxybenzyl)-2-methyl-3-oxo-3,4-dihydro-2H-benzo[b][1,4]oxazine-6-carboxylate (275 mg) was purified by Chiral HPLC with the following conditions Column: ChiralPak ID 10*250 mm, 5 μm; Mobile Phase A: Hexanes, Mobile Phase B: IPA; Flow rate: 5 mL/min; Gradient: 10% B hold; Runtime: 35 minutes, Detector: 220 nm. The first peak was collected and concentrated to give 0.064 g and arbitrarily assigned as methyl (R)-4-(4-methoxybenzyl)-2-methyl-3-oxo-3,4-dihydro-2H-benzo[b][1,4]oxazine-6-carboxylate MS: (ES, m/z): 342 [M+H]+. The second peak was collected and concentrated to give 0.066 g arbitrarily assigned methyl (S)-4-(4-methoxybenzyl)-2-methyl-3-oxo-3,4-dihydro-2H-benzo[b][1,4]oxazine-6-carboxylate. MS: (ES, m/z): 342 [M+H]+.

Step 3. Synthesis of (R)—N-hydroxy-4-(4-methoxybenzyl)-2-methyl-3-oxo-3,4-dihydro-2H-benzo[b][1,4]oxazine-6-carboxamide Intermediate methyl (R)-4-(4-methoxybenzyl)-2-methyl-3-oxo-3,4-dihydro-2H-benzo[b][1,4]oxazine-6-carboxylate (0.030 g, 0.088 mmol, 1.0 equiv) was dissolved in Tetrahydrofuran (0.5 mL) and Methanol (0.5 mL). NH$_2$OH (0.3 ml, 4.54 mmol, 50% in water, 51 equiv) and 1N aq. NaOH (0.3 mL, 3.4 equiv) were added. The resulting solution was stirred for 2 hours at room temperature. The reaction was concentrated to dryness. Purified by preparative-HPLC with the following conditions: Waters reversed phase HPLC: 23 mL/min, 8 min gradient 0%-35% Acetonitrile, 0.1% formic acid on a Waters XBridge Prep C18 OBD 5 μm, 19×50 mm column. Fractions were lyophilized to afford 0.025 g (90% yield) of (R)—N-hydroxy-4-(4-methoxybenzyl)-2-methyl-3-oxo-3,4-dihydro-2H-benzo[b][1,4]oxazine-6-carboxamide. MS: (ES, m/z): 343 [M+H]+.

Example 38. 8-fluoro-N-hydroxy-4-(4-methoxybenzyl)-3-oxo-3,4-dihydro-2H-benzo[b][1,4]oxazine-6-carboxamide (I-163)

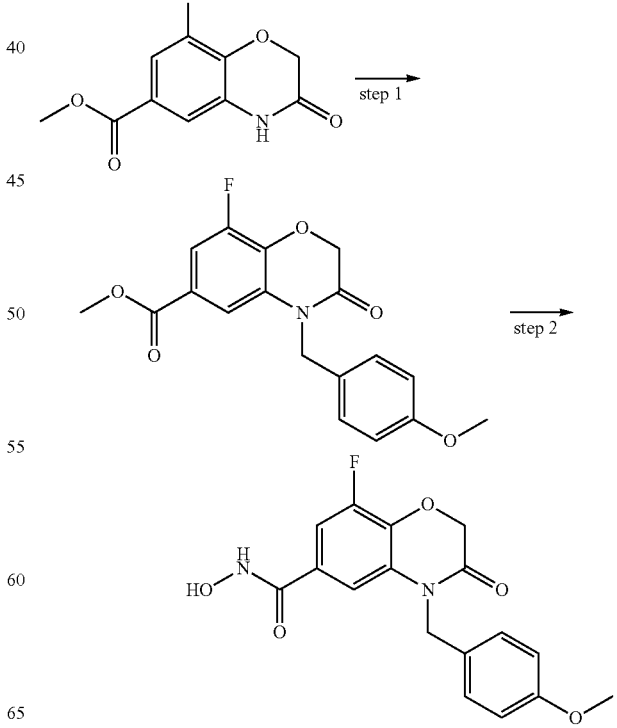

Step 1: Methyl 8-fluoro-4-(4-methoxybenzyl)-3-oxo-3,4-dihydro-2H-benzo[b][1,4]oxazine-6-carboxylate Into a 25-mL round-bottom flask, was placed methyl 8-fluoro-3-oxo-3,4-dihydro-2H-benzo[b][1,4]oxazine-6-carboxylate (100 mg, 0.44 mmol, 1.00 equiv), N,N-dimethylformamide (3 mL), 1-(chloromethyl)-4-methoxybenzene (0.07 mL, 0.49 mmol, 1.10 equiv), Cs$_2$CO$_3$ (362 mg, 1.11 mmol, 2.52 equiv). The resulting solution was stirred for 2 h at room temperature (25° C.) and then diluted with 15 mL of water, extracted with 2×15 mL of ethyl acetate, dried over anhydrous sodium sulfate and concentrated under vacuum. The residue was purified via preparative-TLC (eluting with ethyl acetate/petroleum ether (1:3)) to afford methyl 8-fluoro-4-(4-methoxybenzyl)-3-oxo-3,4-dihydro-2H-benzo[b][1,4]oxazine-6-carboxylate (108 mg, 70%) as a white solid. MS: (ESI, m/z): 346[M+H]$^+$.

Step 2: 8-fluoro-N-hydroxy-4-(4-methoxybenzyl)-3-oxo-3,4-dihydro-2H-benzo[b][1,4]oxazine-6-carboxamide Into a 25-mL round-bottom flask, was placed methyl 8-fluoro-4-(4-methoxybenzyl)-3-oxo-3,4-dihydro-2H-benzo[b][1,4]oxazine-6-carboxylate (108 mg, 0.31 mmol, 1.00 equiv), THF/MeOH (4/1) (3 mL), NH$_2$OH (50% in water) (1.24 mL, 18.77 mmol, 60.00 equiv). This was followed by the addition of NaOH (1M) (0.63 mL, 0.63 mmol, 2.00 equiv). The resulting solution was stirred for 1 h at room temperature (28° C.). The solids were filtered out. The crude product was purified via Prep-HPLC with the following conditions: Column, XBridge Prep C18 OBD Column, 19×150 mm 5 μm; mobile phase, water (0.1% FA) and ACN (15.0% ACN up to 45.0% in 7 min); Detector, UV 254 nm. The collected fraction was lyophilized to afford 8-fluoro-N-hydroxy-4-(4-methoxybenzyl)-3-oxo-3,4-dihydro-2H-benzo[b][1,4]oxazine-6-carboxamide (39.3 mg, 36%) as a white solid. $^1$H-NMR: (DMSO 300 MHz, ppm): δ 11.23 (s, 1H), 9.11 (s, 1H), 7.38-7.31 (m, 2H), 7.23 (d, J=8.7 Hz, 2H), 6.90 (d, J=8.7 Hz, 2H), 5.13 (s, 2H), 4.95 (s, 2H), 3.72 (s, 3H). MS: (ESI, m/z): 347[M+H]$^+$.

The compounds below were synthesized according to the procedures outlined above for Example 38.

Example 39. N-hydroxy-1-(4-methoxybenzyl)-2-oxo-2,4-dihydro-1H-benzo[d][1,3]oxazine-7-carboxamide (I-165)

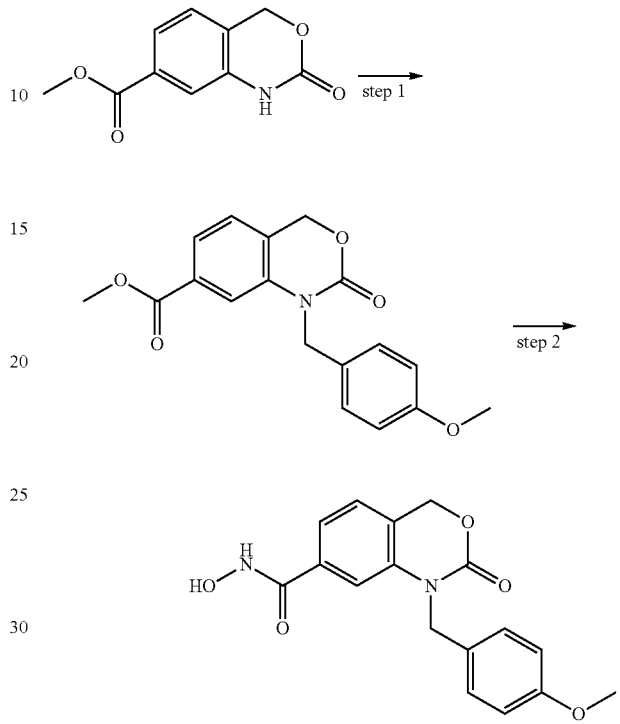

Step 1: Methyl 1-(4-methoxybenzyl)-2-oxo-2,4-dihydro-1H-benzo[d][1,3]oxazine-7-carboxylate Into a 8-mL vial, was placed methyl 2-oxo-2,4-dihydro-1H-benzo[d][1,3]oxazine-7-carboxylate (70 mg, 0.34 mmol, 1.00 equiv), N,N-dimethylformamide (2 mL), Cs$_2$CO$_3$ (275 mg, 0.84 mmol, 2.50 equiv), 1-(chloromethyl)-4-methoxybenzene (0.05 mL, 0.37 mmol, 1.10 equiv). The resulting solution was stirred for 4 h at room temperature (27° C.) and then diluted with 30 mL of water. The resulting solution was extracted with 3×30 mL of ethyl acetate, washed with 2×30 mL of brine, dried over anhydrous sodium sulfate and concentrated under vacuum. The residue was purified via

| Comp. No. | Structure | IUPAC Name | $^1$H NMR | (ESI, m/z) [M + H]$^+$ |
|---|---|---|---|---|
| I-164 | ![structure] | 4-(4-(1H-pyrazol-1-yl)benzyl)-8-fluoro-N-hydroxy-3-oxo-3,4-dihydro-2H-benzo[b][1,4]oxazine-6-carboxamide | (DMSO, 300 MHz, ppm): 11.22 (s, 1H), 9.09 (s, 1H), 8.48 (s, 1H), 7.91 (d, J = 8.4 Hz, 2H), 7.73 (s, 1H), 7.43 (d, J = 8.7 Hz, 2H), 7.39-7.35 (m, 1H), 7.29 (s, 1H), 6.54-6.53 (m, 1H), 5.24 (s, 2H), 5.00 (s, 2H) | 383 | column chromatography on silica gel (eluting with ethyl acetate/petroleum ether (1:4)) to afford methyl 1-(4-methoxybenzyl)-2-oxo-2,4-dihydro-1H-benzo[d][1,3]oxazine-7-carboxylate (85 mg, 77%) as a white solid. MS: (ESI, m/z): 328[M+H]$^+$.

Step 2: N-hydroxy-1-(4-methoxybenzyl)-2-oxo-2,4-dihydro-1H-benzo[d][1,3]oxazine-7-carboxamide Into a 8-mL vial, was placed methyl 1-(4-methoxybenzyl)-2-oxo-2,4-dihydro-1H-benzo[d][1,3]oxazine-7-carboxylate (85 mg, 0.26 mmol, 1.00 equiv), THF/MeOH (4:1)(2 mL), NH$_2$OH (50% in water) (1.03 mL, 15.59 mmol, 60.00 equiv), NaOH (1M) (0.52 mL, 0.52 mmol, 2.00 equiv). The resulting solution was stirred for 2 h at room temperature (27° C.). The crude product was purified via Prep-HPLC with the following conditions: Column, XBridge C18 OBD Prep Column, 100A, 5 μm, 19 mm×250 mm; mobile phase, water (0.1% FA) and ACN (20.0% ACN up to 31.0% in 7 min); Detector, UV 254 nm. The collected fraction was lyophilized to afford N-hydroxy-1-(4-methoxybenzyl)-2-oxo-2,4-dihydro-1H-benzo[d][1,3]oxazine-7-carboxamide (36.2 mg, 42%) as a off-white solid. $^1$H-NMR (DMSO, 400 MHz) δ (ppm): 11.20 (br, 1H), 9.06 (br, 1H), 7.44-7.42 (m, 1H), 7.34-7.30 (m, 2H), 7.23 (d, J=8.8 Hz, 2H), 6.89 (d, J=8.8 Hz, 2H), 5.38 (s, 2H), 5.08 (s, 2H), 3.71 (s, 3H). MS: (ESI, m/z): 329 [I+H]$^+$.

The compounds below were synthesized according to the procedures outlined above for Example 39.

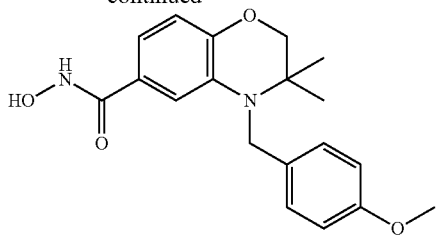

Step 1: Methyl 4-(4-methoxybenzyl)-3,3-dimethyl-3,4-dihydro-2H-benzo[b][1,4]oxazine-6-carboxylate Into a 8-mL vial, was placed methyl 3,3-dimethyl-3,4-dihydro-2H-benzo[b][1,4]oxazine-6-carboxylate (66.5 mg, 0.30 mmol, 1.00 equiv), N,N-dimethylformamide (3 mL), 1-(chloromethyl)-4-methoxybenzene (0.07 mL, 0.45 mmol, 1.50 equiv), Cs$_2$CO$_3$ (195 mg, 0.60 mmol, 2.00 equiv), KI (6 mg, 0.04 mmol, 0.13 equiv). The resulting solution was stirred for overnight at 80° C. and then cooled to room temperature. The resulting solution was diluted with 30 mL of water, extracted with 3×30 mL of ethyl acetate, washed with 30 mL of brine, dried over anhydrous sodium sulfate and concentrated under vacuum. The residue was purified via column chromatography on silica gel (eluting with ethyl acetate/petroleum ether (1:3)) to afford methyl 4-(4-methoxybenzyl)-3,3-dimethyl-3,4-dihydro-2H-benzo[b][1,4]oxazine-6-carboxylate (85 mg, 83%) as yellow oil. MS: (ESI, m/z): 342[M+H]$^+$.

| Comp. No. | Structure | IUPAC Name | $^1$H NMR | (ESI, m/z) [M + H]$^+$ |
|---|---|---|---|---|
| I-166 | ![structure] | 1-(4-(1H-pyrazol-1-yl)benzyl)-N-hydroxy-2-oxo-1,4-dihydro-2H-benzo[d][1,3]oxazine-7-carboxamide | (DMSO, 400 MHz, ppm): 11.20 (br, 1H), 9.04 (br, 1H), 8.46 (d, J = 2.4 Hz, 1H), 7.80 (d, J = 8.8 Hz, 2H), 7.72 (s, 1H), 7.46-7.41 (m, 3H), 7.36 (d, J = 8.0 Hz, 1H), 7.30 (s, 1H), 6.53-6.52 (m, 1H), 5.43 (s, 2H), 5.18 (s, 2H) | 365 |

Example 40. N-hydroxy-4-(4-methoxybenzyl)-3,3-dimethyl-3,4-dihydro-2H-benzo[b][1,4]oxazine-6-carboxamide (I-167)

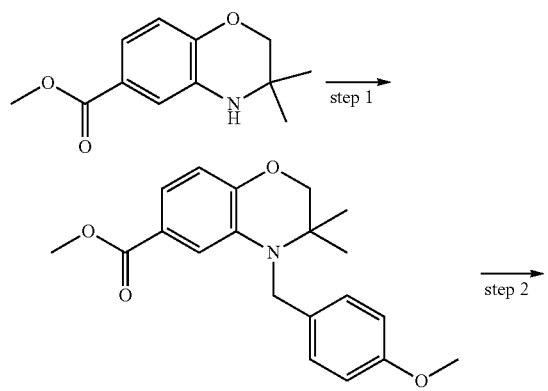

Step 2: N-hydroxy-4-(4-methoxybenzyl)-3,3-dimethyl-3,4-dihydro-2H-benzo[b][1,4]oxazine-6-carboxamide Into a 8-mL vial, was placed methyl 4-(4-methoxybenzyl)-3,3-dimethyl-3,4-dihydro-2H-benzo[b][1,4]oxazine-6-carboxylate (85 mg, 0.25 mmol, 1.00 equiv), THF/MeOH (4/1)(2 mL), NH$_2$OH (50% in water) (0.99 mL, 15.00 mmol, 60.00 equiv), NaOH (1M) (0.5 mL, 0.50 mmol, 2.00 equiv). The resulting solution was stirred for overnight at room temperature (25° C.). The solids were filtered out. The crude product was purified by Prep-HPLC with the following conditions: Column, XSelect CSH Prep C18 OBD Column, 5 μm, 19*150 mm; mobile phase, water (0.1% FA) and ACN (13.0% ACN up to 40.0% in 25 min); Detector, UV 254/220 nm. mL product was obtained. The collected fraction was lyophilized to afford N-hydroxy-4-(4-methoxybenzyl)-3,3- dimethyl-3,4-dihydro-2H-benzo[b][1,4]oxazine-6-carboxamide (19.8 mg, 23%) as a light brown solid. ¹H-NMR (DMSO, 400 MHz) δ (ppm): 10.81 (s, 1H), 8.72 (s, 1H), 7.23 (d, 0.1=8.4 Hz, 2H), 6.92-6.88 (m, 3H), 6.74 (d, 0.1=8.4 Hz, 2H), 4.40 (s, 2H), 4.01 (s, 2H), 3.73 (s, 3H), 1.18 (s, 6H). MS: (ESI, m/z): 343[M+H]⁺.

The compounds below were synthesized according to the procedures outlined above for Example 40.

| Comp. No. | Structure | IUPAC Name | ¹H NMR | (ESI, m/z) [M + H]⁺ |
|---|---|---|---|---|
| I-168 | 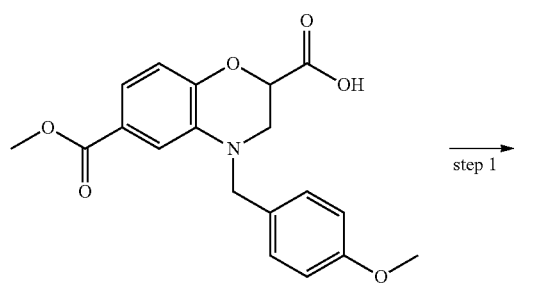 | 4-(4-(1H-pyrazol-1-yl)benzyl)-N-hydroxy-3,3-dimethyl-3,4-dihydro-2H-benzo[b][1,4]oxazine-6-carboxamide | (DMSO, 400 MHz, ppm): 10.84 (s, 1H), 8.72 (s, 1H), 8.46 (s, 1H), 7.78 (d, J = 8.4 Hz, 1H), 7.72 (s, 1H), 7.43 (d, J = 8.4 Hz, 2H), 6.95-6.92 (m, 1H), 6.78-6.75 (m, 2H), 6.52 (s, 1H), 4.51 (s, 2H), 4.05 (s, 2H), 1.21 (s, 6H). | 379 |

Example 41. N6-hydroxy-4-(4-methoxybenzyl)-N2,N2-dimethyl-3,4-dihydro-2H-benzo[b][1,4]oxazine-2,6-dicarboxamide (I-169)

Step 1: Methyl 2-(dimethylcarbamoyl)-4-(4-methoxybenzyl)-3,4-dihydro-2H-benzo[b][1,4]oxazine-6-carboxylate Into a 25-mL round-bottom flask, was placed 4-(4-methoxybenzyl)-6-(methoxycarbonyl)-3,4-dihydro-2H-benzo[b][1,4]oxazine-2-carboxylic acid (50 mg, 0.14 mmol, 1.00 equiv), DMA (2 mL), HATU (62 mg, 0.16 mmol, 1.14 equiv), DIEA (65 μL, 0.39 mmol, 2.78 equiv), dimethylamine hydrochloride (13 mg, 0.16 mmol, 1.14 equiv). The resulting solution was stirred for 1 h at room temperature (25° C.). The resulting solution was diluted with 4 mL of water. The solids were collected by filtration and dried to afford methyl 2-(dimethylcarbamoyl)-4-(4-methoxybenzyl)-3,4-dihydro-2H-benzo[b][1,4]oxazine-6-carboxylate (50 mg, 93%) as yellow oil. MS (ESI, m/z): 385 [M+H]⁺.

Step 2: N⁶-hydroxy-4-(4-meth oxybenzyl)-N²,N²-dimethyl-3,4-dihydro-2H-benzo[b][1,4]oxazine-2,6-dicarboxamide Into a 25-mL round-bottom flask, was placed methyl 2-(dimethylcarbamoyl)-4-(4-methoxybenzyl)-3,4-dihydro-2H-benzo[b][1,4]oxazine-6-carboxylate (50 mg, 0.13 mmol, 1.00 equiv), THF/MeOH (4/1) (2 mL). This was followed by the addition of NH₂OH (50% in water) (1.19 mL, 19.38 mmol, 120 equiv) and NaOH (1M) (0.3 mL, 0.30 mmol, 2.00 equiv) at 0° C. The resulting solution was stirred for 3 h at room temperature (25° C.). The mixture was purified via Prep-HPLC with the following conditions: XBridge Shield RP18 OBD Column, 5 um, 19×150 mm; Mobile Phase A: Water (0.1% FA), Mobile Phase B: ACN; Flow rate: 20 mL/min; Gradient: 20% B to 55% B in 7 min; 254 nm. The collected fraction was lyophilized to afford N6-hydroxy-4-(4-methoxybenzyl)-N2,N2-dimethyl-3,4-dihydro-2H-benzo[b][1,4]oxazine-2,6-dicarboxamide (10.5 mg, 21%) as a pink solid. ¹H-NMR (DMSO, 400 MHz) δ (ppm): 10.95 (br, 1H), 8.82 (br, 1H), 7.23-7.18 (m, 3H), 7.01 (d, J=4.4 Hz, 1H), 6.90 (d, J=8.4 Hz, 2H), 6.80 (d, J=8.4 Hz, 1H), 5.13-5.11 (m, 1H), 4.53-4.36 (m, 1H), 3.73 (s, 3H), 3.40-3.30 (m, 2H), 3.01 (s, 3H), 2.84 (s, 3H). MS (ESI, m/z): 386 [M+H]⁺.

The compounds below were synthesized according to the procedures outlined above for Example 41.

| Comp. No. | Structure | IUPAC Name | ¹H NMR | (ESI, m/z) [M + H]⁺ |
|---|---|---|---|---|
| I-170 | 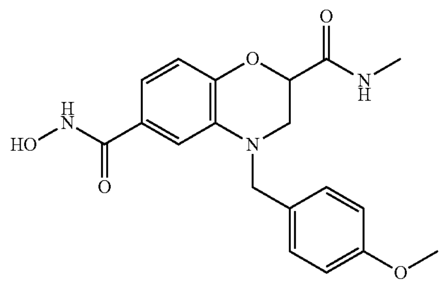 [SMILES: CNC(=O)C1CN(Cc2ccc(OC)cc2)c2cc(C(=O)NO)ccc2O1] | N⁶-hydroxy-4-(4-methoxybenzyl)-N²-methyl-3,4-dihydro-2H-benzo[b][1,4]oxazine-2,6-dicarboxamide | (DMSO, 400 MHz, ppm): 10.96 (br, 1H), 8.84 (br, 1H), 8.01-8.00 (m, 1H), 7.23-7.19 (m, 3H), 7.06-7.03 (m, 1H), 6.90-6.85 (m, 3H), 4.70-4.67 (m, 1H), 4.42 (s, 2H), 3.73 (s, 3H), 3.46-3.42 (m, 1H), 3.33-3.26 (m, 1H), 2.63 (d, J = 4.8 Hz, 3H) | 372 |
| I-171 | 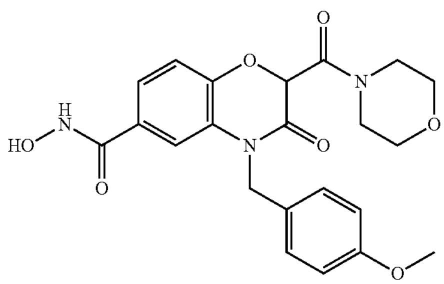 [SMILES: COc1ccc(CN2C(=O)C(C(=O)N3CCOCC3)Oc3ccc(C(=O)NO)cc32)cc1] | N-hydroxy-4-(4-methoxybenzyl)-2-(morpholine-4-carbonyl)-3,4-dihydro-2H-benzo[b][1,4]oxazine-6-carboxamide | (DMSO, 400 MHz, ppm): 10.95 (br, 1H), 8.83 (br, 1H), 7.23-7.19 (m, 3H), 7.02 (d, J = 8.4 Hz, 1H), 6.91 (d, J = 8.4 Hz, 2H), 6.79 (d, J = 8.4 Hz, 1H), 5.18-5.16 (m, 1H), 4.54-4.35 (m, 2H), 3.73 (s, 3H), 3.54-3.36 (m, 10H) | 428 |
| I-172 | 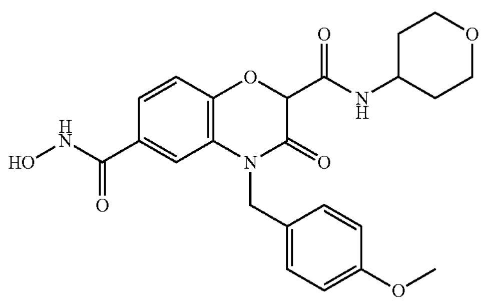 [SMILES: COc1ccc(CN2C(=O)C(C(=O)NC3CCOCC3)Oc3ccc(C(=O)NO)cc32)cc1] | N6-hydroxy-4-(4-methoxybenzyl)-N2-(tetrahydro-2H-pyran-4-yl)-3,4-dihydro-2H-benzo[b][1,4]oxazine-2,6-dicarboxamide | (DMSO, 400 MHz, ppm): 10.96 (br, 1H), 8.83 (br, 1H), 7.97 (d, J = 8.0 Hz, 1H), 7.23-7.19 (m, 3H), 7.04 (d, J = 8.4 Hz, 1H), 6.90-6.87 (m, 3H), 4.67-4.65 (m, 1H), 4.89-4.37 (m, 2H), 3.83-3.79 (m, 3H), 3.73 (s, 3H), 3.47-3.43 (m, 1H), 3.35-325 (m, 3H), 1.66-1.59 (m, 2H), 1.51-1.44 (m, 2H) | 442 |

Example 42. 4-((2,3-dihydro-[1,4]dioxino[2,3-b]pyridin-7-yl)methyl)-N-hydroxy-3-oxo-3,4-dihydro-2H-benzo[b][1,4]oxazine-6-carboxamide (I-173)

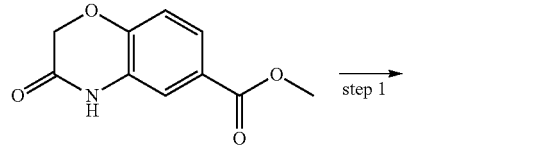

Step 1: Methyl 4-((2,3-dihydro-[1,4]dioxino[2,3-b]pyridin-7-yl)methyl)-3-oxo-3,4-dihydro-2H-benzo[b][1,4]oxazine-6-carboxylate Into a 50-mL 3-necked round-bottom flask purged and maintained with an inert atmosphere of nitrogen, was placed (2,3-dihydro-[1,4]dioxino[2,3-b]pyridin-7-yl)methanol (100 mg, 0.60 mmol, 1.00 equiv), tetrahydrofuran (4 mL), methyl 3-oxo-3,4-dihydro-2H-benzo[b][1,4]oxazine-6-carboxylate (124 mg, 0.60 mmol, 1.00 equiv), PPh₃ (235 mg, 0.90 mmol, 1.50 equiv), this was followed by the addition of DIAD (0.17 mL, 0.90 mmol, 1.50 equiv) dropwise with stirring at 0° C. The resulting solution was stirred overnight at room temperature (25° C.) and then concentrated under vacuum. The residue was purified via preparative TLC (eluting with ethyl acetate/petroleum ether (1:1)) to afford methyl 4-((2,3-dihydro-[1,4]dioxino[2,3-b]pyridin-7-yl)methyl)-3-oxo-3,4-dihydro-2H-benzo[b][1,4]oxazine-6-carboxylate (160 mg, 75%) as a yellow solid. MS: (ESI, m/z): 357[M+H]+.

Step 2: 4-((2,3-dihydro-[1,4]dioxino[2,3-b]pyridin-7-yl)methyl)-N-hydroxy-3-oxo-3,4-dihydro-2H-benzo[b][1,4]oxazine-6-carboxamide Into a 50-mL round-bottom flask, was placed methyl 4-((2,3-dihydro-[1,4]dioxino[2,3-b]pyridin-7-yl)methyl)-3-oxo-3,4-dihydro-2H-benzo[b][1,4]oxazine-6-carboxylate (PH-FMA-PJ94-2113-1) (160 mg, 0.45 mmol, 1.00 equiv), THF/MeOH (4/1) (5 mL), NH$_2$OH (50% in water) (1.80 mL, 26.97 mmol, 60.00 equiv), NaOH (1M) (0.90 mL, 0.90 mmol, 2.00 equiv). The resulting solution was stirred for 2 h at room temperature (25° C.). The solids were filtered out. The crude product was purified via Prep-HPLC with the following conditions: Column, XBridge Prep C18 OBD Column, 19×150 mm, 5 um; mobile phase, water (10 mmol/L NH$_4$HCO$_3$) and ACN (25.0% ACN up to 55.0% in 7 min); Detector, UV 254 nm. The collected fraction was lyophilized to afford 4-((2,3-dihydro-[1,4]dioxino[2,3-b]pyridin-7-yl)methyl)-N-hydroxy-3-oxo-3,4-dihydro-2H-benzo[b][1,4]oxazine-6-carboxamide (25.7 mg, 16%) as a white solid. $^1$H-NMR: (DMSO 300 MHz, ppm): δ 10.60 (s, 1H), 8.97 (s, 1H), 7.74 (s, 1H), 7.45-7.43 (m, 1H), 7.41 (d, J=8.1 Hz, 1H), 7.18 (s, 1H), 7.06 (d, J=8.1 Hz, 1H), 5.10 (s, 2H), 4.85 (s, 2H), 4.38-4.35 (m, 2H), 4.23-4.20 (m, 2H). MS: (ESI, m/z): 358[M+H]+.

The compounds below were synthesized according to the procedures outlined above for Example 42.

| Comp. No. | Structure | IUPAC Name | $^1$H NMR | (ESI, m/z) [M + H]+ |
|---|---|---|---|---|
| I-174 | 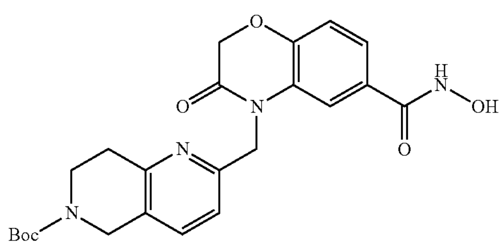 [SMILES: CC(C)(C)OC(=O)N1CCc2nc(CN3C(=O)COc4ccc(C(=O)NO)cc43)ccc2C1] | tert-butyl 2-((6-(hydroxycarbamoyl)-3-oxo-2,3-dihydro-4H-benzo[b][1,4]oxazin-4-yl)methyl)-7,8-dihydro-1,6-naphthyridine-6(5H)-carboxylate | (DMSO, 400 MHz, ppm): 11.10 (s, 1H), 8.96 (s, 1H), 7.56-7.54 (m, 1H), 7.41-7.38 (m, 2H), 7.09-7.06 (m, 2H), 5.17 (s, 2H), 4.85 (s, 2H), 4.50 (s, 2H), 3.66-3.63 (m, 2H), 2.86-2.83 (m, 2H), 1.42 (s, 9H) | 455 |
| I-175 | 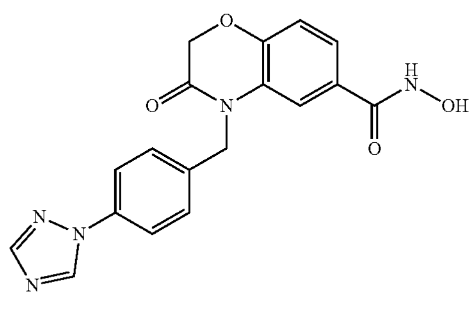 [SMILES: O=C(NO)c1ccc2c(c1)N(Cc1ccc(-n3cncn3)cc1)C(=O)CO2] | 4-(4-(1H-1,2,4-triazol-1-yl)benzyl)-N-hydroxy-3-oxo-3,4-dihydro-2H-benzo[b][1,4]oxazine-6-carboxamide | (DMSO, 300 MHz, ppm): 11.12 (br, 1H), 9.26 (s, 1H), 8.96 (br, 1H), 8.22 (s, 1H), 7.83 (d, J = 8.4 Hz, 2H), 7.50-7.41 (m, 4H), 7.10 (d, J = 9.0 Hz, 1H), 5.26 (s, 2H), 4.91 (s, 2H). | 366 |
| I-176 | 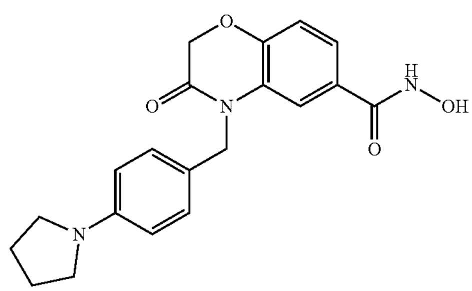 [SMILES: O=C(NO)c1ccc2c(c1)N(Cc1ccc(N3CCCC3)cc1)C(=O)CO2] | N-hydroxy-3-oxo-4-(4-(pyrrolidin-1-yl)benzyl)-3,4-dihydro-2H-benzo[b][1,4]oxazine-6-carboxamide | (DMSO, 300 MHz, ppm): 11.11 (s, 1H), 8,98 (s, 1H), 7.51 (s, 1H), 7.40 736 (m, 1H), 7.11-7.02 (m, 3H), 6.48 (d, J = 8.7 Hz, 2H), 5.06 (s, 2H), 4.82 (s, 2H), 3.19-3,15 (m, 4H), 1.94-1.90 (m, 4H) | 368 |
| I-177 | 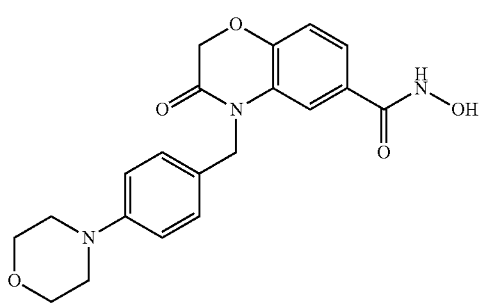 [SMILES: O=C(NO)c1ccc2c(c1)N(Cc1ccc(N3CCOCC3)cc1)C(=O)CO2] | N-hydroxy-4-(4-morpholinobenzyl)-3-oxo-3,4-dihydro-2H-benzo[b][1,4]oxazine-6-carboxamide | (DMSO, 300 MHz, ppm): 11.12 (s, 1H), 8.99 (s, 1H), 7.48 (s, 1H), 7.41 7.38 (m, 1H), 7.16 (d, J = 8.7 Hz, 2H), 7.06 (d, J = 8.4 Hz, 1H), 6.90 (d, J = 8.7 Hz, 2H), 5.09 (s, 2H), 4.84 (s, 2H), 3.72-3.69 (m, 4H), 3.08-3.05 (m, 4H) | 384 |

| Comp. No. | Structure | IUPAC Name | ¹H NMR | (ESI, m/z) [M + H]⁺ |
|---|---|---|---|---|
| I-178 | 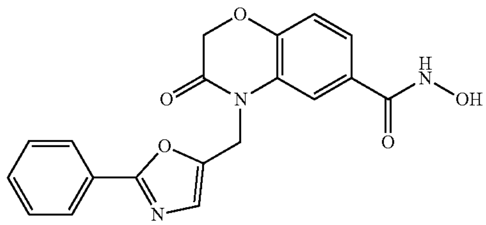 [SMILES: O=C(NO)c1ccc2c(c1)N(Cc1cnc(-c3ccccc3)o1)C(=O)CO2] | N-hydroxy-3-oxo-4-((2-phenyloxazol-5-yl)methyl)-3,4-dihydro-2H-benzo[b][1,4]oxazine-6-carboxamide | (DMSO, 400 MHz, ppm): 11.22 (s, 1H), 9.07 (s, 1H), 7.94-7.92 (m, 2H), 7.82 (s, 1H), 7.52-7.45 (m, 4H), 7.29 (s, 1H), 7.08 (d, J = 8.4 Hz, 1H), 5.31 (s, 2H), 4.81 (s, 2H) | 366 |
| I-179 | 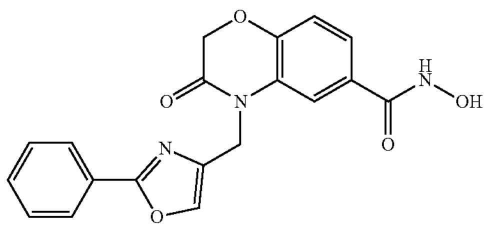 [SMILES: O=C(NO)c1ccc2c(c1)N(Cc1coc(-c3ccccc3)n1)C(=O)CO2] | N-hydroxy-3-oxo-4-((2-phenyloxazol-4-yl)methyl)-3,4-dihydro-2H-benzo[b][1,4]oxazine-6-carboxamide | (DMSO, 400 MHz, ppm): 11.17 (s, 1H), 9.01 (s, 1H), 8.12 (s, 1H), 7.97-7.94 (m, 2H), 7.70 (s, 1H), 7.53-7.52 (m, 3H), 7.45-7.42 (m, 1H), 7.08 (d, J = 8.4 Hz, 1H), 5.11 (s, 2H), 4.81 (s, 2H) | 366 |
| I-180 | 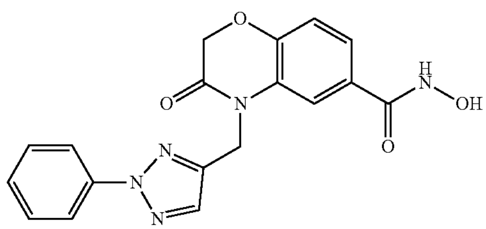 [SMILES: O=C(NO)c1ccc2c(c1)N(Cc1cnn(-c3ccccc3)n1)C(=O)CO2] | N-hydroxy-3-oxo-4-((2-phenyl-2H-1,2,3-triazol-4-yl)methyl)-3,4-dihydro-2H-benzo[b][1,4]oxazine-6-carboxamide | (DMSO, 300 MHz, ppm): 11.16 (br, 1H), 9.00 (br, 1H), 8.02-7.96 (m, 3H), 7.69 (s, 1H), 7.59-7.53 (m, 2H), 7.45-7.40 (m, 2H), 7.09 (d, J = 8.4 Hz, 1H), 5.33 (s, 2H), 4.84 (s, 2H) | 366 |

Example 43. Tert-butyl 6-((6-(hydroxycarbamoyl)-3-oxo-2,3-dihydrobenzo[b][1,4]oxazin-4-yl)methyl)-3,4-dihydroisoquinoline-2(1H)-carboxylate (I-181)

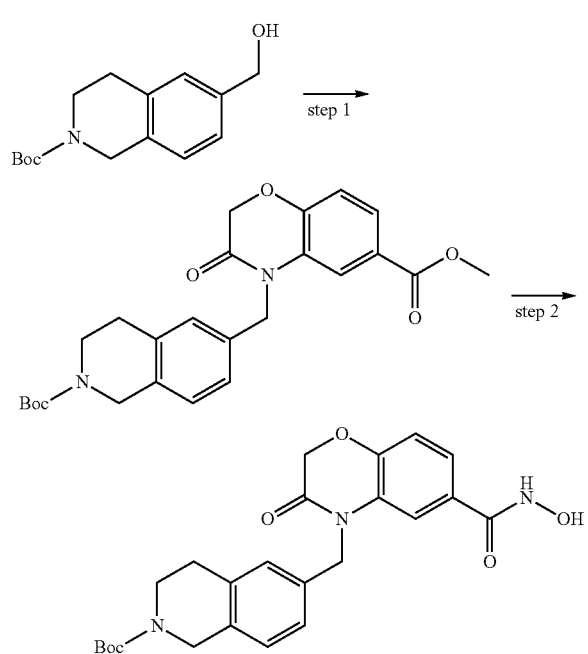

Step 1: Methyl 4-((2-(tert-butoxycarbonyl)-1,2,3,4-tetrahydroisoquinolin-6-yl)methyl)-3-oxo-3,4-dihydro-2H-benzo[b][1,4]oxazine-6-carboxylate Into a 25-mL round-bottom flask, was placed tert-butyl 6-(hydroxymethyl)-3,4-dihydroisoquinoline-2(1H)-carboxylate (83.9 mg, 0.32 mmol, 1.20 equiv), DCM (10 mL), TEA (0.06 mL, 0.40 mmol, 1.50 equiv). This was followed by the addition of MsCl (0.03 mL, 0.32 mmol, 1.2 equiv) dropwise with stirring at 0° C. The resulting solution was stirred for 2 h at 0° C. and then concentrated under vacuum to afford tert-butyl 6-((methylsulfonyloxy)methyl)-3,4-dihydroisoquinoline-2(1H)-carboxylate crude product. The crude product was then dissolved in 10 mL of N,N-dimethylformamide, to the above was the added methyl 3-oxo-3,4-dihydro-2H-benzo[b][1,4]oxazine-6-carboxylate (55 mg, 0.27 mmol, 1.00 equiv), Cs₂CO₃ (173 mg, 0.53 mmol, 2.00 equiv). The resulting solution was stirred for 2 h at room temperature (25° C.) and then diluted with 30 mL of water, extracted with 2×30 mL of ethyl acetate, dried over anhydrous sodium sulfate and concentrated under vacuum. The residue was purified via preparative-TLC (eluting with ethyl acetate/petroleum ether (1:3)) to afford methyl 4-((2-(tert-butoxycarbonyl)-1,2,3,4-tetrahydroisoquinolin-6-yl)methyl)-3-oxo-3,4-dihydro-2H-benzo[b][1,4]oxazine-6-carboxylate (80 mg, 67%) as yellow solid. MS: (ESI, m/z): 453[M+H]⁺.

Step 2: Tert-butyl 6-((6-(hydroxycarbamoyl)-3-oxo-2,3-dihydrobenzo[b][1,4]oxazin-4-yl)methyl)-3,4-dihydroisoquinoline-2(1H)-carboxylate)

Into a 25-mL round-bottom flask, was placed methyl 4-((2-(tert-butoxycarbonyl)-1,2,3,4-tetrahydroisoquinolin-6-yl)methyl)-3-oxo-3,4-dihydro-2H-benzo[b][1,4]oxazine-6-carboxylate (80 mg, 0.18 mmol, 1.00 equiv), THF/MeOH (4/1) (3 mL), NH$_2$OH (50% in water) (0.70 mL, 10.62 mmol, 60.00 equiv). This was followed by the addition of NaOH (1M) (0.35 mL, 0.35 mmol, 2.00 equiv) dropwise with stirring. The resulting solution was stirred for 2 h at room temperature (25° C.). The solids were filtered out. The crude product was purified via Prep-HPLC with the following conditions: Column, XSelect CSH Prep C18 OBD Column, 5 um, 19×150 mm; mobile phase, water (0.1% FA) and ACN (25.0% ACN up to 60.0% in 7 min); Detector, UV 254 & 220 nm. The collected fraction was lyophilized to afford tert-butyl 6-((6-(hydroxycarbamoyl)-3-oxo-2,3-dihydrobenzo[b][1,4]oxazin-4-yl)methyl)-3,4-dihydroisoquinoline-2(1H)-carboxylate (29.2 mg, 36.5%) as a white solid. $^1$H-NMR: (DMSO, 400N11 Hz, ppm): δ 11.13 (s, 1H), 8.97 (s, 1H), 7.39-7.37 (m, 2H), 7.13-7.05 (m, 4H), 5.13 (s, 2H), 4.86 (s, 2H), 4.44 (s, 2H), 3.52-3.49 (m, 2H), 2.73-2.70 (m, 2H), 1.41 (s, 9H). MS: (ESI, m/z): 453[M+H]$^+$.

Example 44. N-hydroxy-4-((1-methyl-1,2,3,4-tetrahydroquinolin-6-yl)methyl)-3-oxo-3,4-dihydro-2H-benzo[b][1,4]oxazine-6-carboxamide (I-182)

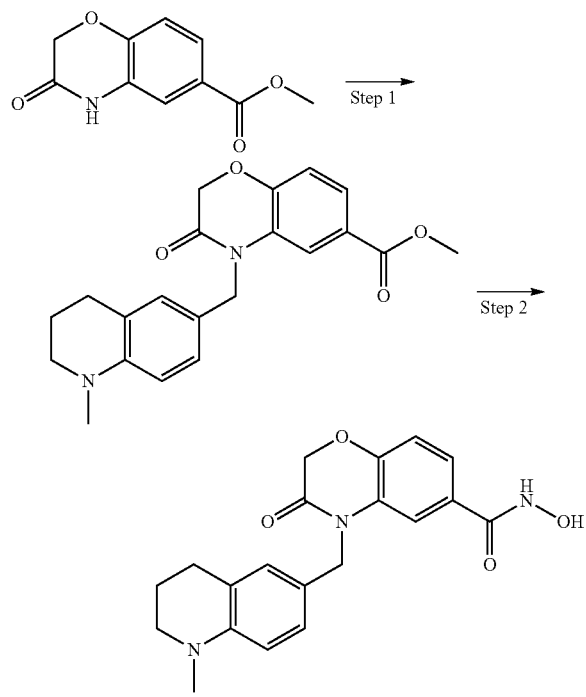

Step 1: Methyl 4-((1-methyl-1,2,3,4-tetrahydroquinolin-6-yl)methyl)-3-oxo-3,4-dihydro-2H-benzo[b][1,4]oxazine-6-carboxylate Into a 20-mL vial, was placed methyl 3-oxo-3,4-dihydro-2H-1,4-benzoxazine-6-carboxylate (83 mg, 0.40 mmol, 1.00 equiv), tetrahydrofuran (5 mL), Cs$_2$CO$_3$ (264 mg, 0.81 mmol, 2.00 equiv), 6-(bromomethyl)-1-methyl-1,2,3,4-tetrahydroquinoline hydrobromide (130 mg, 0.40 mmol, 1.00 equiv). The resulting solution was stirred for overnight at 60° C. and then cooled to room temperature. The resulting solution was diluted with 15 mL of water, extracted with 2×15 mL of ethyl acetate, dried over anhydrous sodium sulfate and concentrated under vacuum. The residue was purified via preparative TLC (eluting with ethyl acetate/petroleum ether (1:3)) to afford methyl-4-((1-methyl-1,2,3,4-tetrahydroquinolin-6-yl)methyl)-3-oxo-3,4-dihydro-2H-benzo[b][1,4]oxazine-6-carboxylate (15 mg, 10%) as yellow oil. MS: (ESI, m/z): 367[M+H]$^-$.

Step 2: N-hydroxy-4-((1-methyl-1,2,3,4-tetrahydroquinolin-6-yl)methyl)-3-oxo-3,4-dihydro-2H-benzo[b][1,4]oxazine-6-carboxamide Into a 25-mL round-bottom flask, was placed methyl 4-((1-methyl-1,2,3,4-tetrahydroquinolin-6-yl)methyl)-3-oxo-3,4-dihydro-2H-benzo[b][1,4]oxazine-6-carboxylate (15 mg, 0.04 mmol, 1.00 equiv), THF/MeOH (4/1)(1 mL), NH$_2$OH (50% in water) (0.16 mL, 2.45 mmol, 60.00 equiv). This was followed by the addition of NaOH (1M) (0.08 mL, 0.08 mmol, 2.00 equiv) dropwise with stirring. The resulting solution was stirred for 2 h at room temperature (25° C.). The solids were filtered out. The crude product was purified via Prep-HPLC with the following conditions: Column, XBridge Shield RP18 OBD Column, 5 μm, 19×150 mm; mobile phase, water (0.1% FA) and ACN (5.0% ACN up to 40.0% in 7 min); Detector, UV 254 nm. The collected fraction was lyophilized to afford N-hydroxy-4-((1-methyl-1,2,3,4-tetrahydroquinolin-6-yl)methyl)-3-oxo-3,4-dihydro-2H-benzo[b][1,4]oxazine-6-carboxamide (2.1 mg, 14%) as a pink solid. $^1$H-NMR: (DMSO, 300 MHz, ppm) δ 11.15 (s, 1H), 9.03 (s, 1H), 7.50 (s, 1H), 7.39-7.36 (m, 1H), 7.05-7.02 (m, 1H), 6.92-6.90 (m, 1H), 6.84 (s, 1H), 6.50-6.47 (m, 1H), 4.99 (s, 2H), 4.81 (s, 2H), 3.14-3.11 (m, 2H), 2.99 (s, 3H), 2.65-2.60 (m, 2H), 1.85-1.84 (m, 2H). MS: (ESI, m/z): 368[M+H]$^+$.

The compounds below were synthesized according to the procedures outlined above for Example 44.

| Comp. No. | Structure | IUPAC Name | $^1$H NMR | (ESI, m/z) [M + H]$^+$ |
|---|---|---|---|---|
| I-183 | 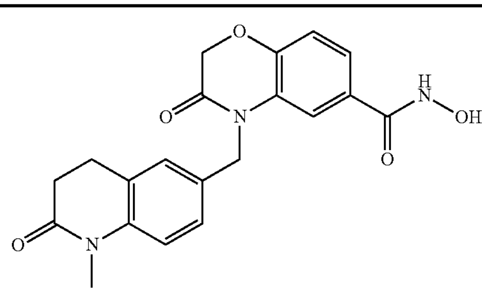 | N-hydroxy-4-((1-methyl-2-oxo-1,2,3,4-tetrahydroquinolin-6-yl)methyl)-3-oxo-3,4-dihydro-2H-benzo[b][1,4]oxazine-6-carboxamide | (DMSO, 400 MHz, ppm): 11.13 (s, 1H), 8.99 (s, 1H), 7.43-7.38 (m, 2H), 7.18-7.03 (m, 4H), 5.13 (s, 2H), 4.86 (s, 2H), 3.21 (s, 3H), 2.83-2.80 (m, 2H), 2.52-2.49 (m, 2H) | 382 |

-continued

| Comp. No. | Structure | IUPAC Name | ¹H NMR | (ESI, m/z) [M + H]⁺ |
|---|---|---|---|---|
| I-184 | 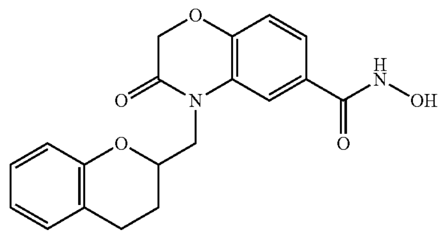 [SMILES: O=C(NO)c1ccc2c(c1)N(CC1CCc3ccccc3O1)C(=O)CO2] | (+/−)-4-(chroman-2-ylmethyl)-N-hydroxy-3-oxo-3,4-dihydro-2H-benzo[b][1,4]oxazine-6-carboxamide | (DMSO, 300 MHz, ppm): 11.20 (s, 1H), 9.03 (s, 1H), 7.84-7.83 (m, 1H), 7.47-7.44 (m, 1H), 7.08-7.00 (m, 3H), 6.82-6.77 (m, 1H), 6.67-6.65 (m, 1H), 4.75 (s, 2H), 4.37-4.24 (m, 3H), 2.79-2.70 (m, 2H), 3.07-102 (m, 1H), 1.78-1.66 (m, 1H) | 355 |
| I-185 | 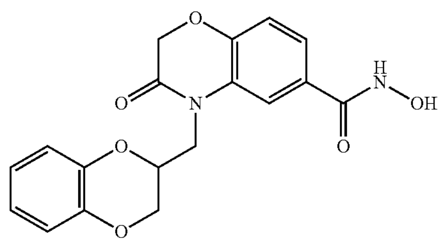 [SMILES: O=C(NO)c1ccc2c(c1)N(CC1COc3ccccc3O1)C(=O)CO2] | (+/−)-4-((2,3-dihydrobenzo[b][1,4]dioxin-2-yl)methyl)-N-hydroxy-3-oxo-3,4-dihydro-2H-benzo[b][1,4]oxazine-6-carboxamide | (DMSO, 300 MHz, ppm): 11.20 (s, 1H), 9.06 (s, 1H), 7.73 (s, 1H), 7 47-7.44 (m, 1H, 7.09-7.06 (m, 1H), 6.90-6.78 (m, 4H), 4.80-4.70 (m, 2H), 4.56-4.51 (m, 1H), 4.38-4.20 (m, 3H), 4.07-4.01 (m, 1H) | 357 |
| I-186 | 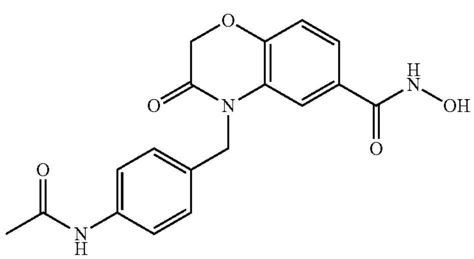 [SMILES: CC(=O)Nc1ccc(CN2C(=O)COc3ccc(C(=O)NO)cc32)cc1] | 4-(4-acetamidobenzyl)-N-hydroxy-3-oxo-3,4-dihydro-2H-benzo[b][1,4]oxazine-6-carboxamide | (DMSO, 300 MHz, ppm): 11.11 (s, 1H), 9.93 (s, 1H), 8.97 (s, 1H), 7.51 (d, J = 8.4 Hz, 2H), 7.38 (d, J = 6.9 Hz, 2H), 7.20 (d, J = 8.4 Hz, 2H), 7.06 (d, J = 9 Hz, 1H), 5.12 (s, 2H), 4.86 (s, 2H), 2.01 (s, 3H) | 356 |
| I-187 | 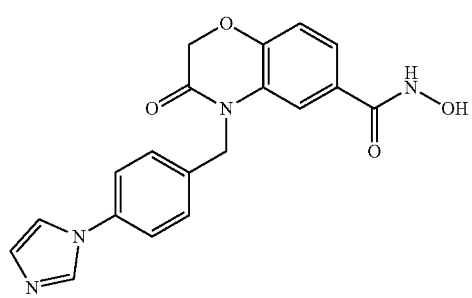 [SMILES: O=C(NO)c1ccc2c(c1)N(Cc1ccc(-n3ccnc3)cc1)C(=O)CO2] | 4-(4-(1H-imidazol-1-yl)benzyl)-N-hydroxy-3-oxo-3,4-dihydro-2H-benzo[b][1,4]oxazine-6-carboxamide | (DMSO, 300 MHz, ppm): 11.13 (br, 1H), 8.98 (br, 1H), 8.22 (s, 1H), 7.12 (s, 1H), 7.62 (d, J = 8.7 Hz, 2H), 7.44-7.40 (m, 4H), 7.10-7.07 (m, 2H), 5.23 (s, 2H), 4.89 (s, 2H). | 365 |
| I-188 | 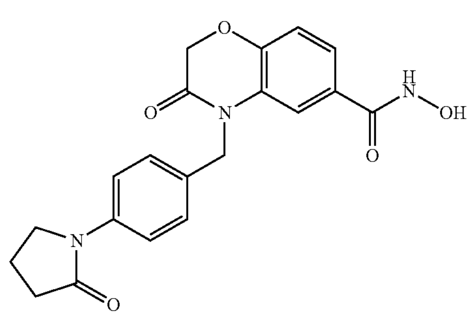 [SMILES: O=C(NO)c1ccc2c(c1)N(Cc1ccc(N3CCCC3=O)cc1)C(=O)CO2] | N-hydroxy-3-oxo-4-(4-(2-oxopyrrolidin-1-yl)benzyl)-3,4-dihydro-2H-benzo[b][1,4]oxazine-6-carboxamide | (DMSO, 300 MHz, ppm): 11.11 (br, 1H), 8.97 (br, 1H), 7.61 (d, J = 8.7 Hz, 2H), 7.40-7.37 (m, 2H), 7.28 (d, J = 8.7 Hz, 2H), 7.06 (d, J = 8.7 Hz, 1H), 5.16 (s, 2H), 4.87 (s, 2H), 3.82-3.77 (m, 2H), 2.46-2.44 (m, 2H), 2.08-2.00 (m, 2H) | 382 |

-continued

| Comp. No. | Structure | IUPAC Name | ¹H NMR | (ESI, m/z) [M + H]⁺ |
|---|---|---|---|---|
| I-189 | 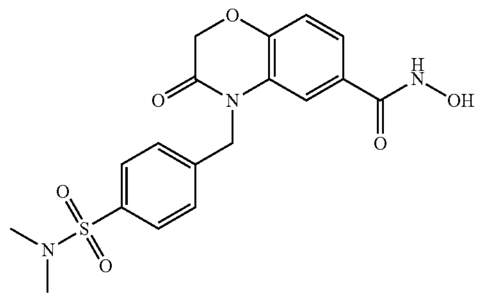 [SMILES: CN(C)S(=O)(=O)c1ccc(CN2C(=O)COc3ccc(C(=O)NO)cc32)cc1] | 4-(4-(N,N-dimethylsulfamoyl)benzyl)-N-hydroxy-3-oxo-3,4-dihydro-2H-benzo[b][1,4]oxazine-6-carboxamide | (DMSO, 300 MHz, ppm): 11.10 (s, 1H), 8.96 (s, 1H), 7.74 (d, J = 8.1 Hz, 2H), 7.56 (d, J = 8.1 Hz, 2H), 7.45-7.41 (m, 1H), 7.34 (s, 1H), 7.11 (d, J = 8.1 Hz, 1H), 5.29 (s, 2H), 4.90 (s, 2H), 2.60 (s, 6H) | 406 |
| I-190 | 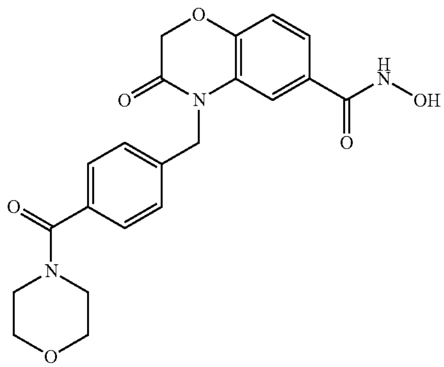 [SMILES: O=C(NO)c1ccc2c(c1)N(Cc1ccc(C(=O)N3CCOCC3)cc1)C(=O)CO2] | N-hydroxy-4-(4-(morpholine-4-carbonyl)benzyl)-3-oxo-3,4-dihydro-2H-benzo[b][1,4]oxazine-6-carboxamide | (DMSO, 300 MHz, ppm): 11.12 (s, 1H), 8.95 (s, 1H), 7.43-7.34 (m, 6H), 7.09 (d, J = 8.1 Hz, 1H), 5.22 (s, 2H), 4.88 (s, 2H), 3.58-3.43 (m, 8H) | 412 |
| I-191 | 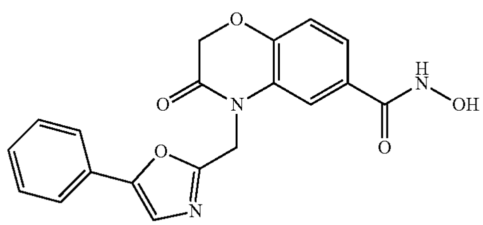 [SMILES: O=C(NO)c1ccc2c(c1)N(Cc1ncc(-c3ccccc3)o1)C(=O)CO2] | N-hydroxy-3-oxo-4-((5-phenyloxazol-2-yl)methyl)-3,4-dihydro-2H-benzo[b][1,4]oxazine-6-carboxamide | (DMSO, 400 MHz, ppm): 11.15 (s, 1H), 9.01 (s, 1H), 7.68-7.65 (m, 3H), 7.61 (s, 1H), 7.48-7.44 (m, 3H), 7.38-7.34 (m, 1H), 7.11 (d, J = 8.4 Hz, 1H), 5.36 (s, 2H), 4.84 (s, 2H) | 366 |
| I-192 | 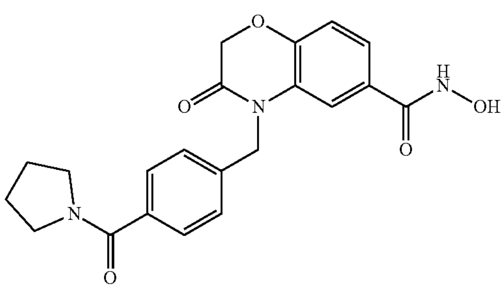 [SMILES: O=C(NO)c1ccc2c(c1)N(Cc1ccc(C(=O)N3CCCC3)cc1)C(=O)CO2] | N-hydroxy-3-oxo-4-(4-(pyrrolidine-1-carbonyl)benzyl)-3,4-dihydro-2H-benzo[b][1,4]oxazine-6-carboxamide | (DMSO, 300 MHz, ppm): 11.11 (br, 1H), 8.96 (br, 1H), 7.49 (d, J = 8.1 Hz, 2H), 7.44-7.40 (m, 2H), 7.34 (d, J = 8.1 Hz, 2H), 7.09 (d, J = 8.1 Hz, 1H), 5.23 (s, 2H), 4.89 (s, 2H), 3.47-3.33 (m, 4H), 1.88-1.77 (m, 4H) | 396 |
| I-193 | 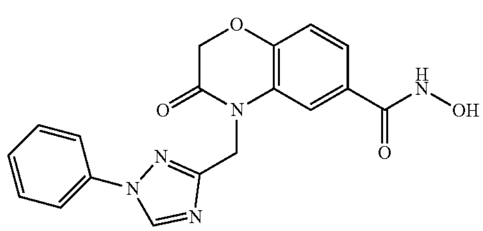 [SMILES: O=C(NO)c1ccc2c(c1)N(Cc1ncn(-c3ccccc3)n1)C(=O)CO2] | N-hydroxy-3-oxo-4-((1-phenyl-1H-1,2,4-triazol-3-yl)methyl)-3,4-dihydro-2H-benzo[b][1,4]oxazine-6-carboxamide | (DMSO, 400 MHz, ppm): 11.12 (s, 1H), 9.21 (s, 1H), 8.97 (s, 1H), 7.81-7.79 (m, 1H), 7.66 (s, 1H), 7.56-7.52 (m, 2H), 7.43-7.39 (m, 2H), 7.09-7.07 (m, 1H), 5.29 (s, 2H), 4.81 (s, 2H) | 366 |

| Comp. No. | Structure | IUPAC Name | $^1$H NMR | (ESI, m/z) [M + H]$^+$ |
|---|---|---|---|---|
| I-213 | 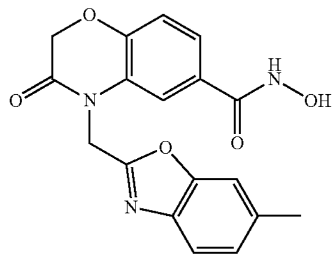 [SMILES: Cc1ccc2nc(CN3C(=O)COc4ccc(C(=O)NO)cc43)oc2c1] | N-hydroxy-4-((6-methylbenzo[d]oxazol-2-yl)methyl)-3-oxo-3,4-dihydro-2H-benzo[b][1,4]oxazine-6-carboxamide | (DMSO, 400 MHz, ppm): 11.11 (s, 1H), 8.99 (s, 1H), 7.60-7.55 (m, 3H), 7.47 (d, J = 8.4 Hz, 1H), 7.18 (d, J = 8.4 Hz, 1H), 7.13 (d, J = 8.0 Hz, 1H), 5.46 (s, 2H), 4.85 (s, 2H), 2.43 (s, 3H) | 354 |

Example 45. 4-(2,4-dimethoxybenzyl)-N-hydroxy-3-oxo-3,4-dihydro-2H-benzo[b][1,4]oxazine-6-carboxamide (I-194)

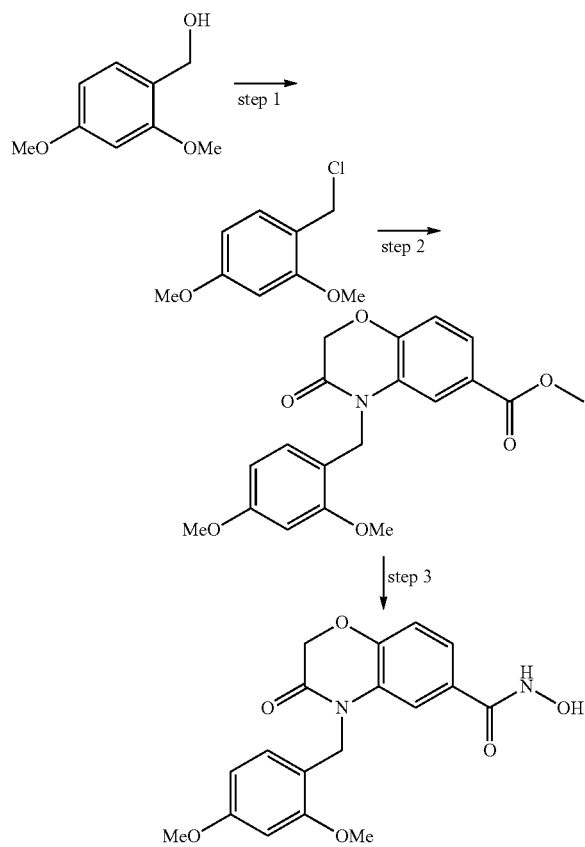

Step 1: 1-(chloromethyl)-2,4-dimethoxybenzene

Into a 50-mL 3-necked round-bottom flask purged and maintained with an inert atmosphere of nitrogen, was placed (2,4-dimethoxyphenyl)methanol (100 mg, 0.59 mmol, 1.00 equiv), dichloromethane (6 mL). This was followed by the addition of thionyl chloride (0.05 mL, 0.71 mmol, 1.20 equiv) dropwise with stirring at 0° C. Then a drop of DMF was added to the mixture. The resulting solution was stirred for 1 h at 0° C. in a water/ice bath. The resulting mixture was concentrated under vacuum to afford 1-(chloromethyl)-2,4-dimethoxybenzene (150 mg, 60% purity) as yellow oil. The product was used to the next step directly without further purification.

Step 2: Methyl 4-(2,4-dimethoxybenzyl)-3-oxo-3,4-dihydro-2H-benzo[b][1,4]oxazine-6-carboxylate Into a 50-mL round-bottom flask, was placed methyl 3-oxo-3,4-dihydro-2H-1,4-benzoxazine-6-carboxylate (99 mg, 0.48 mmol, 1.00 equiv,). N,N-dimethylformamide (6 mL), Cs$_2$CO$_3$ (315 mg, 0.97 mmol, 2.00 equiv) and 1-(chloromethyl)-2,4-dimethoxybenzene (150 mg, 0.48 mmol, 1.00 equiv, 60% purity). The resulting solution was stirred for 18 h at room temperature (16° C.) and then diluted with 20 mL of water, extracted with 3×20 mL of ethyl acetate, dried over anhydrous sodium sulfate and concentrated under vacuum. The residue was purified via column chromatography on silica gel (eluting with ethyl acetate/petroleum ether (1:2)) to afford methyl 4-(2,4-dimethoxybenzyl)-3-oxo-3,4-dihydro-2H-benzo[b][1,4]oxazine-6-carboxylate) (60 mg, 35%) as an off-white solid. MS: (ESI, m/z): 358[M+H]$^+$.

Step 3: 4-(2,4-dimethoxybenzyl)-N-hydroxy-3-oxo-3,4-dihydro-2H-benzo[b][1,4]oxazine-6-carboxamide Into a 10-mL round-bottom flask, was placed methyl 4-(2,4-dimethoxybenzyl)-3-oxo-3,4-dihydro-2H-benzo[b][1,4]oxazine-6-carboxylate (60 mg, 0.17 mmol, 1.00 equiv), THF/MeOH (4/1) (4 mL), NH$_2$OH (50% in water) (1.3 mL, 20.17 mmol, 120.00 equiv), NaOH (1M) (0.34 mL, 0.34 mmol, 2.00 equiv). The resulting solution was stirred for 2 h at room temperature (16° C.). The solids were filtered out. The crude product was purified via Prep-HPLC with the following conditions: Column, XSelect CSH Prep C18 OBD Column, 5 μm, 19*150 mm; mobile phase, water (0.1% FA) and ACN (15.0% ACN up to 55.0% in 7 min); Detector, UV 254 & 220 nm. The collected fraction was lyophilized to afford 4-(2,4-dimethoxybenzyl)-N-hydroxy-3-oxo-3,4-dihydro-2H-benzo[b][1,4]oxazine-6-carboxamide (14.6 mg, 24%) as a white solid. $^1$H-NMR (DMSO, 300 MHz) δ (ppm): 11.13 (s, 1H), 8.95 (s, 1H), 7.39-7.36 (m, 2H), 7.06 (d, J=8.7 Hz, 1H), 6.86 (d, J=8.4 Hz, 1H), 6.61 (d, J=2.4 Hz, 1H), 6.43-6.39 (m, 1H), 5.00 (s, 2H), 4.84 (s, 2H), 3.88 (s, 3H), 3.72 (s, 3H). MS: (ESI, m/z): 359[M+H]$^+$.

Example 46. 4-(2-(4-fluorophenylamino)-2-oxo-ethyl)-N-hydroxy-3-oxo-3,4-dihydro-2H-benzo[b][1,4]oxazine-6-carboxamide (I-195)

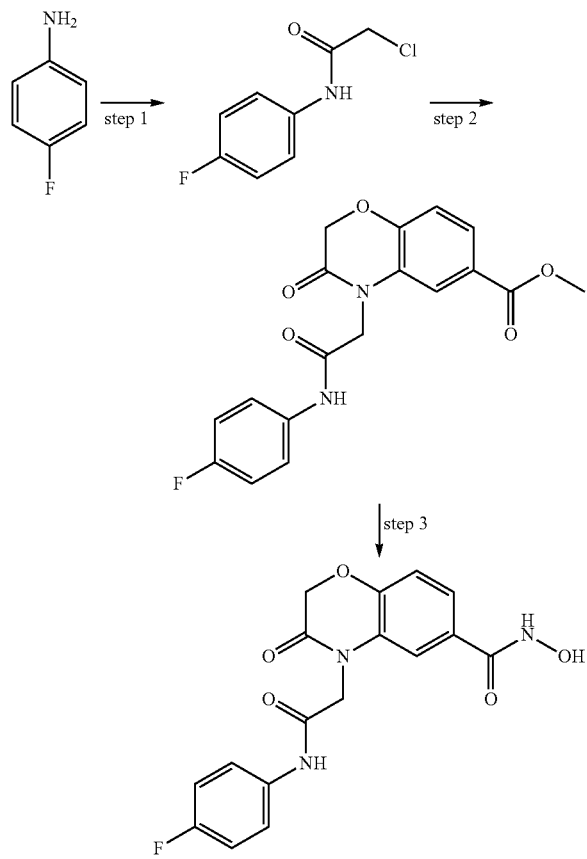

Step 1: 2-chloro-N-(4-fluorophenyl)acetamide

Into a 150-mL round-bottom flask, was placed 4-fluoroaniline (2 g, 18.00 mmol, 1.00 equiv), DCM (40 mL), TEA (5 mL, 35.97 mmol, 2.00 equiv). This was followed by the addition of 2-chloroacetyl chloride (2.03 mL, 27.00 mmol, 1.50 equiv) dropwise with stirring at 0° C. The resulting solution was stirred for 5 h at room temperature (20° C.). The resulting mixture was washed with 1×20 ml of HCl (1 mol/L), 2×20 ml of NaHCO₃ (sat., aq.) and 1×20 mL of brine. The organic layer was dried over anhydrous sodium sulfate and concentrated under vacuum. The residue was purified via column chromatography on silica gel (eluting with ethyl acetate/petroleum ether (1:10)) to afford 2-chloro-N-(4-fluorophenyl)acetamide (2.4 g, 71%) as an off-white solid. MS (ESI, m/z): 188[M+H]$^+$.

Step 2: Methyl 4-(2-(4-fluorophenylamino)-2-oxo-ethyl)-3-oxo-3,4-dihydro-2H-benzo[b][1,4]oxazine-6-carboxylate Into a 50-mL round-bottom flask, was placed methyl 3-oxo-3,4-dihydro-2H-1,4-benzoxazine-6-carboxylate (200 mg, 0.97 mmol, 1.00 equiv), DMF (3 mL), Cs₂CO₃ (805 mg, 2.47 mmol, 2.55 equiv), 2-chloro-N-(4-fluorophenyl)acetamide (273 mg, 1.46 mmol, 1.50 equiv). The resulting solution was stirred for 1 h at room temperature (24° C.). The solids were filtered out. The crude product was purified via reversed phase column with the following conditions: Column, C18 silica gel, 40 g, 20-45 μm, 100A; Mobile phase: water with 0.5% FA and CH₃CN (10% CH₃CN up to 72% in 30 min); Detector, UV 254 nm. The collected fraction was concentrated under vacuum to afford methyl 4-(2-(4-fluorophenylamino)-2-oxoethyl)-3-oxo-3,4-dihydro-2H-benzo[b][1,4]oxazine-6-carboxylate (100 mg, 29%) as a white solid. MS (ESI, m/z): 359 [M+H]$^+$.

Step 3: 4-(2-(4-fluorophenylamino)-2-oxoethyl)-N-hydroxy-3-oxo-3,4-dihydro-2H-benzo[b][1,4]oxazine-6-carboxamide Into a 50-mL round-bottom flask, was placed methyl 4-(2-(4-fluorophenylamino)-2-oxoethyl)-3-oxo-3,4-dihydro-2H-benzo[b][1,4]oxazine-6-carboxylate (51 mg, 0.14 mmol, 1.00 equiv), THF/MeOH (4/1)(3 mL). Then NaOH (1M) (0.28 mL, 0.28 mmol, 2.00 equiv) and NH₂OH (50% in water) (1.13 mL, 17.12 mmol, 122 equiv) were added at 0-10° C. The resulting solution was stirred overnight at room temperature (27° C.). The crude product was purified via Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 15% B to 65% B in 7 min; 254/220 nm. The collected fraction was lyophilized to afford 4-(2-(4-fluorophenylamino)-2-oxoethyl)-N-hydroxy-3-oxo-3,4-dihydro-2H-benzo[b][1,4]oxazine-6-carboxamide (13.7 mg, 27%) as an off-white solid. ¹H-NMR: (DMSO, 300 MHz, ppm): δ 11.19 (s, 1H), 10.43 (s, 1H), 9.02 (s, 1H), 7.63-7.59 (m, 2H), 7.48-7.45 (m, 2H), 7.21-7.09 (m, 3H), 4.80-4.77 (m, 4H). MS (ESI, m/z): 360 [M+H]$^+$.

Example 47. N-hydroxy-4-(4-(2-methoxyethoxy)benzyl)-3-oxo-3,4-dihydro-2H-benzo[b][1,4]oxazine-6-carboxamide (I-196)

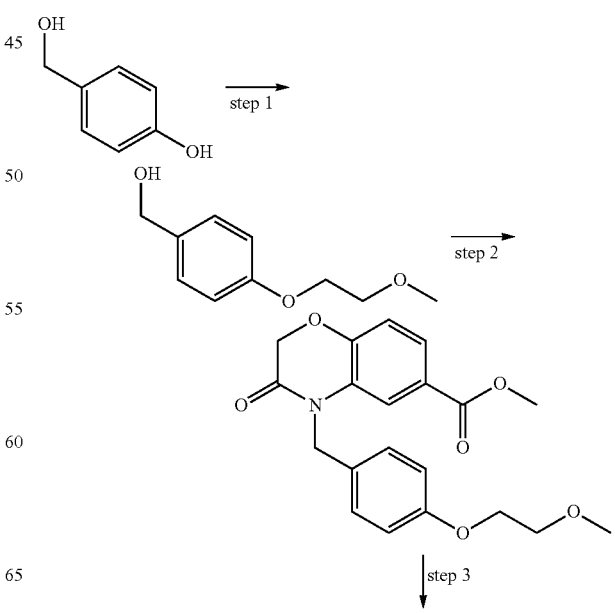

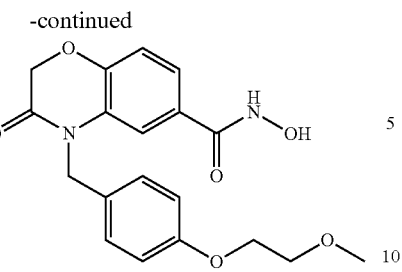

Step 1: (4-(2-methoxyethoxy)phenyl)methanol

Into a 100-mL 3-necked round-bottom flask, was placed 4-(hydroxymethyl)phenol (2.49 g, 20.06 mmol, 1.00 equiv), EtOH (20 mL). This was followed by the addition of NaOH (800 mg, 20.00 mmol, 1.00 equiv) in water (1 mL). After stirred for 30 min at 80° C., 1-bromo-2-methoxyethane (1.90 mL, 20.00 mmol, 1.00 equiv) was added at 80° C. in 20 min. The resulting solution was stirred overnight at 80° C. and then cooled to room temperature, the reaction mixture was concentrated under vacuum. The residue was purified via reversed phase column with the following conditions: Column, C18 silica gel, 120 g, 20-45 um, 100A; Mobile phase: water with 10 mmol/L NH$_4$HCO$_3$ and CH$_3$CN (5% CH$_3$CN up to 60% in 30 min); Detector, UV 254 nm. The collected fraction was concentrated under vacuum to afford (4-(2-methoxyethoxy)phenyl)methanol (1.54 g, 42%) as yellow oil. $^1$H-NMR: (DMSO, 400 MHz, ppm): δ 7.22 (d, J=8.8 Hz, 2H), 6.89 (d, J=8.4 Hz, 2H), 5.06-5.03 (m, 1H), 4.42 (d, J=5.2 Hz, 2H), 4.08-4.06 (m, 2H), 3.66-3.64 (m, 2H), 3.31 (s, 3H).

Step 2: Methyl 4-(4-(2-methoxyethoxy)benzyl)-3-oxo-3,4-dihydro-2H-benzo[b][1,4]oxazine-6-carboxylate Into a 25-mL round-bottom flask purged and maintained with an inert atmosphere of nitrogen, was placed (4-(2-methoxyethoxy)phenyl)methanol (117 mg, 0.64 mmol, 1.00 equiv), THF (20 mL), methyl 3-oxo-3,4-dihydro-2H-1,4-benzoxazine-6-carboxylate (133 mg, 0.64 mmol, 1.00 equiv), PPh$_3$ (253 mg, 0.97 mmol, 1.50 equiv). To this was added DIAD (0.19 mL, 0.97 mmol, 1.50 equiv) dropwise with stirring under 10° C. The resulting solution was stirred overnight at room temperature (22° C.) and then concentrated under vacuum. The residue was purified via column chromatography on silica gel (eluting with ethyl acetate/petroleum ether (1:3)) to afford methyl 4-(4-(2-methoxyethoxy)benzyl)-3-oxo-3,4-dihydro-2H-benzo[b][1,4]oxazine-6-carboxylate (54 mg, 23%) as yellow oil. MS: (ESI, m/z): 372[M+H]$^+$.

Step 3: N-hydroxy-4-(4-(2-methoxyethoxy)benzyl)-3-oxo-3,4-dihydro-2H-benzo[b][1,4]oxazine-6-carboxamide Into a 25-mL round-bottom flask, was placed methyl 4-(4-(2-methoxyethoxy)benzyl)-3-oxo-3,4-dihydro-2H-benzo[b][1,4]oxazine-6-carboxylate (50 mg, 0.13 mmol, 1.00 equiv), THF/MeOH (4/1)(2.5 mL). This was followed by the addition of NH$_2$OH (50% in water) (1.07 mL, 16.19 mmol, 125.00 equiv) and NaOH (1M) (0.25 mL, 0.25 mmol, 2.00 equiv) under 10° C. The resulting solution was stirred for 2 h at room temperature (27° C.). The crude product was purified via Prep-HPLC with the following conditions: Column: XBridge C18 OBD Prep Column, 100 Å, 5 μm, 19 mm×250 mm; Mobile Phase A: Water (0.1% FA), Mobile Phase B: ACN; Flow rate: 20 mL/min; Gradient: 35% B to 55% B in 7 min; 254 nm. The collected fraction was lyophilized to afford N-hydroxy-4-(4-(2-methoxyethoxy)benzyl)-3-oxo-3,4-dihydro-2H-benzo[b][1,4]oxazine-6-carboxamide (16.5 mg, 33%) as off-white solid. $^1$H-NMR: (DMSO, 300 MHz, ppm): δ 11.11 (br, 1H), 8.99 (s, 1H), 7.45 (s, 1H), 7.40 (d, J=8.4 Hz, 1H), 7.21 (d, J=8.7 Hz, 2H), 7.06 (d, J=8.4 Hz, 1H), 6.91 (d, J=8.7 Hz, 2H), 5.12 (s, 2H), 4.86 (s, 2H), 4.07-4.04 (m, 2H), 3.65-3.62 (m, 2H), 3.34 (s, 3H). MS: (ESI, m/z): 373[M+H]$^+$.

The compounds below were synthesized according to the procedures outlined above for Example 47.

| Compd. No. | Structure | IUPAC Name | $^1$H NMR | (ESI, m/z) [M + H]$^+$ |
|---|---|---|---|---|
| I-197 | ![structure] | N-hydroxy-4-(3-(2-methoxyethoxy)benzyl)-3-oxo-3,4-dihydro-2H-benzo[b][1,4]oxazine-6-carboxamide | (DMSO, 300 MHz, ppm): 11.09 (br, 1H), 8.99 (s, 1H), 7.41-7.39 (m, 2H), 7.28-7.22 (m, 1H), 7.09-7.07 (m, 1H), 6.85-6.84 (m, 3H), 5.15 (s, 2H), 4.88 (s, 2H), 4.08-4.05 (m, 2H), 3.65-3.62 (m, 2H), 3.29 (s, 3H) | 373 |

Example 48. N-hydroxy-3-oxo-4-((1-phenylpiperidin-4-yl)methyl)-3,4-dihydro-2H-benzo[b][1,4]oxazine-6-carboxamide (I-198)

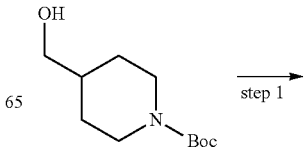

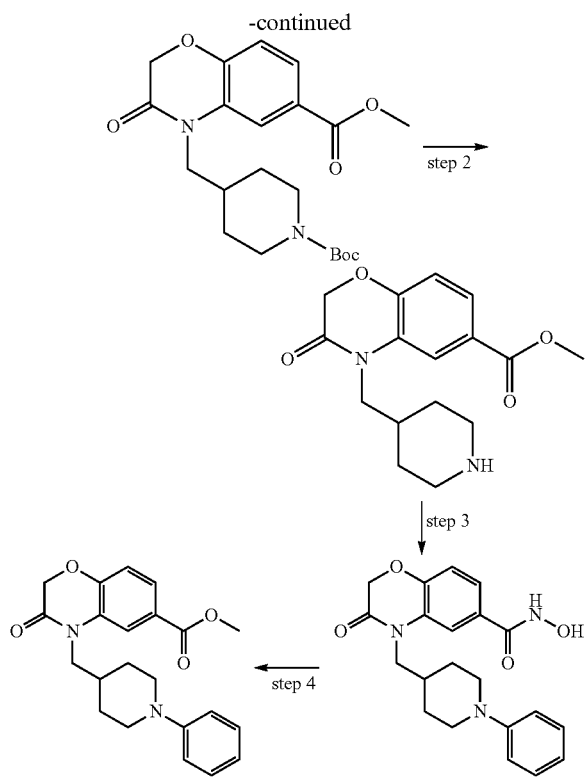

Step 1: Methyl 4-((1-(tert-butoxycarbonyl)piperidin-4-yl)methyl)-3-oxo-3,4-dihydro-2H-benzo[b][1,4]oxazine-6-carboxylate Into a 250-mL round-bottom flask purged and maintained with an inert atmosphere of nitrogen, was placed tert-butyl 4-(hydroxymethyl)piperidine-1-carboxylate (692 mg, 3.21 mmol, 1.00 equiv), THF (50 mL), methyl 3-oxo-3,4-dihydro-2H-1,4-benzoxazine-6-carboxylate (664 mg, 3.21 mmol, 1.00 equiv), PPh$_3$ (1.27 g, 4.84 mmol, 1.50 equiv). This was followed by the addition of DIAD (0.96 mL, 4.84 mmol, 1.50 equiv) dropwise with stirring at 0-10° C. The resulting solution was stirred overnight at room temperature (23° C.) and then concentrated under vacuum. The residue was purified via column chromatography on silica gel (eluting with ethyl acetate/petroleum ether (1:2)) to afford methyl 4-((1-(tert-butoxycarbonyl)piperidin-4-yl)methyl)-3-oxo-3,4-dihydro-2H-benzo[b][1,4]oxazine-6-carboxylate (300 mg, 23%) as a white solid. MS (ESI, m/z): 405[M+H]$^+$.

Step 2: Methyl 3-oxo-4-(piperidin-4-ylmethyl)-3,4-dihydro-2H-benzo[b][1,4]oxazine-6-carboxylate Into a 50-mL round-bottom flask, was placed methyl 4-((1-(tert-butoxycarbonyl)piperidin-4-yl)methyl)-3-oxo-3,4-dihydro-2H-benzo[b][1,4]oxazine-6-carboxylate (170 mg, 0.42 mmol, 1.00 equiv), DCM (3 mL), TFA (1 mL). The resulting solution was stirred for 2 h at room temperature (28° C.) and then concentrated under vacuum. The residue was purified via reversed phase column with the following conditions: Column, C18 silica gel, 40 g, 20-45 μm, 100A; Mobile phase: water with 10 mmol/L NH$_4$HCO$_3$ and CH$_3$CN (5% CH$_3$CN up to 55% in 30 min); Detector, UV 254 nm. The collected fraction was concentrated under vacuum to afford methyl 3-oxo-4-(piperidin-4-ylmethyl)-3,4-dihydro-2H-benzo[b][1,4]oxazine-6-carboxylate (108 mg, 84%) as a light yellow solid. MS (ESI, m/z): 305 [M+H]$^+$.

Step 3: Methyl 3-oxo-4-((1-phenylpiperidin-4-yl)methyl)-3,4-dihydro-2H-benzo[b][1,4]oxazine-6-carboxylate Into a 50-mL round-bottom flask purged and maintained with an inert atmosphere of nitrogen, was placed methyl 3-oxo-4-(piperidin-4-ylmethyl)-3,4-dihydro-2H-benzo[b][1,4]oxazine-6-carboxylate (50 mg, 0.16 mmol, 1.00 equiv), toluene (10 mL), bromobenzene (52 mg, 0.33 mmol, 2.00 equiv), RuPhos (8 mg, 0.02 mmol, 0.10 equiv), 2$^{nd}$ Generation RuPhos precatalyst (26 mg, 0.03 mmol, 0.20 equiv), Cs$_2$CO$_3$ (161 mg, 0.49 mmol, 3.00 equiv). The resulting solution was stirred overnight at 100° C. and then cooled to room temperature, the solids were filtered out and the filtrate was concentrated under vacuum. The residue was purified via column chromatography on silica gel (eluting with ethyl acetate/petroleum ether (1:2)) to afford methyl 3-oxo-4-((1-phenylpiperidin-4-yl)methyl)-3,4-dihydro-2H-benzo[b][1,4]oxazine-6-carboxylate (35 mg, 56%) as a light yellow solid. MS (ESI, m/z): 381 [M+H]$^+$.

Step 4: N-hydroxy-3-oxo-4-((1-phenylpiperidin-4-yl)methyl)-3,4-dihydro-2H-benzo[b][1,4]oxazine-6-carboxamide Into a 50-mL round-bottom flask, was placed methyl 3-oxo-4-((1-phenylpiperidin-4-yl)methyl)-3,4-dihydro-2H-benzo[b][1,4]oxazine-6-carboxylate (48 mg, 0.13 mmol, 1.00 equiv), THF/MeOH (4/1) (2.5 mL). Then NaOH (1M) (0.25 mL, 0.25 mmol, 2.00 equiv) and NH$_2$OH (50% in water) (1.00 mL, 15.15 mmol, 116.00 equiv) were added 0-10° C. The resulting solution was stirred for 2 h at room temperature (20° C.). The crude product was purified via Prep-HPLC with the following conditions: Column: XSelect CSH Prep C18 OBD Column, 5 μm, 19×150 mm; Mobile Phase A: water (0.1% FA), Mobile Phase B: ACN; Flow rate: 20 mL/min; Gradient: 2% B to 25% B in 7 min; UV 254/220 nm. The collected fraction was lyophilized to afford N-hydroxy-3-oxo-4-((1-phenylpiperidin-4-yl)methyl)-3,4-dihydro-2H-benzo[b][1,4]oxazine-6-carboxamide (20.9 mg, 43.4%) as an off-white solid. $^1$H-NMR: (DMSO, 300 MHz, ppm): δ 11.25 (s, 1H), 9.04 (s, 1H), 7.58 (s, 1H), 7.48-4.45 (m, 1H), 7.20-7.15 (m, 2H), 7.08 (d, J=8.4 Hz, 1H), 6.90 (d, J=8.1 Hz, 2H), 6.75-6.70 (m, 1H), 4.73 (s, 2H), 3.92 (d, J=7.2 Hz, 2H), 3.67-3.65 (m, 2H), 2.63-2.55 (m, 2H), 1.92-1.83 (m, 1H), 1.70-1.65 (m, 2H), 1.37-1.34 (m, 2H). MS (ESI, m/z): 382 [M+H]$^+$.

Example 49. N-hydroxy-4-((1-isobutyrylpiperidin-4-yl)methyl)-3-oxo-3,4-dihydro-2H-benzo[b][1,4]oxazine-6-carboxamide (I-199)

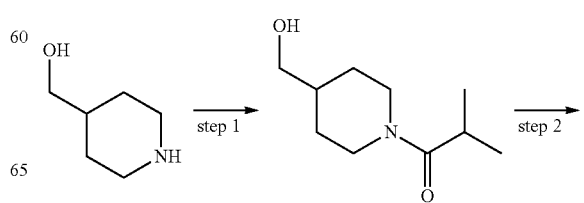

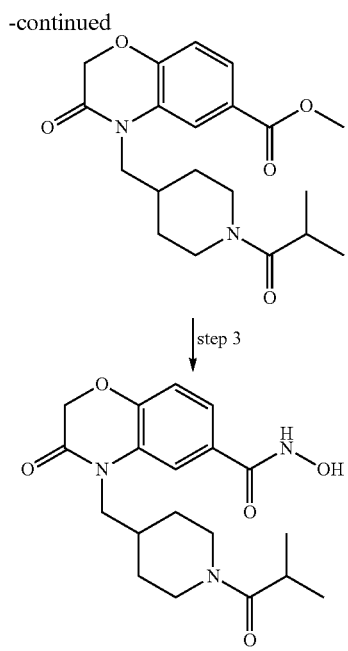

Step 1: 1-(4-(hydroxymethyl)piperidin-1-yl)-2-methylpropan-1-one

Into a 250-mL round-bottom flask, was placed piperidin-4-ylmethanol (4 g, 34.73 mmol, 1.00 equiv), MeOH (60 mL), DIEA (16.41 mL, 104.34 mmol, 3.00 equiv). This was followed by the addition of 2-methylpropanoyl chloride (4.3 mL, 41.29 mmol, 1.20 equiv) dropwise with stirring at 0° C., the resulting solution was stirred for 2 h at 0° C. The reaction was quenched by the addition of 2 mL of water and then concentrated under vacuum. The residue was purified via reversed phase column with the following conditions: Column, C18 silica gel, 120 g, 20-45 μm, 100A; mobile phase water with 0.5% FA and $CH_3CN$ (5% $CH_3CN$ up to 68% in 30 min); Detector, UV 254 nm. The collected fraction was concentrated under vacuum to afford 1-(4-(hydroxymethyl)piperidin-1-yl)-2-methylpropan-1-one ((1 g, 16%) as a white solid. MS (ESI, m/z): 186[M+H]⁺.

Step 2: Methyl 4-((1-isobutyrylpiperidin-4-yl)methyl)-3-oxo-3,4-dihydro-2H-benzo[b][1,4]oxazine-6-carboxylate Into a 250-mL round-bottom flask purged and maintained with an inert atmosphere of nitrogen, was placed 1-(4-(hydroxymethyl)piperidin-1-yl)-2-methylpropan-1-one (200 mg, 1.08 mmol, 1.00 equiv), THF (72 mL), methyl 3-oxo-3,4-dihydro-2H-1,4-benzoxazine-6-carboxylate (224 mg, 1.08 mmol, 1.00 equiv), $PPh_3$ (262 mg, 1.62 mmol, 1.50 equiv). This was followed by the addition of DIAD (0.32 mL, 1.62 mmol, 1.50 equiv) dropwise with stirring at 0° C. The resulting solution was stirred overnight at room temperature (26° C.) and then concentrated under vacuum. The residue was purified via reversed phase column with the following conditions: Column, C18 silica gel, 40 g, 20-45 μm, 100 A; Mobile phase: water with 0.5% FA and $CH_3CN$ (5% CH3CN up to 50% in 30 min); Detector, UV 254 nm. The collected fraction was concentrated under vacuum to afford methyl 4-((1-isobutyrylpiperidin-4-yl)methyl)-3-oxo-3,4-dihydro-2H-benzo[b][1,4]oxazine-6-carboxylate (45 mg, 11%) as a light yellow solid. MS (ESI, m/z): 375 [M+H]⁺.

Step 3: N-hydroxy-4-((1-isobutyrylpiperidin-4-yl)methyl)-3-oxo-3,4-dihydro-2H-benzo[b][1,4]oxazine-6-carboxamide Into a 50-mL round-bottom flask, was placed methyl 4-((1-isobutyrylpiperidin-4-yl)methyl)-3-oxo-3,4-dihydro-2H-benzo[b][1,4]oxazine-6-carboxylate (37 mg, 0.10 mmol, 1.00 equiv), THF/MeOH (4/1) (6 mL). Then NaOH (1M) (0.20 mL, 0.20 mmol, 2.00 equiv) and $NH_2OH$ (50% in water) (0.78 mL, 11.87 mmol, 119 equiv) were added at 0-10° C. The resulting solution was stirred for 1 h at room temperature (25° C.). The crude product was purified via Prep-HPLC with the following conditions: XBridge C18 OBD Prep Column, 100A, 5 μm, 19 mm×250 mm; Mobile Phase A: water (0.1% FA), Mobile Phase B: ACN; Flow rate: 20 mL/min; Gradient: 35% B to 55% B in 7 min; Detector, UV 254 nm. The collected fraction was lyophilized to afford N-hydroxy-4-((1-isobutyrylpiperidin-4-yl)methyl)-3-oxo-3,4-dihydro-2H-benzo[b][1,4]oxazine-6-carboxamide (12.9 mg, 34.7%) as an off-white solid.
¹H-NMR: (DMSO, 400 MHz, ppm): δ 11.25 (s, 1H), 9.07 (s, 1H), 7.55 (s, 1H), 7.46 (d, J=8.0 Hz, 1H), 7.08 (d, J=8.4 Hz, 1H), 4.72 (s, 2H), 4.38-4.35 (m, 1H), 3.94-3.87 (m, 3H), 2.97-2.81 (m, 2H), 2.48-2.40 (m, 1H), 1.89-1.96 (m, 1H), 1.68-1.59 (m, 2H), 1.16-0.98 (m, 8H). MS (ESI, m/z): 376 [M+H]⁺.

Example 50. 4-((1H-indol-3-yl)methyl)-N-hydroxy-3-oxo-3,4-dihydro-2H-benzo[b][1,4]oxazine-6-carboxamide (I-200)

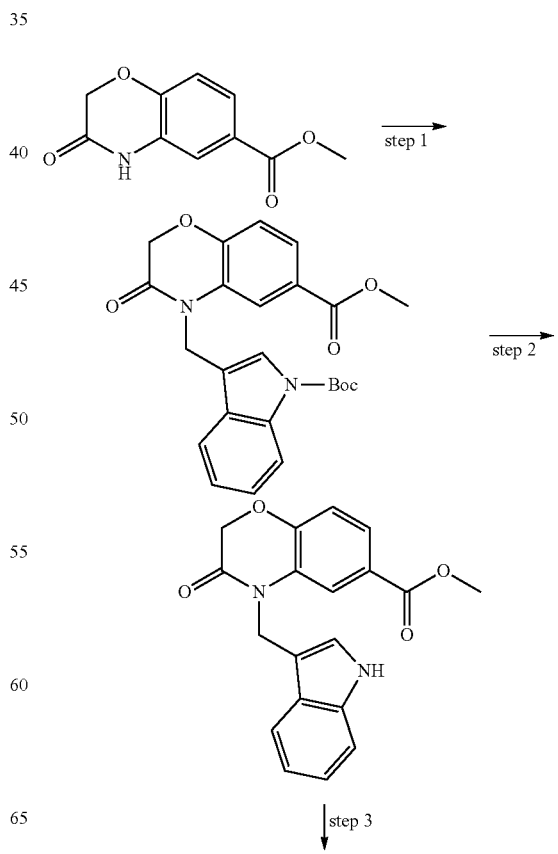

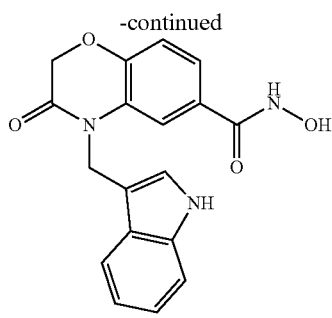

Step 1: Methyl 4-((1-(tert-butoxycarbonyl)-1H-indol-3-yl)methyl)-3-oxo-3,4-dihydro-2H-benzo[b][1,4]oxazine-6-carboxylate Into a 50-mL round-bottom flask, was placed methyl 3-oxo-3,4-dihydro-2H-1,4-benzoxazine-6-carboxylate (134 mg, 0.65 mmol, 1.00 equiv), THF (10 mL), Cs$_2$CO$_3$ (423 mg, 1.30 mmol, 2.00 equiv). Then tert-butyl 3-(bromomethyl)-1H-indole-1-carboxylate (200 mg, 0.65 mmol, 1.00 equiv) was added at 0° C. The resulting solution was stirred for 2 h at room temperature (20° C.). The solids were filtered out and the filtrate was concentrated under vacuum. The residue was purified via reversed phase column with the following conditions: Column, C18 silica gel, 40 g, 20-45 m, 100 A; Mobile phase: water with 0.5% FA and CH$_3$CN (5% CH$_3$CN up to 60% in 30 min); Detector, UV 254 nm. The collected fraction was concentrated under vacuum to afford methyl 4-((1-(tert-butoxycarbonyl)-1H-indol-3-yl)methyl)-3-oxo-3,4-dihydro-2H-benzo[b][1,4]oxazine-6-carboxylate (50 mg, 18%) as a white solid. MS (ESI, m/z): 437 [M+H]$^+$.

Step 2: Methyl 4-((1H-indol-3-yl)methyl)-3-oxo-3,4-dihydro-2H-benzo[b][1,4]oxazine-6-carboxylate Into a 50-mL round-bottom flask, was placed methyl 4-((1-(tert-butoxycarbonyl)-1H-indol-3-yl)methyl)-3-oxo-3,4-dihydro-2H-benzo[b][1,4]oxazine-6-carboxylate (50 mg, 0.11 mmol, 1.00 equiv), DCM (3 mL), TFA (1 mL). The resulting solution was stirred for 2 h at room temperature (27° C.) and then concentrated under vacuum. The residue was purified via reversed phase column with the following conditions: Column, C18 silica gel, 40 g, 20-45 μm, 100 A; Mobile phase: water with 10 mmol/L NH$_4$HCO$_3$ and CH$_3$CN (5% CH$_3$CN up to 50% in 30 min); Detector, UV 254 nm. The collected fraction was concentrated under vacuum to afford methyl 4-((1H-indol-3-yl)methyl)-3-oxo-3,4-dihydro-2H-benzo[b][1,4]oxazine-6-carboxylate (20 mg, 52%) as a light yellow solid. MS (ESI, m/z): 337[M+H]$^+$.

Step 3: 4-((1H-indol-3-yl)methyl)-N-hydroxy-3-oxo-3,4-dihydro-2H-benzo[b][1,4]oxazine-6-carboxamide Into a 50-mL round-bottom flask, was placed methyl 4-((1H-indol-3-yl)methyl)-3-oxo-3,4-dihydro-2H-benzo[b][1,4]oxazine-6-carboxylate (20 mg, 0.06 mmol, 1.00 equiv), THF/MeOH (3 mL). Then NaOH (1M) (0.12 mL, 0.12 mmol, 2.00 equiv) and NH$_2$OH (50% in water) (0.47 mL, 7.14 mmol, 119.00 equiv) were added at 0-10° C. The resulting solution was stirred for 1 h at room temperature (26° C.). The crude product was purified via Prep-HPLC with the following conditions: XBridge C18 OBD Prep Column, 100A, 5 μm, 19 mm×250 mm; Mobile Phase A: water (0.1% FA), Mobile Phase B: ACN; Flow rate: 20 mL/min; Gradient: 25% B to 45% B in 7 min; 254 nm. The collected fraction was lyophilized to afford 4-((1H-indol-3-yl)methyl)-N-hydroxy-3-oxo-3,4-dihydro-2H-benzo[b][1,4]oxazine-6-carboxamide (5.7 mg, 28%) as a pink solid. $^1$H-NMR: (DMSO, 400 MHz, ppm): δ 11.15 (br, 1H), 11.01 (s, 1H), 9.01 (br, 1H), 7.78 (s, 1H), 7.60 (d, J=7.6 Hz, 1H), 7.39-7.32 (m, 3H), 7.08-7.06 (m, 1H), 7.01-6.99 (m, 2H), 5.34 (s, 2H), 4.81 (s, 2H). MS (ESI, m/z): 338 [M+H]$^+$.

Example 51. 4-((1-cyanoindolizin-2-yl)methyl)-N-hydroxy-3-oxo-3,4-dihydro-2H-benzo[b][1,4]oxazine-6-carboxamide (I-201)

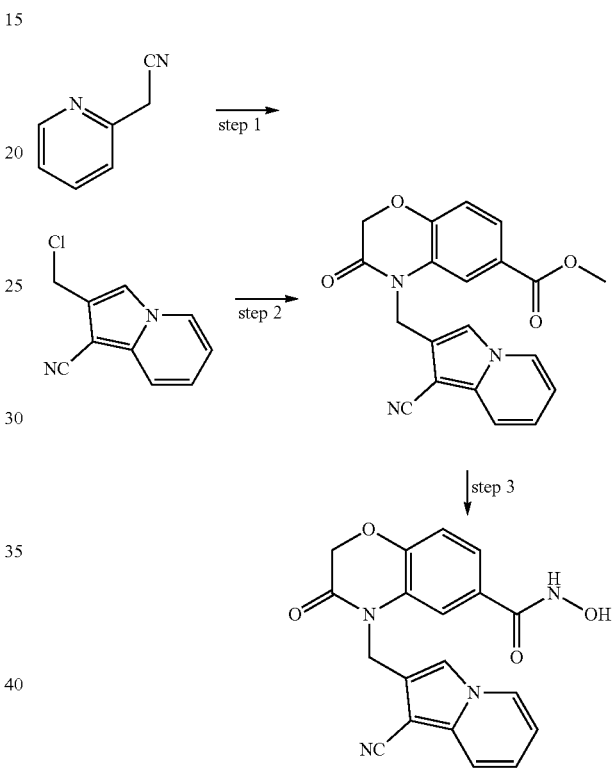

Step 1: 2-(chloromethyl)indolizine-1-carbonitrile

Into a 30-mL sealed tube, was placed 1,3-dichloropropan-2-one (3.87 g, 30.48 mmol, 1.20 equiv), DMF (10 mL), 2-(pyridin-2-yl)acetonitrile (3 g, 25.39 mmol, 1.00 equiv), TMSCl (12.93 mL, 100.30 mmol, 4.00 equiv). The resulting solution was stirred for 4 h at 100° C. and then cooled to room temperature, the resulting mixture was concentrated under vacuum, the crude product was purified via reversed phase column with the following conditions: Column, C18 silica gel, 120 g, 20-45 μm, 100A; mobile phase: water with 0.5% FA and CH$_3$CN (30% CH$_3$CN up to 50% in 40 min); Detector, UV 254 nm. The collected fraction was concentrated under vacuum to afford 2-(chloromethyl)indolizine-1-carbonitrile (1.1 g, 23%) as a yellow solid. MS: (ESI, m/z): 191[M+H]$^-$.

Step 2: Methyl 4-((1-cyanoindolizin-2-yl)methyl)-3-oxo-3,4-dihydro-2H-benzo[b][1,4]oxazine-6-carboxylate Into a 25-mL round-bottom flask, was placed methyl 3-oxo-3,4-dihydro-2H-1,4-benzoxazine-6-carboxylate (182 mg, 0.88 mmol, 1.00 equiv), DMF (10 mL), 2-(chloromethyl)indolizine-1-carbonitrile) (167 mg, 0.88 mmol, 1.00 equiv), $Cs_2CO_3$ (572 mg, 1.76 mmol, 2.00 equiv). The resulting solution was stirred for 2.5 h at room temperature (29° C.). The solids were filtered out and the filtrate was concentrated under vacuum, the crude product was purified via reversed phase column with the following conditions: Column, C18 silica gel, 40 g, 20-45 μm, 100A; Mobile phase: water with 0.1% FA and $CH_3CN$ (5% $CH_3CN$ up to 40% in 30 min); Detector, UV 254 nm. The collected fraction was concentrated under vacuum to afford methyl 4-((1-cyanoindolizin-2-yl)methyl)-3-oxo-3,4-dihydro-2H-benzo[b][1,4]oxazine-6-carboxylate (100 mg, 32%) as an off-white solid. MS: (ESI, m/z): 362[M+H]$^+$.

Step 3: 4-((1-cyanoindolizin-2-yl)methyl)-N-hydroxy-3-oxo-3,4-dihydro-2H-benzo[b][1,4]oxazine-6-carboxamide Into a 25-mL round-bottom flask, was placed methyl 4-((1-cyanoindolizin-2-yl)methyl)-3-oxo-3,4-dihydro-2H-benzo[b][1,4]oxazine-6-carboxylate (50 mg, 0.14 mmol, 1.00 equiv), THF/MeOH (4/1) (2.5 mL). Then $NH_2OH$ (50% in $H_2O$) (1.09 mL, 16.5 mmol, 118.00 equiv) and NaOH (1M) (0.3 mL, 0.3 mmol, 2.00 equiv) were added at 0-10° C. The resulting solution was stirred for 2.5 h at room temperature (26° C.). The crude product was purified via Prep-HPLC with the following conditions: Column: XBridge C18 OBD Prep Column, 100 Å, 5 μm, 19 mm×250 mm; Mobile Phase A: water (0.1% FA), Mobile Phase B: ACN; Flow rate: 20 mL/min; Gradient: 20% B to 40% B in 7 min; 254 nm. The collected fraction was lyophilized to afford 4-((1-cyanoindolizin-2-yl)methyl)-N-hydroxy-3-oxo-3,4-dihydro-2H-benzo[b][1,4]oxazine-6-carboxamide (18.9 mg, 38%) as a light brown solid $^1$H-NMR: (DMSO, 400 MHz, ppm): δ 11.11 (br, 1H), 8.97 (br, 1H), 8.44 (d, J=6.8 Hz, 1H), 7.60-7.58 (m, 2H), 7.46-7.41 (m, 2H), 7.21-7.17 (m, 1H), 7.10 (d, J=8.4 Hz, 1H), 6.91-6.87 (m, 1H), 5.34 (s, 2H), 4.84 (s, 2H). MS: (ESI, m/z): 363[M+H]+.

Example 52. N-hydroxy-3-oxo-4-((4-phenyloxazol-2-yl)methyl)-3,4-dihydro-2H-benzo[b][1,4]oxazine-6-carboxamide (I-202)

Step 1: 2-(benzyloxy)acetamide

Into a 250-mL round-bottom flask, was placed 7 M $NH_3$(g)/MeOH (50 mL) and ethyl 2-(benzyloxy)acetate (15 g, 77.23 mmol, 1.00 equiv). The resulting solution was stirred for 5 h at room temperature (25° C.) and then concentrated under vacuum. The crude product was recrystallized from 200 mL of PE/DCM (20/1) to afford 2-(benzyloxy)acetamide (11 g, 86%) as a white solid. MS: (ESI, m/z): 166[M+H]$^+$.

Step 2: 2-(benzyloxymethyl)-4-phenyloxazole

Into a 30-mL vial, was placed 2-bromo-1-phenylethan-1-one (4 g, 19.98 mmol, 1.00 equiv), DMF (10 mL), 2-(benzyloxy)acetamide (3.3 g, 19.98 mmol, 1.00 equiv). The resulting solution was stirred for 6 h at 130° C. and then cooled to room temperature and concentrated under vacuum, the residue was purified via reversed phase column with the following conditions: Column, C18 silica gel, 120 g, 20-45 m, 100A; Mobile phase: water with 10 mmol/L $NH_4HCO_3$ and $CH_3CN$ (5% $CH_3CN$ up to 70% in 40 min); Detector, UV 254 nm. The collected fraction was concentrated under vacuum to afford 2-(benzyloxymethyl)-4-phenyloxazole (1.1 g, 21%) as a yellow solid. MS: (ESI, m/z): 266[M+H]$^+$.

Step 3: (4-phenyloxazol-2-yl)methanol

Into a 100-mL 3-necked round-bottom flask, was placed 2-(benzyloxymethyl)-4-phenyloxazole (900 mg, 3.39 mmol, 1.00 equiv), DCM (20 mL). This was followed by the addition of $BBr_3$ (1 M) (8.5 mL, 8.5 mmol, 2.50 equiv) dropwise with stirring at −78° C. The resulting solution was stirred for 2 h at room temperature (25° C.) and then the reaction was quenched by the addition of 8 mL of $NaHCO_3$ (sat., aq.) at 0° C. The resulting solution was washed with 3×20 mL of water, dried over anhydrous sodium sulfate and concentrated under vacuum. The residue was purified via column chromatography on silica gel (eluting with ethyl acetate/petroleum ether (1:1)) to afford (4-phenyloxazol-2-yl)methanol (320 mg, 54%) as a yellow solid. MS: (ESI, m/z): 176[M+H]$^+$.

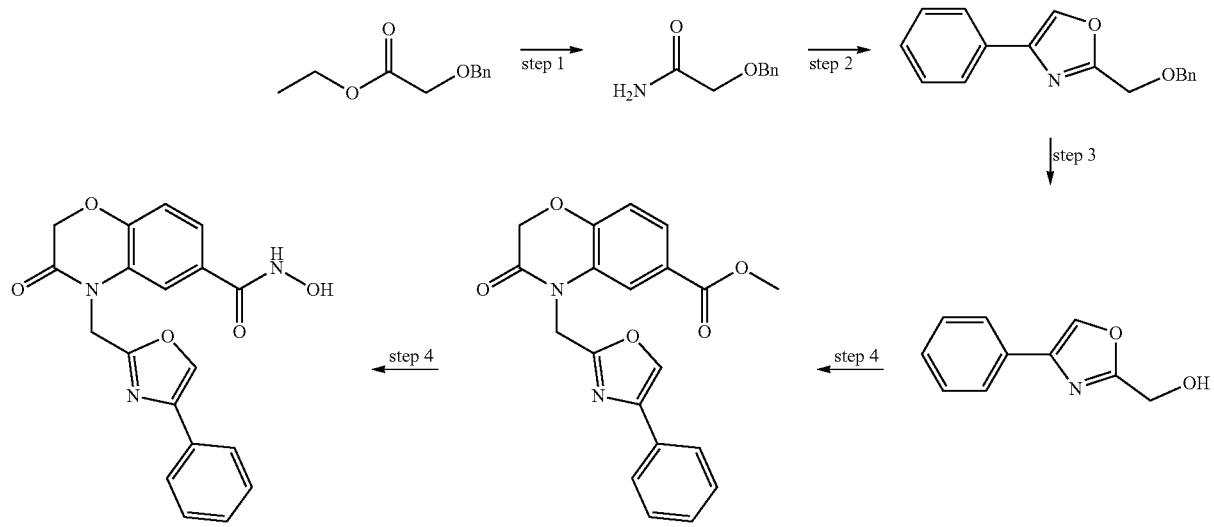

Step 4: Methyl 3-oxo-4-((4-phenyloxazol-2-yl)methyl)-3,4-dihydro-2H-benzo[b][1,4]oxazine-6-carboxylate Into a 30-mL vial, was placed methyl 3-oxo-3,4-dihydro-2H-benzo[b][1,4]oxazine-6-carboxylate (95 mg, 0.46 mmol, 1.00 equiv), THF (10 mL), PPh₃ (180 mg, 0.69 mmol, 1.50 equiv), (4-phenyloxazol-2-yl)methanol (80 mg, 0.46 mmol, 1.00 equiv). This was followed by the addition of DIAD (0.13 mL, 0.68 mmol, 1.50 equiv) dropwise with stirring at 0° C. The resulting solution was stirred overnight at room temperature (25° C.) and then concentrated under vacuum. The residue was purified via column chromatography on silica gel (eluting with ethyl acetate/petroleum ether (1:2)) to afford methyl 3-oxo-4-((4-phenyloxazol-2-yl)methyl)-3,4-dihydro-2H-benzo[b][1,4]oxazine-6-carboxylate (200 mg, 96%, 80% purity) as a yellow solid. MS: (ESI, m/z): 365[M+H]⁺.

Step 5: N-hydroxy-3-oxo-4-((4-phenyloxazol-2-yl)methyl)-3,4-dihydro-2H-benzo[b][1,4]oxazine-6-carboxamide Into a 30-mL vial, was placed methyl 3-oxo-4-((4-phenyloxazol-2-yl)methyl)-3,4-dihydro-2H-benzo[b][1,4]oxazine-6-carboxylate (100 mg, 0.22 mmol, 1.00 equiv, 80% purity), THF/MeOH (4/1) (4 mL). Then NaOH (1M) (0.5 mL, 0.5 mmol, 2.30 equiv) and NH₂OH (50% in water) (2.18 mL, 33.00 mmol, 150.00 equiv) were added at 0-10° C. The resulting solution was stirred for 1 h at room temperature (25° C.). The crude product was purified via Prep-HPLC with the following conditions: Column: XBridge C18 OBD Prep Column, 100A, 5 µm, 19 mm×250 mm; Mobile Phase A: water (0.1% FA), Mobile Phase B: ACN; Flow rate: 20 mL/min; Gradient: 20% B to 45% B in 7 min; 254 nm. The collected fraction was lyophilized to afford N-hydroxy-3-oxo-4-((4-phenyloxazol-2-yl)methyl)-3,4-dihydro-2H-benzo[b][1,4]oxazine-6-carboxamide (24.8 mg, 27%) as an off-white solid. ¹H-NMR: (DMSO, 300 MHz, ppm): δ 11.14 (br, 1H), 9.02 (br, 1H), 8.58 (s, 1H), 7.74-7.69 (m, 3H), 7.48-7.29 (m, 4H), 7.11 (d, J=5.4 Hz, 1H), 5.36 (s, 2H), 4.85 (s, 2H). MS: (ESI, m/z): 366[M+H]⁺.

Example 53. 4-((1H-indazol-3-yl)methyl)-N-hydroxy-3-oxo-3,4-dihydro-2H-benzo[b][1,4]oxazine-6-carboxamide (I-203)

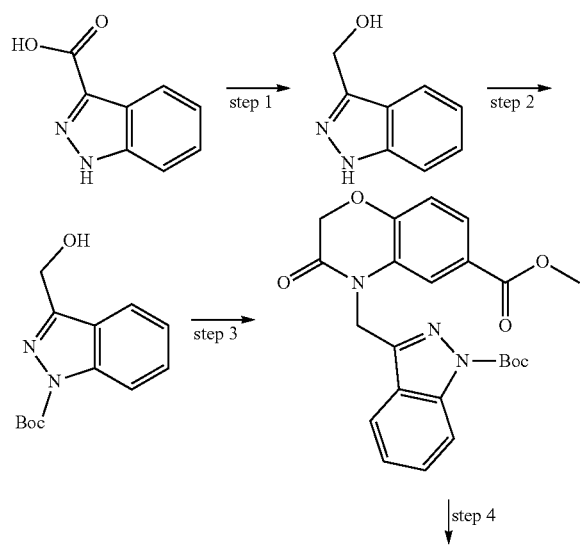

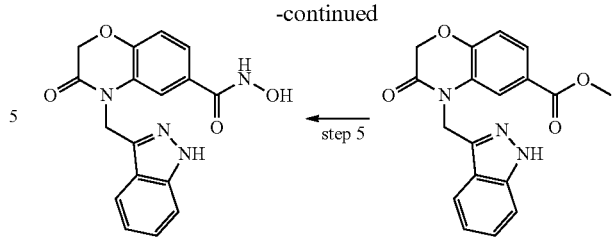

Step 1: (1H-indazol-3-yl)methanol

Into a 250-mL 3-necked round-bottom flask purged and maintained with an inert atmosphere of nitrogen, was placed 1H-indazole-3-carboxylic acid (5 g, 30.84 mmol, 1.00 equiv), THF (25 mL). This was followed by the addition of LiAlH₄ (2.30 g, 60.60 mmol, 2.00 equiv) in portions at 0° C. The resulting solution was stirred for 2 h at room temperature (25° C.) and then the reaction was quenched by the addition of 2.3 mL of water, 6.9 mL of NaOH (1 M) and 2.3 mL of water at 0° C. The solids were filtered out. The filtrate was concentrated under vacuum. The residue was purified via column chromatography on silica gel (eluting with ethyl acetate/petroleum ether (1:1)) to afford (1H-indazol-3-yl)methanol (2.0 g, 44%) as a white solid. MS (ESI, m/z): 149[M+H]⁺.

Step 2: Tert-butyl 3-(hydroxymethyl)-1H-indazole-1-carboxylate

Into a 25-mL round-bottom flask, was placed (1H-indazol-3-yl)methanol (200 mg, 1.35 mmol, 1.00 equiv), THF (5 mL), TEA (0.21 mL, 1.47 mmol, 1.09 equiv), (Boc)₂O (293 mg, 1.34 mmol, 0.99 equiv). The resulting solution was stirred for overnight at room temperature (25° C.) and then concentrated under vacuum. The residue was purified via column chromatography on silica gel (eluting with ethyl acetate/petroleum ether (1:1)) to afford tert-butyl 3-(hydroxymethyl)-1H-indazole-1-carboxylate (130 mg, 39%) as a white solid. MS (ESI, m/z): 249[M+H]⁺.

Step 3: Methyl 4-((1-(tert-butoxycarbonyl)-1H-indazol-3-yl)methyl)-3-oxo-3,4-dihydro-2H-benzo[b][1,4]oxazine-6-carboxylate Into a 30-mL vial purged and maintained with an inert atmosphere of nitrogen, was placed tert-butyl 3-(hydroxymethyl)-1H-indazole-1-carboxylate (80 mg, 0.32 mmol, 1.00 equiv), THF (6 mL), methyl 3-oxo-3,4-dihydro-2H-1,4-benzoxazine-6-carboxylate (66 mg, 0.32 mmol, 1.00 equiv), PPh₃ (126 mg, 0.48 mmol, 1.50 equiv). This was followed by the addition of DIAD (0.10 mL, 0.48 mmol, 1.50 equiv) dropwise with stirring at 0° C. The resulting solution was stirred for overnight at room temperature (25° C.) and then concentrated under vacuum. The residue was purified via reversed phase column with the following conditions: Column, C18 silica gel, 40 g, 20-45 µm, 100A; Mobile phase: water with 10 mmol/L NH₄HCO₃ and CH₃CN (5% CH₃CN up to 80% in 30 min); Detector, UV 254 nm. The collected fraction was concentrated under vacuum to afford methyl 4-((1-(tert-butoxycarbonyl)-1H-indazol-3-yl)methyl)-3-oxo-3,4-dihydro-2H-benzo[b][1,4]oxazine-6-carboxylate (100 mg, 71%) as a white solid. MS (ESI, m/z): 438[M+H]⁺.

Step 4: Methyl 4-((1H-indazol-3-yl)methyl)-3-oxo-3,4-dihydro-2H-benzo[b][1,4]oxazine-6-carboxylate Into a 25-mL round-bottom flask, was placed methyl 4-((1-(tert-butoxycarbonyl)-1H-indazol-3-yl)methyl)-3-oxo-3,4-dihydro-2H-benzo[b][1,4]oxazine-6-carboxylate (100 mg, 0.23 mmol, 1.00 equiv), DCM (3 mL), TFA (1 mL). The resulting solution was stirred for 1.5 h at room temperature (25° C.) and then concentrated under vacuum.

The residue was purified via reversed phase column with the following conditions: Column, C18 silica gel, 40 g, 20-45 μm, 100A; Mobile phase: water with 10 mmol/L NH$_4$HCO$_3$ and CH$_3$CN (5% CH$_3$CN up to 70% in 20 min); Detector, UV 254 nm. The collected fraction was concentrated under vacuum to afford methyl 4-((1H-indazol-3-yl)methyl)-3-oxo-3,4-dihydro-2H-benzo[b][1,4]oxazine-6-carboxylate (50 mg, 65%) as a white solid. MS (ESI, m/z): 338[M+H]$^+$.

Step 5: 4-((1H-indazol-3-yl)methyl)-N-hydroxy-3-oxo-3,4-dihydro-2H-benzo[b][1,4]oxazine-6-carboxamide Into a 25-mL round-bottom flask, was placed methyl 4-((1H-indazol-3-yl)methyl)-3-oxo-3,4-dihydro-2H-benzo[b][1,4]oxazine-6-carboxylate (50 mg, 0.15 mmol, 1.00 equiv), THF/MeOH (4/1)(1 mL). This was followed by the addition of NH$_2$OH (50% in water) (1.17 mL, 17.71 mmol, 119.49 equiv) and NaOH (1M) (0.3 mL, 0.3 mmol, 2.00 equiv) at 0-10° C. The resulting solution was stirred for 3 h at room temperature (25° C.). The mixture was purified via Prep-HPLC with the following conditions: Column, XSelect CSH Prep C18 OBD Column, 100A, 5 μm, 19×150 mm; Mobile phase A: water (0.1% FA), Mobile phase B: ACN (25.0% B up to 50.0% B in 7 min); Detector, UV 254/220 nm. The collected fraction was lyophilized to afford 4-((H-indazol-3-yl)methyl)-N-hydroxy-3-oxo-3,4-dihydro-2H-benzo[b][1,4]oxazine-6-carboxamide (31.7 mg, 63%) as a white solid. $^1$H-NMR: (DMSO, 400 MHz, ppm): δ 12.98 (s, 1H), 11.12 (br, 1H), 8.99 (br, 1H), 7.89 (s, 1H), 7.77 (d, J=8.0 Hz, 1H), 7.48 (d, J=8.4 Hz, 1H), 7.36-7.32 (m, 2H), 7.12-7.09 (m, 1H), 7.02 (d, J=8.4 Hz, 1H), 5.51 (s, 2H), 4.83 (s, 2H). MS (ESI, m/z): 339 [M+H]$^-$.

Example 54. N-hydroxy-3-oxo-4-[(5-phenyl-1H-pyrazol-3-yl)methyl]-3,4-dihydro-2H-1,4-benzoxazine-6-carboxamide (I-204)

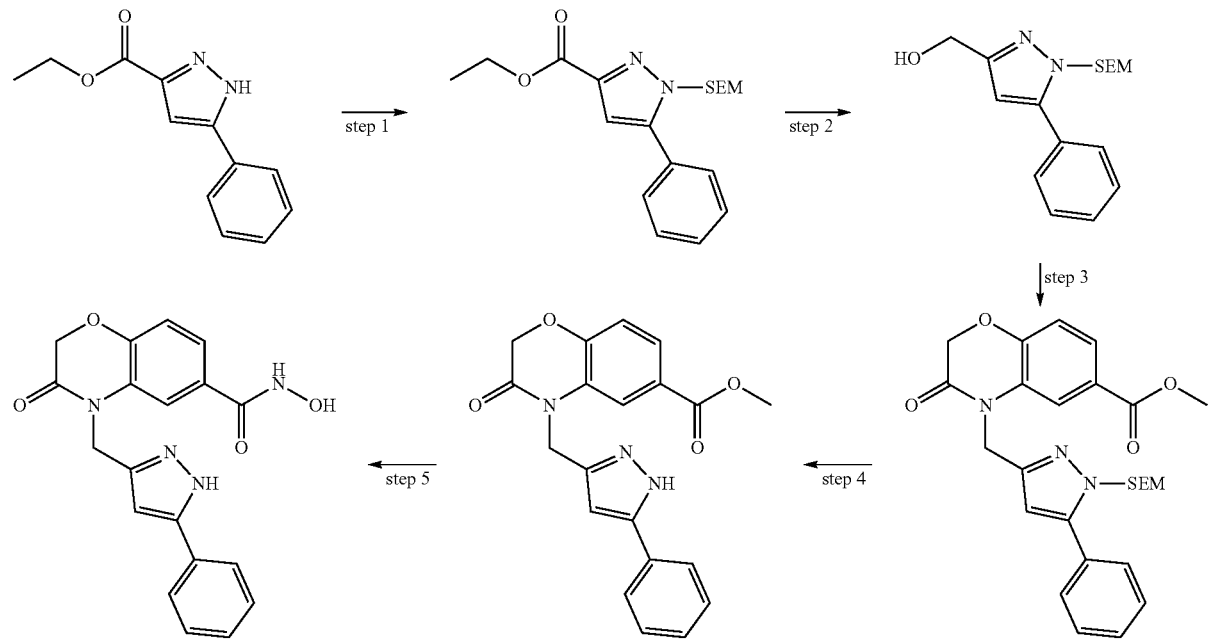

Step 1: Ethyl 5-phenyl-1-[[2-(trimethylsilyl)ethoxy]methyl]-1H-pyrazole-3-carboxylate Into a 50-mL 3-necked round-bottom flask purged and maintained with an inert atmosphere of nitrogen, was placed ethyl 5-phenyl-1H-pyrazole-3-carboxylate (1 g, 4.62 mmol, 1.00 equiv), THF (10 mL). This was followed by the addition of NaH (297 mg, 7.43 mmol, 1.61 equiv, 60%) in portions at 0° C. The resulting solution was stirred for 15 min at room temperature (25° C.). To this was added SEMCl (0.96 mL, 5.92 mmol, 1.28 equiv) at 0° C. The resulting solution was stirred for 1 h at room temperature (25° C.) and then poured into 10 mL of water/ice. The resulting solution was extracted with 3×15 mL of dichloromethane, dried over anhydrous sodium sulfate and concentrated under vacuum. The residue was purified via column chromatography on silica gel (eluting with ethyl acetate/petroleum ether (1:3)) to afford ethyl 5-phenyl-1-[[2-(trimethylsilyl)ethoxy]methyl]-1H-pyrazole-3-carboxylate) (1.2 g, 75%) as light yellow oil. MS (EST, m/z): 347 [M+H]$^+$

Step 2: (5-phenyl-1-[[2-(trimethylsilyl)ethoxy]methyl]-1H-pyrazol-3-yl)methanol Into a 50-mL 3-necked round-bottom flask purged and maintained with an inert atmosphere of nitrogen, was placed ethyl 5-phenyl-1-[[2-(trimethylsilyl)ethoxy]methyl]-1H-pyrazole-3-carboxylate (600 mg, 1.73 mmol, 1.00 equiv), THF (5 mL). This was followed by the addition of LiAlH$_4$ (132 mg, 3.48 mmol, 2.01 equiv) in portions at 0° C. The resulting solution was stirred for 2 h at room temperature (25° C.) and then the reaction was quenched by the addition of 0.13 mL of water, 0.39 mL of NaOH (1 M) and 0.13 mL of water. The solids were filtered out. The filtrate was concentrated under vacuum. The residue was purified via column chromatography on silica gel (eluting with ethyl acetate/petroleum ether (1:1)) to afford (5-phenyl-1-[[2-(trimethylsilyl)ethoxy]methyl]-1H-pyrazol-3-yl)methanol (400 mg, 76%) as yellow oil. MS (ESI, m/z): 305[M+H]⁺.

Step 3: Methyl 3-oxo-4-[(5-phenyl-1-[[2-(trimethylsilyl)ethoxy]methyl]-1H-pyrazol-3-yl)methyl]-3,4-dihydro-2H-1,4-benzoxazine-6-carboxylate Into a 30-mL vial purged and maintained with an inert atmosphere of nitrogen, was placed (5-phenyl-1-[[2-(trimethylsilyl)ethoxy]methyl]-1H-pyrazol-3-yl)methanol (200 mg, 0.66 mmol, 1.00 equiv), THF (6 mL), methyl 3-oxo-3,4-dihydro-2H-1,4-benzoxazine-6-carboxylate (137 mg, 0.66 mmol, 1.00 equiv), PPh₃ (259 mg, 0.99 mmol, 1.50 equiv). This was followed by the addition of DIAD (0.20 mL, 0.98 mmol, 1.50 equiv) dropwise with stirring at 0° C. The resulting solution was stirred for overnight at room temperature (25° C.) and then concentrated under vacuum. The residue was purified via column chromatography on silica gel (eluting with ethyl acetate/petroleum ether (1:3)) to afford methyl 3-oxo-4-[(5-phenyl-1-[[2-(trimethyl silyl)ethoxy]methyl]-1H-pyrazol-3-yl)methyl]-3,4-dihydro-2H-1,4-benzoxazine-6-carboxylate (300 mg, 93%) as white oil. MS (ESI, m/z): 494[M+H]⁺.

Step 4: Methyl 3-oxo-4-[(5-phenyl-1H-pyrazol-3-yl)methyl]-3,4-dihydro-2H-1,4-benzoxazine-6-carboxylate Into a 25-mL round-bottom flask, was placed methyl 3-oxo-4-[(5-phenyl-1-[[2-(trimethylsilyl)ethoxy]methyl]-1H-pyrazol-3-yl)methyl]-3,4-dihydro-2H-1,4-benzoxazine-6-carboxylate (150 mg, 0.30 mmol, 1.00 equiv), DCM (3 mL), TFA (1 mL). The resulting solution was stirred for 1 h at room temperature (25° C.) and then concentrated under vacuum. The residue was purified via Prep-TLC (eluting with ethyl acetate/petroleum ether (1:3)) to afford methyl 3-oxo-4-[(5-phenyl-1H-pyrazol-3-yl)methyl]-3,4-dihydro-2H-1,4-benzoxazine-6-carboxylate (100 mg, 92%) as a white solid. MS (ESI, m/z): 364 [M+H]⁺.

Step 5: N-hydroxy-3-oxo-4-[(5-phenyl-1H-pyrazol-3-yl)methyl]-3,4-dihydro-2H-1,4-benzoxazine-6-carboxamide Into a 25-mL round-bottom flask, was placed methyl 3-oxo-4-[(5-phenyl-1H-pyrazol-3-yl)methyl]-3,4-dihydro-2H-1,4-benzoxazine-6-carboxylate (60 mg, 0.17 mmol, 1.00 equiv), THF/MeOH (4/1)(2 mL). Then NH₂OH (50% in water) (1.31 mL, 19.83 mmol, 120.10 equiv) and NaOH (1M) (0.3 mL, 0.3 mmol, 2.00 equiv) were added at 0-10° C. The resulting solution was stirred for 3 h at room temperature (25° C.). The crude product was purified via Prep-HPLC with the following conditions: Column, XSelect CSH Prep C18 OBD Column, 100A, 5 µm, 19×150 mm; Mobile phase A: water (0.1% FA), Mobile phase B: ACN (20.0% B up to 50.0% B in 7 min); Detector, UV 254 nm. The collected fraction was lyophilized to afford N-hydroxy-3-oxo-4-[(5-phenyl-1H-pyrazol-3-yl)methyl]-3,4-dihydro-2H-1,4-benzoxazine-6-carboxamide (28.7 mg, 48%) as a white solid. ¹H-NMR: (DMSO, 400 MHz, ppm): δ 13.22 (br, 1H), 11.15 (s, 1H), 8.98 (s, 1H), 7.73-7.67 (m, 3H), 7.42-7.32 (m, 4H), 7.05 (d, J=8.0 Hz, 1H), 6.56 (s, 1H), 5.13 (s, 2H), 4.81 (s, 2H). MS (ESI, m/z): 365 [M+H]⁺.

Example 55. N-hydroxy-3-oxo-4-((1-phenyl-1H-imidazol-4-yl)methyl)-3,4-dihydro-2H-benzo[b][1,4]oxazine-6-carboxamide (I-205)

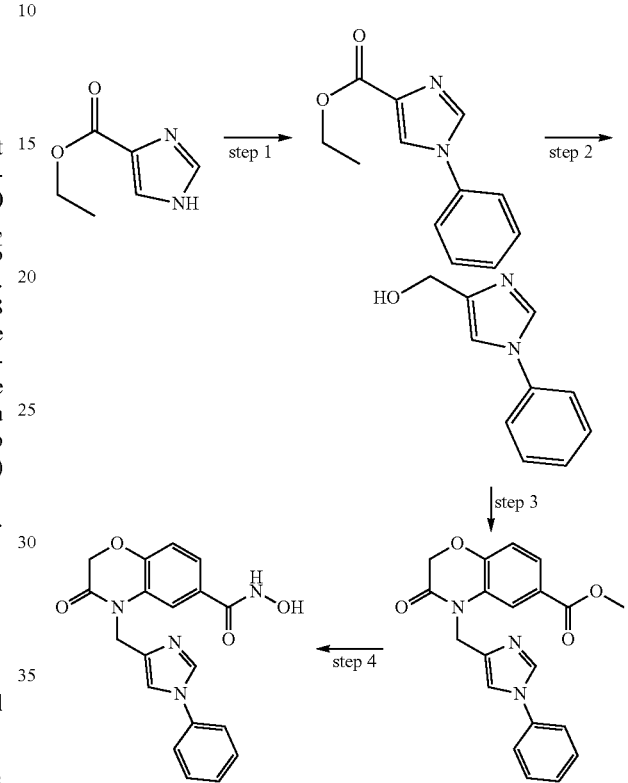

Step 1: Ethyl 1-phenyl-1H-imidazole-4-carboxylate

Into a 250-mL 3-necked round-bottom flask purged and maintained with an inert atmosphere of nitrogen, was placed ethyl 1H-imidazole-4-carboxylate (5 g, 35.68 mmol, 1.00 equiv), DMF (30 mL), iodobenzene (4.80 mL, 42.84 mmol, 1.20 equiv), Cu(OAc)₂ (646 mg, 3.56 mmol, 0.10 equiv), Cs₂CO₃ (23.2 g, 71.21 mmol, 2.00 equiv). The resulting solution was stirred for overnight at 110° C. and then cooled to room temperature, the mixture was poured into 200 mL of water, extracted with 2×60 mL of dichloromethane, washed with 2×40 mL of brine, dried over anhydrous sodium sulfate and concentrated under vacuum. The residue was purified via column chromatography on silica gel (eluting with ethyl acetate/petroleum ether (1:1)) to afford ethyl 1-phenyl-1H-imidazole-4-carboxylate (1.5 g, 19%) as a white solid. MS (ESI, m/z): 217 [M+H]⁺.

Step 2: (1-phenyl-1H-imidazol-4-yl)methanol

Into a 25-mL 3-necked round-bottom flask purged and maintained with an inert atmosphere of nitrogen, was placed ethyl 1-phenyl-1H-imidazole-4-carboxylate (190 mg, 0.88 mmol, 1.00 equiv), THF (10 mL). This was followed by the addition of LiAlH₄ (67 mg, 1.77 mmol, 2.01 equiv) in portions at 0° C. The resulting solution was stirred for 1 h at room temperature (25° C.) and then the reaction was quenched by the addition of 0.07 mL of water, 0.20 mL of NaOH (1M) and 0.07 mL of water. The solids were filtered out. The filtrate was concentrated under vacuum. The residue was purified via column chromatography on silica gel (eluting with methanol/dichloromethane (1/10)) to afford (I-phenyl-1H-imidazol-4-yl)methanol (120 mg, 78%) as a white solid. MS (ESI, m/z): 175 [M+H]⁺.

Step 3: Methyl 3-oxo-4-((1-phenyl-1H-imidazol-4-yl)methyl)-3,4-dihydro-2H-benzo[b][1,4]oxazine-6-carboxylate Into a 30-mL vial purged and maintained with an inert atmosphere of nitrogen, was placed (1-phenyl-1H-imidazol-4-yl)methanol (100 mg, 0.57 mmol, 1.00 equiv), THF (5 mL), methyl 3-oxo-3,4-dihydro-2H-1,4-benzoxazine-6-carboxylate (118 mg, 0.57 mmol, 1.00 equiv), PPh$_3$ (225 mg, 0.85 mmol, 1.50 equiv). This was followed by the addition of DIAD (0.17 mL, 0.88 mmol, 1.50 equiv) dropwise with stirring at 0° C. The resulting solution was stirred for overnight at room temperature (25° C.) and then concentrated under vacuum. The residue was purified via column chromatography on silica gel (eluting with ethyl acetate/petroleum ether (1:1)) to afford methyl 3-oxo-4-((1-phenyl-1H-imidazol-4-yl)methyl)-3,4-dihydro-2H-benzo[b][1,4]oxazine-6-carboxylate (100 mg, 48%) as a white solid. MS (ESI, m/z): 364 [M+H]⁺.

Step 4: N-hydroxy-3-oxo-4-((1-phenyl-1H-imidazol-4-yl)methyl)-3,4-dihydro-2H-benzo[b][1,4]oxazine-6-carboxamide Into a 25-mL round-bottom flask, was placed methyl 3-oxo-4-((1-phenyl-1H-imidazol-4-yl)methyl)-3,4-dihydro-2H-benzo[b][1,4]oxazine-6-carboxylate (60 mg, 0.17 mmol, 1.00 equiv), THF/MeOH (4/1) (2 mL). This was followed by the addition of NH$_2$OH (50% in water) (1.31 mL, 19.82 mmol, 120.00 equiv) and NaOH (1M) (0.3 mL, 0.3 mmol, 2.00 equiv) at 0° C. The resulting solution was stirred for 3 h at room temperature (25° C.). The crude product was purified via Prep-HPLC with the following conditions: Column, XBridge Shield RP18 OBD Column, 100A, 5 µm, 19×150 mm; Mobile phase A: water (0.1% FA), Mobile phase B: ACN (5.0% B up to 55.0% in 7 min); Detector, UV 254 nm. The collected fraction was lyophilized to afford N-hydroxy-3-oxo-4-((1-phenyl-1H-imidazol-4-yl)methyl)-3,4-dihydro-2H-benzo[b][1,4]oxazine-6-carboxamide (22.5 mg, 37%) as a white solid. ¹H-NMR: (DMSO, 400 MHz, ppm): δ 11.15 (s, 1H), 8.98 (s, 1H), 8.22 (s, 1H), 7.74 (s, 1H), 7.63-7.58 (m, 3H), 7.51-7.47 (m, 2H), 7.40-7.32 (m, 2H), 7.05 (d, J=8.4 Hz, 1H), 5.08 (s, 2H), 4.79 (s, 2H). MS (ESI, m/z): 365 [M+H]⁺.

Example 56. 4-((1-cyclopropyl-1H-pyrazol-4-yl)methyl)-N-hydroxy-3-oxo-3,4-dihydro-2H-benzo[b][1,4]oxazine-6-carboxamide (I-206)

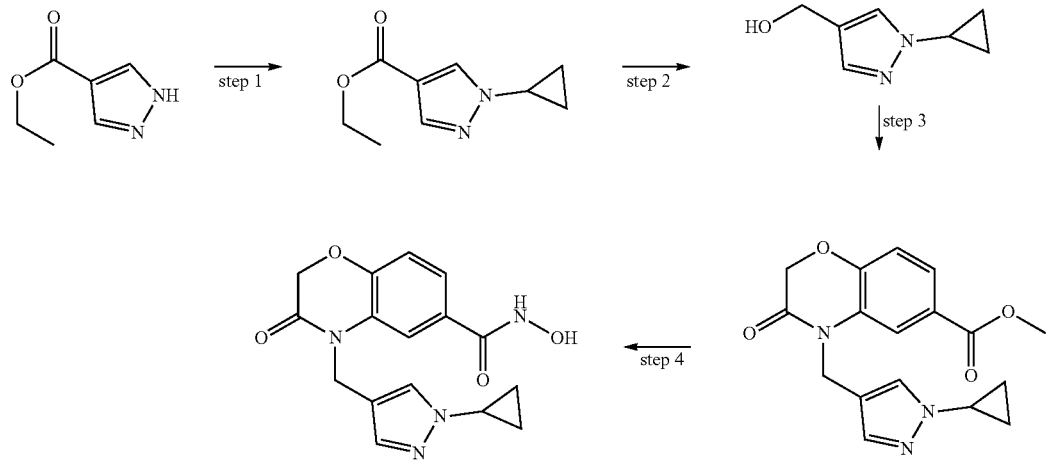

Step 1: Ethyl 1-cyclopropyl-1H-pyrazole-4-carboxylate

Into a 250-mL 3-necked round-bottom flask purged and maintained with an inert atmosphere of O$_2$, was placed ethyl 1H-pyrazole-4-carboxylate (3 g, 21.41 mmol, 1.00 equiv), DCE (50 mL), cyclopropylboronic acid (3.51 g, 40.83 mmol, 1.90 equiv), Na$_2$CO$_3$ (4.54 g, 40.8 mmol, 1.90 equiv), Cu(OAc)$_2$ (3.88 g, 21.36 mmol, 1.00 equiv), bipyridine (3.34 g, 21.41 mmol, 1.00 equiv). The resulting solution was stirred for overnight at 70° C. and then cooled to room temperature. The solids were filtered out. The filtrate was concentrated under vacuum. The residue was purified via reversed phase column with the following conditions: Column, C18 silica gel, 120 g, 20-45 µm, 100A; Mobile phase: water with 0.5% TFA and CH$_3$CN (5% CH$_3$CN up to 80% in 30 min). The collected fraction was concentrated under vacuum to afford ethyl 1-cyclopropyl-1H-pyrazole-4-carboxylate (2.2 g, 57%) as a light yellow solid. MS (ESI, m/z): 181 [M+H]⁺.

Step 2: (1-cyclopropyl-1H-pyrazol-4-yl)methanol

Into a 50-mL round-bottom flask, was placed ethyl 1-cyclopropyl-1H-pyrazole-4-carboxylate (300 mg, 1.66 mmol, 1.00 equiv), THF (10 mL). This was followed by the addition of LiAlH$_4$ (127 mg, 3.35 mmol, 2.01 equiv) in portions at 0° C. The resulting solution was stirred for 1 h at room temperature (25° C.) and then the reaction was quenched by the addition of 0.13 mL of water, 0.38 mL of NaOH (1M) and 0.13 mL of water. The solids were filtered out, the filtrate was concentrated under vacuum. The residue was purified via column chromatography on silica gel (eluting with methanol/dichloromethane (1/10)) to afford (1-cyclopropyl-1H-pyrazol-4-yl)methanol (200 mg, 87%) as a light yellow solid. MS (ESI, m/z): 139[M+H]$^+$.

Step 3: Methyl 4-((1-cyclopropyl-1H-pyrazol-4-yl)methyl)-3-oxo-3,4-dihydro-2H-benzo[b][1,4]oxazine-6-carboxylate Into a 30-mL vial purged and maintained with an inert atmosphere of nitrogen, was placed (1-cyclopropyl-1H-pyrazol-4-yl)methanol (100 mg, 0.72 mmol, 1.00 equiv), THF (5 mL), methyl 3-oxo-3,4-dihydro-2H-1,4-benzoxazine-6-carboxylate (149 mg, 0.72 mmol, 1.00 equiv), PPh$_3$ (284 mg, 1.08 mmol, 1.50 equiv). This was followed by the addition of DIAD (0.22 mL, 1.09 mmol, 1.50 equiv) dropwise with stirring at 0° C. The resulting solution was stirred for overnight at room temperature (25° C.) and then concentrated under vacuum. The residue was purified via column chromatography on silica gel (eluting with ethyl acetate/petroleum ether (1:1)) to afford methyl 4-((1-cyclopropyl-1H-pyrazol-4-yl)methyl)-3-oxo-3,4-dihydro-2H-benzo[b][1,4]oxazine-6-carboxylate (70 mg, 30%) as a light yellow solid. MS (ESI, m/z): 328 [M+H]$^+$.

Step 4: 4-((1-cyclopropyl-1H-pyrazol-4-yl)methyl)-N-hydroxy-3-oxo-3,4-dihydro-2H-benzo[b][1,4]oxazine-6-carboxamide Into a 25-mL round-bottom flask, was placed methyl 4-((1-cyclopropyl-1H-pyrazol-4-yl)methyl)-3-oxo-3,4-dihydro-2H-benzo[b][1,4]oxazine-6-carboxylate (50 mg, 0.15 mmol, 1.00 equiv), THF/MeOH (4/1)(2 mL). This was followed by the addition of NH$_2$OH (50% in water) (1.21 mL, 18.32 mmol, 120.00 equiv) and NaOH (1M) (0.30 mL, 0.30 mmol, 2.00 equiv) at 0° C. The resulting solution was stirred for 3 h at room temperature (25° C.). The crude product was purified via Prep-HPLC with the following conditions: Column, XBridge Shield RP18 OBD Column, 100A, 5 μm, 19×150 mm; Mobile phase A: water (0.1% FA), Mobile phase B: ACN (35.0% B up to 90.0% in 7 min); Detector, UV 254 nm. The collected fraction was lyophilized to afford 4-((1-cyclopropyl-1H-pyrazol-4-yl)methyl)-N-hydroxy-3-oxo-3,4-dihydro-2H-benzo[b][1,4]oxazine-6-carboxamide (23.9 mg, 48%) as a white solid. $^1$H-NMR: (DMSO, 400 MHz, ppm): δ 11.19 (s, 1H), 9.02 (s, 1H), 7.70 (s, 1H), 7.58 (s, 1H), 7.43-7.37 (m, 2H), 7.05 (d, J=8.4 Hz, 1H), 4.96 (s, 2H), 4.76 (s, 2H), 3.68-3.63 (m, 1H), 0.98-0.87 (m, 4H). MS (ESI, m/z): 329 [M+H]$^+$.

Example 57. N-hydroxy-4-((6-methylthiazolo[5,4-b]pyridin-2-yl)methyl)-3-oxo-3,4-dihydro-2H-benzo[b][1,4]oxazine-6-carboxamide (I-207)

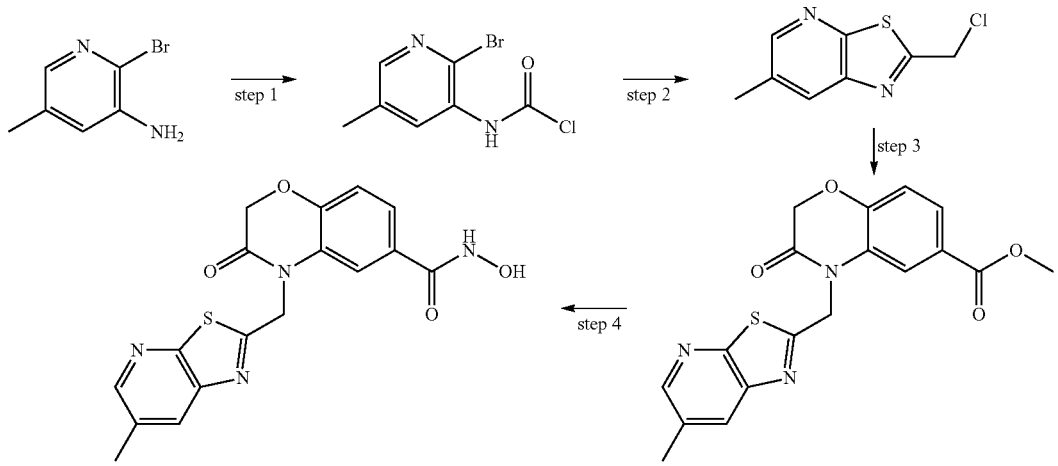

Step 1:
N-(2-bromo-5-methylpyridin-3-yl)-2-chloroacetamide

Into a 100-mL round-bottom flask, was placed 2-bromo-5-methylpyridin-3-amine (1.00 g, 5.35 mmol, 1.00 equiv), dichloromethane (20 mL), triethylamine (2.24 mL, 16.11 mmol, 3.00 equiv). This was followed by the addition of 2-chloroacetyl chloride (0.48 mL, 6.40 mmol, 1.20 equiv) dropwise with stirring at 0° C. The resulting solution was stirred for 2 h at 0° C. and then poured into 50 mL of water. The mixture was extracted with 3×50 mL of ethyl acetate, dried over anhydrous sodium sulfate and concentrated under vacuum. The residue was purified via column chromatography on silica gel (eluting with ethyl acetate/petroleum ether (1:3)) to afford N-(2-bromo-5-methylpyridin-3-yl)-2-chloroacetamide (1.20 g, 85%) as an off-white solid. MS: (ESI, m/z): 263[M+H]$^+$.

Step 2: 2-(chloromethyl)-6-methylthiazolo[5,4-b]pyridine

Into a 20-mL microwave tube, was placed N-(2-bromo-5-methylpyridin-3-yl)-2-chloroacetamide (600 mg, 2.28 mmol, 1.00 equiv), toluene (10 mL), P$_2$S$_5$ (508 mg, 2.28 mmol, 1.00 equiv). The resulting solution was stirred for 30 min at 100° C. and then cooled to room temperature. The resulting mixture was concentrated under vacuum. The residue was diluted with 50 mL of water. The mixture was extracted with 2×50 mL of dichloromethane, dried over anhydrous sodium sulfate and concentrated under vacuum. The residue was purified via column chromatography on silica gel (eluting with ethyl acetate/petroleum ether (1:5)) to afford 2-(chloromethyl)-6-methylthiazolo[5,4-b]pyridine (60 mg, 13%) as yellow oil. MS: (ESI, m/z): 199[M+H]⁺.

Step 3: Methyl 4-((6-methylthiazolo[5,4-b]pyridin-2-yl)methyl)-3-oxo-3,4-dihydro-2H-benzo[b][1,4]oxazine-6-carboxylate Into a 25-mL round-bottom flask, was placed 2-(chloromethyl)-6-methylthiazolo[5,4-b]pyridine (60 mg, 0.30 mmol, 1.00 equiv), N,N-dimethylformamide (3 mL), methyl 3-oxo-3,4-dihydro-2H-1,4-benzoxazine-6-carboxylate (63 mg, 0.30 mmol, 1.00 equiv), $Cs_2CO_3$ (244 mg, 0.75 mmol, 2.50 equiv). The resulting solution was stirred for 2 h at room temperature (25° C.). The reaction mixture was then poured into 15 mL of water, extracted with 2×15 mL of ethyl acetate, dried over anhydrous sodium sulfate and concentrated under vacuum. The residue was purified via preparative TLC (eluting with ethyl acetate/petroleum ether (1:3)) to afford methyl 4-((6-methylthiazolo[5,4-b]pyridin-2-yl)methyl)-3-oxo-3,4-dihydro-2H-benzo[b][1,4]oxazine-6-carboxylate (40 mg, 36%) as yellow oil. MS: (ESI, m/z): 370[M+H]⁻.

Step 4: N-hydroxy-4-((6-methylthiazolo[5,4-b]pyridin-2-yl)methyl)-3-oxo-3,4-dihydro-2H-benzo[b][1,4]oxazine-6-carboxamide Into a 25-mL round-bottom flask, was placed methyl 4-((6-methylthiazolo[5,4-b]pyridin-2-yl)methyl)-3-oxo-3,4-dihydro-2H-benzo[b][1,4]oxazine-6-carboxylate (40 mg, 0.11 mmol, 1.00 equiv), THF/MeOH (4/1) (2 mL), $NH_2OH$ (50% in water) (0.43 mL, 6.49 mmol, 60.00 equiv), NaOH (1M) (0.22 mL, 0.22 mmol, 2.00 equiv). The resulting solution was stirred for 2 h at room temperature (25° C.). The solids were filtered out. The crude product was purified by Prep-HPLC with the following conditions: Column, XBridge C18 OBD Prep Column, 100A, 5 μm, 19 mm×250 mm; mobile phase, water (10 mmol/L NH4HCO3) and ACN (15.0% ACN up to 35.0% in 7 min); Detector, UV/mass 254 & 220 nm. The collected fraction was lyophilized to afford N-hydroxy-4-((6-methylthiazolo[5,4-b]pyridin-2-yl)methyl)-3-oxo-3,4-dihydro-2H-benzo[b][1,4]oxazine-6-carboxamide (6.2 mg, 15%) as a off-white solid. 1H-NMR: (DMSO 300 MHz, ppm): δ 9.00 (s, 1H), 8.46 (s, 1H), 8.20 (s, 1H), 7.60 (s, 1H), 7.44 (d, J=8.4 Hz, 1H), 7.11 (d, J=8.4 Hz, 1H), 5.60 (s, 2H), 4.87 (s, 2H), 2.43 (s, 3H) MS: (ESI, m/z): 371[M+H]+.

The compounds below were synthesized according to the procedures outlined above for Example 57.

| Comp. No. | Structure | IUPAC Name | ¹H NMR | (ESI, m/z) [M + H]⁺ |
|---|---|---|---|---|
| I-208 | 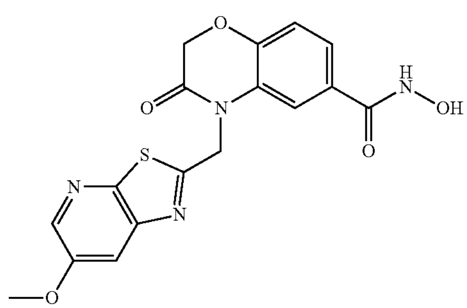 [SMILES: COc1cnc2sc(CN3C(=O)COc4ccc(C(=O)NO)cc43)nc2c1] | N-hydroxy-4-((6-methoxythiazolo[5,4-b]pyridin-2-yl)methyl)-3-oxo-3,4-dihydro-2H-benzo[b][1,4]oxazine-6-carboxamide | (DMSO, 400 MHz, ppm): 11.12 (s, 1H), 9.00 (s, 1H), 8.37 (s, 1H), 8.00 (s, 1H), 7.60 (s, 1H), 7.45 (d, J = 8.4 Hz, 1H), 7.12 (d, J = 8.4 Hz, 1H), 5.61 (s, 2H), 4.87 (s, 2H), 3.88 (s, 3H) | 387 |
| I-209 | 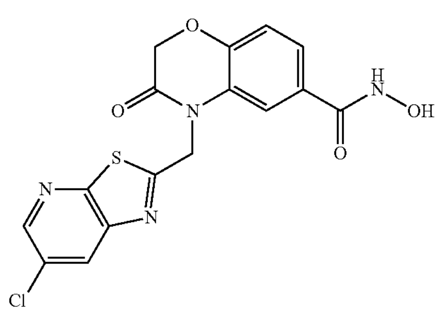 [SMILES: O=C(NO)c1ccc2c(c1)N(Cc1nc3cc(Cl)cnc3s1)C(=O)CO2] | 4-((6-chlorothiazolo[5,4-b]pyridin-2-yl)methyl)-N-hydroxy-3-oxo-3,4-dihydro-2H-benzo[b][1,4]oxazine-6-carboxamide | (DMSO, 400 MHz, ppm): 11.14 (s, 1H), 9.02 (s, 1H), 8.68 (s, 1H), 8.62 (s, 1H), 7.60 (s, 1H), 7.46 (d, J = 8 Hz, 1H), 7.13 (d, J = 8.4 Hz, 1H), 5.65 (s, 2H), 4.89 (s, 2H) | 391 |
| I-210 | 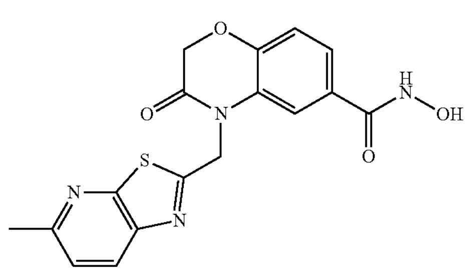 [SMILES: Cc1ccc2nc(CN3C(=O)COc4ccc(C(=O)NO)cc43)sc2n1] | N-hydroxy-4-((5-methylthiazolo[5,4-b]pyridin-2-yl)methyl)-3-oxo-3,4-dihydro-2H-benzo[b][1,4]oxazine-6-carboxamide | (DMSO, 400 MHz, ppm): 11.11 (s, 1H), 8.99 (s, 1H), 8.24 (d, J = 8.4 Hz, 1H), 7.61 (s, 1H), 7.45-7.42 (m, 2H), 7.12 (d, J = 8.4 Hz, 1H), 5.60 (s, 2H), 4.88 (s, 2H), 2.59 (s, 3H) | 371 |

| Comp. No. | Structure | IUPAC Name | ¹H NMR | (ESI, m/z) [M + H]⁺ |
|---|---|---|---|---|
| I-211 | 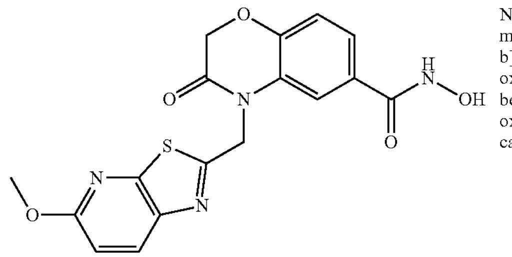 | N-hydroxy-4-((5-methoxythiazolo[5,4-b]pyridin-2-yl)methyl)-3-oxo-3,4-dihydro-2H-benzo[b][1,4]oxazine-6-carboxamide | (DMSO, 400 MHz, ppm): 11.13 (s, 1H), 9.00 (s, 1H), 8.25 (d, J = 8.8 Hz, 1H), 7.63 (s, 1H), 7.44 (d, J = 8.4 Hz, 1H), (d, J = 8.4 Hz, 1H), 6.97 (d, J = 9.2 Hz, 1H), 5.56 (s, 2H), 4.87 (s, 2H), 3.92 (s, 3H) | 387 |
| I-212 | 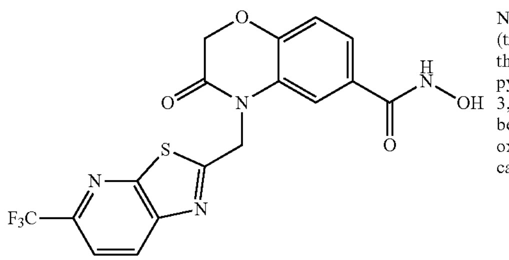 | N-hydroxy-3-oxo-4-((5-(trifluoromethyl)thiazolo[5,4-b]pyridin-2-yl)methyl)-3,4-dihydro-2H-benzo[b][1,4]oxazine-6-carboxamide | (DMSO, 400 MHz, ppm): 11.11 (s, 1H), 9.00 (s, 1H), 8.66 (d, J = 8.4 Hz, 1H), 8.09 (d, J = 8.4 Hz, 1H), 7.60 (s, 1H), 7.47 (d, J = 8.4 Hz, 1H), 7.15 (d, J = 8.4 Hz, 1H), 5.73 (s, 2H), 4.91 (s, 2H) | 425 |

Example 58: N-hydroxy-3-oxo-4-phenyl-3,4-dihydro-2H-benzo[b][1,4]oxazine-6-carboxamide (I-357)

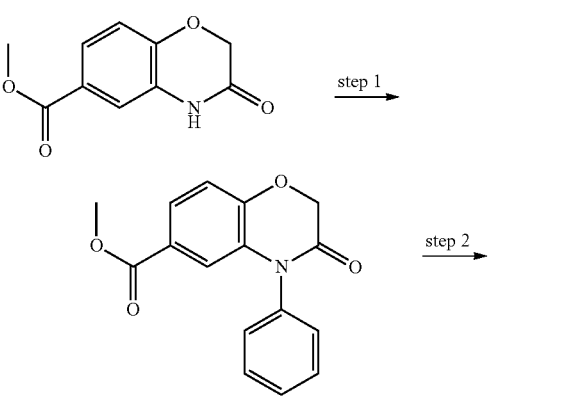

Step 1: Synthesis of methyl 3-oxo-4-phenyl-3,4-dihydro-2H-benzo[b][1,4]oxazine-6-carboxylate To an oven dried 2 mL reaction vial was added methyl 3-oxo-3,4-dihydro-2H-benzo[b][1,4]oxazine-6-carboxylate (0.2 M in DCE, 0.25 mL, 50 µmol), phenylboronic acid (0.2 M in DCE, 0.375 mL, 75 mol), Et₃N (60 µL) and Cu(OAc)₂ (0.2 M in DMSO, 350 µL, 70 µmol). The vial was sealed and shaken at ambient temperature for 3 days. The solvent was removed under reduced pressure and to the residue was added EtOAc (500 µL) and brine (500 ML). The layers were separated and the aqueous layer was extracted with EtOAc (500 µL). The combined organic layers were evaporated to give the crude product as an orange oil, which was used to next step without further purification. LC_MS: M+1 284.

Step 2. Synthesis of N-hydroxy-3-oxo-4-phenyl-3,4-dihydro-2H-benzo[b][1,4]oxazine-6-carboxamide

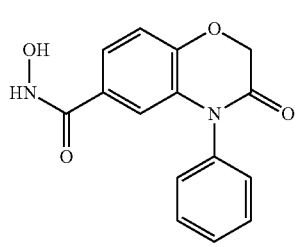

To crude methyl 3-oxo-4-phenyl-3,4-dihydro-2H-benzo[b][1,4]oxazine-6-carboxylate (0.2 M in 4:1 THF/MeOH, 250 µL, 50 µmol) was added NH₂OH (50% in water, 120 µL) and NaOH (1 M in water, 100 µL, 100 µmol). The mixture was shaken at ambient temperature for 3 hours and the solvent was removed under reduced pressure. The residue was dissolved in a mixture of DMSO (500 µL) and HOAc (50 µL) then purified by HPLC to give the titled compound as light yellow solid (3.2 mg, 22% in 2 steps). LCMS: M+1 285.

The following compound was prepared according to the procedures for Example 58.

| Comp. No. | Structure | IUPAC Name | ¹H NMR | (ESI, m/z) [M + H]⁺ |
|---|---|---|---|---|
| I-358 | 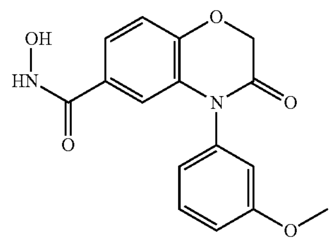 [SMILES: COc1cccc(N2C(=O)COc3ccc(C(=O)NO)cc32)c1] | N-hydroxy-4-(3-methoxyphenyl)-3-oxo-3,4-dihydro-2H-1,4-benzoxazine-6-carboxamide | 315 | 0.79 |

Example 59 N-hydroxy-3-oxo-4-(thiazolo[5,4-b]pyridin-2-ylmethyl)-3,4-dihydro-2H-benzo[b][1,4]oxazine-6-carboxamide (I-359)

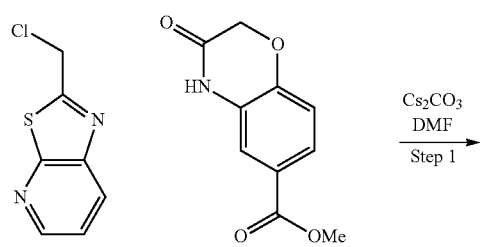

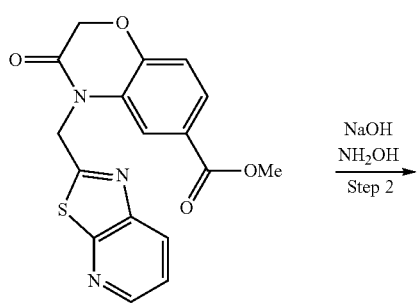

Step-1: Methyl 3-oxo-4-(thiazolo[5,4-b]pyridin-2-ylmethyl)-3,4-dihydro-2H-benzo[b][1,4]oxazine-6-carboxylate 2-(chloromethyl)thiazolo[5,4-b]pyridine (178 mg, 0.965 mmol) was added to a solution of methyl 3-oxo-3,4-dihydro-2H-benzo[b][1,4]oxazine-6-carboxylate (100 mg, 0.483 mmol) and cesium carbonate (315 mg, 0.965 mmol) in DMF (2 mL). The reaction stirred overnight at ambient temperature. The reaction was diluted with ethyl acetate (3 mL) and washed with H₂O. The organic phase was separated and concentrated. The residue was washed with cold MeOH and filtered to afford methyl 3-oxo-4-(thiazolo[5,4-b]pyridin-2-ylmethyl)-3,4-dihydro-2H-benzo[b][1,4]oxazine-6-carboxylate (133.9 mg, 0.377 mmol, 78%) as an off-white solid which was used directly in the next step without further purification. MS: (ES, m/z): 355 [M+H]⁺.

Step-2: N-hydroxy-3-oxo-4-(thiazolo[5,4-b]pyridin-2-ylmethyl)-3,4-dihydro-2H-benzo[b][1,4]oxazine-6-carboxamide methyl 3-oxo-4-(thiazolo[5,4-b]pyridin-2-ylmethyl)-3,4-dihydro-2H-benzo[b][1,4]oxazine-6-carboxylate (133.9 mg, 0.377 mmol) was dissolved in MeOH/THF (1/4) (1 mL) and 50% aqueous hydroxyl amine (0.513 mL, 7.77 mmol). 1N aqueous sodium hydroxide solution (0.388 mL, 0.388 mmol) was added. The resulting solution stirred for 6 hours at ambient temperature, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column). The collected fractions were combined and lyophilized to afford N-hydroxy-3-oxo-4-(thiazolo[5,4-b]pyridin-2-ylmethyl)-3,4-dihydro-2H-benzo[b][1,4]oxazine-6-carboxamide (3.5 mg, 0.009 mmol, 2.5%) as a white solid. MS: (ES, m/z): 356 [M+H]⁺.

Example 60 4-(4-(dimethylcarbamoyl)benzyl)-N-hydroxy-3-oxo-3,4-dihydro-2H-benzo[b][1,4]oxazine-6-carboxamide (I-360)

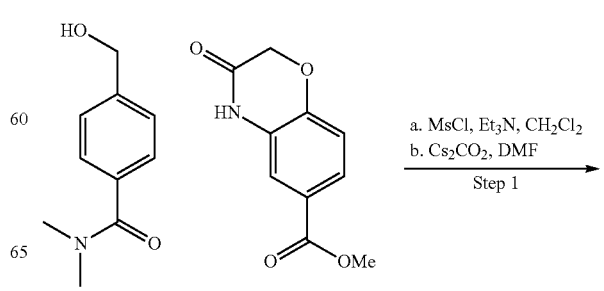

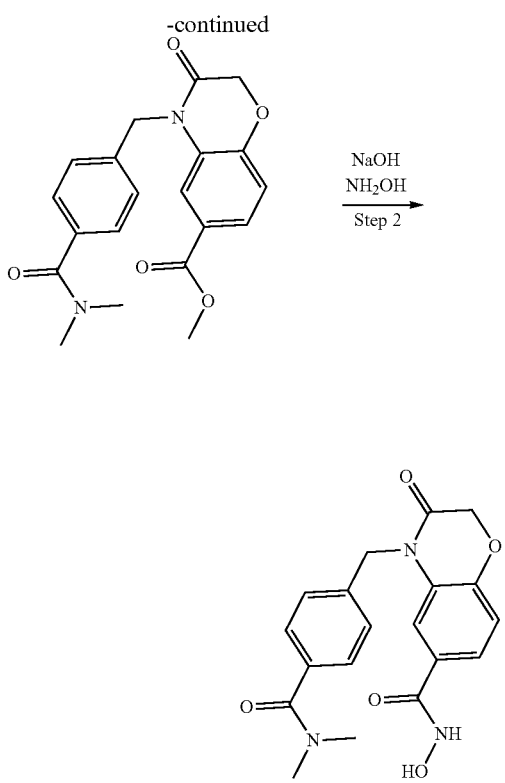

The desired fractions were combined and concentrated to afford methyl 4-(4-(dimethylcarbamoyl)benzyl)-3-oxo-3,4-dihydro-2H-benzo[b][1,4]oxazine-6-carboxylate (157.7 mg, 0.428 mmol, 35.5%) as an off-white solid. MS: (ES, m/z): 368 [M+H]$^+$.

Step-2: 4-(4-(dimethylcarbamoyl)benzyl)-N-hydroxy-3-oxo-3,4-dihydro-2H-benzo[b][1,4]oxazine-6-carboxamide methyl 4-(4-(dimethylcarbamoyl)benzyl)-3-oxo-3,4-dihydro-2H-benzo[b][1,4]oxazine-6-carboxylate (50 mg, 0.136 mmol) was dissolved in MeOH/THF (1/4) (1 mL) and 50% aqueous hydroxyl amine (0.179 mL, 2.71 mmol) and 1N aqueous sodium hydroxide solution (0.271 mL, 0.271 mmol) were added. The resulting solution stirred for 4 hours at ambient temperature, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column). The collected fractions were combined and lyophilized to afford 4-(4-(dimethylcarbamoyl)benzyl)-N-hydroxy-3-oxo-3,4-dihydro-2H-benzo[b][1,4]oxazine-6-carboxamide (4.6 mg, 0.012 mmol, 9.2%) as an orange oil. MS: (ES, m/z): 369 [M+H]$^+$.

The compounds below were synthesized according to the procedures outlined above for Example 60.

| Compnd. No. | Structure | IUPAC Name | $^1$H NMR | MS (ES, m/z) [M + H]$^+$ |
|---|---|---|---|---|
| I-361 | ![structure] | 4-(4-(dimethylamino)benzyl)-N-hydroxy-3-oxo-3,4-dihydro-2H-benzo[b][1,4]oxazine-6-carboxamide | $^1$H NMR (300 MHz, DMSO-d$_6$) δ ppm 2.83 (s, 6 H) 4.82 (s, 2 H) 5.05 (s, 2 H) 6.58-6.72 (m, 2 H) 6.97-7.18 (m, 3 H) 7.37 (dd, J = 8.35, 1.91 Hz, 1H) 7.49 (d, J = 1.76 Hz, 1H) 8.26 (s, 1 H). | 341 |

Step-1: Methyl 4-(4-(dimethylcarbamoyl)benzyl)-3-oxo-3,4-dihydro-2H-benzo[b][1,4]oxazine-6-carboxylate 4-(hydroxymethyl)-N,N-dimethylbenzamide (273 mg, 1.274 mmol), triethylamine (0.168 mL, 1.207 mmol) and methanesulfonyl chloride (0.094 mL, 1.207 mmol) were combined in DCM (1 mL) and were stirred at ambient temperature for 30 minutes. This solution was added to a mixture of methyl 3-oxo-3,4-dihydro-2H-benzo[b][1,4]oxazine-6-carboxylate (264 mg, 1.274 mmol) and cesium carbonate (393 mg, 1.207 mmol) in DMF (3 mL) The reaction stirred at ambient temperature overnight. The reaction was diluted with methylene chloride (10 mL) and washed with H$_2$O (2×5 mL). The organic phases were combined, dried over Na$_2$SO$_4$, filtered and concentrated. The crude product was purified via Biotage (25 g KP-SIL column, 15% EtOAc/Hexanes gradient up to 100% EtOAc).

Example 61 4-(4-carbamoylbenzyl)-N-hydroxy-3-oxo-3,4-dihydro-2H-benzo[b][1,4]oxazine-6-carboxamide (I-362)

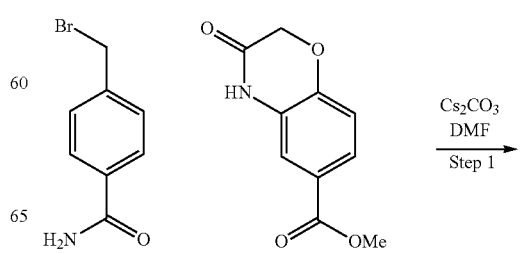

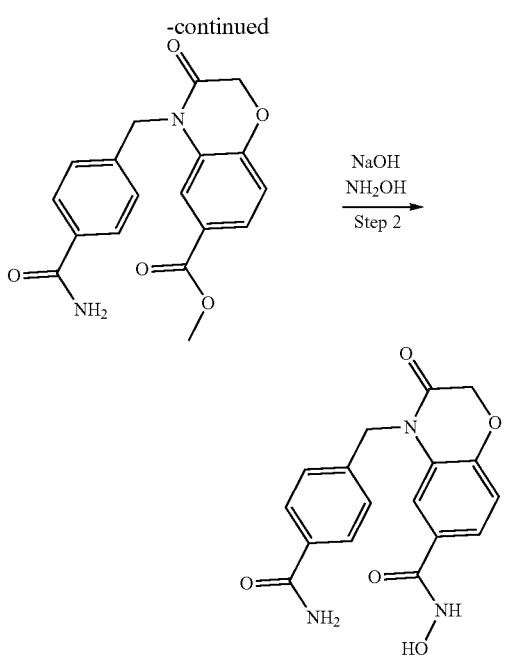

NaOH
NH₂OH
Step 2 mmol) was dissolved in MeOH/THF (1/4) (2.5 mL) and 50% aqueous hydroxyl amine (1.218 mL, 18.44 mmol) and 1N aqueous sodium hydroxide solution (1.844 mL, 1.844 mmol) were added. The resulting solution stirred for 2 hours at ambient temperature, and was then concentrated to dryness. A portion of the crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column). The collected fractions were combined and lyophilized to afford N-hydroxy-3-oxo-4-(thiazolo[5,4-b]pyridin-2-ylmethyl)-3,4-dihydro-2H-benzo[b][1,4]oxazine-6-carboxamide as a light pink solid. MS: (ES, m/z): 341 [M+H]⁺. ¹H NMR (300 MHz, DMSO-d₆) δ ppm 3.14-3.19 (m, 1H) 3.54-3.57 (m, 1H) 4.75-5.03 (m, 3H) 5.23 (s, 3H) 6.94-7.19 (m, 1H) 7.20-7.51 (m, 6H) 7.69-7.98 (m, 3H) 8.16 (s, 1H) 8.98 (brs, 2H) 11.11 (br s, 1H).

The compounds below were synthesized according to the procedures outlined above for Example 61.

| Compd. No. | Structure | IUPAC Name | ¹H NMR | MS (ES, m/z) [M + H]⁺ |
|---|---|---|---|---|
| I-371 | ![structure] | 4-(2-fluoro-5-methoxybenzyl)-N-hydroxy-3-oxo-3,4-dihydro-2H-benzo[b][1,4]oxazine-6-carboxamide | ¹H NMR (400 m/z, DMSO-d₆): δ ppm 11.14 (s, 1H), 8.99 (s, 1H), 7.45-7.42 (m, 2H), 7.21-7.16 (m, 1H), 7.10 (d, J = 8 Hz, 1H), 6.89-6.86 (m, 1H), 6.70-6.77 (m, 1H), 5.18 (s, 2H), 4.88 (s, 2H), 3.68 (s, 3H) | 347 |

Step-1: Methyl 4-(4-carbamoylbenzyl)-3-oxo-3,4-dihydro-2H-benzo[b][1,4]oxazine-6-carboxylate 4-(bromomethyl)benzamide (273 mg, 1.274 mmol) was added to a solution of methyl 3-oxo-3,4-dihydro-2H-benzo[b][1,4]oxazine-6-carboxylate (264 mg, 1.274 mmol) and cesium carbonate (415 mg, 1,274 mmol) in DMF (3 mL), and the reaction stirred overnight at 50° C. The reaction was diluted with ethyl acetate (10 mL) and washed with H₂O (3×3 mL). The organic phases were combined, dried over Na₂SO₄, filtered and concentrated to afford methyl 4-(4-carbamoylbenzyl)-3-oxo-3,4-dihydro-2H-benzo[b][1,4]oxazine-6-carboxylate (313.8 mg, 0.922 mmol, 72.4%) as a light brown solid which was used directly in the next step without further purification. MS: (ES, m/z): 340 [M+H]⁺.

Step-2: 4-(4-carbamoylbenzyl)-N-hydroxy-3-oxo-3,4-dihydro-2H-benzo[b][1,4]oxazine-6-carboxamide methyl 4-(4-carbamoylbenzyl)-3-oxo-3,4-dihydro-2H-benzo[b][1,4]oxazine-6-carboxylate (313.8 mg, 0.922

Example 62 N-hydroxy-4-(imidazo[2,1-b]thiazol-6-ylmethyl)-3-oxo-3,4-dihydro-2H-benzo[b][1,4]oxazine-6-carboxamide (I-363)

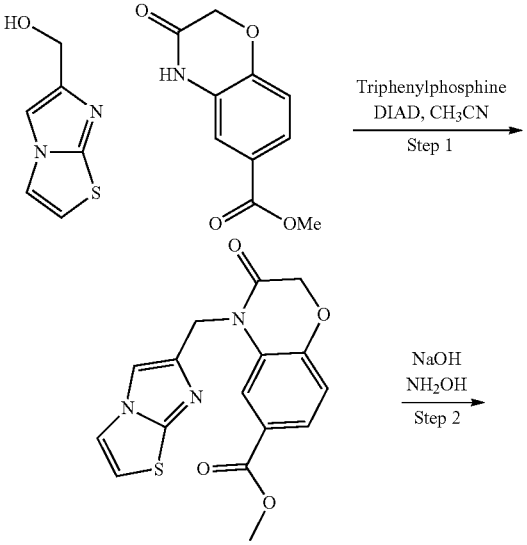

Triphenylphosphine
DIAD, CH₃CN
Step 1

NaOH
NH₂OH
Step 2

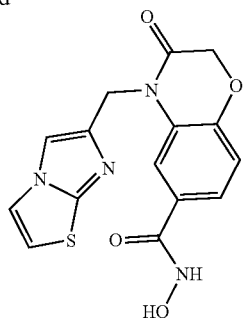

Step-1: Methyl 4-(imidazo[2,1-b]thiazol-6-ylmethyl)-3-oxo-3,4-dihydro-2H-benzo[b][1,4]oxazine-6-carboxylate Methyl 3-oxo-3,4-dihydro-2H-benzo[b][1,4]oxazine-6-carboxylate (112 mg, 0.540 mmol), imidazo[2,1-b]thiazol-6-ylmethanol (200 mg, 1,298 mmol), triphenylphosphine (0.168 mL, 1.207 mmol) and DIAD (0.094 mL, 1.207 mmol) were combined in acetonitrile (1 mL). The reaction was allowed to stir for 16 hours at 50° C. The reaction was diluted with EtOAc (15 mL) and washed with 1N NaOH (5 mL). The organic phase was dried over Na₂SO₄, filtered and concentrated. The crude product was purified via Biotage (25 g KP-SIL column, 12% EtOAc/Hexanes gradient up to 100% EtOAc). The desired fractions were combined and concentrated to afford methyl 4-(imidazo[2,1-b]thiazol-6-ylmethyl)-3-oxo-3,4-dihydro-2H-benzo[b][1,4]oxazine-6-carboxylate (438 mg, 0.510 mmol, 94%; contaminated with triphenylphospine oxide) as a yellow solid. MS: (ES, m/z): 343 [M+H]⁺.

Step-2: N-hydroxy-4-(imidazo[2,1-b]thiazol-6-ylmethyl)-3-oxo-3,4-dihydro-2H-benzo[b][1,4]oxazine-6-carboxamide Methyl 4-(imidazo[2,1-b]thiazol-6-ylmethyl)-3-oxo-3,4-dihydro-2H-benzo[b][1,4]oxazine-6-carboxylate (438 mg, 0.510 mmol) was dissolved in MeOH/THF (1/4) (1 mL) and 50% aqueous hydroxyl amine (0.674 mL, 10.21 mmol) and 1N aqueous sodium hydroxide solution (1.021 mL, 1.021 mmol) were added. The resulting solution stirred for 16 hours at ambient temperature, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column). The collected fractions were combined and lyophilized to afford N-hydroxy-4-(imidazo[2,1-b]thiazol-6-ylmethyl)-3-oxo-3,4-dihydro-2H-benzo[b][1,4]oxazine-6-carboxamide (12.7 mg, 0.037 mmol, 7.2%) as a pale brown solid. MS: (ES, m/z): 344 [M+H]⁺.

The compounds below were synthesized according to the procedures outlined above for Example 62.

| Compnd. No. | Structure | IUPAC Name | ¹H NMR | MS (ES, m/z) [M + H]⁺ |
|---|---|---|---|---|
| I-364 | 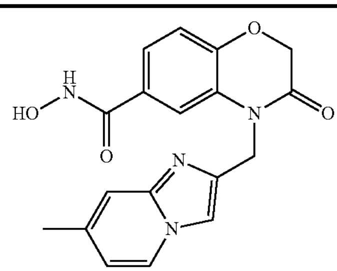 | N-hydroxy-4-((7-methylimidazo[1,2-a]pyridin-2-yl)methyl)-3-oxo-3,4-dihydro-2H-benzo[b][1,4]oxazine-6-carboxamide | ¹H NMR (300 MHz, DMSO-d₆) δ ppm 0.99-1.31 (m, 2H) 3.09-3.33 (m, 1H) 4.78 (s, 1H) 4.95-5.27 (m, 2H) 6.98-7.32 (m, 2H) 7.34-7.52 (m, 1H) 7.53-7.70 (m, 1H) 7.70-7.95 (m, 2H) 8.23 (s, 1H) | 341 |
| I-365 | 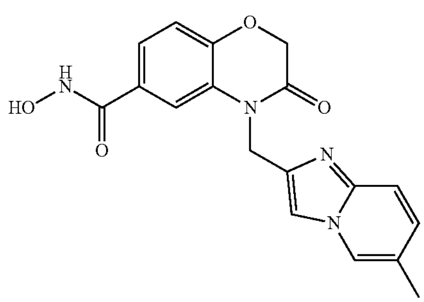 [SMILES: Cc1ccc2nc(CN3C(=O)COc4ccc(C(=O)NO)cc43)cn2c1] | N-hydroxy-4-((6-methylimidazo[1,2-a]pyridin-2-yl)methyl)-3-oxo-3,4-dihydro-2H-benzo[b][1,4]oxazine-6-carboxamide | ¹H NMR (300 MHz, DMSO-d₆) δ ppm 2.23 (s, 3H) 3.33 (br s, 8H) 4.72-4.84 (m, 2H) 5.22 (s, 2H) 6.95-7.13 (m, 2H) 7.18-7.53 (m, 2H) 7.57-7.75 (m, 2H) 8.13-8.30 (m, 1H) | 352 |
| I-366 | 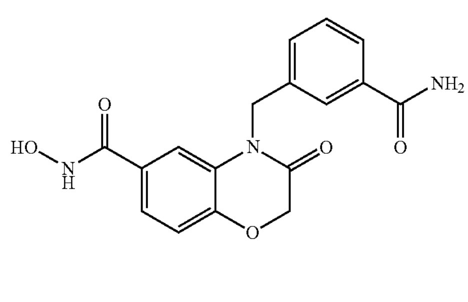 [SMILES: NC(=O)c1cccc(CN2C(=O)COc3ccc(C(=O)NO)cc32)c1] | 4-(3-carbamoylbenzyl)-N-hydroxy-3-oxo-3,4-dihydro-2H-benzo[b][1,4]oxazine-6-carboxamide | N/A | 342 |

| Compnd. No. | Structure | IUPAC Name | ¹H NMR | MS (ES, m/z) [M + H]⁺ |
|---|---|---|---|---|
| I-368 | 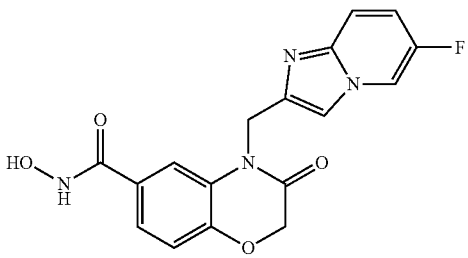 [SMILES: O=C(NO)c1ccc2c(c1)N(Cc1cn3cc(F)ccc3n1)C(=O)CO2] | 4-((6-fluoroimidazo[1,2-a]pyridin-2-yl)methyl)-N-hydroxy-3-oxo-3,4-dihydro-2H-benzo[b][1,4]oxazine-6-carboxamide | N/A | 357 |

Example 63. 4-(3-(dimethylcarbamoyl)benzyl)-N-hydroxy-3-oxo-3,4-dihydro-2H-benzo[b][1,4]oxazine-6-carboxamide (I-367)

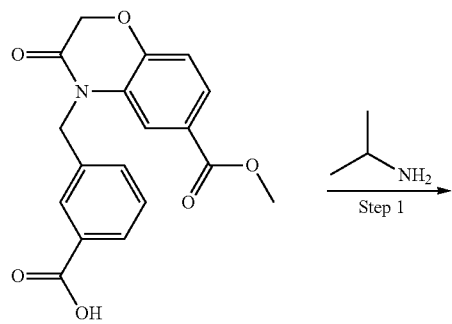

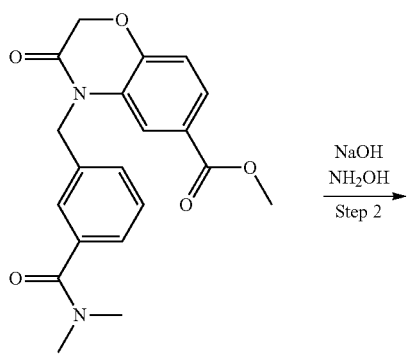

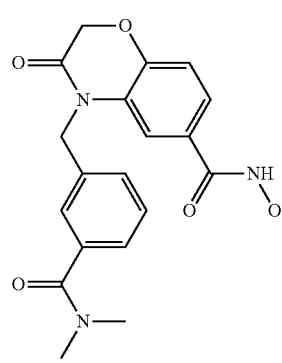

Step-1: Methyl 4-(3-(dimethylcarbamoyl)benzyl)-3-oxo-3,4-dihydro-2H-benzo[b][1,4]oxazine-6-carboxylate Propan-2-amine (0.017 g, 0.302 mmol) was added to a solution of 3-((6-(methoxycarbonyl)-3-oxo-2,3-dihydro-4H-benzo[b][1,4]oxazin-4-yl)methyl)benzoic acid (0.103 g, 0.302 mmol) and triethylamine (0.168 mL, 1.21 mmol) in DCE (1 mL). 2-Chloro-1,3-dimethylimidazolinium chloride (0.076 g, 0.453 mmol) was added and the reaction was allowed to stir at ambient temperature for 1 hour. The reaction was washed with $H_2O$ (2 mL) and the organic layer was separated, dried over $Na_2SO_4$, filtered and concentrated to afford methyl 4-(3-(dimethylcarbamoyl)benzyl)-3-oxo-3,4-dihydro-2H-benzo[b][1,4]oxazine-6-carboxylate as an oil. The crude product was used without further purification. MS: (ES, m/z): 383 [M+H]⁺.

Step-2: 4-(3-(dimethylcarbamoyl)benzyl)-N-hydroxy-3-oxo-3,4-dihydro-2H-benzo[b][1,4]oxazine-6-carboxamide Methyl 4-(3-(dimethylcarbamoyl)benzyl)-3-oxo-3,4-dihydro-2H-benzo[b][1,4]oxazine-6-carboxylate (0.115 g, 0.302 mmol) was dissolved in MeOH/THF (1/4) (1 mL) and 50% aqueous hydroxyl amine (0.399 mL, 6.04 mmol) and 1N aqueous sodium hydroxide solution (0.604 mL, 0.604 mmol) were added. The resulting solution stirred for 4 hours at ambient temperature, and was then concentrated to dryness. The crude product was purified by Prep-HPLC with the following conditions: Waters reversed phase HPLC (23 mL/min, 8 min gradient 0%-35% Acetonitrile, 0.1% formic acid on a Waters XBridge Prep C18 OBD 5 μm, 19×50 mm column). The collected fractions were combined and lyophilized to afford 4-(3-(dimethylcarbamoyl)benzyl)-N-hydroxy-3-oxo-3,4-dihydro-2H-benzo[b][1,4]oxazine-6-carboxamide (11.0 mg, 0.029 mmol, 9.5%) as a white solid. MS: (ES, m/z): 384 [M+H]⁺.

The compounds below were synthesized according to the procedures outlined above for Example 63.

| Compnd. No. | Structure | IUPAC Name | MS (ES, m/z) [M + H]+ |
|---|---|---|---|
| I-369 | 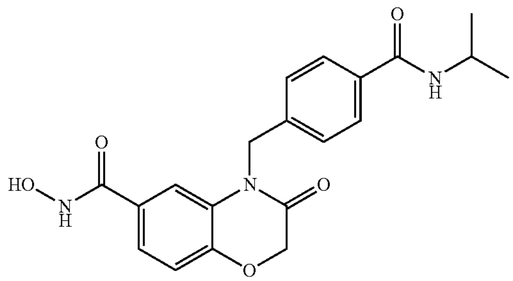 [SMILES: CC(C)NC(=O)c1ccc(CN2C(=O)COc3ccc(C(=O)NO)cc32)cc1] | N-hydroxy-4-(4-(isopropylcarbamoyl)benzyl)-3-oxo-3,4-dihydro-2H-benzo[b][1,4]oxazine-6-carboxamide | 384 |
| I-370 | 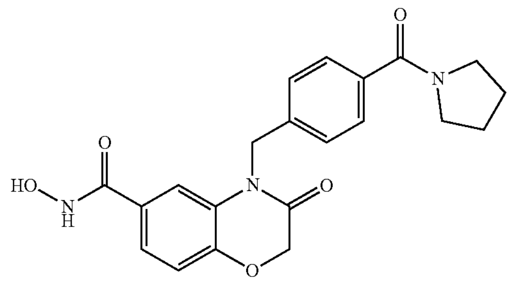 [SMILES: O=C(NO)c1ccc2c(c1)N(Cc1ccc(C(=O)N3CCCC3)cc1)C(=O)CO2] | N-hydroxy-3-oxo-4-(4-(pyrrolidine-1-carbonyl)benzyl)-3,4-dihydro-2H-benzo[b][1,4]oxazine-6-carboxamide | 396 |

Example 64. 4-(2-chloro-4-cyanobenzyl)-N-hydroxy-3-oxo-3,4-dihydro-2H-benzo[b][1,4]oxazine-6-carboxamide (I-372)

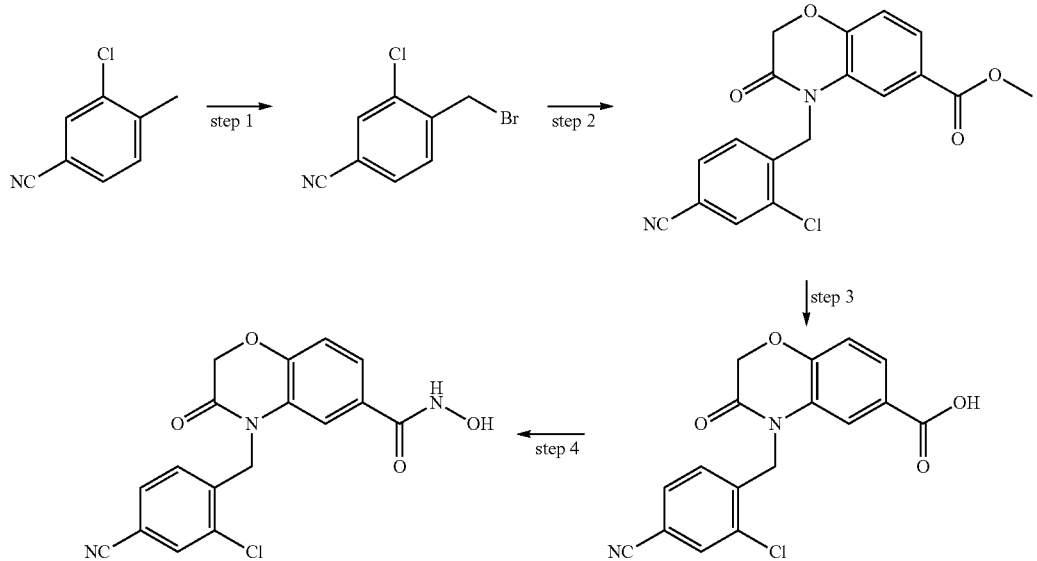

Step 1: 4-(bromomethyl)-3-chlorobenzonitrile

A solution of 3-chloro-4-methylbenzonitrile (1.0 g, 6.60 mmol), NBS (1.4 g, 7.87 mmol), and azobisisobutyronitrile (1.08 g, 6.57 mmol) in carbon tetrachloride (33 mL) stirred for 4 h at 85° C. The resulting mixture was cooled to room temperature, washed with 30 mL of water and 30 mL of brine, dried over anhydrous sodium sulfate, filtered, and concentrated under vacuum. The residue was purified via column chromatography on silica gel (eluting with ethyl acetate/petroleum ether (1:15)) to afford 4-(bromomethyl)-3-chlorobenzonitrile (360 mg, 24%) as yellow oil.

Step 2: Methyl 4-(2-chloro-4-cyanobenzyl)-3-oxo-3,4-dihydro-2H-benzo[b][1,4]oxazine-6-carboxylate A solution of methyl 3-oxo-3,4-dihydro-2H-1,4-benzoxazine-6-carboxylate (271 mg, 1.31 mmol), 4-(bromomethyl)-3-chlorobenzonitrile (450 mg, 1.86 mmol), and cesium carbonate (854 mg, 2.62 mmol) in THF (8 mL)

stirred overnight at room temperature. The reaction mixture was filtered, and the filtrate was concentrated under vacuum. The residue was purified by reversed phase column with the following conditions: Column: C18 column, 40 g, 20-45 um, 100A; Mobile phase: water with 10 mmol/L NH$_4$HCO$_3$ and ACN (5% ACN up to 70% ACN within 30 min); Detector: UV 254 nm. The collected fraction was concentrated under vacuum to afford methyl 4-(2-chloro-4-cyanobenzyl)-3-oxo-3,4-dihydro-2H-benzo[b][1,4]oxazine-6-carboxylate (400 mg, 86%) as a white solid. MS: (ESI, m/z): 357[M+H]$^+$.

Step 3: 4-(2-chloro-4-cyanobenzyl)-3-oxo-3,4-dihydro-2H-benzo[b][1,4]oxazine-6-carboxylic Acid A solution of methyl 4-(2-chloro-4-cyanobenzyl)-3-oxo-3,4-dihydro-2H-benzo[b][1,4]oxazine-6-carboxylate (100 mg, 0.28 mmol) and lithium hydroxide (34 mg, 1.42 mmol) in THF (5 mL) and water (2 mL) stirred overnight at room temperature. The pH value of the reaction mixture was adjusted to 5 with 2 M aqueous HCl solution, and the mixture was extracted with 3×15 mL of ethyl acetate. The organic phase was dried over anhydrous sodium sulfate, filtered, and concentrated under vacuum. The residue was purified by reversed phase column with the following conditions: Column: C18 column, 40 g, 20-45 um, 100A; Mobile phase: water with 10 mmol/L NH$_4$HCO$_3$ and ACN (5% ACN up to 40% ACN within 25 min); Detector: UV 254 nm. The collected fraction was concentrated under vacuum to afford 4-(2-chloro-4-cyanobenzyl)-3-oxo-3,4-dihydro-2H-benzo[b][1,4]oxazine-6-carboxylic acid (PH-FMA-PJ94-2283-3) (45 mg, 47%) as a white solid. MS: (ESI, m/z): 343[M+H]$^+$.

Step 4: 4-(2-chloro-4-cyanobenzyl)-N-hydroxy-3-oxo-3,4-dihydro-2H-benzo[b][1,4]oxazine-6-carboxamide A solution of 4-(2-chloro-4-cyanobenzyl)-3-oxo-3,4-dihydro-2H-benzo[b][1,4]oxazine-6-carboxylic acid (40 mg, 0.12 mmol), isopropyl chloroformate (65 uL, 0.59 mmol), and 4-methylmorpholine (64 µL, 0.58 mmol) in N,N-dimethyl acetamide (2 mL) stirred for 30 min at room temperature, and then hydroxylamine hydrochloride (40 mg, 0.58 mmol) was added. The resulting solution stirred overnight at room temperature. The crude product was purified by Prep-HPLC with the following conditions: Column: XBridge Shield RP18 OBD Column, 5 um, 19×150 mm; Mobile Phase A: water (10 mmol/L NH$_4$HCO$_3$), Mobile Phase B: ACN; Flow rate: 20 mL/min; Gradient: 15% B to 45% B in 7 min; 254 nm. The collected fraction was lyophilized to afford 4-(2-chloro-4-cyanobenzyl)-N-hydroxy-3-oxo-3,4-dihydro-2H-benzo[b][1,4]oxazine-6-carboxamide (10.6 mg, 25%) as a white solid. $^1$H-NMR: (DMSO, 400 MHz, ppm): δ 11.13 (br, 1H), 8.98 (br, 1H), 8.17 (s, 1H), 7.76 (d, J=8 Hz, 1H), 7.47 (d, J=8.8 Hz, 1H), 7.32 (d, J=8.4 Hz, 1H), 7.17-7.12 (m, 2H), 5.20 (s, 2H), 4.91 (s, 2H). MS: (ESI, m/z): 358[M+H]$^+$.

The compound below was synthesized according to the procedures outlined above for Example 64.

| Compnd. No. | Structure | IUPAC Name | $^1$H NMR | MS (ES, m/z) [M + H]$^+$ |
|---|---|---|---|---|
| I-373 | 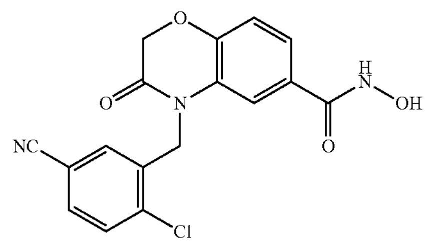 [SMILES: N#Cc1ccc(Cl)c(CN2C(=O)COc3ccc(C(=O)NO)cc32)c1] | 4-(2-chloro-5-cyanobenzyl)-N-hydroxy-3-oxo-3,4-dihydro-2H-benzo[b][1,4]oxazine-6-carboxamide | (DMSO, 400 MHz, ppm): 11.14 (br, 1H), 8.98 (br, 1H), 7.84-7.79 (m, 2H), 7.72 (s, 1H), 7.47 (d, J = 8.4 Hz, 1H), 7.13 (s, 2H), 5.14 (s, 2H), 4.95 (s, 2H) | 358 |

Example 65—In Vitro Histone Deacetylase Assay

The enzymatic HDAC8 assay was performed using electrophoretic mobility shift assay. Full length human recombinant HDAC8 protein was expressed in baculoviral system and purified by affinity chromatography. The enzymatic reactions were assembled in 384 well plates in a total volume of 25 µL in a reaction buffer composing: 100 mM HEPES, pH7.5, 25 mM KCl, 0.1% bovine serum albumin, 0.01% Triton X-100, 1% DMSO (from compounds) 2 µM of the fluorescently labeled peptide substrate and enzyme. The enzyme was added at a final concentration of 1 nM. The peptide substrate RHKK(Ac)—NH2 was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 µL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition (Pinh) is determined using the following equation: Pinh=(PSR0%−PSRinh)/(PSR0%−PSR100%)*100, where PSRinh is the product sum ratio in the presence of inhibitor, PSR0% is the average product sum ration in the absence of inhibitor and PSR100% is the average product sum ratio in 100%-inhibition control samples. The IC$_{50}$ values of inhibitors were determined by fitting the %-inhibition curves with 4 parameter dose-response model using XLfit 4 software. Ranges of IC$_{50}$ values for compounds of the invention are disclosed in Table 1:

Table 1 provides the compounds arranged according to Inhibition of proliferation of HDAC8. The compounds are separated into four groups: IC50≤25 nM, IC50>25 nM≤100 nM, IC50>100 nM≤1 µM, IC50>1 µM.

| Compounds with HDAC8 IC$_{50}$ ≤ 25 nM |
| --- |
| I-9 |
| I-15 |
| I-16 |
| I-17 |
| I-24 |
| I-27 |
| I-35 |
| I-36 |
| I-37 |
| I-38 |
| I-62 |
| I-64 |
| I-69 |
| I-70 |
| I-71 |
| I-72 |
| I-73 |
| I-74 |
| I-75 |
| I-77 |
| I-79 |
| I-81 |
| I-82 |
| I-88 |
| I-93 |
| I-94 |
| I-99 |
| I-100 |
| I-101 |
| I-103 |
| I-124 |
| I-128 |
| I-132 |
| I-134 |
| I-141 |
| I-142 |
| I-143 |
| I-144 |
| I-146 |
| I-147 |
| I-151 |
| I-152 |
| I-160 |
| I-161 |
| I-213 |
| I-217 |
| I-218 |
| I-219 |
| I-221 |
| I-222 |
| I-223 |
| I-224 |
| I-242 |
| I-243 |
| I-244 |
| I-245 |
| I-246 |
| I-247 |
| I-248 |
| I-251 |
| I-252 |
| I-254 |
| I-256 |
| I-258 |
| I-259 |
| I-263 |
| I-264 |
| I-270 |
| I-272 |
| I-274 |
| I-285 |
| I-288 |
| I-290 |
| I-296 |

| Compounds with HDAC8 IC$_{50}$ > 25 nM ≤ 100 nM |
| --- |
| I-2 |
| I-4 |
| I-5 |
| I-6 |
| I-10 |
| I-11 |
| I-19 |
| I-31 |
| I-32 |
| I-33 |
| I-34 |
| I-44 |
| I-45 |
| I-50 |
| I-53 |
| I-55 |
| I-56 |
| I-58 |
| I-59 |
| I-60 |
| I-67 |
| I-68 |
| I-76 |
| I-78 |
| I-84 |
| I-95 |
| I-96 |
| I-98 |
| I-102 |
| I-104 |
| I-105 |
| I-118 |
| I-119 |
| I-120 |
| I-121 |
| I-122 |
| I-123 |
| I-127 |
| I-131 |
| I-133 |
| I-135 |
| I-137 |
| I-139 |
| I-145 |
| I-149 |
| I-153 |
| I-154 |
| I-155 |
| I-157 |
| I-159 |
| I-162 |
| I-216 |
| I-250 |
| I-253 |
| I-255 |
| I-262 |
| I-265 |
| I-267 |
| I-268 |
| I-271 |
| I-273 |
| I-275 |
| I-276 |

-continued

I-278
I-280
I-284
I-286
I-292
I-358

Compounds with
HDAC8
IC$_{50}$ > 100 nM ≤ 1 µM

I-3
I-7
I-8
I-12
I-18
I-20
I-21
I-22
I-23
I-25
I-29
I-30
I-39
I-40
I-41
I-42
I-43
I-46
I-48
I-49
I-51
I-52
I-54
I-57
I-61
I-63
I-65
I-66
I-80
I-83
I-85
I-86
I-87
I-89
I-90
I-91
I-92
I-106
I-110
I-111
I-112
I-114
I-115
I-116
I-117
I-125
I-126
I-129
I-130
I-136
I-138
I-148
I-158
I-249
I-257
I-260
I-269
I-277
I-279

-continued

I-281
I-282
I-283
I-357

Compounds with
HDAC8
IC$_{50}$ > 1 µM

I-1
I-13
I-14
I-26
I-28
I-47
I-97
I-107
I-108
I-109
I-113
I-140
I-156

Example 66—HDAC8 Probe Binding Assay

The HDAC8 probe binding assay was performed using a time resolved fluorescence (TRF) assay format. Recombinant N-terminal GST tag full-length human HDAC8 was expressed and purified from baculovirus in Sf9 insect cells (SignalChem, #H90-30G-1000). Each assay was performed in 1536 black well microplates (Corning, #3936) in a final volume of 4 µL in assay buffer containing 50 mM HEPES (pH 7.5), 50 mM KCl, 50 mM NaCl, 0.5 mM GSH (L-Glutathione reduced, Sigma #G4251), 0.03% BGG (0.22 µM filtered, Sigma, #G7516-25G), and 0.01% Triton X-100 (Sigma, #T9284-10L). 20 nL of 10-point, 3-fold serial dilution in DMSO was pre-dispensed into respective wells of 1536 assay plates for a final test concentration range of 25 µM to 1.3 nM respectively. The final concentration in the assay of HDAC8 and probe (a fluorescein labeled pan-HDAC inhibitor) was 2.5 nM and 1.5 nM respectively. 2 µL of 2× probe and 2× anti-GST Terbium (Cisbio, #61GSTXLB) was added to assay plates followed by 2 µL of 2×HDAC8. Plates were incubated for 16 hours at room temperature before time resolved fluorescence was read on the Envision (Excitation at 340 nm, and Emission at 485 nm and 535 nm, Perkin Elmer).

Data from HDAC8 Assays were reported as percent inhibition (inh) compared with control wells based on the following equation: % inh=1−((FLU−AveLow)/(AveHigh−AveLow)) where FLU=measured time resolved fluorescence. AveLow=average time resolved fluorescence of no enzyme control (n=32). AveHigh=average time resolved fluorescence of DMSO control (n=32). IC$_{50}$ values were determined by curve fitting of the standard 4 parameter logistic fitting algorithm included in the Activity Base software package: IDBS XE Designer Model205. Data is fitted using the Levenburg Marquardt algorithm. Ranges of IC$_{50}$ values for compounds of the invention are disclosed in Table 2:

Table 2. provides the compounds arranged according to inhibition of proliferation of HDAC8 determined in a time resolved fluorescence (TRF) assay. The compounds are separated into four groups: IC50≤25 nM, IC50>25 nM≤100 nM, IC50>100 nM≤1 µM, IC50>1 µM.

| Compounds with HDAC8 IC$_{50}$ ≤ 25 nM |
| --- |
| I-33 |
| I-36 |
| I-37 |
| I-38 |
| I-64 |
| I-68 |
| I-74 |
| I-77 |
| I-82 |
| I-94 |
| I-99 |
| I-100 |
| I-101 |
| I-102 |
| I-103 |
| I-104 |
| I-141 |
| I-142 |
| I-143 |
| I-151 |
| I-152 |
| I-160 |
| I-161 |
| I-165 |
| I-166 |
| I-175 |
| I-176 |
| I-178 |
| I-179 |
| I-180 |
| I-181 |
| I-183 |
| I-185 |
| I-186 |
| I-187 |
| I-189 |
| I-191 |
| I-196 |
| I-197 |
| I-201 |
| I-202 |
| I-204 |
| I-243 |
| I-207 |
| I-208 |
| I-209 |
| I-210 |
| I-211 |
| I-213 |
| I-217 |
| I-218 |
| I-220 |
| I-221 |
| I-222 |
| I-223 |
| I-224 |
| I-226 |
| I-227 |
| I-231 |
| I-232 |
| I-233 |
| I-234 |
| I-236 |
| I-237 |
| I-238 |
| I-239 |
| I-240 |
| I-242 |
| I-245 |
| I-246 |
| I-247 |
| I-248 |
| I-251 |
| I-252 |
| I-254 |
| I-255 |
| I-256 |

-continued

| |
| --- |
| I-258 |
| I-259 |
| I-261 |
| I-263 |
| I-264 |
| I-266 |
| I-270 |
| I-340 |
| I-341 |
| I-272 |
| I-274 |
| I-280 |
| I-285 |
| I-287 |
| I-288 |
| I-289 |
| I-290 |
| I-291 |
| I-294 |
| I-318 |
| I-320 |
| I-321 |
| I-323 |
| I-325 |
| I-330 |
| I-331 |
| I-332 |
| I-333 |
| I-334 |
| I-335 |
| I-336 |
| I-337 |
| I-338 |
| I-339 |
| I-343 |
| I-344 |
| I-345 |
| I-346 |
| I-347 |
| I-348 |
| I-350 |
| I-351 |
| I-352 |
| I-355 |
| I-356 |
| I-359 |
| I-361 |
| I-362 |
| I-371 |
| I-372 |
| I-373 |

| Compounds with HDAC8 IC$_{50}$ > 25 nM ≤ 100 nM |
| --- |
| I-27 |
| I-31 |
| I-45 |
| I-50 |
| I-53 |
| I-54 |
| I-58 |
| I-59 |
| I-60 |
| I-62 |
| I-76 |
| I-96 |
| I-98 |
| I-116 |
| I-125 |
| I-135 |
| I-145 |
| I-147 |
| I-149 |
| I-150 |
| I-154 |
| I-157 |
| I-163 |

-continued

| |
|---|
| I-164 |
| I-169 |
| I-170 |
| I-171 |
| I-172 |
| I-173 |
| I-177 |
| I-182 |
| I-188 |
| I-190 |
| I-192 |
| I-193 |
| I-198 |
| I-200 |
| I-203 |
| I-205 |
| I-206 |
| I-212 |
| I-215 |
| I-216 |
| I-225 |
| I-229 |
| I-230 |
| I-244 |
| I-249 |
| I-250 |
| I-253 |
| I-265 |
| I-267 |
| I-268 |
| I-271 |
| I-273 |
| I-184 |
| I-275 |
| I-276 |
| I-277 |
| I-278 |
| I-284 |
| I-286 |
| I-295 |
| I-296 |
| I-298 |
| I-299 |
| I-300 |
| I-302 |
| I-303 |
| I-305 |
| I-306 |
| I-308 |
| I-312 |
| I-317 |
| I-319 |
| I-322 |
| I-324 |
| I-327 |
| I-342 |
| I-349 |
| I-353 |
| I-354 |
| I-357 |
| I-358 |
| I-360 |
| I-363 |
| I-292 |
| I-364 |
| I-365 |
| I-368 |
| I-369 |
| I-370 |

| Compounds with HDAC8 $IC_{50} > 100$ nM $\leq 1$ μM |
|---|
| I-2 |
| I-21 |
| I-23 |
| I-24 |
| I-25 |

-continued

| |
|---|
| I-39 |
| I-41 |
| I-44 |
| I-46 |
| I-57 |
| I-66 |
| I-93 |
| I-130 |
| I-131 |
| I-138 |
| I-159 |
| I-162 |
| I-167 |
| I-168 |
| I-174 |
| I-194 |
| I-195 |
| I-199 |
| I-214 |
| I-228 |
| I-235 |
| I-241 |
| I-257 |
| I-260 |
| I-262 |
| I-269 |
| I-279 |
| I-282 |
| I-283 |
| I-293 |
| I-297 |
| I-301 |
| I-304 |
| I-307 |
| I-310 |
| I-311 |
| I-313 |
| I-314 |
| I-315 |
| I-316 |
| I-326 |
| I-328 |
| I-329 |
| I-367 |

| Compounds with HDAC8 $IC_{50} > 1$ μM |
|---|
| I-20 |
| I-47 |
| I-281 |
| I-309 |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of Formula (I):

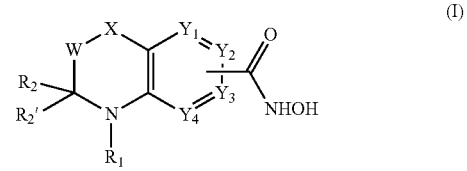

or pharmaceutically acceptable salts thereof, wherein:

$Y_1$, $Y_2$, $Y_3$, and $Y_4$ are each independently C or $CR_3$, provided that when bonded to —C(O)NHOH any of $Y_1$, $Y_2$, $Y_3$, or $Y_4$ is C;

X is selected from the group consisting of $S(O)_2$, $S(O)$, and S;

W is $C(R_4)(R_5)$;

$R_1$ is $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, —$(CH_2)_n$—$R^a$, —$(CH_2)_n$—O—$(CH_2)_p$—$R^a$, —$S(O)_2R^a$, —$C(O)R^a$, or —$C(O)N(R^a)(R^b)$, wherein each alkenyl, alkynyl, cycloalkyl, cycloalkenyl, aryl, heteroaryl, or heterocycle is optionally substituted with one or more —OH, halogen, oxo, —$NO_2$, —$NH_2$, —CN, —$C_1$-$C_6$ alkyl, —$C_1$-$C_6$ alkoxy, heterocycle, aryl, heteroaryl, or $R_4$;

$R^a$ is, at each occurrence, halogen, OH, $NH_2$, $C_2$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —$C(O)N(R_{10})(R_{11})$, wherein each alkyl, alkenyl, alkynyl, cycloalkyl, cycloalkenyl, heteroaryl, or heterocycle is optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl, and wherein each aryl is optionally substituted with one or more —OH, $R_{4'}$, $R_{5'}$, halogen, oxo, $(CH_2)_nOR_6$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl;

$R^b$ is at each occurrence, hydrogen, halogen, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —$C(O)N(R_{10})(R_{11})$, wherein each alkyl, alkenyl, alkynyl, cycloalkyl, cycloalkenyl, aryl, heteroaryl, or heterocycle is optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl;

or $R^a$ and $R^b$ can combine with the carbon or nitrogen to which they are attached to form a $C_3$-$C_8$ cycloalkyl, or 3- to 8-membered heterocycle optionally substituted with one or more substituents selected from $R_{4'}$ and $R_{5'}$, wherein $R_{4'}$ and $R_{5'}$ independently at each occurrence are H or —$C_1$-$C_6$ alkyl;

$R_2$ and $R_{2'}$ are each independently hydrogen, $C_1$-$C_6$ alkyl, $C_1$-$C_6$ alkoxy, —OH, halogen, —$NO_2$, —$NH_2$, —CN, $C_2$-$C_6$ alkenyl, $C_2$-$C_6$ alkynyl, $C_3$-$C_8$ cycloalkyl, $C_4$-$C_8$ cycloalkenyl, aryl, heteroaryl, or 3- to 8-membered heterocycle, wherein each alkyl, alkenyl, alkynyl, cycloalkyl, cycloalkenyl, aryl, heteroaryl, or heterocycle is optionally substituted with one or more —OH, halogen, oxo, —$NO_2$, —$NH_2$, —CN, —$C_1$-$C_6$ alkyl, or —$C_1$-$C_6$ alkoxy; or $R_2$ and $R_{2'}$ can combine with the carbon to which they are attached to form an oxo group, $C_3$-$C_8$ cycloalkyl, or 3- to 8-membered heterocycle;

$R_3$ is independently, at each occurrence, hydrogen, halogen, —OH, —CN, —$NO_2$, —$NH_2$, $C_1$-$C_3$ alkyl, or $C_1$-$C_3$ alkoxy;

each $R_4$ or $R_5$ is each independently, at each occurrence, hydrogen, halogen, —OH, —$NH_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_4$-$C_8$ cycloalkenyl, aryl, heteroaryl, 3- to 8-membered heterocycle, or —$C(O)N(R_{10})(R_{11})$, wherein each alkyl, alkenyl, alkynyl, cycloalkyl, cycloalkenyl, heteroaryl, or heterocycle is optionally substituted with one or more —OH, $R_{4'}$, $R_{5'}$, halogen, oxo, $(CH_2)_nOR_6$, —$NO_2$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl, and wherein aryl is optionally substituted with one or more —OH, $R_{4'}$, $R_{5'}$, halogen, oxo, $(CH_2)_nOR_6$, —$OR_6$, —$N(R_6)(R_7)$, $C(O)OR_6$, —$C(O)N(R_6)(R_7)$, —$S(O)_2R_6$, —$S(O)R_6$, —$S(R_6)$, —$C(O)R_6$, —$S(O)_2N(R_6)(R_7)$, —CN, $C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl; or $R_4$ and $R_5$ can combine with the carbon or nitrogen to which they are attached to form an oxo group, $C_3$-$C_8$ cycloalkyl, or 3- to 8-membered heterocycle optionally substituted with one or more substituents selected from $R_{4'}$ and $R_{5'}$;

$R_{4'}$ and $R_{5'}$ are, independently at each occurrence, H or —$C_1$-$C_6$ alkyl; or $R_{4'}$ and $R_{5'}$ together when attached to the same atom form a $C_3$-$C_8$ spirocycloalkyl ring; or $R_{4'}$ and $R_{5'}$ together when attached to the same atom form a $C_3$-$C_8$ spiroheterocycloalkyl ring; or $R_{4'}$ and $R_{5'}$ together when attached to adjacent atoms form an aryl ring, a heteroaryl ring, a $C_3$-$C_8$ cycloalkyl, or a 3- to 8-membered heterocycle, wherein the spirocycloalkyl, spiroheterocycloalkyl, heteroaryl, cycloalkyl or heterocycle is optionally substituted with one or more groups selected from OH, halogen, —$C_1$-$C_6$ alkyl and $C(O)OR_6$;

$R_6$ and $R_7$ are each independently selected from the group consisting of hydrogen, $C_1$-$C_6$ alkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, $C_3$-$C_8$ cycloalkyl, $C_3$-$C_8$ cycloalkenyl, aryl, heteroaryl, heterocycle, —$S(O)_2NR_8R_9$, —$S(O)_2R_8$, —$C(O)R_8$, —$CO_2R_8$, —$S(O)R_8$, and —$S(O)NR_8R_9$, wherein each alkyl, alkenyl, alkynyl, cycloalkyl, cycloalkenyl, aryl, heteroaryl, or heterocycle is optionally substituted with one or more —OH, halogen, oxo, —$NO_2$, —$NH_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl; or $R_6$ and $R_7$ together with the atom to which they are attached form a $C_3$-$C_8$ cycloalkyl or a 3- to 8-membered heterocycle, wherein the cycloalkyl or the heterocycle is optionally substituted with one or more groups selected from halogen, oxo and $C_1$-$C_6$ alkyl;

$R_8$ and $R_9$ are each independently $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, heteroaryl, or 3- to 8-membered heterocycle, wherein each is optionally substituted with one or more —OH, halogen, oxo, —NO$_2$, —NH$_2$, —CN, —$C_1$-$C_6$ alkyl, —$C_1$-$C_6$ alkoxy, $C_1$-$C_6$ alkylamino, $C_1$-$C_6$ dialkylamino, $C_1$-$C_6$ hydroxyalkyl, heterocycle, aryl, or heteroaryl;

$R_{10}$ and $R_{11}$ are each independently hydrogen, $C_1$-$C_6$ alkyl, aryl, $C_1$-$C_6$ alkylaryl or 3- to 8-membered heterocycle, wherein aryl, alkylaryl and heterocycle are optionally substituted with one or more groups selected from halogen, $C_1$-$C_6$ alkyl, and $C_1$-$C_6$ alkoxy; or $R_{10}$ and $R_{11}$ can combine to form a 3- to 8-membered heterocycle optionally substituted with one or more $R_{12}$;

$R_{12}$ is H or $C_1$-$C_6$ alkyl or two adjacent $R_{12}$ can combine to form an aryl or heteroaryl group;

n is an integer from 1 to 6; and p is an integer from 0 to 2.

2. The compound of claim 1, wherein $Y_1$, $Y_2$, and $Y_3$ are $CR_3$.

3. The compound of claim 1, wherein $Y_1$, $Y_2$, and $Y_4$ are $CR_3$.

4. The compound of claim 1, wherein $Y_1$, $Y_3$, and $Y_4$ are $CR_3$.

5. The compound of claim 1, wherein $Y_2$, $Y_3$, and $Y_4$ are $CR_3$.

6. The compound claim 1, wherein $R_1$ is —(CH$_2$)$_n$—R$^a$.

7. The compound of claim 6, wherein R$^a$ is optionally substituted aryl.

8. The compound of claim 6, wherein n is 1.

9. The compound of claim 1, wherein $R_2$ and $R_2'$ can combine with the carbon to form an oxo.

10. The compound of claim 1, wherein W is CH$_2$.

11. The compound of claim 1, wherein $R_4$ is H and $R_5$ is —C(O)N(R$_{10}$)(R$_{11}$).

12. The compound of claim 1 having the formula (IA):

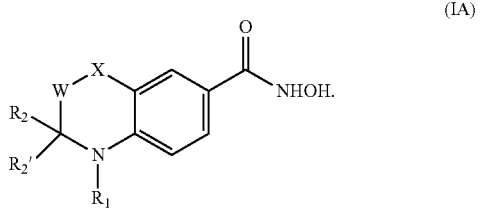

(IA)

13. The compound of claim 6, wherein n is 1 and R$^a$ is optionally substituted aryl, optionally substituted heteroaryl, or optionally substituted 3- to 8-membered heterocycle.

14. The compound of claim 6, wherein n is 1 and R$^a$ is aryl optionally substituted with one or more —OH, $R_{4'}$, $R_{5'}$, halogen, oxo, (CH$_2$)$_n$OR$_6$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

15. The compound of claim 6, wherein n is 1 and R$^a$ is heteroaryl optionally substituted with one or more —OH, $R_{4'}$, $R_{5'}$, halogen, oxo, (CH$_2$)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

16. The compound of claim 6, wherein n is 1 and R$^a$ is 3- to 8-membered heterocycle optionally substituted with one or more —OH, $R_{4'}$, $R_{5'}$, halogen, oxo, (CH$_2$)$_n$OR$_6$, —NO$_2$, —OR$_6$, —N(R$_6$)(R$_7$), C(O)OR$_6$, —C(O)N(R$_6$)(R$_7$), —S(O)$_2$R$_6$, —S(O)R$_6$, —S(R$_6$), —C(O)R$_6$, —S(O)$_2$N(R$_6$)(R$_7$), —CN, —$C_1$-$C_6$ alkyl, —$C_1$-$C_6$ haloalkyl, —$C_1$-$C_6$ alkoxy, $C_1$-$C_6$ alkylamino, $C_1$-$C_6$ dialkylamino, $C_1$-$C_6$ hydroxyalkyl, $C_3$-$C_8$ cycloalkyl, $C_3$-$C_8$ cycloalkylalkyl, arylalkyl, heterocycle, aryl, or heteroaryl.

17. The compound of claim 1, having the formula IA-3a, IA-3b, IA-3c, IA-3d, IA-4a, IA-4b, IA-4c, or IA-4d:

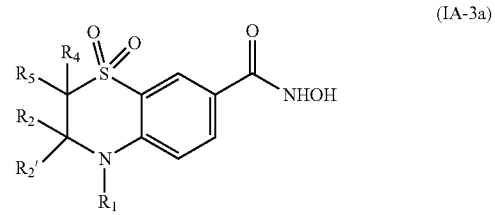

(IA-3a)

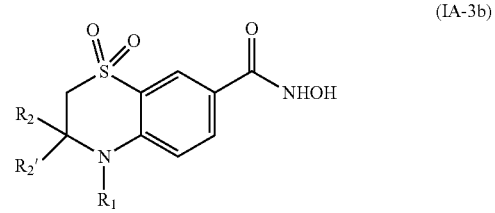

(IA-3b)

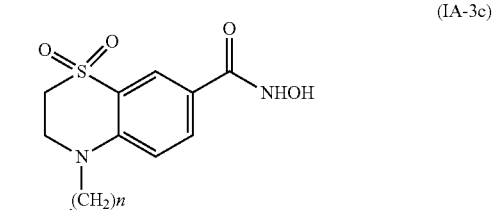

(IA-3c)

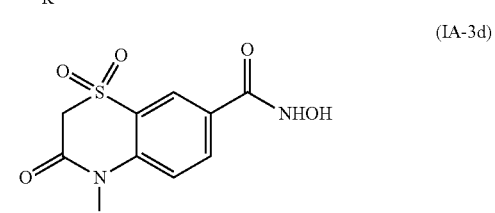

(IA-3d)

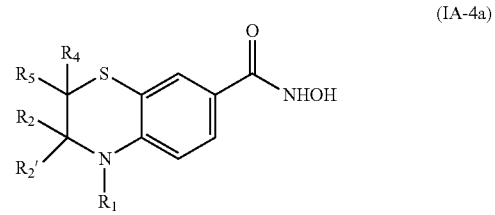

(IA-4a)

(IA-4b)
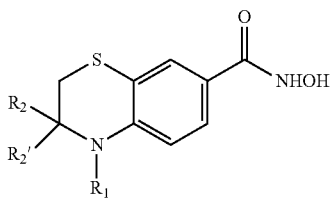

(IA-4c)
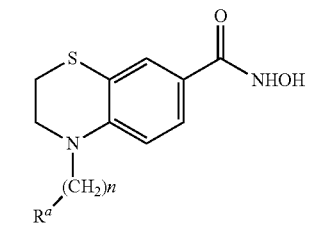

(IA-4d)
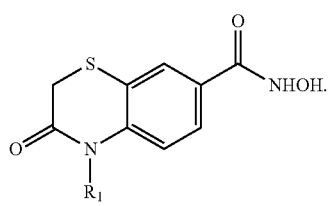

18. The compound of claim 1, having the formula IB-3a, IB-3b, IB-3c, IB-3d, IB-4a, IB-4b, IB-4c, or IB-4d:

(IB-3a)
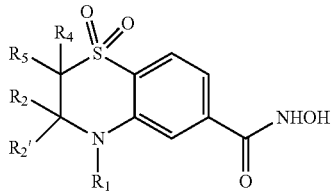

(IB-3b)
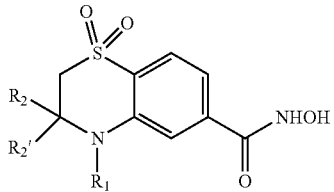

(IB-3c)
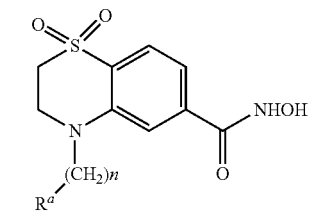

(IB-3d)
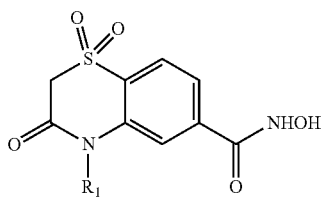

(IB-4a)
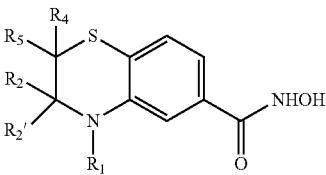

(IB-4b)
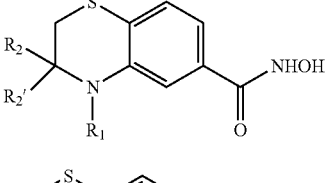

(IB-4c)
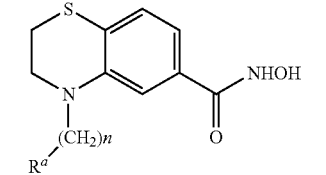

(IB-4d)
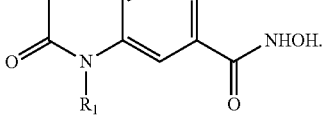

19. A compound selected from:
N-hydroxy-4-(3-((trifluoromethyl)sulfonyl)benzyl)-3,4-dihydro-2H-benzo[b][1,4]thiazine-6-carboxamide-1,1-dioxide (I-15);
N-hydroxy-4-(1-(4-(methylsulfonyl)phenyl)ethyl)-3,4-dihydro-2H-benzo[b][1,4]thiazine-6-carboxamide-1,1-dioxide (I-16);
N-hydroxy-4-(4-(trifluoromethyl)benzyl)-3,4-dihydro-2H-benzo[b][1,4]thiazine-6-carboxamide 1,1-dioxide (I-79);
N-hydroxy-4-(4-methoxybenzyl)-3,4-dihydro-2H-benzo[b][1,4]thiazine-7-carboxamide-1,1-dioxide (I-80);
N-hydroxy-4-(3-(trifluoromethyl)benzyl)-3,4-dihydro-2H-benzo[b][1,4]thiazine-6-carboxamide-1,1-dioxide (I-81);
N-hydroxy-4-(4-(methylsulfonyl)benzyl)-3,4-dihydro-2H-benzo[b][1,4]thiazine-6-carboxamide-1,1-dioxide (I-82);
or a pharmaceutically acceptable salt thereof.

20. A pharmaceutical composition comprising a compound of claim 1, and a pharmaceutically acceptable carrier.

* * * * *